US006335182B1

(12) United States Patent
Loosmore et al.

(10) Patent No.: US 6,335,182 B1
(45) Date of Patent: Jan. 1, 2002

(54) **RECOMBINANT *HAEMOPHILUS INFLUENZAE* ADHESIN PROTEINS**

(75) Inventors: Sheena M. Loosmore, Aurora; Yan Ping Yang; Michel H. Klein, both of Willowdale, all of (CA)

(73) Assignee: Aventis Pasteur Limited, Toronto (CA)

(*) Notice: Subject to any disclaimer, the term of this patent is extended or adjusted under 35 U.S.C. 154(b) by 0 days.

(21) Appl. No.: 09/268,347

(22) Filed: Mar. 16, 1999

(51) Int. Cl.[7] .............................................. C12N 15/09

(52) U.S. Cl. .................... 435/69.3; 536/23.1; 536/23.7; 536/24.1; 536/24.33; 435/69.1; 435/71.1; 435/252.3; 435/320.1; 435/243; 424/256.1; 424/200.1

(58) Field of Search .............................. 536/23.1, 23.7, 536/24.1, 24.33; 435/69.1, 252.3, 320.1, 69.3, 71.1; 424/256.1, 200.1

(56) References Cited

U.S. PATENT DOCUMENTS

| | | | |
|---|---|---|---|
| 4,258,029 | A | 3/1981 | Moloney et al. |
| 4,496,538 | A | 1/1985 | Gordon |
| 4,855,283 | A | 8/1989 | Lockhoff et al. |
| 4,952,496 | A | 8/1990 | Studier et al. |
| 5,194,254 | A | 3/1993 | Barber et al. |
| 5,646,259 | A | 7/1997 | St. Gene, III et al. |
| 5,808,024 | A | 9/1998 | Sasaki et al. |
| 5,843,463 | A | 12/1998 | Krivan et al. |

FOREIGN PATENT DOCUMENTS

| | | |
|---|---|---|
| WO | 95/34308 | 1/1995 |
| WO | 96 02648 | 2/1996 |
| WO | 96 30519 | 10/1996 |
| WO | 96/30519 | * 10/1996 |

OTHER PUBLICATIONS

Geme, J.W.S. et al :"Characterization of the Genetic Locus Encoding *Haemophilus Influenzae* Type B Surface Fibrils", Journal of Bacteriology, U.S., Washington, D.C. vol. 178, No. 21, Nov. 1996, pp. 6281–6287.

Barenkamp, S.J. et al.: "Identification of a Second Family of High–Molecular–Weight Adhesion Proteins Expressed by Non–Typeable *Haemophilus influenzae*.", Molecular Microbiology, GB, Blackwell Scientific, Oxford, vol. 19, No. 6, 1996, pp. 1215–1223.

St. Geme III, J.W. et al: "Prevalence and distribution of the hmw and hia genes and the HMW and Hia adhesins among genetically diverse strains of nontypeable *Haemophilus influenzae*", Infection and Immunity, US, American Society for Microbiology, Washington, vol. 66, No. 1, Jan. 1998, pp. 364–368.

Barbour, M.L., R.T. Mayon–White, C. Coles, D.W.M. Crook, and E.R. Moxon. 1995. The impact of conjugate vaccine on carriage of *Haemophilus influenzae* type b. J. Infect. Dis. 171:93–98.

Berkowitz et al. 1987. J. Pediatr. 110:509.

Claesson et al. 1989. J. Pediatr. 114:97.

Black, S.B., H.R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.

Nitta, D.M., M.A. Jackson, V.F. Burry, and L.C. Olson. 1995. Invasive *Haemophilus influenzae* type f disease. Pediatr. Infect. Dis. J. 14:157–160.

Waggoner–Fountain, L.A., J.O. Hendley, E.J. Cody, V.A. Perriello, and L.G. Donowitz. 1995. The emergence of *Haemophilus influenzae* types e and f as significant pathogens. Clin. Infect. Dis. 21:1322–1324.

Madore, D.V. 1996. Impact of immunization on *Haemophilus influenzae* type b disease. Infectious Agents and Disease 5:8–20.

Bluestone, C.D. 1982. Current concepts in otolaryngology. Otitis media in children: to treat or not to treat? N. Engl. J. Med. 306:1399–1404.

Barenkamp, S.J., and E. Leininger. 1992. Cloning, expression, and DNA sequence analysis of genes encoding nontypeable *Haemophilus influenzae* high–molecular–weight surface–exposed proteins related to filamentous hemagglutinin of *Bordetella pertussis*. Infect. Immun. 60:1302–1313.

St. Geme III, J.W., S. Falkow, and S.J. Barenkamp. 1993. High–molecular–weight proteins of nontypeable *Haemophilus influenzae* mediate attachment to human epithelial cells. Proc. Natl. Acad. Sci. USA 90:2875–2879.

Barenkamp, S.J. 1996. Immunization with high–molecular–weight adhesion proteins of nontypeable *Haemophilus influenzae* modifies experimental otitis media in chinchillas. Infect. Immun. 64:1246–1251.

St. Geme, J.W. and D. Cutter. 1995. Evidence that surface fibrils expressed by *Haemophilus influenzae* type b promote attachment to human epithelial cells. Molec. Microbiol. 15:77–85.

Barenkamp, S.J. and J.W. St. Geme. 1996. Identification of a second family of high–molecular–weight adhesion proteins expressed by non–typable *Haemophilus influenzae*. Molec. Microbiol. 19:1215–1223.

St. Geme, J.W., D. Cutter, and S.J. Barenkamp. 1996. Characterization of the genetic locus encoding *Haemophilus influenzae* type b surface fibrils. J. Bact. 178:6281–6287.

Patient, M.E., and D.K. Summers. 1993. ColE1 multimer formation triggers inhibition of *Escherichia coli* cell division. Molec. Microbiol. 9:1089–1095.

O'Hagan, DT. 1992. Oral delivery of vaccines. Formulation and clinical pharmaco kinetic considerations. Clin. Pharmacokinet 22 (t) : 1–10.

(List continued on next page.)

*Primary Examiner*—Jennifer E. Graser
(74) *Attorney, Agent, or Firm*—Sim & McBurney

(57) ABSTRACT

Recombinant production of Hia protein, in full-length and N-terminally truncated forms, of non-typeable strains of *Haemophilus influenzae*, is described. The nucleic acid and deduced amino acid sequences of Hia genes of various strains of non-typeable and type c *Haemophilus influenzae* also are described.

24 Claims, 201 Drawing Sheets

OTHER PUBLICATIONS

Ulmer et al. 1993. Curr. Opinion Invest. Drugs 2:983–989.

Lockhoff, O., 1991. Glycolipids as immunomodulators: Synthesis and properties 1611–1620.

Nixon–George A., et al., 1990. The adjuvant effect of stearyltyrosine on a recombinant subunit hepatitis B surface antigen. J. Immunol 144 (12) :4798–4802.

Yang, Y–P., S.M. Loosmore, B.J. Underdown, and M.H. Klein. 1998. Nasopharyngeal colonization with nontypeable *Haemophilus influenzae* in chinchillas. Infect. Immun. 66:1973–1980.

Tabor, S., and C.C. Richardson. 1985. A bacteriophage T7 RNA polymerase/promoter system for controlled exclusive expression of specific genes. Proc. Natl. Acad. Sci. USA 82:1074–1078.

Laemmli, U.K. 1970. Cleavage of structural proteins during the assembly of the head of bacteriophage $T_4$. Nature 227:680–685.

Loosmore, S.M., Y–P. Yang, D.C. Coleman, J.M. Shortreed, D.M. England, and M.H. Klein. 1997. Outer membrane protein D15 is conserved among *Haemophilus influenzae* species and may represent a universal protective antigen against invasive disease. Infect. Immun. 65:3701–3707.

Needleman, S.B. and Wunsch, C.D. 1970, J. Mol. Biol. 48:443–453.

Sellers, P.H. 1974 On the theory and computation of evolutionary distances. J. Appl. Math(Siam) 26:787–793.

Waterman, M.S., Smith, T.F. and Beyer, W.A. 1976. Advan. Math. 20:367–387.

Smith, T.F. and Waterman, M.S. 1981 Identification of common molecular subsequences. J. Mol. Biol. 147:195–197.

Sobel, E. and Martinez, H.M. 1985 A multiple Sequence Alignment Program. Nucleic Acid Res. 14:363–374.

* cited by examiner

Restriction map of DS-2008-2-3, pT7 hia (11).

pT7 hia (11)

FIG.1B

Oligonucleotides used to PCR amplify the full-length strain 11 *hia* gene for expression studies.

```
sense

     EcoR I Nde I
       ↓      ↓
               M  N  K  I  F  N  V  I  W  N    P                              SEQ ID NO:2
5'   GCGAATTCATATGAACAAAATTTTTAACGTTATTTGGAAT  3'                    5038.SL  SEQ ID NO:1

antisense

       K  T  G  V  A  A  G  V  G  Y  Q  W  *  *                               SEQ ID NO:5
5'     AAAACAGGCGTTGCAGCAGGTGTTGGTTACCAGTGGTAATAG                3'           SEQ ID NO:4
3'     TTTTGTCCGCAACGTCGTCCACAACCAATGGTCACCATTATCTTAAGGCCTAGGCG  5'  5039.SL  SEQ ID NO:3
                                                 ↑     ↑
                                             EcoR I BamH I
```

Construction of DS-2092-1 and DS-2092-40, plasmids containing tandem T7 hia (11) genes.

FIG.4

Sites for N-terminal truncations of rHia proteins.

MNKIFNVIWNVVTQTWVVVSE$^{21}$LTRTHTKCASAT$^{33}$VAVAV$^{38}$LATLLSATVEANAN$^{52}$TPVTNKLKAYGD (SEQ ID NO.6)

Construction of plasmids expressing truncated hia (11) genes.

FIG.5B

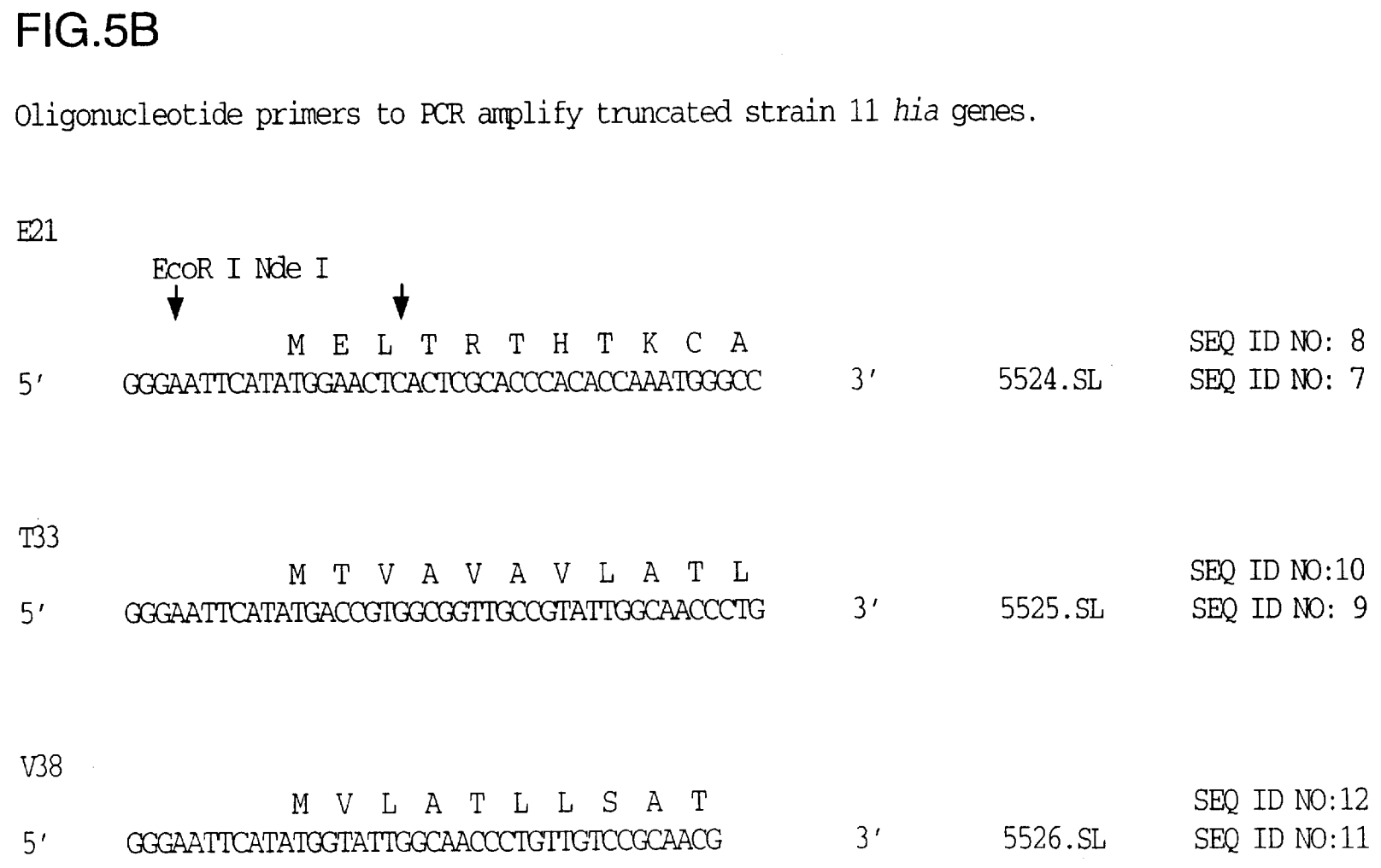

Oligonucleotide primers to PCR amplify truncated strain 11 *hia* genes.

E21

EcoR I Nde I

| | | | | |
|---|---|---|---|---|
| | M E L T R T H T K C A | | | SEQ ID NO: 8 |
| 5′ | GGGAATTCATATGGAACTCACTCGCACCCACACCAAATGGGCC | 3′ | 5524.SL | SEQ ID NO: 7 |

T33

| | | | | |
|---|---|---|---|---|
| | M T V A V A V L A T L | | | SEQ ID NO:10 |
| 5′ | GGGAATTCATATGACCGTGGCGGTTGCCGTATTGGCAACCCTG | 3′ | 5525.SL | SEQ ID NO: 9 |

V38

| | | | | |
|---|---|---|---|---|
| | M V L A T L L S A T | | | SEQ ID NO:12 |
| 5′ | GGGAATTCATATGGTATTGGCAACCCTGTTGTCCGCAACG | 3′ | 5526.SL | SEQ ID NO:11 |

```
            M  N  T  P  V  T  N  K  L  K  A                        SEQ ID NO:14
5'   GGGAATTCATATGAATACTCCTGTTACGAATAAGTTGAAGGCT   3'   5527.SL   SEQ ID NO:13
```

antisense

```
      H  T  I  T  F  A  L  A  K  D  L  G                           SEQ ID NO:17
5'   CACACCATTACCTTTGCGCTAGCGAAAGACCTTGGTGG        3'             SEQ ID NO:16
3'   GTGTGGTAATGGAAACGCGATCGCTTTCTGGAACCACCCTAGGGC 5'   5528.SL   SEQ ID NO:15
                         ↑           ↑        ↑
                       Nhe I       Sty I    BamH I
```

Construction of BK-96-2-11,
a plasmid containing T7 V38 hia(11) and cer.

FIG.6B

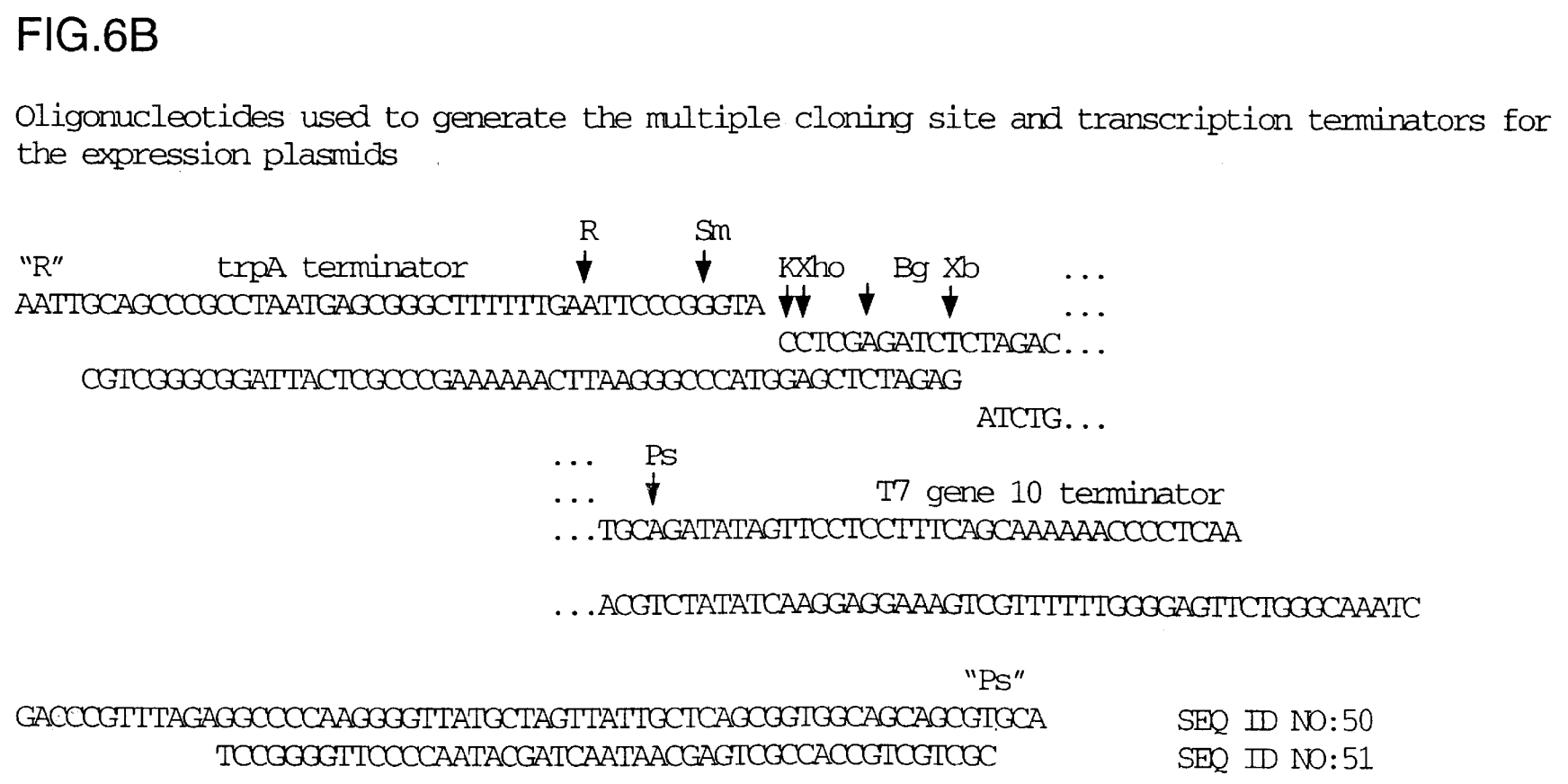

Oligonucleotides used to generate the multiple cloning site and transcription terminators for the expression plasmids

```
                                           R      Sm
"R"          trpA terminator                               KXho    Bg Xb      ...
AATTGCAGCCCGCCTAATGAGCGGGCTTTTTTTTGAATTCCCGGGTA                                ...
                                                    CCTCGAGATCTCTAGAC...
   CGTCGGGCGGATTACTCGCCCGAAAAAACTTAAGGGCCCATGGAGCTCTAGAG
                                                                ATCTG...
                                       ...   Ps
                                       ...               T7 gene 10 terminator
                                       ...TGCAGATATAGTTCCTCCTTTCAGCAAAAAACCCCTCAA

                                       ...ACGTCTATATCAAGGAGGAAAGTCGTTTTTTGGGGAGTTCTGGCAAATC

                                                               "Ps"
GACCCGTTTAGAGGCCCCAAGGGGTTATGCTAGTTATTGCTCAGCGGTGGCAGCAGCGTGCA        SEQ ID NO:50
           TCCGGGGTTCCCCAATACGATCAATAACGAGTCGCCACCGTCGTCGC              SEQ ID NO:51
```

Construction of DS-2242-1 and DS-242-2, plasmids containing T7 hia (33) and cer.

FIG.7B

Oligonucleotides used to generate the 5′-end of the strain 33 *hia* gene for expression studies.

```
Nde I
↓
  M  N  K  I  F  N  V  I  W  N  V  M  T  Q  T  W  A  V  V  S  E  L  T  R  A  H  T  K...
TATGAACAAAATTTTTAACGTTATTTGGAATGTTATGACTCAAACTTGGGCTGTCG
                                                     TATCTGAACTCACTCGCGCCCACACCA...
  ACTTGTTTTAAAAATTGCAATAAACCTTACAATACTGAGTTT
                                            GAACCCGACAGCATAGACTTGAGTGAGCGCGGGTGTGGT...

                                                                                 ...

                                                        ...  R  A  S  A  T  V  A  A    SEQ ID NO:54

                                                        ...AACGTGCCTCCGCAACCGTGGCAGCCG SEQ ID NO:52

                                                        ...TTGCACGGAGGCGTTGGCACCGTC    SEQ ID NO:53
                                                                                 ↑
                                                        ...                      AlwN I
```

Construction of DS-2340-2-3,
a plasmid containing T7 V38 hia (33) and cer.

FIG.8B

Oligonucleotides used to PCR amplify the strain 33 hia gene from the V38 codon to the SnaB I site.

sense

```
             Nde I
             ↓M  V  L  A  T  V  L  S  A  T                              SEQ ID NO:61
5'    GGGAATTCATATGGTATTGGCGACCGTATTGTCTGCAACG    3'    6286.SL          SEQ ID NO:60
```

antisense

```
                                 SnaB I
                                 ↓
       D  E  T  T  A  T  V  G  N  L  R  K  L                                  SEQ ID NO:20
5'    GACGAAACCACCGCAACCGTAGGCAATTTACGTAAATTGAAGCTTCG    3'                   SEQ ID NO:19
3'    CTGCTTTGGTGGCGTTGGCATCCGTTAAATGCATTTAACTTCGAAGC    5'    6287.SL        SEQ ID NO:18
```

Construction of DS-2447-2,
a plasmid containing tandem T7 V38 hia (11) cassettes and cer.

Construction of DS-2448-17,
a plasmid containing tandem T7 V38 hia(33) cassettes and cer.

Purification of rHia (V38) from E. coli

1. Prestained molecular weight markers
2. E. coli whole cell lysate
3. Crude extract
4. Purified rHia protein The Stability of rHia (V38/SB11)

Anti-rHia (V38) Antibody Titers in Mice

Anti-V38 rHia (SB11) Antibody Titers in BALB/c Mice

Anti-V38 rHia (SB11) Antibody Titers in Guinea Pigs

FIG.17

Oligonucleotides used to PCR amplify additional *hia* genes.

sense

| | | | | |
|---|---|---|---|---|
| | M N K I F N V | | | SEQ ID NO:22 |
| 5′ | TTAAATATAAGGTAAATAAAAATGAACAAAATTTTTAACGTT | 3′ | 5040.SL | SEQ ID NO:21 |

antisense

| | | | | |
|---|---|---|---|---|
| | K T G V A A G V G Y Q W * * | | | SEQ ID NO:5 |
| 5′ | AAAACAGGCGTTGCAGCAGGTGTTGGTTACCAGTGGTAATAG | 3′ | | SEQ ID NO:4 |
| 3′ | TTTTGTCCGCAACGTCGTCCACAACCAATGGTCACCATTATCTTAAGGCCTAGGCG | 5′ | 5039.SL | SEQ ID NO:3 |

EcoR I BamH I

FIG.18A

NTHi strain 33 Hia

```
                              MET  ASN  LYS...
G A A T T C G G C T T A A A T A A A A A T G A A C A A ...
          10                  20                      ...
                        ...  ILE  PHE  ASN  VAL  ILE  TRP  ASN  VAL  MET  THR  GLN
                        ...A A T T T T T A A C G T T A T T T G G A A T G T T A T G A C T C A
                        ...  30                 40                  50                  60

  THR  TRP  ALA  VAL  VAL  SER  GLU  LEU  THR...
A A C T T G G G C T G T C G T A T C T G A A C T C A C ...
          70                  80                      ...
                        ...  ARG  ALA  HIS  THR  LYS  ARG  ALA  SER  ALA  THR  VAL
                        ...T C G C G C C C A C A C C A A A C G T G C C T C C G C A A C C G T
                        ...  90                 100                 110                 120

  ALA  ALA  ALA  VAL  LEU  ALA  THR  VAL  LEU...
G G C A G C C G C T G T A T T G G C G A C C G T A T T ...
          130                 140                     ...
                        ...  SER  ALA  THR  VAL  GLN  ALA  SER  ALA  GLY  SER  THR
                        ...G T C T G C A A C G G T T C A G G C G A G T G C A G G C A G T A C
                        ...  150                160                 170                 180

  THR  GLY  THR  ASN  SER  LEU  ASN  VAL  TYR...
G A C A G G T A C A A A T A G T T T G A A T G T T T A ...
          190                 200                     ...
```

FIG.18B

... GLY LYS ASN ASN SER ASN PHE ASN SER ALA ASN
...T G G A A A G A A T A A T T C G A A T T T C A A T T C A G C C A A
... 210 220 230 240

ASN SER ILE ALA ASP LEU ASN LYS GLN...
T A A T T C A A T A G C A G A T T T A A A T A A A C A ...
250 260 ...

... ASN ASP SER VAL TYR ASP GLY LEU LEU ASN LEU
...A A A T G A T A G T G T T T A C G A T G G T T T A T T A A A T C T
... 270 280 290 300

ASN GLU LYS GLY THR ASP LYS SER LYS...
G A A T G A A A A A G G T A C G G A T A A G T C A A A ...
310 320 ...

... PHE LEU VAL ALA ASP GLU THR THR ALA THR VAL
...A T T C C T G G T T G C T G A C G A A A C C A C C G C A A C C G T
... 330 340 350 360

GLY ASN LEU ARG LYS LEU GLY TRP VAL...
A G G C A A T T T A C G T A A A T T G G G T T G G G T ...
370 380 ...

... VAL SER THR LYS ASN SER THR LYS GLU GLU SER
...A G T A T C A A C C A A A A A C A G T A C G A A A G A A G A A A G
... 390 400 410 420

FIG.18C

```
 ASN  GLN  VAL  LYS  GLN  ALA  ASP  GLU  VAL...
C A A T C A A G T C A A A C A G G C G G A T G A A G T ...
                430                 440                 ...
                                    ...  LEU  PHE  GLU  GLY  LYS  ASP  GLY  VAL  THR  VAL  THR
                                    ...G T T G T T T G A A G G C A A A G A C G G T G T A A C G G T T A C
                                    ...  450                 460                 470                 480

 SER  LYS  SER  GLU  ASN  GLY  LYS  HIS  THR...
T T C C A A A T C T G A A A A C G G C A A A C A C A C ...
                490                 500                 ...
                                    ...  VAL  THR  PHE  ALA  LEU  ALA  ASN  ASP  LEU  ASN  VAL
                                    ...C G T T A C T T T T G C C C T T G C G A A T G A C C T T A A T G T
                                    ...  510                 520                 530                 540

 LYS  ASN  ALA  THR  VAL  SER  ASP  LYS  LEU...
A A A A A A C G C A A C C G T T A G C G A T A A A T T ...
                550                 560                 ...
                                    ...  SER  LEU  GLY  ALA  ASN  GLY  LYS  LYS  VAL  ASP  ILE
                                    ...A T C G C T T G G T G C A A A C G G C A A G A A A G T C G A T A T
                                    ...  570                 580                 590                 600

 THR  SER  ASP  ALA  ASN  GLY  LEU  LYS  PHE...
T A C C A G T G A T G C A A A C G G C T T G A A A T T ...
                610                 620                 ...
```

FIG.18D

```
                                   ...  ALA  LYS  GLN  GLY  THR  ASN  GLY  GLN  ASN  GLY  ASN
                                   ...T G C G A A A C A G G G T A C G A A T G G T C A A A A C G G T A A
                                   ...  630                 640                 650                 660

 VAL  HIS  LEU  ASN  GLY  ILE  ALA  SER  THR...
T G T T C A C T T A A A C G G T A T T G C T T C G A C ...
               670                 680                ...
                                   ...  LEU  ASP  ASP  PRO  ARG  VAL  GLY  GLY  LYS  THR  ALA
                                   ...T T T A G A T G A T C C T C G T G T G G G T G G A A A A A C A G C
                                   ...  690                 700                 710                 720

 HIS  LEU  THR  LYS  GLU  ILE  SER  ASP  THR...
A C A C C T T A C A A A A G A A A T C A G C G A T A C ...
               730                 740                ...
                                   ...  GLU  ARG  ASN  ARG  ALA  ALA  SER  VAL  GLY  ASP  VAL
                                   ...A G A A C G T A A C C G T G C T G C G A G C G T G G G C G A T G T
                                   ...  750                 760                 770                 780

 LEU  ASN  ALA  GLY  TRP  ASN  ILE  ARG  GLY...
A T T G A A T G C G G G T T G G A A T A T T C G T G G ...
               790                 800                ...
                                   ...  ALA  LYS  THR  ILE  GLY  GLY  THR  VAL  ASP  ASN  VAL
                                   ...C G C A A A A A C G A T T G G C G G T A C A G T G G A T A A T G T
                                   ...  810                 820                 830                 840
```

FIG.18E

```
  ASP  PHE  VAL  SER  THR  TYR  ASP  THR  VAL...
T G A T T T T G T T T C A A C T T A T G A C A C T G T ...
             850              860                  ...
                          ...  GLU  PHE  ALA  SER  GLY  ALA  ASN  ALA  ASN  VAL  SER
                          ...T G A A T T T G C C A G C G G C G C A A A C G C A A A T G T G A G
                          ...  870            880            890            900

  VAL  THR  THR  ASP  ASP  ASN  LYS  LYS  THR...
C G T T A C G A C T G A T G A T A A C A A A A A A A C ...
             910              920                  ...
                          ...  THR  VAL  ARG  VAL  ASP  VAL  THR  GLY  LEU  PRO  VAL
                          ...A A C C G T C C G T G T G G A T G T A A C A G G C T T G C C G G T
                          ...  930            940            950            960

  GLN  TYR  VAL  THR  GLU  ASP  SER  LYS  THR...
C C A A T A T G T T A C G G A A G A C A G C A A A A C ...
             970              980                  ...
                          ...  VAL  VAL  LYS  VAL  GLY  ASN  GLU  TYR  TYR  GLU  ALA
                          ...C G T T G T G A A A G T G G G C A A T G A G T A T T A C G A A G C
                          ...  990           1000           1010           1020

  LYS  GLN  ASP  GLY  SER  ALA  ASP  MET  ASP...
C A A G C A A G A C G G T T C G G C G G A T A T G G A ...
            1030             1040                  ...
```

FIG.18F

```
... LYS LYS VAL GLU ASN GLY LYS LEU ALA LYS THR
...T A A A A A A G T C G A A A A T G G C A A G C T G G C G A A A A C
... 1050 1060 1070 1080

LYS VAL LYS LEU VAL SER ALA ASN GLY...
T A A A G T G A A A T T G G T A T C G G C A A A C G G ...
1090 1100 ...
... THR ASN PRO VAL LYS ILE SER ASN VAL ALA ASP
...T A C A A A T C C G G T G A A A A T C A G C A A T G T T G C G G A
... 1110 1120 1130 1140

GLY THR GLU ASP THR ASP ALA VAL SER...
C G G C A C G G A A G A T A C C G A T G C G G T C A G ...
1150 1160 ...
... PHE LYS GLN LEU LYS ALA LEU GLN ASP LYS GLN
...C T T T A A G C A G T T G A A A G C C T T G C A A G A T A A A C A
... 1170 1180 1190 1200

VAL THR LEU SER ALA SER ASN ALA TYR...
G G T T A C G T T A A G T G C G A G C A A T G C T T A ...
1210 1220 ...
... ALA ASN GLY GLY SER ASP ALA ASP GLY GLY LYS
...T G C C A A T G G C G G T A G C G A T G C C G A C G G C G G C A A
... 1230 1240 1250 1260
```

FIG.18G

```
ALA THR GLN THR LEU GLY ASN ASP LEU...
GGCAACTCAAACTTTAGGCAATGATTT...
1270 1280 ...
... ASN PHE LYS PHE LYS SER THR ASP SER GLU LEU
...GAATTTTAAATTTAAATCCACAGACAGCGAGTT
... 1290 1300 1310 1320

LEU ASN ILE LYS ALA ALA GLY ASP THR...
GTTGAACATCAAAGCAGCAGGTGACAC...
1330 1340 ...
... VAL THR PHE THR PRO LYS LYS GLY SER VAL GLN
...GGTTACCTTTACGCCGAAAAAAGGTTCGGTGCA
... 1350 1360 1370 1380

VAL GLY ASP ASP GLY LYS ALA THR ILE...
GGTTGGCGATGATGGTAAGGCTACGAT...
1390 1400 ...
... GLN ASP GLY ALA LYS THR THR THR GLY LEU VAL
...TCAAGACGGCGCGAAAACAACTACCGGTTTGGT
... 1410 1420 1430 1440

GLU ALA SER GLU LEU VAL ASP SER LEU...
TGAGGCTTCTGAATTGGTTGACAGCCT...
1450 1460 ...
```

FIG.18H

```
                                    ...  ASN  LYS  LEU  GLY  TRP  LYS  VAL  GLY  VAL  GLY  LYS
                                    ...G A A C A A A T T G G G C T G G A A A G T G G G C G T T G G T A A
                                    ... 1470           1480            1490            1500

  ASP  GLY  THR  GLY  ALA  THR  ASP  GLY  THR...
A G A C G G C A C A G G A G C G A C C G A T G G C A C ...
           1510            1520          ...
                                    ...  HIS  THR  ASP  THR  LEU  VAL  LYS  SER  GLY  ASP  LYS
                                    ...G C A T A C C G A C A C T T T A G T G A A G T C G G G C G A T A A
                                    ... 1530           1540            1550            1560

  VAL  THR  LEU  LYS  ALA  GLY  ASP  ASN  LEU...
A G T A A C T T T G A A A G C C G G C G A T A A T C T ...
           1570            1580          ...
                                    ...  LYS  VAL  LYS  GLN  GLU  GLY  THR  ASN  PHE  THR  TYR
                                    ...G A A G G T C A A A C A A G A G G G T A C A A A C T T C A C T T A
                                    ... 1590           1600            1610            1620

  VAL  LEU  ARG  ASP  GLU  LEU  THR  GLY  VAL...
C G T G C T C A G A G A T G A A T T G A C G G G C G T ...
           1630            1640          ...
                                    ...  LYS  SER  VAL  GLU  PHE  LYS  ASP  THR  GLU  ASN  GLY
                                    ...A A A G A G C G T G G A G T T T A A A G A C A C G G A G A A T G G
                                    ... 1650           1660            1670            1680
```

FIG.18I

```
ALA ASN GLY ALA SER THR LYS ILE THR...
T G C A A A C G G T G C A A G C A C G A A G A T T A C ...
1690 1700 ...
... LYS ASP GLY LEU THR ILE THR PRO ALA ASN ASP
...C A A A G A C G G C T T G A C C A T T A C G C C G G C A A A C G A
... 1710 1720 1730 1740

ALA ASN GLY ALA ALA ALA THR ASP ALA...
T G C G A A T G G T G C G G C G G C G A C T G A T G C ...
1750 1760 ...
... ASP LYS ILE LYS VAL ALA SER ASP GLY ILE SER
...T G A C A A G A T T A A A G T G G C T T C A G A C G G C A T T A G
... 1770 1780 1790 1800

ALA GLY ASN LYS ALA VAL LYS ASN VAL...
T G C G G G T A A T A A A G C A G T T A A A A A C G T ...
1810 1820 ...
... VAL SER GLY LEU LYS LYS PHE GLY ASP ALA ASN
...T G T G A G C G G A C T G A A G A A A T T T G G T G A T G C G A A
... 1830 1840 1850 1860

PHE ASN PRO LEU THR SER SER ALA ASP...
T T T C A A T C C G C T G A C T A G C T C A G C C G A ...
1870 1880 ...
```

FIG.18J

```
                          ...  ASN  LEU  THR  LYS  GLN  TYR  ASP  ASN  ALA  TYR  LYS
                          ...C A A C T T A A C G A A A C A A T A T G A C A A T G C C T A T A A
                          ... 1890           1900           1910           1920

 GLY  LEU  THR  ASN  LEU  ASP  GLU  LYS  SER...
A G G C T T G A C C A A T C T G G A T G A A A A A A G ...
          1930           1940          ...
                          ...  LYS  GLY  LYS  GLN  THR  PRO  THR  VAL  ALA  ASP  ASN
                          ...T A A A G G C A A G C A A A C T C C G A C C G T T G C T G A C A A
                          ... 1950           1960           1970           1980

 THR  ALA  ALA  THR  VAL  GLY  ASP  LEU  ARG...
T A C C G C T G C A A C C G T G G G C G A T T T G C G ...
          1990           2000          ...
                          ...  GLY  LEU  GLY  TRP  VAL  ILE  SER  ALA  ASP  LYS  THR
                          ...C G G T T T G G G C T G G G T C A T T T C T G C A G A C A A A A C
                          ... 2010           2020           2030           2040

 THR  GLY  GLU  SER  LYS  GLU  TYR  SER  ALA...
C A C A G G C G A G T C A A A G G A A T A T A G C G C ...
          2050           2060          ...
                          ...  GLN  VAL  ARG  ASN  ALA  ASN  GLU  VAL  LYS  PHE  LYS
                          ...G C A A G T G C G T A A C G C C A A T G A A G T G A A A T T C A A
                          ... 2070           2080           2090           2100
```

FIG.18K

```
SER   GLY   ASN   GLY   ILE   ASN   VAL   SER   GLY...
G A G C G G C A A C G G T A T C A A T G T T T C C G G ...
              2110                    2120              ...
                        ...  LYS   THR   LEU   ASP   ASN   GLY   THR   ARG   GLU   ILE   THR
                        ...T A A A A C A T T G G A T A A C G G T A C G C G C G A A A T T A C
                        ... 2130              2140                2150               2160

PHE   GLU   LEU   ALA   LYS   ASP   GLU   ASN   ALA...
T T T T G A A T T G G C T A A A G A C G A A A A T G C ...
              2170                    2180              ...
                        ...  ILE   ALA   PHE   GLY   SER   GLY   SER   LYS   ALA   LEU   ARG
                        ...C A T T G C T T T C G G T T C T G G C T C A A A A G C C T T G C G
                        ... 2190              2200                2210               2220

ASP   ASN   THR   VAL   ALA   ILE   GLY   THR   GLY...
C G A T A A C A C G G T G G C G A T T G G T A C G G G ...
              2230                    2240              ...
                        ...  ASN   VAL   VAL   ASN   ALA   GLU   LYS   SER   GLY   ALA   PHE
                        ...C A A C G T T G T G A A T G C G G A A A A A T C T G G T G C A T T
                        ... 2250              2260                2270               2280

GLY   ASP   PRO   ASN   TYR   ILE   GLU   ASP   LYS...
C G G C G A T C C G A A C T A C A T C G A A G A T A A ...
              2290                    2300              ...
```

FIG.18L

```
                          ...  ALA  GLY  GLY  SER  TYR  ALA  PHE  GLY  ASN  ASP  ASN
                          ...A G C C G G T G G C A G C T A C G C T T T C G G T A A C G A T A A
                          ... 2310          2320          2330          2340

ARG  ILE  THR  SER  LYS  ASN  THR  PHE  VAL...
C C G T A T T A C T T C T A A A A A C A C T T T T G T ...
          2350          2360          ...
                          ...  LEU  GLY  ASN  GLY  VAL  ASN  ALA  LYS  TYR  LYS  ALA
                          ...G T T G G G T A A T G G A G T T A A T G C G A A A T A T A A A G C
                          ... 2370          2380          2390          2400

ASN  GLY  ASP  VAL  ASP  THR  GLU  THR  VAL...
C A A T G G A G A T G T T G A T A C G G A A A C C G T ...
          2410          2420          ...
                          ...  THR  VAL  LYS  ASP  LYS  ASP  GLY  LYS  GLU  THR  THR
                          ...A A C T G T T A A G G A C A A A G A C G G T A A A G A G A C T A C
                          ... 2430          2440          2450          2460

VAL  THR  VAL  PRO  LYS  ALA  LEU  GLY  ALA...
C G T T A C T G T T C C T A A A G C G T T A G G G G C ...
          2470          2480          ...
                          ...  THR  VAL  GLU  ASN  SER  VAL  TYR  LEU  GLY  ASN  LYS
                          ...T A C G G T T G A A A A C T C C G T T T A T T T G G G T A A T A A
                          ... 2490          2500          2510          2520
```

FIG.18M

```
SER THR ALA THR LYS ASP LYS GLY LYS...
A T C G A C T G C G A C A A A A G A T A A G G G T A A ...
2530 2540 ...
... ASN LEU LYS SER ASP GLY THR ALA GLY ASN THR
...A A A T C T G A A A T C T G A T G G T A C G G C G G G T A A C A C
... 2550 2560 2570 2580

THR THR ALA GLY THR THR GLY THR VAL...
T A C A A C T G C T G G T A C A A C G G G T A C G G T ...
2590 2600 ...
... ASN GLY PHE ALA GLY ALA THR ALA HIS GLY ALA
...A A A C G G C T T T G C C G G T G C A A C G G C G C A C G G T G C
... 2610 2620 2630 2640

VAL SER VAL GLY ALA SER GLY GLU GLU...
G G T T T C T G T C G G C G C A A G C G G C G A A G A ...
2650 2660 ...
... ARG ARG ILE GLN ASN VAL ALA ALA GLY GLU ILE
...A A G A C G T A T C C A A A A C G T T G C G G C A G G C G A A A T
... 2670 2680 2690 2700

SER ALA THR SER THR ASP ALA ILE ASN...
T T C C G C T A C T T C C A C C G A T G C G A T T A A ...
2710 2720 ...
```

FIG.18N

```
                              ...  GLY  SER  GLN  LEU  TYR  ALA  VAL  ALA  LYS  GLY  VAL
                              ...C G G C A G C C A G T T G T A T G C C G T G G C A A A A G G G G T
                              ... 2730               2740                2750               2760

 THR  ASN  LEU  ALA  GLY  GLN  VAL  ASN  LYS...
A A C A A A C C T T G C T G G A C A A G T G A A T A A ...
          2770                2780           ...
                              ...  VAL  GLY  LYS  ARG  ALA  ASP  ALA  GLY  THR  ALA  SER
                              ...A G T G G G C A A A C G T G C A G A T G C A G G T A C A G C A A G
                              ... 2790               2800                2810               2820

 ALA  LEU  ALA  ALA  SER  GLN  LEU  PRO  GLN...
T G C A T T A G C G G C T T C A C A G T T A C C A C A ...
          2830                2840           ...
                              ...  ALA  SER  MET  SER  GLY  LYS  SER  MET  VAL  SER  ILE
                              ...A G C C T C T A T G T C A G G T A A A T C A A T G G T T T C T A T
                              ... 2850               2860                2870               2880

 ALA  GLY  SER  SER  TYR  GLN  GLY  GLN  SER...
T G C G G G A A G T A G T T A T C A A G G T C A A A G ...
          2890                2900           ...
                              ...  GLY  LEU  ALA  ILE  GLY  VAL  SER  ARG  ILE  SER  ASP
                              ...T G G T T T A G C T A T C G G G G T A T C A A G A A T T T C C G A
                              ... 2910               2920                2930               2940
```

FIG.18O

```
  ASN   GLY   LYS   VAL   ILE   ILE   ARG   LEU   SER...
T A A T G G C A A A G T G A T T A T T C G C T T G T C ...
              2950                2960              ...
                                  ...  GLY   THR   THR   ASN   SER   GLN   GLY   LYS   THR   GLY   VAL
                                  ...A G G C A C A A C C A A T A G C C A A G G T A A A A C A G G C G T
                                  ... 2970              2980                2990                3000

  ALA   ALA   GLY   VAL   GLY   TYR   GLN   TRP   ***
T G C A G C A G G T G T T G G T T A C C A G T G G T A ...
              3010                3020              ...

                                  ...A T A G A A T T C
                                  ... 3030
```

NTHi strain 32 *hia*

```
GAATTCGGCTTTAAATATAAGGTAAATAAA ...
         10        20        30 ...
                              MET ASN LYS ILE PHE ASN VAL ILE TRP ASN
                           ...AATGAACAAAATTTTTAACGTTATTTGGAA
                           ...         40        50        60

VAL VAL THR GLN THR TRP VAL VAL VAL SER...
TGTTGTGACTCAAACTTGGGTTGTCGTATC ...
         70        80        90 ...
                           ... GLU LEU THR ARG THR HIS THR LYS CYS ALA
                           ...TGAACTCACTCGCACCCACACCAAATGCGC
                           ...        100       110       120

SER ALA THR VAL ALA VAL ALA VAL LEU ALA...
CTCCGCCACCGTGGCAGTTGCCGTATTGGC ...
        130       140       150 ...
                           ... THR LEU LEU SER ALA THR VAL GLN ALA ASN
                           ...AACCCTGTTGTCCGCAACGGTTCAGGCGAA
                           ...        160       170       180

ALA THR ASP GLU ASN GLU ASP ASP GLU GLU...
TGCTACCGATGAAAACGAAGATGATGAAGA ...
        190       200       210 ...
```

FIG.19B

```
                              ...  GLU LEU GLU PRO VAL GLN ARG SER VAL LEU
                              ...A G A G T T A G A A C C C G T A C A A C G C T C T G T T T T
                              ...              220                 230                240

 ARG TRP SER PHE LYS SER ALA LYS GLU GLY...
A A G G T G G A G C T T C A A A T C C G C T A A G G A A G G ...
          250                 260                270 ...
                              ...  THR GLY GLU GLN GLU GLY THR THR GLU VAL
                              ...C A C T G G A G A A C A A G A G G G A A C A A C A G A G G T
                              ...              280                 290                300

 ILE ASN LEU ASN THR ASP SER SER GLY ASN...
A A T A A A T T T G A A C A C A G A T T C A T C A G G A A A ...
          310                 320                330 ...
                              ...  ALA VAL GLY SER SER THR ILE THR PHE LYS
                              ...T G C A G T A G G A A G C A G C A C A A T C A C C T T C A A
                              ...              340                 350                360

 ALA GLY ASP ASN LEU LYS ILE LYS GLN SER...
A G C C G G C G A C A A C C T G A A A A T C A A A C A A A G ...
          370                 380                390 ...
                              ...  GLY ASN ASP PHE THR TYR SER LEU LYS LYS
                              ...C G G C A A T G A C T T C A C C T A C T C G C T G A A A A A
                              ...              400                 410                420
```

FIG.19C

```
   GLU   LEU   LYS   ASN   LEU   THR   SER   VAL   GLU   THR...
A G A G C T G A A A A A C C T G A C C A G T G T T G A A A C ...
                  430                   440                   450 ...
                                         ...   GLU   LYS   LEU   SER   PHE   GLY   ALA   ASN   GLY   ASN
                                         ...T G A A A A A T T A T C G T T T G G C G C A A A C G G C A A
                                         ...               460                   470                   480

   LYS   VAL   ASP   ILE   THR   SER   ASP   ALA   ASN   GLY...
T A A A G T T G A T A T T A C C A G T G A T G C A A A T G G ...
                  490                   500                   510 ...
                                         ...   LEU   LYS   LEU   ALA   LYS   THR   GLY   ASN   GLY   ASN
                                         ...C T T G A A A T T G G C G A A A A C A G G T A A C G G A A A
                                         ...               520                   530                   540

   GLY   GLN   ASN   SER   ASN   VAL   HIS   LEU   ASN   GLY...
T G G T C A A A A C A G T A A T G T T C A C T T A A A C G G ...
                  550                   560                   570 ...
                                         ...   ILE   ALA   SER   THR   LEU   THR   ASP   THR   LEU   ALA
                                         ...T A T T G C T T C G A C T T T G A C C G A T A C G C T T G C
                                         ...               580                   590                   600

   GLY   GLY   THR   THR   GLY   HIS   VAL   ASP   THR   ASN...
C G G T G G C A C A A C A G G A C A C G T T G A C A C C A A ...
                  610                   620                   630 ...
```

FIG.19D

```
                                             ...  ILE  ASP  ALA  VAL  ASN  TYR  HIS  ARG  ALA  ALA
                                             ...C A T T G A T G C G G T T A A T T A T C A T C G C G C T G C
                                             ...            640             650             660

SER  VAL  GLN  ASP  VAL  LEU  ASN  SER  GLY  TRP...
A A G C G T A C A A G A T G T G T T A A A C A G C G G T T G ...
          670             680             690 ...
                                             ...  ASN  ILE  GLN  GLY  ASN  GLY  ASN  ASN  VAL  ASP
                                             ...G A A T A T C C A A G G C A A T G G A A A C A A T G T C G A
                                             ...            700             710             720

PHE  VAL  ARG  THR  TYR  ASP  THR  VAL  ASP  PHE...
T T T T G T C C G T A C T T A C G A C A C C G T G G A C T T ...
          730             740             750 ...
                                             ...  VAL  ASN  GLY  ALA  ASN  ALA  ASN  VAL  SER  VAL
                                             ...T G T C A A T G G C G C G A A T G C C A A T G T G A G C G T
                                             ...            760             770             780

THR  ALA  ASP  THR  ALA  HIS  LYS  LYS  THR  THR...
T A C G G C T G A T A C G G C T C A C A A A A A G A C A A C ...
          790             800             810 ...
                                             ...  VAL  ARG  VAL  ASP  VAL  THR  GLY  LEU  PRO  VAL
                                             ...T G T C C G T G T G G A T G T A A C A G G C T T G C C G G T
                                             ...            820             830             840
```

FIG.19E

```
GLN  TYR  VAL  THR  GLU  ASP  GLY  LYS  THR  VAL...
T C A A T A T G T T A C G G A A G A C G G C A A A A C C G T ...
           850                 860                870 ...
                         ...  VAL  LYS  VAL  GLY  ASN  GLU  TYR  TYR  LYS  ALA
                         ...T G T G A A A G T G G G C A A T G A G T A T T A C A A A G C
                         ...            880                 890                900

LYS  ASP  ASP  GLY  SER  ALA  ASP  MET  ASN  GLN...
C A A A G A T G A C G G T T C G G C G G A T A T G A A T C A ...
           910                 920                930 ...
                         ...  LYS  VAL  GLU  ASN  GLY  GLU  LEU  ALA  LYS  THR
                         ...A A A A G T C G A A A A C G G C G A G C T G G C G A A A A C
                         ...            940                 950                960

LYS  VAL  LYS  LEU  VAL  SER  ALA  SER  GLY  THR...
C A A A G T G A A A T T G G T A T C G G C A A G C G G T A C ...
           970                 980                990 ...
                         ...  ASN  PRO  VAL  LYS  ILE  SER  ASN  VAL  ALA  ASP
                         ...A A A T C C G G T G A A A A T T A G C A A T G T T G C A G A
                         ...           1000                1010               1020

GLY  THR  GLU  ASP  THR  ASP  ALA  VAL  SER  PHE...
C G G C A C G G A A G A C A C C G A T G C G G T C A G C T T ...
          1030                1040               1050 ...
```

FIG.19F

```
                                     ...   LYS  GLN  LEU  LYS  ALA  LEU  GLN  ASP  LYS  GLN
                                     ...T A A G C A A T T A A A A G C C T T G C A A G A C A A A C A
                                     ...            1060                1070                1080

 VAL  THR  LEU  SER  THR  SER  ASN  ALA  TYR  ALA...
G G T T A C G T T G A G C A C G A G C A A T G C T T A T G C ...
               1090                1100                1110 ...
                                     ...   ASN  GLY  GLY  THR  ASP  ASN  ASP  GLY  GLY  LYS
                                     ...C A A T G G C G G T A C A G A T A A C G A C G G C G G C A A
                                     ...            1120                1130                1140

 ALA  THR  GLN  THR  LEU  SER  ASN  GLY  LEU  ASN...
G G C A A C T C A A A C T T T A A G C A A T G G T T T G A A ...
               1150                1160                1170 ...
                                     ...   PHE  LYS  PHE  LYS  SER  SER  ASP  GLY  GLU  LEU
                                     ...T T T T A A A T T T A A A T C T A G C G A T G G C G A G T T
                                     ...            1180                1190                1200

 LEU  LYS  ILE  SER  ALA  THR  GLY  ASP  THR  VAL...
G T T G A A A A T T A G C G C G A C C G G C G A T A C G G T ...
               1210                1220                1230 ...
                                     ...   THR  PHE  THR  PRO  LYS  LYS  GLY  SER  VAL  GLN
                                     ...T A C T T T T A C G C C G A A A A A A G G T T C G G T A C A
                                     ...            1240                1250                1260
```

FIG.19G

```
 VAL  GLY  ASP  ASP  GLY  LYS  ALA  SER  ILE  SER...
G G T T G G C G A T G A T G G C A A G G C T T C A A T T T C ...
            1270            1280            1290 ...
                                 ...  LYS  GLY  ALA  ASN  THR  THR  GLU  GLY  LEU  VAL
                                 ...A A A A G G T G C A A A T A C A A C T G A A G G T T T G G T
                                 ...            1300            1310            1320

 GLU  ALA  SER  GLU  LEU  VAL  GLU  SER  LEU  ASN...
T G A G G C T T C T G A A T T G G T T G A A A G C C T G A A ...
            1330            1340            1350 ...
                                 ...  LYS  LEU  GLY  TRP  LYS  VAL  GLY  VAL  GLU  LYS
                                 ...C A A A C T G G G T T G G A A A G T A G G G G T T G A G A A
                                 ...            1360            1370            1380

 VAL  GLY  SER  GLY  GLU  LEU  ASP  GLY  THR  SER...
A G T C G G C A G C G G C G A G C T T G A T G G T A C A T C ...
            1390            1400            1410 ...
                                 ...  LYS  GLU  THR  LEU  VAL  LYS  SER  GLY  ASP  LYS
                                 ...C A A G G A A A C T T T A G T G A A G T C G G G C G A T A A
                                 ...            1420            1430            1440

 VAL  THR  LEU  LYS  ALA  GLY  ASP  ASN  LEU  LYS...
A G T A A C T T T G A A A G C C G G C G A C A A T C T G A A ...
            1450            1460            1470 ...
```

FIG.19H

```
                              ... VAL  LYS  GLN  GLU  GLY  THR  ASN  PHE  THR  TYR
                              ...G G T C A A A C A A G A G G G C A C A A A C T T C A C T T A
                              ...          1480                1490                1500

ALA  LEU  LYS  ASP  GLU  LEU  THR  GLY  VAL  LYS...
C G C G C T C A A A G A T G A A T T G A C G G G C G T G A A ...
        1510                1520                1530 ...
                              ... SER  VAL  GLU  PHE  LYS  ASP  THR  ALA  ASN  GLY
                              ...G A G C G T G G A G T T T A A A G A C A C G G C G A A T G G
                              ...          1540                1550                1560

ALA  ASN  GLY  ALA  SER  THR  LYS  ILE  THR  LYS...
T G C A A A C G G T G C A A G C A C G A A G A T T A C C A A ...
        1570                1580                1590 ...
                              ... ASP  GLY  LEU  THR  ILE  THR  LEU  ALA  ASN  GLY
                              ...A G A C G G C T T G A C C A T T A C G C T G G C A A A C G G
                              ...          1600                1610                1620

ALA  ASN  GLY  ALA  THR  VAL  THR  ASP  ALA  ASP...
T G C G A A T G G T G C G A C G G T G A C T G A T G C C G A ...
        1630                1640                1650 ...
                              ... LYS  ILE  LYS  VAL  ALA  SER  ASP  GLY  ILE  SER
                              ...C A A G A T T A A A G T T G C T T C G G A C G G C A T T A G
                              ...          1660                1670                1680
```

FIG.19I

```
 ALA  GLY  ASN  LYS  ALA  VAL  LYS  ASN  VAL  ALA...
C G C G G G T A A T A A A G C A G T T A A A A A C G T C G C ...
              1690                1700                1710 ...
                              ... ALA  GLY  GLU  ILE  SER  ALA  THR  SER  THR  ASP
                              ...G G C A G G C G A A A T T T C T G C C A C T T C C A C C G A
                              ...              1720                1730                1740

 ALA  ILE  ASN  GLY  SER  GLN  LEU  TYR  ALA  VAL...
T G C G A T T A A C G G A A G C C A G T T G T A T G C C G T ...
              1750                1760                1770 ...
                              ... ALA  LYS  GLY  VAL  THR  ASN  LEU  ALA  GLY  GLN
                              ...G G C A A A A G G G G T A A C A A A C C T T G C T G G A C A
                              ...              1780                1790                1800

 VAL  ASN  ASN  LEU  GLU  GLY  LYS  VAL  ASN  LYS...
A G T G A A T A A T C T T G A G G G C A A A G T G A A T A A ...
              1810                1820                1830 ...
                              ... VAL  GLY  LYS  ARG  ALA  ASP  ALA  GLY  THR  ALA
                              ...A G T G G G C A A A C G T G C A G A T G C A G G T A C T G C
                              ...              1840                1850                1860

 SER  ALA  LEU  ALA  ALA  SER  GLN  LEU  PRO  GLN...
A A G T G C A T T A G C G G C T T C A C A G T T A C C A C A ...
              1870                1880                1890 ...
```

FIG.19J

```
                              ...   ALA   THR   MET   PRO   GLY   LYS   SER   MET   VAL   SER
                              ...A G C C A C T A T G C C A G G T A A A T C A A T G G T T T C
                              ...               1900                1910                1920

  ILE   ALA   GLY   SER   SER   TYR   GLN   GLY   GLN   ASN...
T A T T G C G G G A A G T A G T T A T C A A G G T C A A A A ...
                1930                1940                1950 ...
                              ...   GLY   LEU   ALA   ILE   GLY   VAL   SER   ARG   ILE   SER
                              ...T G G T T T A G C T A T C G G G G T A T C A A G A A T T T C
                              ...               1960                1970                1980

  ASP   ASN   GLY   LYS   VAL   ILE   ILE   ARG   LEU   SER...
C G A T A A T G G C A A A G T G A T T A T T C G C T T G T C ...
                1990                2000                2010 ...
                              ...   GLY   THR   THR   ASN   SER   GLN   GLY   LYS   THR   GLY
                              ...A G G C A C A A C C A A T A G T C A A G G T A A A A C A G G
                              ...               2020                2030                2040

  VAL   ALA   ALA   GLY   VAL   GLY   TYR   GLN   TRP   ***
C G T T G C A G C A G G T G T T G G T T A C C A G T G G T A ...

                              ...A T A G A A T T C
```

NIHi strain 29 Hia

```
                                       MET  ASN  LYS ...
T T A A A T A T A A G G T A A A T A A A A A T G A A C A A A...
          10                  20                  30...
                          ... ILE  PHE  ASN  VAL  ILE  TRP  ASN  VAL  VAL  THR
                          ... A T T T T T A A C G T T A T T T G G A A T G T T G T G A C T
                          ...                 40                  50                  60

GLN  THR  TRP  VAL  VAL  VAL  SER  GLU  LEU  THR ...
C A A A C T T G G G T T G T C G T A T C T G A A C T C A C T...
          70                  80                  90...
                          ... ARG  ALA  HIS  THR  LYS  CYS  ALA  SER  ALA  THR
                          ... C G C G C C C A C A C C A A A T G C G C C T C C G C C A C C
                          ...                100                 110                 120

VAL  ALA  VAL  ALA  VAL  LEU  ALA  THR  ALA  LEU ...
G T G G C G G T T G C C G T A T T G G C A A C T G C G T T G...
         130                 140                 150...
                          ... SER  ALA  THR  ALA  GLU  ALA  ASN  ASN  ASN  THR
                          ... T C T G C A A C G G C T G A A G C G A A C A A C A A T A C T
                          ...                160                 170                 180

SER  VAL  THR  ASN  GLY  LEU  ASN  ALA  TYR  GLY ...
T C T G T T A C G A A T G G G T T G A A T G C T T A T G G C...
         190                 200                 210...
```

FIG.20B

```
                                            ... ASP   THR   ASN   PHE   ASN   THR   THR   ASN   ASN   SER
                                            ... G A T A C T A A T T T T A A T A C A A C C A A T A A T T C G
                                            ...                 220                 230                 240

ILE   ALA   ASP   LEU   GLU   LYS   HIS   VAL   GLN   ASP ...
A T A G C A G A T T T G G A A A A A C A C G T T C A A G A T...
                  250                 260                 270...
                                            ... ALA   TYR   LYS   GLY   LEU   LEU   ASN   LEU   ASN   GLU
                                            ... G C T T A T A A A G G C T T A T T A A A T C T G A A T G A A
                                            ...                 280                 290                 300

LYS   ASP   THR   ASN   LYS   SER   SER   PHE   LEU   VAL ...
A A A G A T A C A A A T A A G T C A A G T T T C T T G G T T...
                  310                 320                 330...
                                            ... ALA   ASP   ASN   THR   ALA   ALA   THR   VAL   GLY   ASN
                                            ... G C C G A C A A T A C C G C C G C A A C C G T A G G C A A T
                                            ...                 340                 350                 360

LEU   ARG   LYS   LEU   GLY   TRP   VAL   LEU   SER   SER ...
T T G C G T A A A T T G G G C T G G G T A T T G T C T A G C...
                  370                 380                 390...
                                            ... LYS   ASN   GLY   THR   ARG   ASN   GLU   LYS   SER   TYR
                                            ... A A A A A C G G C A C A A G G A A C G A G A A A A G C T A T
                                            ...                 400                 410                 420
```

FIG.20C

```
GLN  VAL  LYS  GLN  ALA  ASP  GLU  VAL  LEU  PHE ...
C A A G T A A A A C A A G C T G A T G A A G T T C T C T T T...
                430                 440                 450...
                                   ... THR  GLY  SER  GLY  ALA  ALA  THR  VAL  SER  SER
                                   ... A C T G G A T C T G G T G C T G C A A C G G T T A G T T C C
                                   ...                460                 470                 480

SER  SER  LYS  ASP  GLY  LYS  HIS  THR  ILE  THR ...
A G C T C T A A A G A C G G T A A A C A T A C C A T T A C C...
                490                 500                 510...
                                   ... ILE  SER  VAL  THR  LYS  GLY  SER  PHE  ALA  GLU
                                   ... A T T T C T G T T A C C A A A G G T A G T T T T G C T G A G
                                   ...                520                 530                 540

VAL  LYS  THR  ASP  ALA  THR  THR  GLY  GLY  GLN ...
G T A A A A A C T G A T G C A A C T A C T G G A G G T C A A...
                550                 560                 570...
                                   ... VAL  ASN  ALA  ASP  ARG  GLY  LYS  VAL  LYS  ALA
                                   ... G T A A A C G C C G A C C G T G G T A A A G T G A A A G C T
                                   ...                580                 590                 600

GLU  ASP  GLU  ASN  GLY  ALA  ASP  VAL  ASP  LYS ...
G A G G A C G A G A A T G G A G C T G A T G T T G A T A A G...
                610                 620                 630...
```

FIG.20D

```
                                      ... LYS  VAL  ALA  THR  VAL  LYS  ASP  VAL  ALA  LYS
                                      ... A A A G T T G C A A C T G T A A A A G A T G T T G C T A A G
                                      ...                640              650              660

ALA  ILE  ASN  ASP  ALA  ALA  THR  PHE  VAL  LYS ...
G C G A T T A A C G A T G C C G C A A C T T T C G T G A A A...
            670              680              690...
                                      ... VAL  GLU  SER  THR  ASP  ASP  ASP  ILE  GLU  ASN
                                      ... G T G G A A A G C A C A G A T G A T G A C A T T G A A A A T
                                      ...                700              710              720

GLY  ALA  ALA  GLY  LYS  ASN  GLU  THR  THR  ASP ...
G G T G C T G C A G G C A A A A A T G A A A C T A C A G A C...
            730              740              750...
                                      ... GLN  ALA  LEU  LYS  ALA  GLY  ASP  THR  LEU  THR
                                      ... C A A G C T C T C A A A G C A G G C G A C A C C T T A A C C
                                      ...                760              770              780

LEU  LYS  ALA  GLY  LYS  ASN  LEU  LYS  ALA  LYS ...
T T A A A A G C G G G T A A A A A C T T A A A A G C T A A G...
            790              800              810...
                                      ... LEU  ASP  GLN  ASN  GLY  LYS  SER  VAL  THR  PHE
                                      ... T T A G A C C A A A A T G G T A A A T C A G T A A C C T T T
                                      ...                820              830              840
```

FIG.20E

```
ALA  LEU  ALA  LYS  ASP  LEU  ASP  VAL  THR  SER ...
G C T T T A G C G A A A G A C C T T G A T G T G A C C T C T...
              850                 860                 870...
                           ... ALA  LYS  VAL  SER  ASP  LYS  LEU  SER  ILE  GLY
                           ... G C G A A A G T G A G T G A T A A G T T G T C T A T T G G T
                           ...                880                 890                 900

LYS  ASP  THR  ASN  LYS  VAL  ASP  ILE  THR  SER ...
A A A G A T A C G A A T A A A G T T G A T A T T A C C A G T...
              910                 920                 930...
                           ... ASP  ALA  ASN  GLY  LEU  LYS  LEU  ALA  LYS  THR
                           ... G A T G C A A A T G G C T T G A A A T T G G C G A A A A C A
                           ...                940                 950                 960

GLY  ASN  GLY  ASN  GLY  GLN  ASN  GLY  ASN  VAL ...
G G T A A C G G A A A T G G T C A A A A C G G T A A T G T C...
              970                 980                 990...
                           ... HIS  LEU  ASN  GLY  ILE  ALA  SER  THR  LEU  THR
                           ... C A C T T A A A T G G T A T T G C T T C G A C T T T G A C C
                           ...               1000                1010                1020

ASP  THR  ILE  THR  GLY  MET  THR  THR  GLN  ALA ...
G A T A C C A T T A C A G G T A T G A C A A C A C A A G C A...
             1030                1040                1050...
```

FIG.20F

... SER ASN GLY VAL ALA VAL GLN ASN HIS ASN
... A G C A A T G G C G T G G C T G T G C A G A A T C A T A A T
... 1060 1070 1080

ARG ALA ALA SER VAL ALA ASP VAL LEU ASN ...
C G T G C T G C G A G T G T G G C T G A T G T A T T A A A T...
1090 1100 1110...

... ALA GLY TRP ASN ILE GLN GLY ASN GLY ALA
... G C A G G C T G G A A T A T T C A A G G C A A C G G A G C G
... 1120 1130 1140

SER VAL ASP PHE VAL ASN ALA TYR ASP THR ...
A G C G T T G A T T T T G T C A A T G C T T A C G A C A C A...
1150 1160 1170...

... VAL ASP PHE VAL ASN GLY THR ASN THR ASN
... G T A G A T T T T G T C A A T G G T A C A A A C A C C A A T
... 1180 1190 1200

VAL ASN VAL THR THR ASP THR ALA HIS LYS ...
G T G A A C G T T A C G A C T G A T A C G G C T C A C A A A...
1210 1220 1230...

... LYS THR THR VAL ARG VAL ASP VAL THR GLY
... A A G A C A A C C G T C C G T G T G G A T G T A A C A G G C
... 1240 1250 1260

FIG.20G

LEU PRO VAL GLN TYR VAL THR GLU ASP GLY ...
T T G C C G G T T C A A T A T G T T A C G G A A G A C G G C...
1270 1280 1290...

... LYS THR VAL VAL LYS VAL ASP ASN LYS TYR
... A A A A C C G T T G T G A A A G T G G A C A A T A A G T A T
... 1300 1310 1320

TYR GLU ALA LYS GLN ASP GLY SER ALA ASP ...
T A C G A A G C T A A G C A A G A C G G T T C G G C G G A T...
1330 1340 1350...

... MET ASP LYS LYS VAL GLU ASN GLY GLU LEU
... A T G G A T A A A A A A G T C G A A A A T G G C G A G C T G
... 1360 1370 1380

ALA LYS THR LYS VAL LYS LEU VAL SER ALA ...
G C G A A A A C C A A A G T G A A A T T G G T G T C G G C A...
1390 1400 1410...

... SER GLY GLN ASN PRO VAL LYS ILE SER ASN
... A G C G G T C A A A A T C C G G T G A A A A T C A G C A A T
... 1420 1430 1440

VAL ALA GLU GLY THR GLU GLU ASN ASP ALA ...
G T T G C G G A A G G C A C G G A A G A A A A C G A T G C G...
1450 1460 1470...

FIG.20H

```
... VAL SER PHE LYS GLN LEU LYS ALA LEU GLN
... G T C A G C T T T A A G C A A T T G A A A G C C T T G C A A
...                 1480                1490                1500

GLU LYS GLN VAL THR LEU THR ALA SER ASN ...
G A G A A A C A G G T T A C T T T A A C T G C G A G C A A T...
          1510                1520                1530...
... ALA TYR ALA ASN GLY GLY ASN ASP ALA ASP
... G C T T A T G C C A A T G G T G G T A A C G A T G C C G A C
...                 1540                1550                1560

GLY GLY LYS ALA THR GLN THR LEU ASN ASN ...
G G C G G C A A G G C A A C T C A A A C T T T A A A C A A T...
          1570                1580                1590...
... GLY LEU ASN PHE LYS PHE LYS SER THR ASP
... G G T T T G A A T T T T A A A T T T A A A T C C A C A G A C
...                 1600                1610                1620

GLY GLU LEU LEU ASN ILE LYS VAL GLU ASN ...
G G C G A G T T G T T G A A C A T C A A A G T A G A A A A T...
          1630                1640                1650...
... ASP THR VAL THR PHE THR PRO LYS LYS GLY
... G A C A C A G T T A C C T T T A C G C C G A A A A A A G G T
...                 1660                1670                1680
```

FIG.20I

```
SER VAL GLN VAL GLY GLU ASP GLY LYS ALA ...
T C G G T A C A G G T T G G C G A A G A C G G T A A G G C T...
          1690                1700              1710...
                      ... THR ILE GLN ASN GLY THR LYS THR THR ASP
                      ... A C G A T T C A A A A T G G T A C G A A A A C A A C C G A C
                      ...                1720              1730             1740

GLY LEU VAL GLU ALA SER GLU LEU VAL GLU ...
G G T T T G G T T G A A G C T T C C G A A T T G G T T G A A...
          1750                1760              1770...
                      ... SER LEU ASN LYS LEU GLY TRP LYS VAL GLY
                      ... A G C C T G A A C A A A C T G G G C T G G A A A G T G G G C
                      ...                1780              1790             1800

VAL ASP LYS ASP GLY SER GLY GLU LEU ASP ...
G T T G A T A A A G A C G G C A G C G G C G A G C T T G A T...
          1810                1820              1830...
                      ... GLY ALA SER ASN GLU THR LEU VAL LYS SER
                      ... G G T G C A T C C A A T G A A A C T T T A G T G A A G T C G
                      ...                1840              1850             1860

GLY ASP LYS VAL THR LEU LYS ALA GLY GLU ...
G G C G A T A A A G T A A C T T T G A A A G C C G G C G A G...
          1870                1880              1890...
```

FIG.20J

```
                              ... ASN LEU LYS VAL LYS GLN ASP GLY THR ASN
                              ... A A T C T G A A G G T C A A A C A A G A C G G C A C A A A C
                              ...           1900           1910           1920

PHE THR TYR ALA LEU LYS ASP GLU LEU THR ...
T T C A C T T A C G C G C T C A A A G A T G A A T T G A C G...
        1930           1940           1950...
                              ... GLY VAL LYS SER VAL GLU PHE LYS ASP THR
                              ... G G C G T G A A G A G C G T G G A G T T T A A A G A C A C G
                              ...           1960           1970           1980

ALA ASN GLY SER ASN GLY ALA SER THR LYS ...
G C G A A T G G T T C A A A C G G T G C A A G C A C G A A G...
        1990           2000           2010...
                              ... ILE THR LYS ASP GLY LEU THR ILE THR SER
                              ... A T T A C C A A A G A C G G C T T G A C C A T T A C G T C G
                              ...           2020           2030           2040

ALA ASN GLY ALA ASN GLY ALA ALA ALA THR ...
G C A A A C G G T G C G A A T G G T G C G G C G G C G A C T...
        2050           2060           2070...
                              ... ASP ALA ASP LYS ILE LYS VAL ALA SER ASP
                              ... G A T G C G G A C A A G A T T A A A G T G G C T T C A G A C
                              ...           2080           2090           2100
```

FIG.20K

```
GLY  ILE  SER  ALA  GLY  ASN  LYS  ALA  VAL  LYS ...
G G C A T C A G T G C G G G T A A T A A A G C G G T T A A A...
              2110                2120                2130...
                                   ... ASN  VAL  VAL  SER  GLY  LEU  LYS  LYS  PHE  GLY
                                   ... A A C G T T G T G A G C G G A C T G A A G A A A T T T G G T
                                   ...            2140                2150                2160

ASP  ALA  ASN  PHE  ASN  PRO  LEU  THR  SER  SER ...
G A T G C G A A T T T C A A T C C A C T G A C C A G T T C C...
              2170                2180                2190...
                                   ... ALA  ASP  ASN  LEU  THR  LYS  GLN  TYR  ASP  ASP
                                   ... G C C G A C A A C T T A A C G A A A C A A T A T G A C G A T
                                   ...            2200                2210                2220

ALA  TYR  LYS  GLY  LEU  THR  ASN  LEU  ASP  GLU ...
G C C T A T A A A G G C T T G A C C A A T T T G G A T G A A...
              2230                2240                2250...
                                   ... LYS  GLY  ALA  ASP  LYS  GLN  THR  LEU  THR  VAL
                                   ... A A A G G T G C G G A C A A G C A A A C T C T G A C T G T T
                                   ...            2260                2270                2280

ALA  ASP  ASN  THR  ALA  ALA  THR  VAL  GLY  ASP ...
G C C G A C A A T A C T G C C G C A A C C G T G G G C G A T...
              2290                2300                2310...
```

FIG.20L

```
                              ... LEU ARG GLY LEU GLY TRP VAL ILE SER ALA
                              ... T T G C G C G G C T T G G G C T G G G T C A T T T C T G C G
                              ...              2320                2330               2340

ASP LYS THR THR GLY GLU LEU ASN LYS GLU ...
G A C A A A A C C A C A G G C G A A C T C A A T A A G G A A...
              2350                2360                2370...
                              ... TYR ASN ALA GLN VAL ARG ASN ALA ASN GLU
                              ... T A C A A C G C G C A A G T G C G T A A C G C C A A T G A A
                              ...              2380                2390               2400

VAL LYS PHE LYS SER GLY ASN GLY ILE HIS ...
G T G A A A T T C A A G A G C G G C A A C G G T A T C C A T...
              2410                2420                2430...
                              ... VAL SER GLY LYS THR VAL ASN GLY ARG ARG
                              ... G T T T C C G G T A A A A C G G T C A A C G G T A G G C G C
                              ...              2440                2450               2460

GLU ILE THR PHE GLU LEU ALA LYS ASP GLU ...
G A A A T T A C T T T T G A A T T G G C T A A A G A C G A A...
              2470                2480                2490...
                              ... ASN ALA ILE ALA PHE GLY TYR GLY SER LYS
                              ... A A T G C C A T T G C T T T C G G T T A T G G C T C A A A A
                              ...              2500                2510               2520
```

FIG.20M

```
ALA   LEU   ARG   ASP   ASN   THR   VAL   ALA   ILE   GLY ...
G C C T T G C G C G A T A A C A C G G T G G C A A T T G G T...
            2530                2540                2550...
                                ...  THR   GLY   ASN   VAL   VAL   ASN   ALA   GLU   LYS   SER
                                ... A C G G G C A A C G T T G T G A A T G C G G A A A A A T C T
                                ...                2560                2570                2580

GLY   ALA   PHE   GLY   ASP   PRO   ASN   TYR   ILE   GLU ...
G G T G C A T T C G G C G A T C C G A A C T A C A T C G A A...
            2590                2600                2610...
                                ...  ASP   LYS   ALA   GLY   GLY   SER   TYR   ALA   PHE   GLY
                                ... G A T A A A G C C G G T G G C A G C T A C G C T T T C G G T
                                ...                2620                2630                2640

ASN   ASP   ASN   ARG   ILE   THR   SER   LYS   ASN   THR ...
A A C G A T A A C C G T A T T A C T T C T A A A A A C A C T...
            2650                2660                2670...
                                ...  PHE   VAL   LEU   GLY   ASN   GLY   VAL   ASN   ALA   LYS
                                ... T T T G T G T T G G G T A A T G G A G T T A A T G C G A A A
                                ...                2680                2690                2700

TYR   LYS   ALA   ASN   GLY   ASP   VAL   ASP   THR   GLU ...
T A T A A A G C C A A T G G A G A T G T T G A T A C G G A A...
            2710                2720                2730...
```

FIG.20N

```
... THR VAL THR VAL LYS ASP LYS ASP GLY LYS
... A C C G T A A C C G T T A A G G A C A A A G A C G G T A A A
...                2740                2750                2760

GLU THR THR VAL THR VAL PRO LYS ALA LEU ...
G A G A C T A C C G T T A C T G T T C C T A A A G C G T T A...
          2770                2780                2790...
... GLY ALA THR VAL GLU ASN SER VAL TYR LEU
... G G G G C T A C G G T T G A A A A C T C C G T T T A T T T G
...                2800                2810                2820

GLY ASN LYS SER THR ALA THR LYS ASP LYS ...
G G T A A T A A A T C G A C T G C G A C A A A A G A T A A G...
          2830                2840                2850...
... GLY LYS ASN LEU LYS SER ASP GLY THR ALA
... G G T A A A A A C C T G A A A T C T G A T G G T A C G G C G
...                2860                2870                2880

GLY ASN THR THR THR ALA GLY THR THR GLY ...
G G T A A C A C T A C A A C T G C T G G C A C A A C G G G T...
          2890                2900                2910...
... THR VAL ASN GLY PHE ALA GLY ALA THR ALA
... A C G G T A A A C G G C T T T G C C G G T G C A A C G G C G
...                2920                2930                2940
```

FIG.20O

```
HIS   GLY   ALA   VAL   SER   VAL   GLY   ALA   SER   GLY ...
C A C G G T G C G G T T T C T G T C G G C G C A A G C G G C...
            2950             2960             2970...
                              ... GLU   GLU   ARG   ARG   ILE   GLN   ASN   VAL   ALA   ALA
                              ... G A A G A A A G A C G T A T C C A A A A C G T C G C G G C A
                              ...             2980             2990             3000

GLY   GLU   ILE   SER   ALA   THR   SER   THR   ASP   ALA ...
G G C G A A A T T T C C G C C A C T T C C A C C G A T G C G...
            3010             3020             3030...
                              ... ILE   ASN   GLY   SER   GLN   LEU   TYR   ALA   VAL   ALA
                              ... A T T A A C G G C A G C C A G T T G T A T G C T G T G G C A
                              ...             3040             3050             3060

LYS   GLY   VAL   THR   ASN   LEU   ALA   GLY   GLN   VAL ...
A A A G G G G T A A C A A A T C T T G C T G G A C A A G T G...
            3070             3080             3090...
                              ... ASN   LYS   VAL   GLY   LYS   ARG   ALA   ASP   ALA   GLY
                              ... A A T A A A G T G G G C A A A C G T G C A G A T G C A G G T
                              ...             3100             3110             3120

THR   ALA   SER   ALA   LEU   ALA   ALA   SER   GLN   LEU ...
A C A G C A A G T G C A T T A G C A G C T T C A C A G T T A...
            3130             3140             3150...
```

FIG.20P

```
                                ... PRO GLN ALA SER MET PRO GLY LYS SER MET
                                ... C C A C A A G C C T C T A T G C C A G G T A A A T C A A T G
                                ...                 3160                3170                3180

VAL SER ILE ALA GLY SER SER TYR GLN GLY ...
G T T T C T A T T G C G G G A A G T A G T T A T C A A G G T...
          3190                3200                3210...
                                ... GLN ASN GLY LEU ALA ILE GLY VAL SER ARG
                                ... C A A A A T G G T T T A G C T A T C G G G G T A T C A C G A
                                ...                 3220                3230                3240

ILE SER ASP ASN GLY LYS 'VAL ILE ILE ARG ...
A T T T C C G A T A A T G G C A A A G T G A T T A T T C G C...
          3250                3260                3270...
                                ... LEU SER GLY THR THR ASN SER GLN GLY LYS
                                ... T T G T C A G G C A C A A C C A A T A G C C A A G G T A A A
                                ...                 3280                3290                3300

THR GLY VAL ALA ALA GLY VAL GLY TYR GLN ...
A C A G G C G T T G C A G C A G G T G T T G G T T A C C A G...
          3310                3320                3330...
                                ... TRP ***
                                ... T G G T A A T A G A A T T C C G G A T C C G C
                                ...                 3340                3350
```

FIG.21A

NTHi strain M4071 Hia

```
                MET  ASN  LYS  ILE  PHE  ASN  VAL...
G C G A A T T C A T A T G A A C A A A A T T T T T A A C G T ...
                  10                  20                  30 ...
                    ...  ILE  TRP  ASN  VAL  MET  THR  GLN  THR  TRP  ALA
                    ...T A T T T G G A A T G T T A T G A C T C A A A C T T G G G C
                    ...               40                  50                  60

 VAL  VAL  SER  GLU  LEU  THR  ARG  ALA  HIS  THR...
T G T C G T A T C T G A A C T C A C T C G C G C C C A C A C ...
                  70                  80                  90 ...
                    ...  LYS  ARG  ALA  SER  ALA  THR  VAL  ALA  THR  ALA
                    ...C A A A C G T G C C T C C G C A A C C G T G G C A A C C G C
                    ...               100                 110                 120

 VAL  LEU  ALA  THR  LEU  LEU  SER  THR  THR  VAL...
C G T A T T G G C G A C G T T G T T G T C T A C A A C A G T ...
                  130                 140                 150 ...
                    ...  GLN  ALA  THR  THR  THR  GLY  GLY  THR  THR  SER
                    ...T C A G G C G A C A A C T A C T G G C G G T A C G A C A A G
                    ...               160                 170                 180

 THR  ASN  GLY  LEU  LYS  ALA  TYR  GLY  SER  THR...
T A C A A A C G G T T T G A A A G C T T A T G G A A G T A C ...
                  190                 200                 210 ...
```

FIG.21B

```
                            ... ASN ASN PRO ASN PHE ASN ALA ALA GLY ASN
                            ...G A A T A A T C C G A A T T T C A A T G C T G C A G G T A A
                            ...             220                 230                  240

SER ALA THR ASP LEU ALA ARG GLN PHE ASP...
C T C T G C A A C T G A T T T A G C T A G A C A G T T T G A ...
              250                 260                 270 ...
                            ... GLY ALA TYR ASP GLY LEU LEU ASN LEU ASN
                            ...T G G T G C T T A T G A C G G T T T A T T A A A T C T A A A
                            ...             280                 290                  300

GLU LYS ASP ALA ASN LYS ASN LEU LEU VAL...
T G A A A A A G A T G C G A A T A A A A A T C T G T T G G T ...
              310                 320                 330 ...
                            ... THR ASP ASP LYS ALA ALA THR VAL GLY ASN
                            ...G A C T G A T G A T A A G G C G G C G A C C G T A G G C A A
                            ...             340                 350                  360

LEU ARG LYS LEU GLY TRP VAL LEU SER SER...
T T T G C G T A A A T T G G G T T G G G T A T T G T C T A G ...
              370                 380                 390 ...
                            ... LYS ASN GLY THR ARG ASN GLU LYS SER GLN
                            ...T A A A A A C G G C A C A A G G A A C G A G A A A A G C C A
                            ...             400                 410                  420
```

FIG.21C

```
GLN  VAL  LYS  HIS  ALA  ASP  GLU  VAL  LEU  PHE...
A C A A G T C A A A C A C G C G G A T G A A G T G T T G T T ...
               430                440                450 ...
                          ...  GLU  GLY  LYS  ASP  GLY  VAL  THR  VAL  THR  SER
                          ...T G A A G G C A A A G A C G G T G T A A C G G T T A C T T C
                          ...                460                470                480

LYS  SER  GLU  ASN  GLY  LYS  HIS  THR  VAL  THR...
C A A A T C T G A A A A C G G T A A A C A C A C C G T T A C ...
               490                500                510 ...
                          ...  PHE  THR  LEU  GLU  LYS  ASP  LEU  ASN  VAL  LYS
                          ...T T T T A C C C T T G A G A A A G A C C T T A A T G T A A A
                          ...                520                530                540

ASN  ALA  THR  VAL  SER  ASP  LYS  LEU  SER  LEU...
A A A C G C A A C C G T T A G C G A T A A A T T A T C G C T ...
               550                560                570 ...
                          ...  GLY  ALA  ASN  GLY  ASN  LYS  VAL  ASP  ILE  THR
                          ...T G G T G C A A A C G G C A A T A A A G T C G A T A T T A C
                          ...                580                590                600

SER  ASP  THR  ASN  GLY  LEU  LYS  PHE  ALA  LYS...
C A G T G A T A C A A A C G G C T T G A A A T T T G C G A A ...
               610                620                630 ...
```

FIG.21D

```
                                  ...  PRO SER THR ASN GLY GLN ASN GLY ASN VAL
                                  ...A C C A A G T A C G A A T G G T C A A A A C G G T A A T G T
                                  ...            640             650            660

HIS LEU ASN GLY ILE ALA SER THR LEU THR...
T C A C T T A A A C G G T A T T G C C T C T A C C T T A A C ...
            670            680            690 ...
                                  ...  ASP THR ILE THR GLY THR THR LYS SER ALA
                                  ...T G A C A C A A T T A C A G G T A C A A C A A A A T C T G C
                                  ...            700             710            720

THR ASN GLY VAL ASP VAL GLN ASN HIS ASN...
A A C T A A T G G T G T A G A T G T G C A G A A T C A T A A ...
            730            740            750 ...
                                  ...  ARG ALA ALA SER VAL ALA ASP VAL LEU ASN
                                  ...T C G T G C T G C G A G T G T A G C T G A T G T A T T G A A
                                  ...            760             770            780

ALA GLY TRP ASN ILE GLN GLY ASN GLY ALA...
T G C A G G C T G G A A T A T T C A A G G C A A C G G A G C ...
            790            800            810 ...
                                  ...  SER VAL ASP PHE VAL ASN THR TYR ASP THR
                                  ...G A G C G T T G A T T T T G T C A A T A C T T A C G A C A C
                                  ...            820             830            840
```

FIG.21E

```
 VAL  ASP  PHE  VAL  ASN  GLY  LEU  ASN  THR  ASN...
A G T A G A T T T T G T C A A T G G T T T A A A T A C C A A ...
              850                 860                 870 ...
                            ...  VAL  ASN  VAL  THR  THR  ASP  THR  ALA  HIS  ASN
                            ...T G T G A A C G T T A C G A C T G A T A C G G C T C A C A A
                            ...             880                 890                 900

 LYS  LYS  THR  THR  VAL  ARG  VAL  ASP  VAL  THR...
C A A A A A G A C A A C C G T C C G T G T G G A T G T A A C ...
              910                 920                 930 ...
                            ...  GLY  LEU  PRO  VAL  GLN  TYR  VAL  THR  GLU  ASP
                            ...G G G C T T G C C G G T C C A A T A T G T T A C G G A A G A
                            ...             940                 950                 960

 GLY  GLU  THR  VAL  VAL  LYS  VAL  GLY  ASN  GLU...
C G G C G A A A C C G T T G T G A A A G T G G G C A A T G A ...
              970                 980                 990 ...
                            ...  TYR  TYR  GLU  ALA  LYS  GLN  ASP  GLY  SER  ALA
                            ...G T A T T A C G A A G C C A A G C A A G A C G G T T C G G C
                            ...             1000                1010                1020

 ASP  MET  ASP  LYS  LYS  VAL  GLU  ASN  GLY  LYS...
G G A T A T G G A T A A A A A A G T C G A A A A T G G C A A ...
              1030                1040                1050 ...
```

FIG.21F

```
                               ...   LEU  ALA  LYS  THR  LYS  VAL  LYS  LEU  VAL  SER
                               ...G C T G G C G A A A A C T A A A G T T A A A T T G G T A T C
                               ...            1060           1070           1080

ALA  ASN  GLY  THR  ASN  PRO  VAL  LYS  ILE  SER...
G G C A A A C G G T A C A A A T C C G G T G A A A A T C A G ...
          1090           1100           1110 ...
                               ...   ASN  VAL  ALA  ASP  GLY  THR  GLU  ASN  THR  ASP
                               ...C A A T G T T G C G G A C G G C A C G G A A A A T A C C G A
                               ...            1120           1130           1140

ALA  VAL  SER  PHE  LYS  GLN  LEU  LYS  ALA  LEU...
T G C G G T C A G C T T T A A G C A G T T G A A A G C C T T ...
          1150           1160           1170 ...
                               ...   GLN  ASP  LYS  GLN  VAL  THR  LEU  SER  ALA  SER
                               ...G C A A G A C A A A C A G G T T A C G T T A A G T G C G A G
                               ...            1180           1190           1200

ASN  ALA  TYR  ALA  ASN  GLY  GLY  SER  ASP  ALA...
C A A T G C T T A T G C C A A T G G C G G T A G C G A T G C ...
          1210           1220           1230 ...
                               ...   ASP  GLY  GLY  LYS  GLY  ILE  GLN  THR  LEU  SER
                               ...C G A C G G C G G C A A G G G A A T T C A A A C T T T A A G
                               ...            1240           1250           1260
```

FIG.21G

```
ASN GLY LEU ASN PHE LYS PHE LYS SER THR...
C A A T G G T T T G A A T T T T A A A T T T A A A T C C A C ...
            1270              1280              1290 ...
                              ... ASP GLY GLU LEU LEU ASN ILE LYS ALA GLU
                              ...A G A C G G C G A G T T G T T G A A T A T C A A A G C A G A
                              ...          1300              1310              1320

ASN ASP THR VAL THR PHE THR PRO LYS LYS...
A A A T G A C A C G G T T A C C T T T A C G C C G A A A A A ...
            1330              1340              1350 ...
                              ... GLY SER VAL GLN VAL GLY ASP ASP GLY LYS
                              ...A G G T T C G G T G C A G G T T G G C G A T G A T G G T A A
                              ...          1360              1370              1380

ALA THR ILE GLN ASP GLY ALA LYS THR THR...
G G C T A C G A T T C A A G A C G G C G C A A A A A C A A C ...
            1390              1400              1410 ...
                              ... THR GLY LEU VAL GLU ALA SER GLU LEU VAL
                              ...T A C C G G T T T G G T T G A G G C T T C T G A A T T G G T
                              ...          1420              1430              1440

ASP SER LEU ASN LYS LEU GLY TRP LYS VAL...
T G A C A G C C T G A A C A A A T T G G G T T G G A A A G T ...
            1450              1460              1470 ...
```

FIG.21H

```
                                    ...  GLY THR GLY THR ASP GLY THR GLY VAL THR
                                    ...G G G C A C C G G C A C T G A C G G C A C A G G A G T G A C
                                    ...            1480               1490              1500
 ASP GLY THR HIS THR ASP THR LEU VAL LYS...
C G A T G G C A C G C A T A C C G A C A C T T T A G T G A A ...
           1510               1520              1530 ...
                                    ...  SER GLY ASP LYS VAL THR LEU LYS ALA GLY
                                    ...G T C G G G C G A T A A A G T A A C T T T G A A A G C C G G
                                    ...            1540               1550              1560
 ASP ASN LEU LYS VAL LYS GLN GLU GLY THR...
C G A C A A T C T G A A G G T C A A A C A A G A G G G T A C ...
           1570               1580              1590 ...
                                    ...  ASN PHE THR TYR ALA LEU LYS ASP GLU LEU
                                    ...A A A C T T C A C T T A T G C G C T C A A A G A T G A A T T
                                    ...            1600               1610              1620
 THR ASP VAL LYS SER VAL GLU PHE LYS ASP...
G A C G G A C G T G A A G A G C G T G G A G T T T A A A G A ...
           1630               1640              1650 ...
                                    ...  THR ALA ASN GLY ALA ASN GLY ALA SER THR
                                    ...C A C G G C G A A T G G T G C A A A C G G T G C A A G C A C
                                    ...            1660               1670              1680
```

FIG.21I

```
 LYS  ILE  THR  LYS  ASP  GLY  LEU  THR  ILE  THR...
G A A G A T T A C C A A A G A C G G C T T G A C C A T T A C ...
              1690                1700                1710 ...
                          ...  PRO  ALA  ASN  GLY  ALA  GLY  ALA  ALA  GLY  ALA
                          ...G C C G G C A A A C G G T G C G G G T G C G G C A G G T G C
                          ...             1720                1730                1740

 ASN  THR  ALA  ASN  THR  ILE  SER  VAL  THR  LYS...
A A A C A C T G C A A A C A C C A T T A G C G T A A C C A A ...
              1750                1760                1770 ...
                          ...  ASP  GLY  ILE  SER  ALA  GLY  ASN  LYS  ALA  VAL
                          ...A G A C G G C A T T A G C G C G G G T A A T A A A G C A G T
                          ...             1780                1790                1800

 LYS  ASN  VAL  VAL  SER  GLY  LEU  LYS  LYS  PHE...
T A A A A A C G T T G T G A G C G G A C T G A A G A A A T T ...
              1810                1820                1830 ...
                          ...  GLY  ASP  ALA  ASN  PHE  ASP  PRO  LEU  THR  SER
                          ...T G G T G A T G C G A A T T T C G A T C C G C T G A C T A G
                          ...             1840                1850                1860

 SER  ALA  ASP  ASN  LEU  THR  LYS  GLN  TYR  ASP...
C T C A G C C G A C A A C T T A A C G A A A C A A T A T G A ...
              1870                1880                1890 ...
```

FIG.21J

```
                                    ...  ASN  ALA  TYR  LYS  GLY  LEU  THR  ASN  LEU  ASP
                                    ...C A A T G C C T A T A A A G G C T T G A C C A A T C T G G A
                                    ...                1900                1910                1920

 GLU  LYS  SER  LYS  GLY  LYS  GLN  THR  PRO  THR...
T G A A A A A A G T A A A G G C A A G C A A A C T C C G A C ...
           1930                1940                1950 ...
                                    ...  VAL  ALA  ASP  ASN  THR  ALA  ALA  THR  VAL  GLY
                                    ...C G T T G C T G A C A A T A C C G C T G C A A C C G T G G G
                                    ...                1960                1970                1980

 ASP  LEU  ARG  GLY  LEU  GLY  TRP  VAL  ILE  SER...
C G A T T T G C G C G G C T T G G G C T G G G T C A T T T C ...
           1990                2000                2010 ...
                                    ...  ALA  ASP  LYS  THR  LYS  GLY  GLU  LEU  ASN  LYS
                                    ...T G C A G A C A A A A C C A A A G G C G A A C T C A A T A A
                                    ...                2020                2030                2040

 GLU  TYR  ASN  ALA  GLN  VAL  ARG  ASN  ALA  ASN...
G G A A T A C A A C G C A C A A G T G C G T A A C G C T A A ...
           2050                2060                2070 ...
                                    ...  GLU  VAL  LYS  PHE  LYS  SER  GLY  ASN  GLY  ILE
                                    ...T G A A G T G A A A T T C A A G A G C G G C A A C G G T A T
                                    ...                2080                2090                2100
```

FIG.21K

```
   ASN   VAL   SER   GLY   LYS   THR   LEU   ASP   ASN   GLY...
C A A T G T T T C C G G T A A A A C A T T G G A T A A C G G ...
              2110                 2120                2130 ...
                           ...   THR   ARG   GLU   ILE   THR   PHE   GLU   LEU   ALA   LYS
                           ...T A C G C G C G A A A T T A C T T T T G A A T T G G C T A A
                           ...              2140                2150                2160

   ASP   GLU   ASN   ALA   ILE   ALA   PHE   GLY   SER   GLY...
A G A C G A A A A T G C C A T T G C T T T C G G T T C T G G ...
              2170                 2180                2190 ...
                           ...   SER   LYS   ALA   LEU   ARG   ASP   ASN   THR   VAL   ALA
                           ...C T C A A A A G C C T T G C G C G A T A A C A C G G T G G C
                           ...              2200                2210                2220

   ILE   GLY   THR   GLY   ASN   VAL   VAL   ASN   ALA   GLU...
A A T T G G T A C G G G C A A C G T T G T G A A T G C G G A ...
              2230                 2240                2250 ...
                           ...   LYS   SER   GLY   ALA   PHE   GLY   ASP   PRO   ASN   TYR
                           ...A A A A T C T G G T G C A T T C G G C G A T C C G A A C T A
                           ...              2260                2270                2280

   ILE   GLU   ASP   LYS   ALA   GLY   GLY   SER   TYR   ALA...
C A T C G A A G A T A A A G C C G G T G G C A G C T A C G C ...
              2290                 2300                2310 ...
```

FIG.21L

```
                                 ...   PHE   GLY   ASN   ASP   ASN   ARG   ILE   THR   SER   LYS
                                 ...T T T C G G T A A C G A T A A C C G T A T T A C T T C T A A
                                 ...             2320                 2330                 2340

 ASN   THR   PHE   VAL   LEU   GLY   ASN   SER   VAL   ASN...
A A A C A C T T T T G T G T T G G G T A A T A G T G T T A A ...
               2350                 2360                 2370 ...
                                 ...   ALA   LYS   ARG   ASP   ALA   ASN   GLY   ASN   VAL   LEU
                                 ...T G C G A A A C G T G A T G C A A A T G G C A A T G T A C T
                                 ...             2380                 2390                 2400

 THR   GLU   GLU   LYS   GLU   VAL   VAL   GLY   LYS   ASP...
G A C C G A A G A A A A A G A A G T G G T T G G A A A A G A ...
               2410                 2420                 2430 ...
                                 ...   GLY   ALA   LYS   THR   LYS   VAL   THR   VAL   PRO   GLN
                                 ...C G G T G C G A A G A C G A A A G T A A C C G T G C C G C A
                                 ...             2440                 2450                 2460

 ALA   LEU   GLY   GLU   THR   VAL   GLU   ASN   SER   VAL...
A G C C T T A G G C G A A A C C G T A G A A A A T T C T G T ...
               2470                 2480                 2490 ...
                                 ...   TYR   LEU   GLY   ASN   ALA   SER   THR   ALA   THR   LYS
                                 ...T T A T C T C G G T A A T G C T T C A A C T G C G A C A A A
                                 ...             2500                 2510                 2520
```

FIG.21M

```
 ASP   LYS   GLY   LYS   ASN   LEU   LYS   SER   ASP   GLY...
A G A T A A G G G T A A A A A C C T G A A A T C T G A T G G ...
              2530                2540                2550 ...
                                  ...  THR   ALA   GLY   ASN   THR   THR   THR   ALA   GLY   ALA
                                  ...T A C G G C G G T A A C A C T A C A A C T G C T G G C G C
                                  ...            2560                2570                2580

 THR   GLY   THR   VAL   ASN   GLY   PHE   ALA   GLY   ALA...
A A C G G G T A C G G T A A A C G G C T T T G C C G G T G C ...
              2590                2600                2610 ...
                                  ...  THR   ALA   HIS   GLY   ALA   VAL   SER   VAL   GLY   ALA
                                  ...A A C G G C G C A C G G T G C G G T T T C T G T C G G C G C
                                  ...            2620                2630                2640

 SER   GLY   GLU   GLU   ARG   ARG   ILE   GLN   ASN   VAL...
A A G T G G C G A A G A A A G A C G T A T C C A A A A C G T ...
              2650                2660                2670 ...
                                  ...  ALA   ALA   GLY   GLU   ILE   SER   ALA   THR   SER   THR
                                  ...C G C G G C A G G C G A A A T T T C C G C T A C T T C C A C
                                  ...            2680                2690                2700

 ASP   ALA   ILE   ASN   GLY   SER   GLN   LEU   TYR   ALA...
A G A T G C G A T T A A C G G T A G C C A G T T G T A T G C ...
              2710                2720                2730 ...
```

FIG.21N

```
                                    ...  VAL  ALA  LYS  GLY  VAL  THR  ASN  LEU  ALA  GLY
                                    ...T G T G G C A A A A G G G G T A A C A A A C C T T G C T G G
                                    ...           2740                2750                2760

 GLN  VAL  ASN  LYS  VAL  GLY  LYS  ARG  ALA  ASP...
A C A A G T G A A T A A A G T G G G C A A A C G T G C A G A ...
           2770                2780                2790 ...
                                    ...  ALA  GLY  THR  ALA  SER  ALA  LEU  ALA  ALA  SER
                                    ...T G C A G G T A C A G C A A G T G C A T T A G C G G C T T C
                                    ...           2800                2810                2820

 GLN  LEU  PRO  GLN  ALA  SER  MET  PRO  GLY  LYS...
A C A G T T A C C A C A A G C C T C T A T G C C A G G T A A ...
           2830                2840                2850 ...
                                    ...  SER  MET  VAL  SER  ILE  ALA  GLY  SER  SER  TYR
                                    ...A T C A A T G G T T T C T A T T G C G G G A A G T A G T T A
                                    ...           2860                2870                2880

 GLN  GLY  GLN  SER  GLY  LEU  ALA  ILE  GLY  VAL...
T C A A G G T C A A A G T G G T T T A G C T A T C G G G G T ...
           2890                2900                2910 ...
                                    ...  SER  ARG  ILE  SER  ASP  ASN  GLY  LYS  VAL  ILE
                                    ...A T C A A G A A T T T C C G A T A A T G G C A A A G T G A T
                                    ...           2920                2930                2940
```

FIG.21O

```
 ILE  ARG  LEU  SER  GLY  THR  THR  ASN  SER  GLN...
T A T T C G C T T G T C A G G C A C A A C C A A T A G C C A ...
             2950                2960                2970 ...
                        ...  GLY  LYS  THR  GLY  VAL  ALA  ALA  GLY  VAL  GLY
                        ...A G G T A A A A C A G G C G T T G C A G C A G G T G T T G G
                        ...            2980                2990                3000

 TYR  GLN  TRP  ***  ***  ASN  SER  GLY  SER
T T A C C A G T G G T A A T A G A A T T C C G G A T C C G C
             3010                3020                3030
```

FIG.22A

NTHi strain K9 hia sequence

```
MET ASN LYS ILE PHE ASN VAL ILE TRP ASN ...
A T G A A C A A A A T T T T T A A C G T T A T T T G G A A T...
10 20 30...
... VAL MET THR GLN THR TRP ALA VAL VAL SER
... G T T A T G A C T C A A A C T T G G G C T G T C G T A T C T
... 40 50 60

GLU LEU THR ARG ALA HIS THR LYS ARG ALA ...
G A A C T C A C T C G C G C C C A C A C C A A A C G T G C C...
70 80 90...
... SER ALA THR VAL ALA THR ALA VAL LEU ALA
... T C C G C A A C C G T G G C G A C C G C C G T A T T G G C G
... 100 110 120

THR GLN LEU SER ALA THR ALA GLU ALA ASN ...
A C G C A G T T G T C T G C A A C G G C T G A A G C G A A C...
130 140 150...
... SER SER ALA SER VAL THR SER ARG LEU ASN
... A G T A G T G C T T C T G T T A C G A G T A G G T T G A A T
... 160 170 180

VAL TYR GLY ASP THR ASN THR LYS PHE ASN ...
G T T T A T G G C G A T A C G A A T A C T A A A T T C A A T...
190 200 210...
```

FIG.22B

```
                                            ... ALA  ALA  ASN  ASN  SER  ILE  ALA  ASP  LEU  ASN
                                            ... G C A G C C A A T A A T T C A A T A G C A G A T T T A A A T
                                            ...                220               230              240
LYS  GLN  ASN  ASP  GLY  VAL  HIS  ASP  GLY  LEU ...
A A A C A A A A T G A T G G T G T T C A C G A T G G T T T A...
             250              260              270...
                                            ... LEU  ASN  LEU  ASN  GLU  ASN  GLY  ALA  ASN  LYS
                                            ... T T A A A T C T G A A T G A A A A C G G T G C G A A T A A A
                                            ...                280               290              300
LYS  LEU  LEU  VAL  ASP  ASP  ASN  THR  ALA  ALA ...
A A G C T G T T G G T G G A T G A C A A T A C T G C G G C G...
             310              320              330...
                                            ... THR  VAL  GLY  ASP  LEU  ARG  LYS  LEU  GLY  TRP
                                            ... A C C G T A G G C G A T T T A C G T A A A T T G G G C T G G
                                            ...                340               350              360
VAL  VAL  SER  THR  LYS  ASN  GLY  LYS  GLU  ASN ...
G T C G T A T C A A C C A A A A A T G G C A A G G A A A A T...
             370              380              390...
                                            ... GLU  LYS  SER  GLN  GLN  VAL  LYS  GLN  ALA  ASP
                                            ... G A G A A A A G C C A A C A A G T C A A A C A G G C G G A T
                                            ...                400               410              420
```

FIG.22C

```
GLU VAL LEU PHE LYS GLY SER LYS GLY GLY ...
G A A G T G T T G T T T A A A G G C A G C A A A G G C G G T...
430 440 450...
... VAL GLN VAL THR SER THR SER GLU ASN GLY
... G T G C A G G T T A C T T C C A C C T C T G A A A A C G G C
... 460 470 480

LYS HIS ALA ILE THR PHE ALA LEU ALA LYS ...
A A A C A C G C C A T T A C C T T T G C T T T A G C G A A A...
490 500 510...
... ASP LEU ASP MET ARG THR ALA THR VAL SER
... G A C C T T G A T A T G A G A A C T G C G A C T G T G A G T
... 520 530 540

ASP THR LEU THR ILE GLY GLY SER THR THR ...
G A T A C C T T A A C G A T T G G C G G T A G T A C T A C T...
550 560 570...
... THR GLY SER ALA THR THR PRO LYS VAL ASN
... A C A G G T A G T G C A A C A A C A C C A A A A G T G A A T
... 580 590 600

VAL THR SER THR ALA SER GLY LEU ASN PHE ...
G T G A C T A G C A C G G C A A G C G G C T T G A A C T T T...
610 620 630...
```

FIG.22D

```
                                         ... ALA  LYS  GLY  ALA  THR  GLY  ALA  ASN  GLY  ASP
                                         ... G C G A A A G G C G C T A C A G G T G C T A A T G G C G A T
                                         ...                640                650                660

THR  THR  VAL  HIS  LEU  THR  ASN  ILE  ALA  SER ...
A C T A C G G T T C A C T T G A C T A A T A T T G C T T C A...
              670              680              690...
                                         ... THR  LEU  GLN  ASP  THR  LEU  LEU  ASN  THR  GLY
                                         ... A C T T T G C A A G A T A C T C T A T T G A A T A C T G G G
                                         ...                700                710                720

VAL  VAL  SER  LYS  LEU  ASP  GLY  ASN  GLY  ILE ...
G T T G T G A G T A A A T T A G A T G G T A A T G G T A T T...
              730              740              750...
                                         ... THR  ALA  ASP  GLU  LYS  LYS  ARG  ALA  ALA  SER
                                         ... A C T G C T G A C G A G A A A A A A C G T G C G G C A A G C
                                         ...                760                770                780

VAL  GLN  ASP  VAL  LEU  ASN  SER  GLY  TRP  ASN ...
G T T C A A G A T G T T T T A A A T A G T G G T T G G A A T...
              790              800              810...
                                         ... ILE  LYS  GLY  VAL  LYS  THR  GLY  ALA  THR  THR
                                         ... A T C A A G G G T G T T A A A A C A G G T G C G A C G A C T
                                         ...                820                830                840
```

FIG.22E

```
SER   ASP   ASN   VAL   ASP   PHE   VAL   ARG   THR   TYR ...
T C T G A T A A C G T T G A T T T T G T C C G T A C T T A C...
                850                 860                 870...
                              ... ASP   THR   VAL   GLU   PHE   LEU   SER   GLY   SER   GLU
                              ... G A C A C A G T T G A G T T T T T G A G C G G A A G T G A A
                              ...                 880                 890                 900

GLU   THR   THR   LEU   VAL   THR   VAL   ASP   SER   GLU ...
G A A A C T A C A C T G G T T A C A G T G G A T A G T G A A...
                910                 920                 930...
                              ... SER   ASN   GLY   LYS   SER   THR   LYS   VAL   LYS   ILE
                              ... A G T A A T G G A A A A T C T A C T A A A G T T A A A A T C
                              ...                 940                 950                 960

GLY   ALA   LYS   THR   SER   VAL   ILE   LYS   GLU   LYS ...
G G T G C G A A G A C C T C T G T T A T C A A A G A A A A A...
                970                 980                 990...
                              ... ASP   GLY   LYS   LEU   PHE   THR   GLY   LYS   ALA   ASN
                              ... G A C G G T A A G T T A T T T A C T G G A A A A G C T A A T
                              ...                1000                1010                1020

LYS   ASP   THR   ASN   GLN   VAL   ALA   SER   ASN   ASN ...
A A A G A C A C A A A T C A A G T C G C A A G T A A T A A T...
               1030                1040                1050...
```

FIG.22F

```
                                     ... ALA ALA ASP ASP THR ASP GLU GLY LYS GLY
                                     ... G C A G C T G A T G A T A C G G A T G A G G G C A A A G G C
                                     ...           1060           1070           1080

LEU VAL THR ALA GLU THR VAL ILE ASN ALA ...
T T A G T C A C T G C A G A G A C T G T T A T C A A T G C A...
          1090           1100           1110...
                                     ... VAL ASN LYS ALA GLY TRP ARG ILE LYS THR
                                     ... G T A A A C A A G G C T G G T T G G A G A A T T A A A A C A
                                     ...           1120           1130           1140

THR GLY ALA ASN ASN GLN ALA GLY GLN PHE ...
A C G G G T G C T A A T A A T C A A G C T G G T C A G T T T...
          1150           1160           1170...
                                     ... GLU THR VAL THR SER GLY THR ASN VAL THR
                                     ... G A A A C T G T C A C A T C A G G C A C A A A T G T A A C C
                                     ...           1180           1190           1200

PHE ALA ASP GLY ASN GLY THR THR ALA VAL ...
T T T G C T G A T G G C A A T G G T A C A A C T G C A G T C...
          1210           1220           1230...
                                     ... VAL THR GLY ASP ALA THR ASN GLY ILE THR
                                     ... G T A A C T G G C G A T G C T A C C A A T G G T A T T A C T
                                     ...           1240           1250           1260
```

FIG.22G

```
VAL  LYS  TYR  GLU  ALA  LYS  VAL  GLY  ASP  GLY ...
G T T A A A T A C G A A G C G A A A G T T G G C G A C G G C...
          1270                1280                1290...
                                   ... LEU  LYS  ILE  GLY  ASN  ASP  GLN  LYS  ILE  THR
                                   ...T T G A A G A T T G G T A A C G A C C A A A A A A T C A C T
                                   ...          1300                1310                1320

ALA  ASP  THR  THR  ALA  LEU  THR  VAL  THR  GLY ...
G C A G A T A C G A C C G C A C T T A C T G T G A C G G G C...
          1330                1340                1350...
                                   ... GLY  LYS  VAL  THR  ALA  PRO  ASP  ALA  THR  ASN
                                   ...G G T A A A G T T A C T G C C C C T G A T G C A A C C A A T
                                   ...          1360                1370                1380

GLY  LYS  LYS  LEU  VAL  ASN  ALA  SER  GLY  LEU ...
G G T A A G A A A C T T G T T A A T G C A A G T G G T T T A...
          1390                1400                1410...
                                   ... ALA  ASP  ALA  LEU  ASN  LYS  LEU  SER  TRP  THR
                                   ...G C T G A T G C G T T A A A C A A A T T A A G T T G G A C T
                                   ...          1420                1430                1440

ALA  LYS  ALA  GLU  ALA  ASP  THR  ALA  ASN  GLY ...
G C A A A A G C T G A A G C A G A T A C T G C T A A T G G C...
          1450                1460                1470...
```

FIG.22H

```
                                   ... GLY GLU LEU ASP GLY THR ALA ASP GLU LYS
                                   ... G G C G A G C T T G A T G G A A C T G C A G A T G A A A A A
                                   ...              1480                1490                1500

GLU VAL LYS ALA GLY GLU THR VAL THR PHE ...
G A A G T T A A A G C A G G C G A A A C G G T A A C C T T T...
              1510                1520                1530...
                                   ... LYS ALA GLY LYS ASN LEU LYS VAL LYS GLN
                                   ... A A A G C G G G C A A G A A C T T A A A A G T G A A A C A A
                                   ...              1540                1550                1560

ASP GLY ALA ASN PHE THR TYR SER LEU GLN ...
G A T G G T G C G A A C T T T A C T T A T T C A C T G C A A...
              1570                1580                1590...
                                   ... ASP ALA LEU THR GLY LEU THR SER ILE THR
                                   ... G A T G C T T T A A C A G G C T T A A C G A G C A T T A C T
                                   ...              1600                1610                1620

LEU GLY THR GLY ASN ASN GLY ALA LYS THR ...
T T A G G T A C A G G A A A T A A T G G T G C G A A A A C T...
              1630                1640                1650...
                                   ... GLU ILE ASN LYS ASP GLY LEU THR ILE THR
                                   ... G A A A T C A A C A A A G A C G G C T T A A C C A T C A C A
                                   ...              1660                1670                1680
```

FIG.22I

```
PRO   ALA   ASN   GLY   ALA   GLY   ALA   ASN   ASN   ALA ...
C C A G C A A A T G G T G C G G G T G C A A A T A A T G C A...
            1690                1700                1710...
                                ...  ASN   THR   ILE   SER   VAL   THR   LYS   ASP   GLY   ILE
                                ... A A C A C C A T C A G C G T A A C C A A A G A C G G C A T T
                                ...                1720                1730                1740

SER   ALA   GLY   GLY   GLN   SER   VAL   LYS   ASN   VAL ...
A G T G C G G G C G G T C A G T C G G T T A A A A A C G T T...
            1750                1760                1770...
                                ...  VAL   SER   GLY   LEU   LYS   LYS   PHE   GLY   ASP   ALA
                                ... G T G A G C G G A C T G A A G A A A T T T G G T G A T G C G
                                ...                1780                1790                1800

ASN   PHE   ASP   PRO   LEU   THR   SER   SER   ALA   ASP ...
A A T T T C G A T C C G C T G A C T A G C T C C G C C G A C...
            1810                1820                1830...
                                ...  ASN   LEU   THR   LYS   GLN   TYR   ASP   ASP   ALA   TYR
                                ... A A C T T A A C G A A A C A A T A T G A C G A T G C C T A T
                                ...                1840                1850                1860

LYS   GLY   LEU   THR   ASN   LEU   ASP   GLU   LYS   GLY ...
A A A G G C T T G A C C A A T T T G G A T G A A A A A G G T...
            1870                1880                1890...
```

FIG.22J

```
                                  ... ALA ASP LYS GLN THR LEU THR VAL ALA ASP
                                  ... G C G G A C A A G C A A A C T C T G A C T G T T G C C G A C
                                  ...              1900                1910               1920

ASN THR ALA ALA THR VAL GLY ASP LEU ARG ...
A A T A C T G C C G C A A C C G T G G G C G A T T T G C G C...
            1930                1940               1950...
                                  ... GLY LEU GLY TRP VAL ILE SER ALA ASP LYS
                                  ... G G C T T G G G C T G G G T C A T T T C T G C G G A C A A A
                                  ...              1960                1970               1980

THR THR GLY GLU LEU ASP LYS GLU TYR ASN ...
A C C A C A G G C G A A C T C G A T A A G G A A T A C A A C...
            1990                2000               2010...
                                  ... ALA GLN VAL ARG ASN ALA ASN GLU VAL LYS
                                  ... G C G C A A G T G C G T A A C G C C A A T G A A G T G A A A
                                  ...              2020                2030               2040

PHE LYS SER GLY ASN GLY ILE ASN VAL SER ...
T T C A A A A G C G G C A A C G G T A T C A A T G T T T C C...
            2050                2060               2070...
                                  ... GLY LYS THR VAL ASN GLY ARG ARG GLU ILE
                                  ... G G T A A A A C T G T C A A C G G T A G G C G T G A A A T T
                                  ...              2080                2090               2100
```

FIG.22K

```
THR   PHE   GLU   LEU   ALA   LYS   GLY   GLU   VAL   VAL ...
A C T T T T G A A T T G G C T A A A G G C G A A G T G G T T...
              2110                2120                2130...
                                  ... LYS   SER   ASN   GLU   PHE   THR   VAL   LYS   GLU   THR
                                  ... A A A T C G A A T G A A T T T A C T G T C A A A G A A A C C
                                  ...             2140                2150                2160

ASN   GLY   LYS   GLU   THR   SER   LEU   VAL   LYS   VAL ...
A A T G G C A A G G A A A C G A G C C T G G T T A A A G T T...
              2170                2180                2190...
                                  ... GLY   ASP   LYS   TYR   TYR   SER   LYS   GLU   ASP   ILE
                                  ... G G C G A T A A A T A T T A C A G C A A A G A G G A T A T T
                                  ...             2200                2210                2220

ASP   PRO   ALA   THR   GLY   LYS   PRO   LYS   VAL   THR ...
G A C C C A G C A A C C G G T A A A C C G A A A G T T A C A...
              2230                2240                2250...
                                  ... ASN   GLY   ASN   ALA   VAL   ALA   ALA   LYS   TYR   GLN
                                  ... A A T G G C A A T G C A G T T G C T G C G A A A T A T C A A
                                  ...             2260                2270                2280

ASP   LYS   ASP   GLY   LYS   VAL   VAL   SER   ALA   ASP ...
G A T A A A G A T G G C A A A G T C G T T T C T G C T G A C...
              2290                2300                2310...
```

FIG.22L

```
                                    ... GLY SER SER ASN THR ALA VAL THR LEU THR
                                    ... G G C A G C A G C A A T A C C G C T G T T A C C C T A A C C
                                    ...           2320           2330          2340
ASN LYS GLY TYR GLY TYR VAL THR GLY ASN ...
A A C A A A G G T T A T G G C T A T G T A A C A G G T A A C...
         2350           2360         2370...
                                    ... GLN VAL ALA ASP ALA ILE ALA LYS SER GLY
                                    ... C A A G T G G C A G A T G C G A T T G C G A A A T C A G G C
                                    ...           2380           2390          2400
PHE GLU LEU GLY LEU ALA ASP ALA GLU LYS ...
T T T G A G C T T G G T T T G G C T G A T G C A G A A A A A...
         2410           2420         2430...
                                    ... ALA LYS ALA ALA PHE GLY ASP GLU THR LYS
                                    ... G C G A A A G C T G C G T T T G G C G A T G A A A C A A A A
                                    ...           2440           2450          2460
ALA LEU SER SER ASP LYS LEU GLU THR VAL ...
G C C T T G T C T T C T G A T A A A T T G G A A A C C G T A...
         2470           2480         2490...
                                    ... ASN ALA ASN ASP LYS VAL ARG PHE ALA ASN
                                    ... A A T G C C A A C G A C A A A G T C C G T T T T G C T A A T
                                    ...           2500           2510          2520
```

FIG.22M

```
GLY LEU ASN THR LYS VAL SER ALA ALA THR ...
G G T T T A A A T A C C A A A G T G A G C G C G G C A A C G...
2530 2540 2550...
... VAL GLU SER ILE ASP ALA ASN GLY ASP LYS
... G T G G A A A G C A T C G A T G C A A A C G G C G A T A A A
... 2560 2570 2580

VAL THR THR THR PHE VAL LYS THR ASP VAL ...
G T G A C T A C A A C C T T T G T G A A A A C C G A T G T G...
2590 2600 2610...
... GLU LEU PRO LEU THR GLN ILE TYR ASN THR
... G A A T T G C C T T T A A C G C A A A T C T A C A A T A C C
... 2620 2630 2640

ASP ALA ASN GLY LYS LYS ILE VAL LYS ASN ...
G A T G C A A A C G G T A A G A A A A T C G T T A A A A A T...
2650 2660 2670...
... GLY ASP LYS TRP TYR TYR THR LYS ASP ASP
... G G C G A T A A A T G G T A T T A C A C G A A A G A T G A C
... 2680 2690 2700

GLY SER THR ASP MET THR LYS GLU VAL THR ...
G G C T C A A C T G A T A T G A C T A A A G A A G T T A C C...
2710 2720 2730...
```

FIG.22N

```
                                   ... LEU GLY ASN VAL ASP SER ASP GLY LYS LYS
                                   ...CTTGGCAATGTGGATTCAGACGGCAAGAAA
                                   ...          2740          2750          2760

VAL VAL LYS GLU ASP ASN LYS TRP TYR HIS ...
GTTGTGAAAGAAGACAACAAGTGGTATCAC...
          2770          2780          2790...
                                   ... VAL LYS SER ASP GLY SER THR ASP LYS THR
                                   ...GTTAAATCTGATGGTTCTACGGATAAAACA
                                   ...          2800          2810          2820

GLN VAL VAL GLU GLU ALA LYS VAL SER THR ...
CAGGTGGTCGAAGAAGCTAAAGTTTCTACC...
          2830          2840          2850...
                                   ... ASP GLU LYS HIS VAL VAL SER LEU ASP PRO
                                   ...GATGAAAAACACGTTGTCAGCCTTGATCCA
                                   ...          2860          2870          2880

ASN ASP GLN SER LYS GLY LYS GLY VAL VAL ...
AATGATCAATCAAAAGGTAAAGGCGTGGTC...
          2890          2900          2910...
                                   ... ILE ASN ASN MET ALA ASN GLY GLU ILE SER
                                   ...ATTAACAATATGGCTAATGGCGAAATTTCT
                                   ...          2920          2930          2940
```

FIG.22O

```
ALA THR SER THR ASP ALA ILE ASN GLY SER ...
G C C A C T T C C A C C G A T G C G A T T A A C G G A A G T...
          2950                2960                2970...
                    ... GLN LEU TYR ALA VAL ALA LYS GLY VAL THR
                    ... C A G T T G T A T G C C G T G G C A A A A G G G G T A A C A
                    ...           2980                2990                3000

ASN LEU ALA GLY GLN VAL ASN ASN LEU GLU ...
A A C C T T G C T G G A C A A G T G A A T A A T C T T G A G...
          3010                3020                3030...
                    ... GLY LYS VAL ASN LYS VAL GLY LYS ARG ALA
                    ... G G C A A A G T G A A T A A A G T G G G C A A A C G T G C A
                    ...           3040                3050                3060

ASP ALA GLY THR ALA SER ALA LEU ALA ALA ...
G A T G C A G G T A C T G C A A G T G C A T T A G C G G C T...
          3070                3080                3090...
                    ... SER GLN LEU PRO GLN ALA THR MET PRO GLY
                    ... T C A C A G T T A C C A C A A G C C A C T A T G C C A G G T
                    ...           3100                3110                3120

LYS SER MET VAL SER ILE ALA GLY SER SER ...
A A A T C A A T G G T T T C T A T T G C G G G A A G T A G T...
          3130                3140                3150...
```

FIG.22P

```
                                        ... TYR GLN GLY GLN ASN GLY LEU ALA ILE GLY
                                        ... T A T C A A G G T C A A A A T G G T T T A G C T A T C G G G
                                        ...             3160                3170                3180

VAL SER ARG ILE SER ASP ASN GLY LYS VAL ...
G T A T C A A G A A T T T C C G A T A A T G G C A A A G T G...
            3190                3200                3210...
                                        ... ILE ILE ARG LEU SER GLY THR THR ASN SER
                                        ... A T T A T T C G C T T G T C A G G C A C A A C C A A T A G T
                                        ...             3220                3230                3240

GLN GLY LYS THR GLY VAL ALA ALA GLY VAL ...
C A A G G T A A A A C A G G C G T T G C A G C A G G T G T T...
            3250                3260                3270...
                                        ... GLY TYR GLN TRP ***
                                        ... G G T T A C C A G T G G T A A T A G A A T T C C G G A T C C
                                        ...             3280                3290                3300
```

FIG.23A

NTHi strain K22 Hia

```
                 MET  ASN  LYS  ILE  PHE  ASN...
GCGAATTCATATGAACAAAATTTTTAA ...
        10         20          ...
                ...  VAL  ILE  TRP  ASN  VAL  VAL  THR  GLN  THR  TRP  VAL
                ...CGTTATTTGGAATGTTGTGACTCAAACTTGGGT
                ...  30            40            50            60

 VAL  VAL  SER  GLU  LEU  THR  ARG  ALA  HIS...
TGTCGTATCTGAACTCACTCGCGCCCA ...
        70         80          ...
                ...  THR  LYS  CYS  ALA  SER  ALA  THR  VAL  ALA  VAL  ALA
                ...CACCAAATGCGCCTCCGCCACCGTGGCGGTTGC
                ...  90            100           110           120

 VAL  LEU  ALA  THR  ALA  LEU  SER  ALA  THR...
CGTATTGGCAACTGCGTTGTCTGCAAC ...
        130        140         ...
                ...  ALA  GLU  ALA  ASN  ASN  ASN  THR  SER  VAL  THR  ASN
                ...GGCTGAAGCGAACAACAATACTTCTGTTACGAA
                ...  150           160           170           180
```

FIG.23B

```
GLY   LEU   ASN   ALA   TYR   GLY   ASP   THR   ASN...
T G G G T T G A A T G C T T A T G G C G A T A C T A A ...
            190                     200             ...
                    ...  PHE   ASN   THR   THR   ASN   ASN   SER   ILE   ALA   ASP   LEU
                    ...T T T T A A T A C A A C C A A T A A T T C G A T A G C A G A T T T
                    ...  210                 220                 230                 240

GLU   LYS   HIS   VAL   GLN   ASP   ALA   TYR   LYS...
G G A A A A A C A C G T T C A A G A T G C T T A T A A ...
            250                     260             ...
                    ...  GLY   LEU   LEU   ASN   LEU   ASN   GLU   LYS   ASP   THR   ASN
                    ...A G G C T T A T T A A A T C T G A A T G A A A A A G A T A C A A A
                    ...  270                 280                 290                 300

LYS   SER   SER   PHE   LEU   VAL   ALA   ASP   ASN...
T A A G T C A A G T T T C T T G G T T G C C G A C A A ...
            310                     320             ...
                    ...  THR   ALA   ALA   THR   VAL   GLY   ASN   LEU   ARG   LYS   LEU
                    ...T A C C G C C G C A A C C G T A G G C A A T T T G C G T A A A T T
                    ...  330                 340                 350                 360

GLY   TRP   VAL   LEU   SER   SER   LYS   ASN   GLY...
G G G C T G G G T A T T G T C T A G C A A A A A C G G ...
            370                     380             ...
```

FIG.23C

```
                                  ...  THR ARG ASN GLU LYS SER TYR GLN VAL LYS GLN
                                  ...C A C A A G G A A C G A G A A A A G C T A T C A A G T A A A A C A
                                  ...  390                  400                  410                  420

ALA ASP GLU VAL LEU PHE THR GLY SER...
A G C T G A T G A A G T T C T C T T T A C T G G A T C ...
            430                  440              ...
                                  ...  GLY ALA ALA THR VAL SER SER SER SER LYS ASP
                                  ...T G G T G C T G C A A C G G T T A G T T C C A G C T C T A A A G A
                                  ...  450                  460                  470                  480

GLY LYS HIS THR ILE THR ILE SER VAL...
C G G T A A A C A T A C C A T T A C C A T T T C T G T ...
            490                  500              ...
                                  ...  THR LYS GLY SER PHE ALA GLU VAL LYS THR ASP
                                  ...T A C C A A A G G T A G T T T T G C T G A G G T A A A A A C T G A
                                  ...  510                  520                  530                  540

ALA THR THR GLY GLY GLN VAL ASN ALA...
T G C A A C T A C T G G A G G T C A A G T A A A C G C ...
            550                  560              ...
                                  ...  ASP ARG GLY LYS VAL LYS ALA GLU ASP GLU ASN
                                  ...C G A C C G T G G T A A A G T G A A A G C T G A G G A C G A G A A
                                  ...  570                  580                  590                  600
```

FIG.23D

```
GLY ALA ASP VAL ASP LYS LYS VAL ALA...
T G G A G C T G A T G T T G A T A A G A A A G T T G C ...
610 620 ...
... THR VAL LYS ASP VAL ALA LYS ALA ILE ASN ASP
...A A C T G T A A A A G A T G T T G C T A A G G C G A T T A A C G A
... 630 640 650 660

ALA ALA THR PHE VAL LYS VAL GLU SER...
T G C C G C A A C T T T C G T G A A A G T G G A A A G ...
670 680 ...
... THR ASP ASP ASP ILE GLU ASN GLY ALA ALA GLY
...C A C A G A T G A T G A C A T T G A A A A T G G T G C T G C A G G
... 690 700 710 720

LYS ASN GLU THR THR ASP GLN ALA LEU...
C A A A A A T G A A A C T A C A G A C C A A G C T C T ...
730 740 ...
... LYS ALA GLY ASP THR LEU THR LEU LYS ALA GLY
...C A A A G C A G G C G A C A C C T T A A C C T T A A A A G C G G G
... 750 760 770 780

LYS ASN LEU LYS ALA LYS LEU ASP GLN...
T A A A A A C T T A A A A G C T A A G T T A G A C C A ...
790 800 ...
```

FIG.23E

```
                                   ...  ASN  GLY  LYS  SER  VAL  THR  PHE  ALA  LEU  ALA  LYS
                                   ...A A A T G G T A A A T C A G T A A C C T T T G C T T T A G C G A A
                                   ...  810            820            830            840

ASP  LEU  ASP  VAL  THR  SER  ALA  LYS  VAL...
A G A C C T T G A T G T G A C C T C T G C G A A A G T ...
          850            860        ...
                                   ...  SER  ASP  LYS  LEU  SER  ILE  GLY  LYS  ASP  THR  ASN
                                   ...G A G T G A T A A G T T G T C T A T T G G T A A A G A T A C G A A
                                   ...  870            880            890            900

LYS  VAL  ASP  ILE  THR  SER  ASP  ALA  ASN...
T A A A G T T G A T A T T A C C A G T G A T G C A A A ...
          910            920        ...
                                   ...  GLY  LEU  LYS  LEU  ALA  LYS  THR  GLY  ASN  GLY  ASN
                                   ...T G G C T T G A A A T T G G C G A A A A C A G G T A A C G G A A A
                                   ...  930            940            950            960

GLY  GLN  ASN  GLY  ASN  VAL  HIS  LEU  ASN...
T G G T C A A A A C G G T A A T G T C C A C T T A A A ...
          970            980        ...
                                   ...  GLY  ILE  ALA  SER  THR  LEU  THR  ASP  THR  ILE  THR
                                   ...T G G T A T T G C T T C G A C T T T G A C C G A T A C C A T T A C
                                   ...  990            1000           1010           1020
```

FIG.23F

```
   GLY   MET   THR   THR   GLN   ALA   SER   ASN   GLY...
 A G G T A T G A C A A C A C A A G C A A G C A A T G G ...
              1030              1040              ...
                                  ...   VAL   ALA   VAL   GLN   ASN   HIS   ASN   ARG   ALA   ALA   SER
                                  ...C G T G G C T G T G C A G A A T C A T A A T C G T G C T G C G A G
                                  ... 1050              1060              1070              1080

   VAL   ALA   ASP   VAL   LEU   ASN   ALA   GLY   TRP...
 T G T G G C T G A T G T A T T A A A T G C A G G C T G ...
              1090              1100              ...
                                  ...   ASN   ILE   GLN   GLY   ASN   GLY   ALA   SER   VAL   ASP   PHE
                                  ...G A A T A T T C A A G G C A A C G G A G C G A G C G T T G A T T T
                                  ... 1110              1120              1130              1140

   VAL   ASN   ALA   TYR   ASP   THR   VAL   ASP   PHE...
 T G T C A A T G C T T A C G A C A C A G T A G A T T T ...
              1150              1160              ...
                                  ...   VAL   ASN   GLY   THR   ASN   THR   ASN   VAL   ASN   VAL   THR
                                  ...T G T C A A T G G T A C A A A C A C C A A T G T G A A C G T T A C
                                  ... 1170              1180              1190              1200

   THR   ASP   THR   ALA   HIS   LYS   LYS   THR   THR...
 G A C T G A T A C G G C T C A C A A A A A G A C A A C ...
              1210              1220              ...
```

FIG.23G

```
                                      ...  VAL ARG VAL ASP VAL THR GLY LEU PRO VAL GLN
                                      ...C G T C C G T G T G G A T G T A A C A G G C T T G C C G G T T C A
                                      ... 1230           1240           1250           1260

TYR VAL THR GLU ASP GLY LYS THR VAL...
A T A T G T T A C G G A A G A C G G C A A A A C C G T ...
          1270           1280           ...
                                      ...  VAL LYS VAL ASP ASN LYS TYR TYR GLU ALA LYS
                                      ...T G T G A A A G T G G A C A A T A A G T A T T A C G A A G C T A A
                                      ... 1290           1300           1310           1320

GLN ASP GLY SER ALA ASP MET ASP LYS...
G C A A G A C G G T T C G G C G G A T A T G G A T A A ...
          1330           1340           ...
                                      ...  LYS VAL GLU ASN GLY GLU LEU ALA LYS THR LYS
                                      ...A A A A G T C G A A A A T G G C G A G C T G G C G A A A A C C A A
                                      ... 1350           1360           1370           1380

VAL LYS LEU VAL SER ALA SER GLY GLN...
A G T G A A A T T G G T G T C G G C A A G C G G T C A ...
          1390           1400           ...
                                      ...  ASN PRO VAL LYS ILE SER ASN VAL ALA GLU GLY
                                      ...A A A T C C G G T G A A A A T C A G C A A T G T T G C G G A A G G
                                      ... 1410           1420           1430           1440
```

FIG.23H

```
 THR  GLU  GLU  ASN  ASP  ALA  VAL  SER  PHE...
C A C G G A A G A A A A C G A T G C G G T C A G C T T ...
           1450                1460                ...
                                ...  LYS  GLN  LEU  LYS  ALA  LEU  GLN  GLU  LYS  GLN  VAL
                                ...T A A G C A A T T G A A A G C C T T G C A A G A G A A A C A G G T
                                ... 1470                1480                1490                1500

 THR  LEU  THR  ALA  SER  ASN  ALA  TYR  ALA...
T A C T T T A A C T G C G A G C A A T G C T T A T G C ...
           1510                1520                ...
                                ...  ASN  GLY  GLY  ASN  ASP  ALA  ASP  GLY  GLY  LYS  ALA
                                ...C A A T G G T G G T A A C G A T G C C G A C G G C G G C A A G G C
                                ... 1530                1540                1550                1560

 THR  GLN  THR  LEU  ASN  ASN  GLY  LEU  ASN...
A A C T C A A A C T T T A A A C A A T G G T T T G A A ...
           1570                1580                ...
                                ...  PHE  LYS  PHE  LYS  SER  THR  ASP  GLY  GLU  LEU  LEU
                                ...T T T T A A A T T T A A A T C C A C A G A C G G C G A G T T G T T
                                ... 1590                1600                1610                1620

 ASN  ILE  LYS  VAL  GLU  ASN  ASP  THR  VAL...
G A A C A T C A A A G T A G A A A A T G A C A C A G T ...
           1630                1640                ...
```

FIG.23I

```
                               ...  THR PHE THR PRO LYS LYS GLY SER VAL GLN VAL
                               ...T A C C T T T A C G C C G A A A A A A G G T T C G G T A C A G G T
                               ... 1650                1660                1670                1680
 GLY GLU ASP GLY LYS ALA THR ILE GLN...
T G G C G A A G A C G G T A A G G C T A C G A T T C A ...
          1690                1700                ...
                               ...  ASN GLY THR LYS THR THR ASP GLY LEU VAL GLU
                               ...A A A T G G T A C G A A A A C A A C C G A C G G T T T G G T T G A
                               ... 1710                1720                1730                1740
 ALA SER GLU LEU VAL GLU SER LEU ASN...
A G C T T C C G A A T T G G T T G A A A G C C T G A A ...
          1750                1760                ...
                               ...  LYS LEU GLY TRP LYS VAL GLY VAL ASP LYS ASP
                               ...C A A A C T G G G C T G G A A A G T G G G C G T T G A T A A A G A
                               ... 1770                1780                1790                1800
 GLY SER GLY GLU LEU ASP GLY ALA SER...
C G G C A G C G G C G A G C T T G A T G G T G C A T C ...
          1810                1820                ...
                               ...  ASN GLU THR LEU VAL LYS SER GLY ASP LYS VAL
                               ...C A A T G A A A C T T T A G T G A A G T C G G G C G A T A A A G T
                               ... 1830                1840                1850                1860
```

FIG.23J

```
 THR   LEU   LYS   ALA   GLY   GLU   ASN   LEU   LYS...
A A C T T T G A A A G C C G G C G A G A A T C T G A A ...
            1870                        1880                ...
                                      ...   VAL   LYS   GLN   ASP   GLY   THR   ASN   PHE   THR   TYR   ALA
                                      ...G G T C A A A C A A G A C G G C A C A A A C T T C A C T T A C G C
                                      ... 1890                 1900                     1910                     1920

 LEU   LYS   ASP   GLU   LEU   THR   GLY   VAL   LYS...
G C T C A A A G A T G A A T T G A C G G G C G T G A A ...
            1930                        1940                ...
                                      ...   SER   VAL   GLU   PHE   LYS   ASP   THR   ALA   ASN   GLY   SER
                                      ...G A G C G T G G A G T T T A A A G A C A C G G C G A A T G G T T C
                                      ... 1950                 1960                     1970                     1980

 ASN   GLY   ALA   SER   THR   LYS   ILE   THR   LYS...
A A A C G G T G C A A G C A C G A A G A T T A C C A A ...
            1990                        2000                ...
                                      ...   ASP   GLY   LEU   THR   ILE   THR   SER   ALA   ASN   GLY   ALA
                                      ...A G A C G G C T T G A C C A T T A C G T C G G C A A A C G G T G C
                                      ... 2010                 2020                     2030                     2040

 ASN   GLY   ALA   ALA   ALA   THR   ASP   ALA   ASP...
G A A T G G T G C G G C G G C G A C T G A T G C G G A ...
            2050                        2060                ...
```

FIG.23K

```
                         ... LYS ILE LYS VAL ALA SER ASP GLY ILE SER ALA
                         ...CAAGATTAAAGTGGCTTCAGACGGCATCAGTGC
                         ... 2070      2080      2090      2100

GLY ASN LYS ALA VAL LYS ASN VAL VAL...
GGGTAATAAAGCGGTTAAAAACGTTGT...
          2110      2120
                                   ...
                         ... SER GLY LEU LYS LYS PHE GLY ASP ALA ASN PHE
                         ...GAGCGGACTGAAGAAATTTGGTGATGCGAATTT
                         ... 2130      2140      2150      2160

ASN PRO LEU THR SER SER ALA ASP ASN...
CAATCCACTGACCAGTTCCGCCGACAA...
          2170      2180
                                   ...
                         ... LEU THR LYS GLN TYR ASP ASP ALA TYR LYS GLY
                         ...CTTAACGAAACAATATGACGATGCCTATAAAGG
                         ... 2190      2200      2210      2220

LEU THR ASN LEU ASP GLU LYS GLY ALA...
CTTGACCAATTTGGATGAAAAAGGTGC...
          2230      2240
                                   ...
                         ... ASP LYS GLN THR LEU THR VAL ALA ASP ASN THR
                         ...GGACAAGCAAACTCTGACTGTTGCCGACAATAC
                         ... 2250      2260      2270      2280
```

FIG.23L

```
 ALA  ALA  THR  VAL  GLY  ASP  LEU  ARG  GLY...
T G C C G C A A C C G T G G G C G A T T T G C G C G G ...
              2290           2300           ...
                        ...  LEU  GLY  TRP  VAL  ILE  SER  ALA  ASP  LYS  THR  THR
                        ...C T T G G G C T G G G T C A T T T C T G C G G A C A A A A C C A C
                        ... 2310           2320           2330           2340

 GLY  GLU  LEU  ASN  LYS  GLU  TYR  ASN  ALA...
A G G C G A A C T C A A T A A G G A A T A C A A C G C ...
              2350           2360           ...
                        ...  GLN  VAL  ARG  ASN  ALA  ASN  GLU  VAL  LYS  PHE  LYS
                        ...G C A A G T G C G T A A C G C C A A T G A A G T G A A A T T C A A
                        ... 2370           2380           2390           2400

 SER  GLY  ASN  GLY  ILE  HIS  VAL  SER  GLY...
G A G C G G C A A C G G T A T C C A T G T T T C C G G ...
              2410           2420           ...
                        ...  LYS  THR  VAL  ASN  GLY  ARG  ARG  GLU  ILE  THR  PHE
                        ...T A A A A C G G T C A A C G G T A G G C G C G A A A T T A C T T T
                        ... 2430           2440           2450           2460

 GLU  LEU  ALA  LYS  ASP  GLU  ASN  ALA  ILE...
T G A A T T G G C T A A A G A C G A A A A T G C C A T ...
              2470           2480           ...
```

FIG.23M

```
                                  ... ALA PHE GLY TYR GLY SER LYS ALA LEU ARG ASP
                                  ...TGCTTTCGGTTATGGCTCAAAAGCCTTGCGCGA
                                  ... 2490       2500       2510       2520

ASN THR VAL ALA ILE GLY THR GLY ASN...
TAACACGGTGGCAATTGGTACGGGCAA ...
         2530       2540       ...
                                  ... VAL VAL ASN ALA GLU LYS SER GLY ALA PHE GLY
                                  ...CGTTGTGAATGCGGAAAAATCTGGTGCATTCGG
                                  ... 2550       2560       2570       2580

ASP PRO ASN TYR ILE GLU ASP LYS ALA...
CGATCCGAACTACATCGAAGATAAAGC ...
         2590       2600       ...
                                  ... GLY GLY SER TYR ALA PHE GLY ASN ASP ASN ARG
                                  ...CGGTGGCAGCTACGCTTTCGGTAACGATAACCG
                                  ... 2610       2620       2630       2640

ILE THR SER LYS ASN THR PHE VAL LEU...
TATTACTTCTAAAAACACTTTTGTGTT ...
         2650       2660       ...
                                  ... GLY ASN GLY VAL ASN ALA LYS TYR LYS ALA ASN
                                  ...GGGTAATGGAGTTAATGCGAAATATAAAGCCAA
                                  ... 2670       2680       2690       2700
```

FIG.23N

```
  GLY   ASP   VAL   ASP   THR   GLU   THR   VAL   THR...
T G G A G A T G T T G A T A C G G A A A C C G T A A C ...
              2710                    2720            ...
                                            ...   VAL   LYS   ASP   LYS   ASP   GLY   LYS   GLU   THR   THR   VAL
                                            ...C G T T A A G G A C A A A G A C G G T A A A G A G A C T A C C G T
                                            ... 2730              2740                 2750                 2760

  THR   VAL   PRO   LYS   ALA   LEU   GLY   ALA   THR...
T A C T G T T C C T A A A G C G T T A G G G G C T A C ...
              2770                    2780            ...
                                            ...   VAL   GLU   ASN   SER   VAL   TYR   LEU   GLY   ASN   LYS   SER
                                            ...G G T T G A A A A C T C C G T T T A T T T G G G T A A T A A A T C
                                            ... 2790              2800                 2810                 2820

  THR   ALA   THR   LYS   ASP   LYS   GLY   LYS   ASN...
G A C T G C G A C A A A A G A T A A G G G T A A A A A ...
              2830                    2840            ...
                                            ...   LEU   LYS   SER   ASP   GLY   THR   ALA   GLY   ASN   THR   THR
                                            ...C C T G A A A T C T G A T G G T A C G G C G G G T A A C A C T A C
                                            ... 2850              2860                 2870                 2880

  THR   ALA   GLY   THR   THR   GLY   THR   VAL   ASN...
A A C T G C T G G C A C A A C G G G T A C G G T A A A ...
              2890                    2900            ...
```

FIG.23O

```
                 ...   GLY  PHE  ALA  GLY  ALA  THR  ALA  HIS  GLY  ALA  VAL
                 ...C G G C T T T G C C G G T G C A A C G G C G C A C G G T G C G G T
                 ... 2910                2920                2930              2940

 SER  VAL  GLY  ALA  SER  GLY  GLU  GLU  ARG...
T T C T G T C G G C G C A A G C G G C G A A G A A A G ...
           2950                2960          ...
                 ...   ARG  ILE  GLN  ASN  VAL  ALA  ALA  GLY  GLU  ILE  SER
                 ...A C G T A T C C A A A A C G T C G C G G C A G G C G A A A T T T C
                 ... 2970                2980                2990              3000

 ALA  THR  SER  THR  ASP  ALA  ILE  ASN  GLY...
C G C C A C T T C C A C C G A T G C G A T T A A C G G ...
           3010                3020          ...
                 ...   SER  GLN  LEU  TYR  ALA  VAL  ALA  LYS  GLY  VAL  THR
                 ...C A G C C A G T T G T A T G C T G T G G C A A A A G G G G T A A C
                 ... 3030                3040                3050              3060

 ASN  LEU  ALA  GLY  GLN  VAL  ASN  LYS  VAL...
A A A T C T T G C T G G A C A A G T G A A T A A A G T ...
           3070                3080          ...
                 ...   GLY  LYS  ARG  ALA  ASP  ALA  GLY  THR  ALA  SER  ALA
                 ...G G G C A A A C G T G C A G A T G C A G G T A C A G C A A G T G C
                 ... 3090                3100                3110              3120
```

FIG.23P

```
 LEU   ALA   ALA   SER   GLN   LEU   PRO   GLN   ALA...
ATTAGCAGCTTCACAGTTACCACAAGC...
       3130             3140                      ...
                         ...  SER   MET   PRO   GLY   LYS   SER   MET   VAL   SER   ILE   ALA
                         ...CTCTATGCCAGGTAAATCAATGGTTTCTATTGC
                         ... 3150             3160            3170             3180

 GLY   SER   SER   TYR   GLN   GLY   GLN   ASN   GLY...
GGGAAGTAGTTATCAAGGTCAAAATGG...
       3190             3200                      ...
                         ...  LEU   ALA   ILE   GLY   VAL   SER   ARG   ILE   SER   ASP   ASN
                         ...TTTAGCTATCGGGGTATCACGAATTTCCGATAA
                         ... 3210             3220            3230             3240

 GLY   LYS   VAL   ILE   ILE   ARG   LEU   SER   GLY...
TGGCAAAGTGATTATTCGCTTGTCAGG...
       3250             3260                      ...
                         ...  THR   THR   ASN   SER   GLN   GLY   LYS   THR   GLY   VAL   ALA
                         ...CACAACCAATAGCCAAGGTAAAACAGGCGTTGC
                         ... 3270             3280            3290             3300

 ALA   GLY   VAL   GLY   TYR   GLN   TRP   ***
AGCAGGTGTTGGTTACCAGTGGTAATA...
       3310             3320                      ...

                         ...GAATTGATCCGC
                         ... 3330
```

FIG.24A

*H. influenzae* type c strain API *hia* sequence

```
MET   ASN   LYS   ILE   PHE   ASN   VAL   ILE   TRP   ASN ...
A T G A A C A A A A T T T T T A A C G T T A T T T G G A A T...
                  10                  20                  30...
                                   ...  VAL   MET   THR   GLN   THR   TRP   VAL   VAL   VAL   SER
                                   ... G T T A T G A C T C A A A C T T G G G T T G T C G T A T C T
                                   ...                  40                  50                  60

GLU   LEU   THR   ARG   THR   HIS   THR   LYS   ARG   ALA ...
G A A C T C A C T C G C A C C C A C A C C A A A C G C G C C...
                  70                  80                  90...
                                   ...  SER   ALA   THR   VAL   GLU   THR   ALA   VAL   LEU   ALA
                                   ... T C C G C A A C C G T G G A G A C C G C C G T A T T G G C G
                                   ...                 100                 110                 120

THR   LEU   LEU   PHE   ALA   THR   VAL   GLN   ALA   ASN ...
A C A C T G T T G T T T G C A A C G G T T C A G G C G A A T...
                 130                 140                 150...
                                   ...  ALA   THR   ASP   GLU   ASP   GLU   GLU   LEU   ASP   PRO
                                   ... G C T A C C G A T G A A G A T G A A G A G T T A G A C C C C
                                   ...                 160                 170                 180

VAL   VAL   ARG   THR   ALA   PRO   VAL   LEU   SER   PHE ...
G T A G T A C G C A C T G C T C C C G T G T T G A G C T T C...
                 190                 200                 210...
```

FIG.24B

```
... HIS SER ASP LYS GLU GLY THR GLY GLU LYS
... C A T T C C G A T A A A G A A G G C A C G G G A G A A A A A
...                 220                 230                 240

GLU VAL THR GLU ASN SER ASN TRP GLY ILE ...
G A A G T T A C A G A A A A T T C A A A T T G G G G A A T A...
          250                 260                 270...
... TYR PHE HIS ASN LYS GLY VAL LEU LYS ALA
... T A T T T C C A C A A T A A A G G A G T A C T A A A A G C C
...                 280                 290                 300

GLY ALA ILE THR LEU LYS ALA GLY ASP ASN ...
G G A G C A A T C A C C C T C A A A G C C G G C G A C A A C...
          310                 320                 330...
... LEU LYS ILE LYS GLN SER THR ASN ALA SER
... C T G A A A A T C A A A C A A A G C A C C A A T G C C A G T
...                 340                 350                 360

SER PHE THR TYR SER LEU LYS LYS ASP LEU ...
A G C T T C A C C T A C T C G C T G A A A A A A G A C C T C...
          370                 380                 390...
... THR ASP LEU THR SER VAL ALA THR GLU LYS
... A C A G A T C T G A C C A G T G T T G C A A C T G A A A A A
...                 400                 410                 420
```

FIG.24C

```
LEU   SER   PHE   GLY   ALA   ASN   GLY   ASP   LYS   VAL ...
T T A T C G T T T G G C G C A A A C G G C G A T A A A G T T...
              430                     440                450...
                                      ...  ASP   ILE   THR   SER   ASP   ALA   ASN   GLY   LEU   LYS
                                      ... G A T A T T A C C A G T G A T G C A A A T G G C T T G A A A
                                      ...                460                  470                  480

LEU   ALA   LYS   THR   GLY   ASN   GLY   ASN   VAL   HIS ...
T T G G C G A A A A C A G G T A A C G G A A A T G T T C A T...
              490                     500                510...
                                      ...  LEU   ASN   GLY   LEU   ASP   SER   THR   LEU   PRO   ASP
                                      ... T T G A A T G G T T T G G A T T C A A C T T T G C C T G A T
                                      ...                520                  530                  540

ALA   VAL   THR   ASN   THR   GLY   VAL   LEU   SER   SER ...
G C G G T A A C G A A T A C A G G T G T G T T A A G T T C A...
              550                     560                570...
                                      ...  SER   SER   PHE   THR   PRO   ASN   ASP   VAL   GLU   LYS
                                      ... T C A A G T T T T A C A C C T A A T G A T G T T G A A A A A
                                      ...                580                  590                  600

THR   ARG   ALA   ALA   THR   VAL   LYS   ASP   VAL   LEU ...
A C A A G A G C T G C A A C T G T T A A A G A T G T T T T A...
              610                     620                630...
```

FIG.24D

```
                         ... ASN ALA GLY TRP ASN ILE LYS GLY ALA LYS
                         ... A A T G C A G G T T G G A A C A T T A A A G G T G C T A A A
                         ...               640                 650               660

THR ALA GLY GLY ASN VAL GLU SER VAL ASP ...
A C T G C T G G A G G T A A T G T T G A G A G T G T T G A T...
          670                 680             690...
                         ... LEU VAL SER ALA TYR ASN ASN VAL GLU PHE
                         ... T T A G T G T C C G C T T A T A A T A A T G T T G A A T T T
                         ...               700                 710               720

ILE THR GLY ASP LYS ASN THR LEU ASP VAL ...
A T T A C A G G C G A T A A A A A C A C G C T T G A T G T T...
          730                 740             750...
                         ... VAL LEU THR ALA LYS GLU ASN GLY LYS THR
                         ... G T A T T A A C A G C T A A A G A A A A C G G T A A A A C A
                         ...               760                 770               780

THR GLU VAL LYS PHE THR PRO LYS THR SER ...
A C C G A A G T G A A A T T C A C A C C G A A A A C C T C T...
          790                 800             810...
                         ... VAL ILE LYS GLU LYS ASP GLY LYS LEU PHE
                         ... G T T A T C A A A G A A A A A G A C G G T A A G T T A T T T
                         ...               820                 830               840
```

FIG.24E

```
THR   GLY   LYS   GLU   ASN   ASN   ASP   THR   ASN   LYS ...
A C T G G A A A A G A G A A T A A C G A C A C A A A T A A A...
                850                 860                 870...
                                  ... VAL   THR   SER   ASN   THR   ALA   THR   ASP   ASN   THR
                                  ... G T T A C A A G T A A C A C G G C G A C T G A T A A T A C A
                                  ...                 880                 890                 900

ASP   GLU   GLY   ASN   GLY   LEU   VAL   THR   ALA   LYS ...
G A T G A G G G T A A T G G C T T A G T C A C T G C A A A A...
                910                 920                 930...
                                  ... ALA   VAL   ILE   ASP   ALA   VAL   ASN   LYS   ALA   GLY
                                  ... G C T G T G A T T G A T G C T G T G A A C A A G G C T G G T
                                  ...                 940                 950                 960

TRP   ARG   VAL   LYS   THR   THR   THR   ALA   ASN   GLY ...
T G G A G A G T T A A A A C A A C T A C T G C T A A T G G T...
                970                 980                 990...
                                  ... GLN   ASN   GLY   ASP   PHE   ALA   THR   VAL   ALA   SER
                                  ... C A A A A T G G C G A C T T C G C A A C T G T T G C G T C A
                                  ...                1000                1010                1020

GLY   THR   ASN   VAL   THR   PHE   GLU   SER   GLY   ASP ...
G G C A C A A A T G T A A C C T T T G A A A G T G G C G A T...
               1030                1040                1050...
```

FIG.24F

```
                          ... GLY THR THR ALA SER VAL THR LYS ASP THR
                          ... G G T A C A A C A G C G T C A G T A A C T A A A G A T A C T
                          ...                 1060                1070                1080

ASN GLY ASN GLY ILE THR VAL LYS TYR ASP ...
A A C G G C A A T G G C A T C A C T G T T A A G T A C G A C...
              1090                1100                1110...
                          ... ALA LYS VAL GLY ASP GLY LEU LYS PHE ASP
                          ... G C G A A A G T T G G C G A C G G C T T G A A A T T T G A T
                          ...                 1120                1130                1140

SER ASP LYS LYS ILE VAL ALA ASP THR THR ...
A G C G A T A A A A A A A T C G T T G C A G A T A C G A C C...
              1150                1160                1170...
                          ... ALA LEU THR VAL THR GLY GLY LYS VAL ALA
                          ... G C A C T T A C T G T G A C A G G T G G T A A G G T A G C T
                          ...                 1180                1190                1200

GLU ILE ALA LYS GLU ASP ASP LYS LYS LYS ...
G A A A T T G C T A A A G A A G A T G A C A A G A A A A A A...
              1210                1220                1230...
                          ... LEU VAL ASN ALA GLY ASP LEU VAL THR ALA
                          ... C T T G T T A A T G C A G G C G A T T T G G T A A C A G C T
                          ...                 1240                1250                1260
```

FIG.24G

```
LEU GLY ASN LEU SER TRP LYS ALA LYS ALA ...
T T A G G T A A T C T A A G T T G G A A A G C A A A A G C T...
1270 1280 1290...
... GLU ALA ASP THR ASP THR ASP GLY ALA LEU
... G A G G C T G A T A C T G A T A C T G A T G G T G C G C T T
... 1300 1310 1320

GLU GLY ILE SER LYS ASP GLN GLU VAL LYS ...
G A G G G G A T T T C A A A A G A C C A A G A A G T C A A A...
1330 1340 1350...
... ALA GLY GLU THR VAL THR PHE LYS ALA GLY
... G C A G G C G A A A C G G T A A C C T T T A A A G C G G G C
... 1360 1370 1380

LYS ASN LEU LYS VAL LYS GLN ASP GLY ALA ...
A A G A A C T T A A A A G T G A A A C A G G A T G G T G C G...
1390 1400 1410...
... ASN PHE THR TYR SER LEU GLN ASP ALA LEU
... A A C T T T A C T T A T T C A C T G C A A G A T G C T T T A
... 1420 1430 1440

THR GLY LEU THR SER ILE THR LEU GLY GLY ...
A C G G G T T T A A C G A G C A T T A C T T T A G G T G G T...
1450 1460 1470...
```

FIG.24H

```
                                  ... THR THR ASN GLY GLY ASN ASP ALA LYS THR
                                  ... A C A A C T A A T G G C G G A A A T G A T G C G A A A A C C
                                  ...          1480                1490               1500

VAL ILE ASN LYS ASP GLY LEU THR ILE THR ...
G T C A T C A A C A A A G A C G G T T T A A C C A T C A C G...
           1510                1520                1530...
                                  ... PRO ALA GLY ASN GLY GLY THR THR GLY THR
                                  ... C C A G C A G G T A A T G G C G G T A C G A C A G G T A C A
                                  ...          1540                1550               1560

ASN THR ILE SER VAL THR LYS ASP GLY ILE ...
A A C A C C A T C A G C G T A A C C A A A G A T G G C A T T...
           1570                1580                1590...
                                  ... LYS ALA GLY ASN LYS ALA ILE THR ASN VAL
                                  ... A A A G C A G G T A A T A A A G C T A T T A C T A A T G T T
                                  ...          1600                1610               1620

ALA SER GLY LEU ARG ALA TYR ASP ASP ALA ...
G C G A G T G G T T T A A G A G C T T A T G A C G A T G C G...
           1630                1640                1650...
                                  ... ASN PHE ASP VAL LEU ASN ASN SER ALA THR
                                  ... A A T T T T G A T G T T T T A A A T A A C T C T G C A A C T
                                  ...          1660                1670               1680
```

FIG.24I

```
ASP  LEU  ASN  ARG  HIS  VAL  GLU  ASP  ALA  TYR ...
G A T T T A A A T A G A C A C G T T G A A G A T G C T T A T...
            1690            1700             1710...
                                ... LYS  GLY  LEU  LEU  ASN  LEU  ASN  GLU  LYS  ASN
                                ... A A A G G T T T A T T A A A T C T A A A T G A A A A A A A T
                                ...            1720             1730             1740

ALA  ASN  LYS  GLN  PRO  LEU  VAL  THR  ASP  SER ...
G C A A A T A A A C A A C C G T T G G T G A C T G A C A G C...
            1750            1760             1770...
                                ... THR  ALA  ALA  THR  VAL  GLY  ASP  LEU  ARG  LYS
                                ... A C G G C G G C G A C T G T A G G C G A T T T A C G T A A A
                                ...            1780             1790             1800

LEU  GLY  TRP  VAL  VAL  SER  THR  LYS  ASN  GLY ...
T T G G G T T G G G T A G T A T C A A C C A A A A A C G G T...
            1810            1820             1830...
                                ... THR  LYS  GLU  GLU  SER  ASN  GLN  VAL  LYS  GLN
                                ... A C G A A A G A A G A A A G C A A T C A A G T T A A A C A A
                                ...            1840             1850             1860

ALA  ASP  GLU  VAL  LEU  PHE  THR  GLY  ALA  GLY ...
G C T G A T G A A G T C C T C T T T A C C G G A G C C G G T...
            1870            1880             1890...
```

FIG.24J

```
                                  ... ALA ALA THR VAL THR SER LYS SER GLU ASN
                                  ... G C T G C T A C G G T T A C T T C C A A A T C T G A A A A C
                                  ...          1900              1910              1920

GLY LYS HIS THR ILE THR VAL SER VAL ALA ...
G G T A A A C A T A C G A T T A C C G T T A G T G T G G C T...
          1930              1940              1950...
                                  ... GLU THR LYS ALA ASP SER GLY LEU GLU LYS
                                  ... G A A A C T A A A G C G G A T A G C G G T C T T G A A A A A
                                  ...          1960              1970              1980

ASP GLY ASP THR ILE LYS LEU LYS VAL ASP ...
G A T G G C G A T A C T A T T A A G C T C A A A G T G G A T...
          1990              2000              2010...
                                  ... ASN GLN ASN THR ASP ASN VAL LEU THR VAL
                                  ... A A T C A A A A C A C T G A T A A T G T T T T A A C T G T T
                                  ...          2020              2030              2040

GLY ASN ASN GLY THR ALA VAL THR LYS GLY ...
G G T A A T A A T G G T A C T G C T G T C A C T A A A G G T...
          2050              2060              2070...
                                  ... GLY PHE GLU THR VAL LYS THR GLY ALA THR
                                  ... G G C T T T G A A A C T G T T A A A A C T G G A G C G A C T
                                  ...          2080              2090              2100
```

FIG.24K

```
ASP  ALA  ASP  ARG  GLY  LYS  VAL  THR  VAL  LYS ...
G A T G C A G A T C G C G G T A A A G T A A C T G T A A A A...
              2110                 2120                2130...
                                            ... ASP  ALA  THR  ALA  ASN  ASP  ALA  ASP  LYS  LYS
                                            ... G A T G C T A C T G C T A A T G A C G C T G A T A A G A A A
                                            ...               2140                2150                2160

VAL  ALA  THR  VAL  LYS  ASP  VAL  ALA  THR  ALA ...
G T C G C A A C T G T A A A A G A T G T T G C A A C C G C A...
              2170                 2180                2190...
                                            ... ILE  ASN  SER  ALA  ALA  THR  PHE  VAL  LYS  THR
                                            ... A T T A A T A G T G C G G C G A C T T T T G T G A A A A C A
                                            ...               2200                2210                2220

GLU  ASN  LEU  THR  THR  SER  ILE  ASP  GLU  ASP ...
G A G A A T T T A A C T A C C T C T A T T G A T G A A G A T...
              2230                 2240                2250...
                                            ... ASN  PRO  THR  ASP  ASN  GLY  LYS  ASP  ASP  ALA
                                            ... A A T C C T A C A G A T A A C G G C A A A G A T G A C G C A
                                            ...               2260                2270                2280

LEU  LYS  ALA  GLY  ASP  THR  LEU  THR  PHE  LYS ...
C T T A A A G C G G G C G A T A C C T T A A C C T T T A A A...
              2290                 2300                2310...
```

FIG.24L

```
... ALA GLY LYS ASN LEU LYS VAL LYS ARG ASP
... G C A G G T A A A A A C C T G A A A G T T A A A C G T G A T
...                 2320                2330                2340

GLY LYS ASN ILE THR PHE ASP LEU ALA LYS ...
G G A A A A A A T A T T A C T T T T G A C T T G G C G A A A...
          2350                2360                2370...
... ASN LEU GLU VAL LYS THR ALA LYS VAL SER
... A A C C T T G A G G T G A A A A C T G C G A A A G T G A G T
...                 2380                2390                2400

ASP THR LEU THR ILE GLY GLY ASN THR PRO ...
G A T A C T T T A A C G A T T G G C G G G A A T A C A C C T...
          2410                2420                2430...
... THR GLY GLY THR THR ALA THR PRO LYS VAL
... A C A G G T G G C A C T A C T G C G A C G C C A A A A G T G
...                 2440                2450                2460

ASN ILE THR SER THR ALA ASP GLY LEU ASN ...
A A T A T T A C T A G C A C G G C T G A T G G T T T G A A T...
          2470                2480                2490...
... PHE ALA LYS GLU THR ALA ASP ALA SER GLY
... T T T G C A A A A G A A A C A G C C G A T G C C T C G G G T
...                 2500                2510                2520
```

FIG.24M

```
SER LYS ASN VAL TYR LEU LYS GLY ILE ALA ....
T C T A A G A A T G T T T A T T T G A A A G G T A T T G C G ....
                    2540                    2550....
                                                        THR THR LEU THR GLU PRO SER ALA GLY ALA
                                                    ... A C A A C T T T A A C T G A G C C A A G C G C G G G A G C G
                                                            2560                    2570                    2580

LYS SER SER HIS VAL ASP LEU ASN VAL ASP ....
A A G T C T T C A C A C G T T G A T T T A A A T G T G G A T ....
                    2600                    2610....
                                                        ALA THR LYS LYS SER ASN ALA ALA SER ILE
                                                    ... G C G A C G A A A A A A T C C A A T G C A G C A A G T A T T
                                                            2620                    2630                    2640

GLU ASP VAL LEU ARG ALA GLY TRP ASN ILE ....
G A A G A T G T A T T G C G C G C A G G T T G G A A T A T T ....
                    2650                    2660                    2670....
                                                        GLN GLY ASN GLY ASN ASN VAL ASP TYR VAL
                                                    ... C A A G G T A A T G G T A A T A A T G T T G A T T A T G T A
                                                            2680                    2690                    2700

ALA THR TYR ASP THR VAL ASN PHE THR ASP ....
G C G A C G T A T G A C A C A G T A A A C T T T A C C G A T ....
                    2710                    2720                    2730....
```

FIG.24N

```
                              ... ASP SER THR GLY THR THR THR VAL THR VAL
                              ... G A C A G C A C A G G T A C A A C A A C G G T A A C C G T A
                              ...           2740                2750                2760

THR GLN LYS ALA ASP GLY LYS GLY ALA ASP ...
A C C C A A A A A G C A G A T G G C A A A G G T G C T G A C...
          2770                2780                2790...
                              ... VAL LYS ILE GLY ALA LYS THR SER VAL ILE
                              ... G T T A A A A T C G G T G C G A A A A C T T C T G T T A T C
                              ...           2800                2810                2820

LYS ASP HIS ASN GLY LYS LEU PHE THR GLY ...
A A A G A C C A C A A C G G C A A A C T G T T T A C A G G C...
          2830                2840                2850...
                              ... LYS ASP LEU LYS ASP ALA ASN ASN GLY ALA
                              ... A A A G A C C T G A A A G A T G C G A A T A A T G G T G C A
                              ...           2860                2870                2880

THR VAL SER GLU ASP ASP GLY LYS ASP THR ...
A C C G T T A G T G A A G A T G A T G G C A A A G A C A C C...
          2890                2900                2910...
                              ... GLY THR GLY LEU VAL THR ALA LYS THR VAL
                              ... G G C A C A G G C T T A G T T A C T G C A A A A A C T G T G
                              ...           2920                2930                2940
```

FIG.24O

```
ILE   ASP   ALA   VAL   ASN   LYS   SER   GLY   TRP   ARG ...
A T T G A T G C A G T A A A T A A A A G C G G T T G G A G G...
            2950                 2960                 2970...
                          ... VAL   THR   GLY   GLU   GLY   ALA   THR   ALA   GLU   THR
                          ... G T A A C C G G T G A G G G C G C G A C T G C C G A A A C C
                          ...            2980                 2990                 3000

GLY   ALA   THR   ALA   VAL   ASN   ALA   GLY   ASN   ALA ...
G G T G C A A C C G C C G T G A A T G C G G G T A A C G C T...
            3010                 3020                 3030...
                          ... GLU   THR   VAL   THR   SER   GLY   THR   SER   VAL   ASN
                          ... G A A A C C G T T A C A T C A G G C A C G A G C G T G A A C
                          ...            3040                 3050                 3060

PHE   LYS   ASN   GLY   ASN   ALA   THR   THR   ALA   THR ...
T T C A A A A A C G G C A A T G C G A C C A C A G C G A C C...
            3070                 3080                 3090...
                          ... VAL   SER   LYS   ASP   ASN   GLY   ASN   ILE   ASN   VAL
                          ... G T A A G C A A A G A T A A T G G C A A C A T C A A T G T C
                          ...            3100                 3110                 3120

LYS   TYR   ASP   VAL   ASN   VAL   GLY   ASP   GLY   LEU ...
A A A T A C G A T G T A A A T G T T G G T G A C G G C T T G...
            3130                 3140                 3150...
```

FIG.24P

```
... LYS ILE GLY ASP ASP LYS LYS ILE VAL ALA
... A A G A T T G G C G A T G A C A A A A A A A T C G T T G C A
...                 3160                3170                3180

ASP THR THR THR LEU THR VAL THR GLY GLY ...
G A C A C G A C C A C A C T T A C T G T A A C A G G T G G T...
            3190                3200                3210...
... LYS VAL SER VAL PRO ALA GLY ALA ASN SER
... A A G G T G T C T G T T C C T G C T G G T G C T A A T A G T
...                 3220                3230                3240

VAL ASN ASN ASN LYS LYS LEU VAL ASN ALA ...
G T T A A T A A C A A T A A G A A A C T T G T T A A T G C A...
            3250                3260                3270...
... GLU GLY LEU ALA THR ALA LEU ASN ASN LEU
... G A G G G T T T A G C G A C T G C T T T A A A C A A C C T A
...                 3280                3290                3300

SER TRP THR ALA LYS ALA ASP LYS TYR ALA ...
A G C T G G A C G G C A A A A G C C G A T A A A T A T G C A...
            3310                3320                3330...
... ASP GLY GLU SER GLU GLY GLU THR ASP GLN
... G A T G G C G A G T C A G A G G G C G A A A C C G A C C A A
...                 3340                3350                3360
```

FIG.24Q

```
GLU   VAL   LYS   ALA   GLY   ASP   LYS   VAL   THR   PHE ...
G A A G T C A A A G C A G G C G A C A A A G T A A C C T T T...
               3370                3380                3390...
                                    ... LYS   ALA   GLY   LYS   ASN   LEU   LYS   VAL   LYS   GLN
                                    ... A A A G C A G G C A A G A A C T T A A A A G T G A A A C A G
                                    ...                3400                3410                3420

SER   GLU   LYS   ASP   PHE   THR   TYR   SER   LEU   GLN ...
T C T G A A A A A G A C T T T A C T T A T T C A C T G C A A...
               3430                3440                3450...
                                    ... ASP   THR   LEU   THR   GLY   LEU   THR   SER   ILE   THR
                                    ... G A C A C T T T A A C A G G C T T A A C G A G C A T T A C T
                                    ...                3460                3470                3480

LEU   GLY   GLY   THR   ALA   ASN   GLY   ARG   ASN   ASP ...
T T A G G T G G T A C A G C T A A T G G C A G A A A T G A T...
               3490                3500                3510...
                                    ... THR   GLY   THR   VAL   ILE   ASN   LYS   ASP   GLY   LEU
                                    ... A C G G G A A C C G T C A T C A A C A A A G A C G G C T T A
                                    ...                3520                3530                3540

THR   ILE   THR   LEU   ALA   ASN   GLY   ALA   ALA   ALA ...
A C C A T C A C G C T G G C A A A T G G T G C T G C G G C A...
               3550                3560                3570...
```

FIG.24R

```
                                 ... GLY  THR  ASP  ALA  SER  ASN  GLY  ASN  THR  ILE
                                 ... G G C A C A G A T G C G T C T A A C G G A A A C A C C A T C
                                 ...                3580               3590               3600

SER  VAL  THR  LYS  ASP  GLY  ILE  SER  ALA  GLY ...
A G T G T A A C C A A A G A C G G C A T T A G T G C G G G T...
          3610               3620               3630...
                                 ... ASN  LYS  GLU  ILE  THR  ASN  VAL  LYS  SER  ALA
                                 ... A A T A A A G A A A T T A C C A A T G T T A A G A G T G C T
                                 ...                3640               3650               3660

LEU  LYS  THR  TYR  LYS  ASP  THR  GLN  ASN  THR ...
T T A A A A A C C T A T A A A G A T A C T C A A A A C A C T...
          3670               3680               3690...
                                 ... ALA  GLY  ALA  THR  GLN  PRO  ALA  ALA  ASN  THR
                                 ... G C A G G T G C A A C T C A A C C T G C G G C T A A T A C A
                                 ...                3700               3710               3720

ALA  GLU  VAL  ALA  LYS  GLN  ASP  LEU  VAL  ASP ...
G C T G A A G T A G C C A A A C A A G A C T T G G T T G A T...
          3730               3740               3750...
                                 ... LEU  THR  LYS  PRO  ALA  THR  GLY  ALA  ALA  GLY
                                 ... T T A A C T A A A C C T G C G A C A G G T G C A G C T G G A
                                 ...                3760               3770               3780
```

FIG.24S

```
ASN  GLY  ALA  ASP  ALA  LYS  ALA  PRO  ASP  THR ...
A A T G G T G C A G A T G C A A A A G C T C C C G A T A C C...
          3790                3800                3810...
                              ... THR  ALA  ALA  THR  VAL  GLY  ASP  LEU  ARG  GLY
                              ... A C A G C T G C A A C C G T A G G C G A C T T G C G T G G T
                              ...           3820                3830                3840

LEU  GLY  TRP  VAL  LEU  SER  ALA  LYS  LYS  THR ...
T T G G G C T G G G T G C T T T C A G C T A A G A A A A C T...
          3850                3860                3870...
                              ... ALA  ASP  GLU  THR  GLN  ASP  LYS  GLU  PHE  HIS
                              ... G C A G A T G A A A C A C A A G A T A A A G A G T T C C A C
                              ...           3880                3890                3900

ALA  ALA  VAL  LYS  ASN  ALA  ASN  GLU  VAL  GLU ...
G C C G C C G T T A A A A A C G C A A A T G A A G T T G A G...
          3910                3920                3930...
                              ... PHE  VAL  GLY  LYS  ASN  GLY  ALA  THR  VAL  SER
                              ... T T C G T G G G T A A A A A C G G T G C A A C C G T G T C T
                              ...           3940                3950                3960

ALA  LYS  THR  ASP  ASN  ASN  GLY  LYS  HIS  THR ...
G C A A A A A C T G A T A A C A A C G G A A A A C A T A C T...
          3970                3980                3990...
```

FIG.24T

```
                                      ... VAL THR ILE ASP VAL ALA GLU ALA LYS VAL
                                      ... G T A A C G A T T G A T G T T G C A G A A G C C A A A G T T
                                      ...              4000                4010                4020
GLY ASP GLY LEU GLU LYS ASP THR ASP GLY ...
G G T G A T G G T C T T G A A A A A G A T A C T G A C G G C...
          4030                4040                4050...
                                      ... LYS ILE LYS LEU LYS VAL ASP ASN THR ASP
                                      ... A A G A T T A A A C T C A A A G T A G A T A A T A C A G A T
                                      ...              4060                4070                4080
GLY ASN ASN LEU LEU THR VAL ASP ALA THR ...
G G G A A T A A T C T A T T A A C C G T T G A T G C A A C A...
          4090                4100                4110...
                                      ... LYS GLY ALA SER VAL ALA LYS GLY GLU PHE
                                      ... A A A G G T G C A T C C G T T G C C A A G G G C G A G T T T
                                      ...              4120                4130                4140
ASN ALA VAL THR THR ASP ALA THR THR ALA ...
A A T G C C G T A A C A A C A G A T G C A A C T A C A G C C...
          4150                4160                4170...
                                      ... GLN GLY THR ASN ALA ASN GLU ARG GLY LYS
                                      ... C A A G G C A C A A A T G C C A A T G A G C G C G G T A A A
                                      ...              4180                4190                4200
```

FIG.24U

```
VAL   VAL   VAL   LYS   GLY   SER   ASN   GLY   ALA   THR ...
G T G G T T G T C A A G G G T T C A A A T G G T G C A A C T...
              4210                4220                4230...
                                  ... ALA   THR   GLU   THR   ASP   LYS   LYS   LYS   VAL   ALA
                                  ... G C T A C C G A A A C T G A C A A G A A A A A A G T G G C A
                                  ...               4240                4250                4260

THR   VAL   GLY   ASP   VAL   ALA   LYS   ALA   ILE   ASN ...
A C T G T T G G C G A C G T T G C T A A A G C G A T T A A C...
              4270                4280                4290...
                                  ... ASP   ALA   ALA   THR   PHE   VAL   LYS   VAL   GLU   ASN
                                  ... G A C G C A G C A A C T T T C G T G A A A G T G G A A A A T
                                  ...               4300                4310                4320

ASP   ASP   SER   ALA   THR   ILE   ASP   ASP   SER   PRO ...
G A C G A C A G T G C T A C G A T T G A T G A T A G C C C A...
              4330                4340                4350...
                                  ... THR   ASP   ASP   GLY   ALA   ASN   ASP   ALA   LEU   LYS
                                  ... A C A G A T G A T G G C G C A A A T G A T G C T C T C A A A
                                  ...               4360                4370                4380

ALA   GLY   ASP   THR   LEU   THR   LEU   LYS   ALA   GLY ...
G C A G G C G A C A C C T T G A C C T T A A A A G C G G G T...
              4390                4400                4410...
```

FIG.24V

```
                                             ... LYS   ASN   LEU   LYS   VAL   LYS   ARG   ASP   GLY   LYS
                                             ... A A A A A C T T A A A A G T T A A A C G T G A T G G T A A A
                                             ...                4420                4430                4440

ASN   ILE   THR   PHE   ALA   LEU   ALA   ASN   ASP   LEU ...
A A T A T T A C T T T T G C C C T T G C G A A C G A C C T T...
             4450                4460                4470...
                                             ... SER   VAL   LYS   SER   ALA   THR   VAL   SER   ASP   LYS
                                             ... A G T G T A A A A A G C G C A A C C G T T A G C G A T A A A
                                             ...                4480                4490                4500

LEU   SER   LEU   GLY   THR   ASN   GLY   ASN   LYS   VAL ...
T T A T C G C T T G G T A C A A A C G G C A A T A A A G T C...
             4510                4520                4530...
                                             ... ASN   ILE   THR   SER   ASP   THR   LYS   GLY   LEU   ASN
                                             ... A A T A T C A C A A G C G A C A C C A A A G G C T T G A A C
                                             ...                4540                4550                4560

PHE   ALA   LYS   ASP   SER   LYS   THR   GLY   ASP   ASP ...
T T C G C T A A A G A T A G T A A G A C A G G C G A T G A T...
             4570                4580                4590...
                                             ... ALA   ASN   ILE   HIS   LEU   ASN   GLY   ILE   ALA   SER
                                             ... G C T A A T A T T C A C T T A A A T G G C A T T G C T T C A
                                             ...                4600                4610                4620
```

FIG.24W

```
THR  LEU  THR  ASP  THR  LEU  LEU  ASN  SER  GLY ...
A C T T T A A C T G A T A C A T T G T T A A A T A G T G G T...
          4630                4640                4650...
                              ... ALA  THR  THR  ASN  LEU  GLY  GLY  ASN  GLY  ILE
                              ... G C G A C A A C C A A T T T A G G T G G T A A T G G T A T T
                              ...               4660                4670                4680

THR  ASP  ASN  GLU  LYS  LYS  ARG  ALA  ALA  SER ...
A C T G A T A A C G A G A A A A A A C G C G C G G C G A G C...
          4690                4700                4710...
                              ... VAL  LYS  ASP  VAL  LEU  ASN  ALA  GLY  TRP  ASN
                              ... G T T A A A G A T G T C T T G A A T G C G G G T T G G A A T
                              ...               4720                4730                4740

VAL  ARG  GLY  VAL  LYS  PRO  ALA  SER  ALA  ASN ...
G T T C G T G G T G T T A A A C C G G C A T C T G C A A A T...
          4750                4760                4770...
                              ... ASN  GLN  VAL  GLU  ASN  ILE  ASP  PHE  VAL  ALA
                              ... A A T C A A G T G G A G A A T A T C G A C T T T G T A G C A
                              ...               4780                4790                4800

THR  TYR  ASP  THR  VAL  ASP  PHE  VAL  SER  GLY ...
A C C T A C G A C A C A G T G G A C T T T G T T A G T G G A...
          4810                4820                4830...
```

FIG.24X

```
                                ... ASP  LYS  ASP  THR  THR  SER  VAL  THR  VAL  GLU
                                ... G A T A A A G A C A C C A C G A G T G T A A C T G T T G A A
                                ...            4840                4850                4860

SER  LYS  ASP  ASN  GLY  LYS  ARG  THR  GLU  VAL ...
A G T A A A G A T A A T G G C A A G A G A A C C G A A G T T...
         4870                4880           4890...
                                ... LYS  ILE  GLY  ALA  LYS  THR  SER  VAL  ILE  LYS
                                ... A A A A T C G G T G C G A A G A C T T C T G T T A T C A A A
                                ...            4900                4910                4920

ASP  HIS  ASN  GLY  LYS  LEU  PHE  THR  GLY  LYS ...
G A C C A C A A C G G C A A A C T G T T T A C A G G C A A A...
         4930                4940           4950...
                                ... GLU  LEU  LYS  ASP  ALA  ASN  ASN  ASN  GLY  VAL
                                ... G A G C T G A A G G A T G C T A A C A A T A A T G G C G T A
                                ...            4960                4970                4980

THR  VAL  THR  GLU  THR  ASP  GLY  LYS  ASP  GLU ...
A C T G T T A C C G A A A C C G A C G G C A A A G A C G A G...
         4990                5000           5010...
                                ... GLY  ASN  GLY  LEU  VAL  THR  ALA  LYS  ALA  VAL
                                ... G G T A A T G G T T T A G T G A C T G C A A A A G C T G T G
                                ...            5020                5030                5040
```

FIG.24Y

```
ILE   ASP   ALA   VAL   ASN   LYS   ALA   GLY   TRP   ARG ...
A T T G A T G C C G T G A A T A A G G C T G G T T G G A G A...
              5050                5060                5070...
                                  ...  VAL   LYS   THR   THR   GLY   ALA   ASN   GLY   GLN   ASN
                                  ... G T T A A A A C A A C A G G T G C T A A T G G T C A G A A T
                                  ...                5080                5090                5100

ASP   ASP   PHE   ALA   THR   VAL   ALA   SER   GLY   THR ...
G A T G A C T T C G C A A C T G T T G C G T C A G G C A C A...
              5110                5120                5130...
                                  ...  ASN   VAL   THR   PHE   ALA   ASP   GLY   ASN   GLY   THR
                                  ... A A T G T A A C C T T T G C T G A T G G T A A T G G C A C A
                                  ...                5140                5150                5160

THR   ALA   GLU   VAL   THR   LYS   ALA   ASN   ASP   GLY ...
A C T G C C G A A G T A A C T A A A G C A A A C G A C G G T...
              5170                5180                5190...
                                  ...  SER   ILE   THR   VAL   LYS   TYR   ASN   VAL   LYS   VAL
                                  ... A G T A T T A C T G T T A A A T A C A A T G T T A A A G T G
                                  ...                5200                5210                5220

ALA   ASP   GLY   LEU   LYS   LEU   ASP   GLY   ASP   LYS ...
G C T G A T G G C T T A A A A C T A G A C G G C G A T A A A...
              5230                5240                5250...
```

FIG.24Z

```
                                 ... ILE VAL ALA ASP THR THR VAL LEU THR VAL
                                 ... A T C G T T G C A G A C A C G A C C G T A C T T A C T G T G
                                 ...             5260                5270                5280

ALA ASP GLY LYS VAL THR ALA PRO ASN ASN ...
G C A G A T G G T A A A G T T A C A G C T C C G A A T A A T...
            5290                5300                5310...
                                 ... GLY ASP GLY LYS LYS PHE VAL ASP ALA SER
                                 ... G G C G A T G G T A A G A A A T T T G T T G A T G C A A G T
                                 ...             5320                5330                5340

GLY LEU ALA ASP ALA LEU ASN LYS LEU SER ...
G G T T T A G C G G A T G C G T T A A A T A A A T T A A G C...
            5350                5360                5370...
                                 ... TRP THR ALA THR ALA GLY LYS GLU GLY THR
                                 ... T G G A C G G C A A C T G C T G G T A A A G A A G G C A C T
                                 ...             5380                5390                5400

GLY GLU VAL ASP PRO ALA ASN SER ALA GLY ...
G G T G A A G T T G A T C C T G C A A A T T C A G C A G G G...
            5410                5420                5430...
                                 ... GLN GLU VAL LYS ALA GLY ASP LYS VAL THR
                                 ... C A A G A A G T C A A A G C G G G C G A C A A A G T A A C C
                                 ...             5440                5450                5460
```

FIG.24A'

```
PHE   LYS   ALA   GLY   ASP   ASN   LEU   LYS   ILE   LYS ...
T T T A A A G C C G G C G A C A A C C T G A A A A T C A A A...
              5470                5480                5490...
                     ... GLN   SER   GLY   LYS   ASP   PHE   THR   TYR   SER   LEU
                     ... C A A A G C G G C A A A G A C T T T A C C T A C T C G C T G
                     ...               5500                5510                5520

LYS   LYS   GLU   LEU   LYS   ASP   LEU   THR   SER   VAL ...
A A A A A A G A G C T G A A A G A C C T G A C C A G C G T A...
              5530                5540                5550...
                     ... GLU   PHE   LYS   ASP   ALA   ASN   GLY   GLY   THR   GLY
                     ... G A G T T C A A A G A C G C A A A C G G C G G T A C A G G C
                     ...               5560                5570                5580

SER   GLU   SER   THR   LYS   ILE   THR   LYS   ASP   GLY ...
A G T G A A A G C A C C A A G A T T A C C A A A G A C G G C...
              5590                5600                5610...
                     ... LEU   THR   ILE   THR   PRO   ALA   ASN   GLY   ALA   GLY
                     ... T T G A C C A T T A C G C C G G C A A A C G G T G C G G G T
                     ...               5620                5630                5640

ALA   ALA   GLY   ALA   ASN   THR   ALA   ASN   THR   ILE ...
G C G G C A G G T G C A A A C A C T G C A A A C A C C A T T...
              5650                5660                5670...
```

FIG.24B'

```
... SER VAL THR LYS ASP GLY ILE SER ALA GLY
... A G C G T A A C C A A A G A T G G C A T T A G C G C G G T
...                 5680                5690                5700

ASN LYS ALA VAL THR ASN VAL VAL SER GLY ...
A A T A A A G C A G T T A C A A A C G T T G T G A G C G G A...
              5710                5720                5730...
... LEU LYS LYS PHE GLY ASP GLY HIS THR LEU
... C T G A A G A A A T T T G G T G A T G G T C A T A C G T T G
...                 5740                5750                5760

ALA ASN GLY THR VAL ALA ASP PHE GLU LYS ...
G C A A A T G G C A C T G T T G C T G A T T T T G A A A A G...
              5770                5780                5790...
... HIS TYR ASP ASN ALA TYR LYS ASP LEU THR
... C A T T A T G A C A A T G C C T A T A A A G A C T T G A C C
...                 5800                5810                5820

ASN LEU ASP GLU LYS GLY ALA ASP ASN ASN ...
A A T T T G G A T G A A A A A G G C G C G G A T A A T A A T...
              5830                5840                5850...
... PRO THR VAL ALA ASP ASN THR ALA ALA THR
... C C G A C T G T T G C C G A C A A T A C C G C T G C A A C C
...                 5860                5870                5880
```

FIG.24C'

```
VAL   GLY   ASP   LEU   ARG   GLY   LEU   GLY   TRP   VAL ...
G T G G G C G A T T T G C G C G G C T T G G G C T G G G T C...
              5890                5900                5910...
                                  ...  ILE   SER   ALA   ASP   LYS   THR   THR   GLY   GLU   PRO
                                  ... A T T T C T G C G G A C A A A A C C A C A G G C G A A C C C
                                  ...               5920                5930                5940

ASN   GLN   GLU   TYR   ASN   ALA   GLN   VAL   ARG   ASN ...
A A T C A G G A A T A C A A C G C G C A A G T G C G T A A C...
              5950                5960                5970...
                                  ...  ALA   ASN   GLU   VAL   LYS   PHE   LYS   SER   GLY   ASN
                                  ... G C C A A T G A A G T G A A A T T C A A G A G C G G C A A C
                                  ...               5980                5990                6000

GLY   ILE   ASN   VAL   SER   GLY   LYS   THR   LEU   ASN ...
G G T A T C A A T G T T T C C G G T A A A A C A T T G A A C...
              6010                6020                6030...
                                  ...  GLY   THR   ARG   VAL   ILE   THR   PHE   GLU   LEU   ALA
                                  ... G G T A C G C G C G T G A T T A C C T T T G A A T T G G C T
                                  ...               6040                6050                6060

LYS   GLY   GLU   VAL   VAL   LYS   SER   ASN   GLU   PHE ...
A A A G G C G A A G T G G T T A A A T C G A A T G A A T T T...
              6070                6080                6090...
```

FIG.24D'

```
                                   ... THR VAL LYS ASN ALA ASP GLY SER GLU THR
                                   ... A C C G T T A A G A A T G C C G A T G G T T C G G A A A C G
                                   ...            6100           6110           6120
ASN LEU VAL LYS VAL GLY ASP MET TYR TYR ...
A A C T T G G T T A A A G T T G G C G A T A T G T A T T A C...
       6130           6140           6150...
                                   ... SER LYS GLU ASP ILE ASP PRO ALA THR SER
                                   ... A G C A A A G A G G A T A T T G A C C C G G C A A C C A G T
                                   ...            6160           6170           6180
LYS PRO MET THR GLY LYS THR GLU LYS TYR ...
A A A C C G A T G A C A G G T A A A A C T G A A A A A T A T...
       6190           6200           6210...
                                   ... LYS VAL GLU ASN GLY LYS VAL VAL SER ALA
                                   ... A A G G T T G A A A A C G G C A A A G T C G T T T C T G C T
                                   ...            6220           6230           6240
ASN GLY SER LYS THR GLU VAL THR LEU THR ...
A A C G G C A G C A A G A C C G A A G T T A C C C T A A C C...
       6250           6260           6270...
                                   ... ASN LYS GLY SER GLY TYR VAL THR GLY ASN
                                   ... A A C A A A G G T T C C G G C T A T G T A A C A G G T A A C
                                   ...            6280           6290           6300
```

FIG.24E'

```
GLN   VAL   ALA   ASP   ALA   ILE   ALA   LYS   SER   GLY ...
C A A G T G G C T G A T G C G A T T G C G A A A T C A G G C...
               6310                6320                6330...
                                    ... PHE   GLU   LEU   GLY   LEU   ALA   ASP   ALA   ALA   GLU
                                    ... T T T G A G C T T G G T T T G G C T G A T G C G G C A G A A
                                    ...                6340                6350                6360

ALA   GLU   LYS   ALA   PHE   ALA   GLU   SER   ALA   LYS ...
G C T G A A A A A G C C T T T G C A G A A A G C G C A A A A...
               6370                6380                6390...
                                    ... ASP   LYS   GLN   LEU   SER   LYS   ASP   LYS   ALA   GLU
                                    ... G A C A A G C A A T T G T C T A A A G A T A A A G C G G A A
                                    ...                6400                6410                6420

THR   VAL   ASN   ALA   HIS   ASP   LYS   VAL   ARG   PHE ...
A C T G T A A A T G C C C A C G A T A A A G T C C G T T T T...
               6430                6440                6450...
                                    ... ALA   ASN   GLY   LEU   ASN   THR   LYS   VAL   SER   ALA
                                    ... G C T A A T G G T T T A A A T A C C A A A G T G A G C G C G
                                    ...                6460                6470                6480

ALA   THR   VAL   GLU   SER   THR   ASP   ALA   ASN   GLY ...
G C A A C G G T G G A A A G C A C T G A T G C A A A C G G C...
               6490                6500                6510...
```

FIG.24F'

```
                                     ... ASP  LYS  VAL  THR  THR  THR  PHE  VAL  LYS  THR
                                     ... G A T A A A G T G A C C A C A A C C T T T G T G A A A A C C
                                     ...             6520              6530              6540
ASP  VAL  GLU  LEU  PRO  LEU  THR  GLN  ILE  TYR ...
G A T G T G G A A T T G C C T T T A A C G C A A A T C T A C...
            6550              6560              6570...
                                     ... ASN  THR  ASP  ALA  ASN  GLY  ASN  LYS  ILE  VAL
                                     ... A A T A C C G A T G C A A A C G G T A A T A A G A T C G T T
                                     ...             6580              6590              6600
LYS  LYS  ALA  ASP  GLY  LYS  TRP  TYR  GLU  LEU ...
A A A A A A G C T G A C G G A A A A T G G T A T G A A C T G...
            6610              6620              6630...
                                     ... ASN  ALA  ASP  GLY  THR  ALA  SER  ASN  LYS  GLU
                                     ... A A T G C T G A T G G T A C G G C G A G T A A C A A A G A A
                                     ...             6640              6650              6660
VAL  THR  LEU  GLY  ASN  VAL  ASP  ALA  ASN  GLY ...
G T G A C A C T T G G T A A C G T G G A T G C A A A C G G T...
            6670              6680              6690...
                                     ... LYS  LYS  VAL  VAL  LYS  VAL  THR  GLU  ASN  GLY
                                     ... A A G A A A G T T G T G A A A G T A A C C G A A A A T G G T
                                     ...             6700              6710              6720
```

FIG.24G'

```
ALA   ASP   LYS   TRP   TYR   TYR   THR   ASN   ALA   ASP ...
G C G G A T A A G T G G T A T T A C A C C A A T G C T G A C...
                6730                6740                6750...
                                 ... GLY   ALA   ALA   ASP   LYS   THR   LYS   GLY   GLU   VAL
                                 ... G G T G C T G C G G A T A A A A C C A A A G G C G A A G T G
                                 ...             6760                6770                6780

SER   ASN   ASP   LYS   VAL   SER   THR   ASP   GLU   LYS ...
A G C A A T G A T A A A G T T T C T A C C G A T G A A A A A...
                6790                6800                6810...
                                 ... HIS   VAL   VAL   ARG   LEU   ASP   PRO   ASN   ASN   GLN
                                 ... C A C G T T G T C C G C C T T G A T C C G A A C A A T C A A
                                 ...             6820                6830                6840

SER   ASN   GLY   LYS   GLY   VAL   VAL   ILE   ASP   ASN ...
T C G A A C G G C A A A G G C G T G G T C A T T G A C A A T...
                6850                6860                6870...
                                 ... VAL   ALA   ASN   GLY   GLU   ILE   SER   ALA   THR   SER
                                 ... G T G G C T A A T G G C G A A A T T T C T G C C A C T T C C
                                 ...             6880                6890                6900

THR   ASP   ALA   ILE   ASN   GLY   SER   GLN   LEU   TYR ...
A C C G A T G C G A T T A A C G G A A G T C A G T T G T A T...
                6910                6920                6930...
```

FIG.24H'

... ALA VAL ALA LYS GLY VAL THR ASN LEU ALA
... G C C G T G G C A A A A G G G G T A A C A A A C C T T G C T
... 6940 6950 6960

GLY GLN VAL ASN ASN LEU GLU GLY LYS VAL ...
G G A C A A G T G A A T A A T C T T G A G G G C A A A G T G...
6970 6980 6990...

... ASN LYS VAL GLY LYS ARG ALA ASP ALA GLY
... A A T A A A G T G G G C A A A C G T G C A G A T G C A G G T
... 7000 7010 7020

THR ALA SER ALA LEU ALA ALA SER GLN LEU ...
A C A G C A A G T G C A T T A G C G G C T T C A C A G T T A...
7030 7040 7050...

... PRO GLN ALA THR MET PRO GLY LYS SER MET
... C C A C A A G C C A C T A T G C C A G G T A A A T C A A T G
... 7060 7070 7080

VAL ALA ILE ALA GLY SER SER TYR GLN GLY ...
G T T G C T A T T G C G G G A A G T A G T T A T C A A G G T...
7090 7100 7110...

... GLN ASN GLY LEU ALA ILE GLY VAL SER ARG
... C A A A A T G G T T T A G C T A T C G G G G T A T C A A G A
... 7120 7130 7140

FIG.24I'

```
 ILE  SER  ASP  ASN  GLY  LYS  VAL  ILE  ILE  ARG ...
A T T T C C G A T A A T G G C A A A G T G A T T A T T C G C...
              7150              7160              7170...
                                      ...  LEU  SER  GLY  THR  THR  ASN  SER  GLN  GLY  LYS
                                      ... T T G T C A G G C A C A A C C A A T A G T C A A G G T A A A
                                      ...               7180              7190              7200

 THR  GLY  VAL  ALA  ALA  GLY  VAL  GLY  TYR  GLN ...
A C A G G C G T T G C A G C A G G T G T T G G T T A C C A G...
              7210              7220              7230...
                                      ...  TRP  ***
                                      ... T G G T A A T A G A A T T C C G G A T C C G C
                                      ...               7240              7250
```

FIG.25A

NTHi strain 12 *hia* locus

```
    TYR   TYR   HIS   TRP   ***   PRO   THR   PRO  ...
GAATTCTATTACCACTGGTAACCAACACCT ...
         10        20        30 ...
                              ... ALA   ALA   THR   PRO   GLU   THR   ALA   GLN   GLN   ILE
                              ...GCTGCAACGCCAGAAACAGCACAACAAATT
                              ...        40        50        60

HIS   TRP   LEU   HIS   GLN   PHE   THR   LYS   ALA   ARG  ...
CACTGGCTACATCAATTTACCAAAGCTCGC ...
         70        80        90 ...
                              ... ILE   GLN   TRP   ARG   LYS   THR   HIS   SER   LEU   PHE
                              ...ATTCAATGGCGCAAAACCCATTCCTTATTC
                              ...       100       110       120

PHE   LYS   GLU   LYS   PRO   ASP   TYR   ALA   PHE   VAL  ...
TTTAAAGAAAAACCCGATTATGCCTTTGTG ...
        130       140       150 ...
                              ... LEU   ALA   GLU   ASN   GLY   LYS   VAL   GLN   GLU   ILE
                              ...CTGGCAGAAAACGGCAAAGTGCAAGAAATC
                              ...       160       170       180

LYS   ALA   GLU   TYR   ARG   ARG   ILE   ALA   ASN   GLN  ...
AAAGCAGAATATCGCCGCATTGCCAATCAA ...
        190       200       210 ...
```

FIG.25B

```
                                                 ... ILE VAL GLU GLU ALA MET ILE ILE ALA ASN
                                                 ...A T T G T G G A A G A A G C A A T G A T T A T T G C C A A C
                                                 ...            220                 230                 240

ILE CYS ALA ALA GLN PHE LEU HIS GLU GLN ...
A T C T G C G C C G C C C A A T T T T T A C A C G A A C A G ...
             250                260                270 ...
                                                 ... ALA LYS THR GLY ILE PHE ASN ALA HIS SER
                                                 ...G C A A A A A C A G G C A T T T T T C A A C G C C C A C A G C
                                                 ...            280                 290                 300

GLY PHE ASP LYS LYS TYR LEU GLU ASN ALA ...
                                 ________...
G G T T T T G A T A A A A A A T A C T T A G A A A A T G C G ...
             310                320                330 ...
                                                 ... HIS HIS PHE LEU MET ALA ASN LEU ALA ASN
                                                 ...__________6431.SL (________________
                                                 ...C A C C A T T T C T T A A T G G C A A A T T T A G C C A A T
                                                 ...            340                 350                 360

GLU GLN ASN GLN THR GLU LEU ALA GLU ARG ...
G A A C A A A A T C A A A C T G A A C T G G C A G A A C G T ...
             370                380                390 ...
                                                 ... TYR SER VAL GLU ASN LEU ALA THR LEU ASN
                                                 ...T A T T C A G T A G A A A A C T T A G C A A C C T T A A A C
                                                 ...            400                 410                 420
```

FIG.25C

```
GLY   TYR   CYS   GLN   MET   ARG   HIS   ASP   ILE   GLU ...
G G C T A T T G C C A A A T G C G T C A C G A T A T T G A A ...
                430                     440                     450 ...
                                    ... PRO   ILE   GLU   SER   ASP   TYR   LEU   GLU   LEU   ARG
                                    ...C C C A T C G A A A G C G A T T A T T T A G A A C T G C G T
                                    ...                   460                     470                     480

LEU   ARG   ARG   TYR   LEU   THR   PHE   ALA   GLU   PHE ...
T T A C G C C G T T A T T T A A C T T T C G C C G A A T T T ...
                490                     500                     510 ...
                                    ... LYS   SER   GLU   LEU   ALA   PRO   HIS   PHE   GLY   LEU
                                    ...A A A T C A G A A T T A G C A C C G C A C T T T G G T C T T
                                    ...                   520                     530                     540

GLY   LEU   GLU   GLY   TYR   ALA   THR   TRP   THR   SER ...
G G T T T A G A A G G C T A T G C C A C T T G G A C A T C G ...
                550                     560                     570 ...
                                    ... PRO   ILE   ARG   LYS   TYR   SER   ASP   MET   VAL   ASN
                                    ...C C C A T C C G C A A A T A T T C A G A T A T G G T T A A T
                                    ...                   580                     590                     600

HIS   ARG   LEU   ILE   LYS   ALA   VAL   LEU   ALA   LYS ...
                                                            ...
C A T C G C T T A A T C A A A G C C G T G C T G G C A A A A ...
                610                     620                     630 ...
```

FIG.25D

```
                                   ... GLN  PRO  TYR  GLU  LYS  PRO  GLN  ASN  ASP  VAL
                                   ...
                                   ...C A G C C T T A T G A A A A A C C A C A A A A T G A C G T G
                                   ...               640                 650                660

LEU  ALA  ARG  LEU  GLN  GLU  SER  ARG  ARG  GLN ...
_______6432.SL  (______________________________...
T T G G C A C G T T T G C A A G A G T C T C G C C G C C A A ...
            670                 680                 690 ...
                                   ... ASN  ARG  LEU  VAL  GLU  ARG  ASP  ILE  ALA  ASP
                                   ...______________
                                   ...A A T C G C C T A G T G G A A C G T G A T A T T G C C G A T
                                   ...               700                 710                720

TRP  LEU  TYR  CYS  ARG  TYR  LEU  ALA  ASP  LYS ...
T G G C T A T A T T G C C G T T A T C T T G C T G A C A A A ...
            730                 740                 750 ...
                                   ... VAL  ALA  GLU  ASN  VAL  GLU  PHE  ASN  ALA  GLU
                                   ...G T G G C T G A A A A T G T G G A A T T T A A T G C A G A A
                                   ...               760                 770                780

VAL  GLN  ASP  VAL  MET  ARG  ALA  GLY  LEU  ARG ...
G T G C A A G A T G T A A T G C G T G C A G G C T T A C G C ...
            790                 800                 810 ...
```

FIG.25E

```
                                        ... VAL  GLN  LEU  LEU  GLU  ASN  GLY  ALA  SER  LEU
                                        ...G T A C A A C T G C T C G A A A A T G G T G C A T C G C T A
                                        ...                820                 830                 840

PHE  ILE  PRO  ALA  ALA  THR  LEU  HIS  ASN  ASN ...
T T T A T T C C T G C C G C C A C G T T G C A C A A C A A C ...
             850                 860                 870 ...
                                        ... LYS  GLU  GLU  ILE  GLN  LEU  ASN  PRO  ASP  GLU
                                        ...A A A G A A G A A A T A C A G C T A A A C C C T G A C G A A
                                        ...                880                 890                 900

LEU  ALA  LEU  TYR  ILE  LYS  GLY  GLU  ARG  THR ...
C T C G C C C T C T A T A T A A A A G G C G A A C G C A C T ...
             910                 920                 930 ...
                                        ... TYR  LYS  ILE  GLY  ASP  ILE  VAL  LYS  VAL  LYS
                                        ...T A C A A A A T A G G C G A C A T T G T G A A A G T G A A A
                                        ...                940                 950                 960

LEU  THR  GLU  VAL  LYS  GLU  ALA  THR  ARG  SER ...
C T C A C A G A A G T G A A A G A A G C A A C T C G C A G T ...
             970                 980                 990 ...
                                        ... ILE  VAL  GLY  GLU  ILE  LEU  GLN  ***  LEU  PRO
                                        ...A T T G T G G G C G A A A T A C T T C A A T A A A T T G C C
                                        ...                1000                1010                1020
```

FIG.25F

```
   PHE  GLN  TYR  VAL  THR  GLU  ASP  GLY  LYS  THR...
G T T C C A A T A T G T T A C G G A A G A C G G C A A A A C ...
               1030                1040                1050 ...
                                   ...  VAL  VAL  LYS  VAL  GLY  ASN  GLU  TYR  TYR  GLU
                                   ...C G T T G T G A A A G T G G G C A A T G A G T A T T A C G A
                                   ...                1060                1070                1080

   ALA  LYS  GLN  ASP  GLY  SER  ALA  ASP  MET  ASP...
A G C C A A G C A A G A C G G T T C G G C G G A T A T G G A ...
                    (   6295.SL
               1090                1100                1110 ...
                                   ...  LYS  LYS  VAL  LYS  ASN  GLY  GLU  LEU  VAL  LYS
                                   ...T A A A A A A G T C A A A A A T G G C G A G C T G G T G A A
                                   ...
                                   ...                1120                1130                1140

   THR  LYS  VAL  LYS  LEU  VAL  SER  ALA  ASN  GLY...
A A C T A A A G T G A A A T T G G T A T C G G C A A A C G G ...
               1150                1160                1170 ...
                                   ...  THR  ASN  PRO  VAL  LYS  ILE  SER  ASN  VAL  ALA
                                   ...T A C A A A T C C G G T G A A A A T C A G C A A T G T T G C
                                   ...                1180                1190                1200

   GLU  GLY  THR  GLU  ASP  THR  ASP  ALA  VAL  SER...
G G A A G G C A C G G A A G A T A C C G A T G C G G T C A G ...
               1210                1220                1230 ...
```

FIG.25G

```
                               ...  PHE LYS GLN LEU LYS ALA LEU GLN ASN LYS
                               ...C T T T A A G C A G T T G A A A G C C T T G C A A A A C A A
                               ...           1240                1250                1260

GLN VAL THR LEU SER ALA SER ASN ALA TYR...
A C A G G T T A C G T T A A G C G C G A G C A A T G C T T A ...
              1270                1280                1290 ...
                               ...  ALA ASN GLY GLY SER ASP ALA ASP VAL GLY
                               ...T G C C A A T G G C G G T A G C G A T G C C G A C G T C G G
                               ...           1300                1310                1320

LYS VAL THR GLN THR LEU SER ASN GLY LEU...
C A A G G T A A C T C A A A C T T T A A G C A A T G G T T T ...
              1330                1340                1350 ...
                               ...  ASN PHE LYS PHE LYS SER THR ASP GLY GLU
                               ...G A A T T T T A A A T T T A A A T C C A C A G A C G G C G A
                               ...           1360                1370                1380

LEU LEU ASN ILE LYS ALA ASP LYS ASP THR...
G T T G T T G A A C A T C A A A G C A G A C A A G G A C A C ...
              1390                1400                1410 ...
                               ...  VAL THR ILE THR ARG ALA SER GLY ALA ASN
                               ...G G T T A C C A T T A C G C G G G C A A G C G G T G C G A A
                               ...           1420                1430                1440
```

FIG.25H

```
GLY ALA ALA ALA THR ASP ALA ASP LYS ILE...
TGGTGCGGCGGCGACTGATGCCGACAAGAT ...
1450 1460 1470 ...
... LYS VAL ALA SER ASP GLY ILE SER ALA GLY
...TAAAGTGGCTTCAGACGGCATTAGCGCGGG
... 1480 1490 1500

ASN LYS ALA VAL LYS ASN VAL ALA ALA GLY...
TAATAAAGCAGTTAAAAACGTCGCGGCAGG ...
...
1510 1520 1530 ...
... GLU ILE SER ALA THR SER THR ASP ALA ILE
...CGAAATTTCCGCCACTTCCACCGATGCGAT
... ( 6271.SL
... 1540 1550 1560

ASN GLY SER GLN LEU TYR ALA VAL ALA LYS...
TAACGGCAGTCAGTTGTATGCCGTGGCAAA ...
1570 1580 1590 ...
... GLY VAL THR ASN LEU ALA GLY GLN VAL ASN
...GGGGGTAACAAACCTTGCTGGACAAGTGAA
... 1600 1610 1620

LYS VAL GLY LYS ARG ALA ASP ALA GLY THR...
TAAAGTGGGCAAACGTGCAGATGCAGGTAC ...
1630 1640 1650 ...
```

FIG. 25I

```
                                  ALA  SER  ALA  LEU  ALA  ALA  ALA  SER  GLN  LEU  PRO
                               ...AGC  AAG  TGC  ATT  AGC  GGG  CTT  CAC  AGT  TAC  C
                                       1660           1670           1680
                          ...

GLN  ALA  SER  MET  PRO  GLY  LYS  SER  MET  VAL...       SER  ILE  ALA  GLY  SER  SER  TYR  GLN  GLY  GLN
ACA  AGC  CTC  TAT  GCC  GGG  TAA  ATC  AAT  GGT...    ...TTC  TAT  TGC  GGG  AAG  TAG  TTA  TCA  AGG  TCA
          1690           1700           1710                     1720           1730           1740
                                                  ...                                                   ...

SER  GLY  LEU  ALA  ILE  GLY  VAL  SER  ARG  ILE...       SER  ASP  ASN  GLY  LYS  LEU  ILE  ILE  ARG  LEU
AAG  TGG  TTT  AGC  TAT  CGG  GGT  ATC  AAG  AAT...    ...TTC  CGA  TAA  TGG  CAA  ATT  GAT  TAT  TCG  CTT
          1750           1760           1770                     1780           1790           1800
                                                  ...                                                   ...

SER  GLY  THR  THR  ASN  SER  GLN  GLY  LYS  THR...       GLY  VAL  ALA  ALA  GLY  VAL  GLY  TYR  GLN  TRP
GTC  AGG  CAC  ACA  ACC  AAT  AGC  CAA  GGT  AAA  AAC...  AGG  CGT  TGC  AGC  AGG  TGT  TGG  TTA  CCA  GTG
          1810           1820           1830                     1840           1850           1860
                                                       ...

***  ***              ***
GTA  ATA  GAA  TTC
          1870
```

FIG.26A

```
ATG AAC AAA ATT TTT AAC GTT ATT TGG AAT GTT GTG ACT CAA ACT TGG     48
Met Asn Lys Ile Phe Asn Val Ile Trp Asn Val Val Thr Gln Thr Trp
        2130                2135                2140

GTT GTC GTA TCT GAA CTC ACT CGC ACC CAC ACC AAA TGC GCC TCC GCC     96
Val Val Val Ser Glu Leu Thr Arg Thr His Thr Lys Cys Ala Ser Ala
    2145                2150                2155

ACC GTG GCG GTT GCC GTA TTG GCA ACC CTG TTG TCC GCA ACG GTT GAG    144
Thr Val Ala Val Ala Val Leu Ala Thr Leu Leu Ser Ala Thr Val Glu
2160                2165                2170                2175

GCG AAC AAC AAT ACT CCT GTT ACG AAT AAG TTG AAG GCT TAT GGC GAT    192
Ala Asn Asn Asn Thr Pro Val Thr Asn Lys Leu Lys Ala Tyr Gly Asp
                2180                2185                2190

GCG AAT TTT AAT TTC ACT AAT AAT TCG ATA GCA GAT GCA GAA AAA CAA    240
Ala Asn Phe Asn Phe Thr Asn Asn Ser Ile Ala Asp Ala Glu Lys Gln
            2195                2200                2205

GTT CAA GAG GCT TAT AAA GGT TTA TTA AAT CTA AAT GAA AAA AAT GCG    288
Val Gln Glu Ala Tyr Lys Gly Leu Leu Asn Leu Asn Glu Lys Asn Ala
        2210                2215                2220
```

FIG.26B

```
AGT GAT AAA CTG TTG GTG GAG GAC AAT ACT GCG GCG ACC GTA GGC AAT        336
Ser Asp Lys Leu Leu Val Glu Asp Asn Thr Ala Ala Thr Val Gly Asn
    2225                2230                2235

TTG CGT AAA TTG GGC TGG GTA TTG TCT AGC AAA AAC GGC ACA AGG AAC        384
Leu Arg Lys Leu Gly Trp Val Leu Ser Ser Lys Asn Gly Thr Arg Asn
2240                2245                2250                2255

GAG AAA AGC CAA CAA GTC AAA CAT GCG GAT GAA GTG TTG TTT GAA GGC        432
Glu Lys Ser Gln Gln Val Lys His Ala Asp Glu Val Leu Phe Glu Gly
                2260                2265                2270

AAA GGC GGT GTG CAG GTT ACT TCC ACC TCT GAA AAC GGC AAA CAC ACC        480
Lys Gly Gly Val Gln Val Thr Ser Thr Ser Glu Asn Gly Lys His Thr
            2275                2280                2285

ATT ACC TTT GCT TTA GCG AAA GAC CTT GGT GTG AAA ACT GCG ACT GTG        528
Ile Thr Phe Ala Leu Ala Lys Asp Leu Gly Val Lys Thr Ala Thr Val
        2290                2295                2300

AGT GAT ACC TTA ACG ATT GGC GGT GGT GCT GCT GCA GGT GCT ACA ACA        576
Ser Asp Thr Leu Thr Ile Gly Gly Gly Ala Ala Ala Gly Ala Thr Thr
    2305                2310                2315
```

FIG.26C

```
ACA CCG AAA GTG AAT GTA ACT AGT ACA ACT GAT GGC TTG AAG TTC GCT      624
Thr Pro Lys Val Asn Val Thr Ser Thr Thr Asp Gly Leu Lys Phe Ala
2320                2325                2330                2335

AAA GAT GCT GCG GGT GCT AAT GGC GAT ACT ACG GTT CAC TTG AAT GGT      672
Lys Asp Ala Ala Gly Ala Asn Gly Asp Thr Thr Val His Leu Asn Gly
                2340                2345                2350

ATT GGT TCA ACC TTG ACA GAC ACG CTT GTG GGT TCT CCT GCT ACT CAT      720
Ile Gly Ser Thr Leu Thr Asp Thr Leu Val Gly Ser Pro Ala Thr His
            2355                2360                2365

ATT GAC GGA GGA GAT CAA AGT ACG CAT TAC ACT CGT GCA GCA AGT ATC      768
Ile Asp Gly Gly Asp Gln Ser Thr His Tyr Thr Arg Ala Ala Ser Ile
        2370                2375                2380

AAG GAT GTC TTG AAT GCG GGT TGG AAT ATC AAG GGT GTT AAA GCT GGC      816
Lys Asp Val Leu Asn Ala Gly Trp Asn Ile Lys Gly Val Lys Ala Gly
    2385                2390                2395

TCA ACA ACT GGT CAA TCA GAA AAT GTC GAT TTT GTT CAT ACT TAC GAT      864
Ser Thr Thr Gly Gln Ser Glu Asn Val Asp Phe Val His Thr Tyr Asp
2400                2405                2410                2415
```

FIG.26D

```
ACT GTT GAG TTC TTG AGT GCG GAT ACA GAG ACC ACG ACT GTT ACT GTA      912
Thr Val Glu Phe Leu Ser Ala Asp Thr Glu Thr Thr Thr Val Thr Val
                2420                    2425                    2430

GAT AGC AAA GAA AAC GGT AAG AGA ACC GAA GTT AAA ATC GGT GCG AAG      960
Asp Ser Lys Glu Asn Gly Lys Arg Thr Glu Val Lys Ile Gly Ala Lys
            2435                    2440                    2445

ACT TCT GTT ATC AAA GAA AAA GAC GGT AAG TTA TTT ACT GGA AAA GCT     1008
Thr Ser Val Ile Lys Glu Lys Asp Gly Lys Leu Phe Thr Gly Lys Ala
        2450                    2455                    2460

AAC AAA GAG ACA AAT AAA GTT GAT GGT GCT AAC GCG ACT GAA GAT GCA     1056
Asn Lys Glu Thr Asn Lys Val Asp Gly Ala Asn Ala Thr Glu Asp Ala
    2465                    2470                    2475

GAC GAA GGC AAA GGC TTA GTG ACT GCG AAA GAT GTG ATT GAC GCA GTG     1104
Asp Glu Gly Lys Gly Leu Val Thr Ala Lys Asp Val Ile Asp Ala Val
2480                    2485                    2490                    2495

AAT AAG ACT GGT TGG AGA ATT AAA ACA ACC GAT GCT AAT GGT CAA AAT     1152
Asn Lys Thr Gly Trp Arg Ile Lys Thr Thr Asp Ala Asn Gly Gln Asn
                2500                    2505                    2510
```

FIG.26E

```
GGC GAC TTC GCA ACT GTT GCA TCA GGC ACA AAT GTA ACC TTT GCT AGT       1200
Gly Asp Phe Ala Thr Val Ala Ser Gly Thr Asn Val Thr Phe Ala Ser
            2515                2520                2525

GGT AAT GGT ACA ACT GCG ACT GTA ACT AAT GGC ACC GAT GGT ATT ACC       1248
Gly Asn Gly Thr Thr Ala Thr Val Thr Asn Gly Thr Asp Gly Ile Thr
        2530                2535                2540

GTT AAG TAT GAT GCG AAA GTT GGC GAC GGC TTA AAA CTA GAT GGC GAT       1296
Val Lys Tyr Asp Ala Lys Val Gly Asp Gly Leu Lys Leu Asp Gly Asp
    2545                2550                2555

AAA ATC GCT GCA GAT ACG ACC GCA CTT ACT GTG AAT GAT GGT AAG AAC       1344
Lys Ile Ala Ala Asp Thr Thr Ala Leu Thr Val Asn Asp Gly Lys Asn
2560                2565                2570                2575

GCT AAT AAT CCG AAA GGT AAA GTG GCT GAT GTT GCT TCA ACT GAC GAG       1392
Ala Asn Asn Pro Lys Gly Lys Val Ala Asp Val Ala Ser Thr Asp Glu
                2580                2585                2590

AAG AAA TTG GTT ACA GCA AAA GGT TTA GTA ACA GCC TTA AAC AGT CTA       1440
Lys Lys Leu Val Thr Ala Lys Gly Leu Val Thr Ala Leu Asn Ser Leu
            2595                2600                2605
```

FIG.26F

```
AGC TGG ACT ACA ACT GCT GCT GAG GCG GAC GGT GGT ACG CTT GAT GGA    1488
Ser Trp Thr Thr Thr Ala Ala Glu Ala Asp Gly Gly Thr Leu Asp Gly
        2610                    2615                2620

AAT GCA AGT GAG CAA GAA GTT AAA GCG GGC GAT AAA GTA ACC TTT AAA    1536
Asn Ala Ser Glu Gln Glu Val Lys Ala Gly Asp Lys Val Thr Phe Lys
    2625                    2630                2635

GCA GGC AAG AAC TTA AAA GTG AAA CAA GAG GGT GCG AAC TTT ACT TAT    1584
Ala Gly Lys Asn Leu Lys Val Lys Gln Glu Gly Ala Asn Phe Thr Tyr
2640                2645                2650                2655

TCA CTG CAA GAT GCT TTA ACA GGC TTA ACG AGC ATT ACT TTA GGT ACA    1632
Ser Leu Gln Asp Ala Leu Thr Gly Leu Thr Ser Ile Thr Leu Gly Thr
                2660                2665                2670

GGA AAT AAT GGT GCG AAA ACT GAA ATC AAC AAA GAC GGC TTA ACC ATC    1680
Gly Asn Asn Gly Ala Lys Thr Glu Ile Asn Lys Asp Gly Leu Thr Ile
            2675                2680                2685

ACA CCA GCA AAT GGT GCG GGT GCA AAT AAT GCA AAC ACC ATC AGC GTA    1728
Thr Pro Ala Asn Gly Ala Gly Ala Asn Asn Ala Asn Thr Ile Ser Val
        2690                2695                2700
```

FIG.26G

```
ACC AAA GAC GGC ATT AGT GCG GGC GGT CAG TCG GTT AAA AAC GTT GTG      1776
Thr Lys Asp Gly Ile Ser Ala Gly Gly Gln Ser Val Lys Asn Val Val
    2705                2710                2715

AGC GGA CTG AAG AAA TTT GGT GAT GCG AAT TTC GAT CCG CTG ACT AGC      1824
Ser Gly Leu Lys Lys Phe Gly Asp Ala Asn Phe Asp Pro Leu Thr Ser
2720                2725                2730                2735

TCC GCC GAC AAC TTA ACG AAA CAA AAT GAC GAT GCC TAT AAA GGC TTG      1872
Ser Ala Asp Asn Leu Thr Lys Gln Asn Asp Asp Ala Tyr Lys Gly Leu
                2740                2745                2750

ACC AAT TTG GAT GAA AAA GGT ACA GAC AAG CAA ACT CCA GTT GTT GCC      1920
Thr Asn Leu Asp Glu Lys Gly Thr Asp Lys Gln Thr Pro Val Val Ala
            2755                2760                2765

GAC AAT ACC GCC GCA ACC GTG GGC GAT TTG CGC GGC TTG GGC TGG GTC      1968
Asp Asn Thr Ala Ala Thr Val Gly Asp Leu Arg Gly Leu Gly Trp Val
        2770                2775                2780

ATT TCT GCG GAC AAA ACC ACA GGC GGC TCA ACG GAA TAT CAC GAT CAA      2016
Ile Ser Ala Asp Lys Thr Thr Gly Gly Ser Thr Glu Tyr His Asp Gln
    2785                2790                2795
```

FIG.26H

```
GTT CGG AAT GCG AAC GAA GTG AAA TTC AAA AGC GGC AAC GGT ATC AAT      2064
Val Arg Asn Ala Asn Glu Val Lys Phe Lys Ser Gly Asn Gly Ile Asn
2800                2805                2810                2815

GTT TCC GGT AAA ACG GTC AAC GGT AGG CGT GAA ATT ACT TTT GAA TTG      2112
Val Ser Gly Lys Thr Val Asn Gly Arg Arg Glu Ile Thr Phe Glu Leu
                2820                2825                2830

GCT AAA GGT GAA GTG GTT AAA TCG AAT GAA TTT ACC GTC AAA GAA ACC      2160
Ala Lys Gly Glu Val Val Lys Ser Asn Glu Phe Thr Val Lys Glu Thr
            2835                2840                2845

AAT GGA AAG GAA ACG AGC CTG GTT AAA GTT GGC GAT AAA TAT TAC AGC      2208
Asn Gly Lys Glu Thr Ser Leu Val Lys Val Gly Asp Lys Tyr Tyr Ser
        2850                2855                2860

AAA GAG GAT ATT GAC TTA ACA ACA GGT CAG CCT AAA TTA AAA GAT GGC      2256
Lys Glu Asp Ile Asp Leu Thr Thr Gly Gln Pro Lys Leu Lys Asp Gly
    2865                2870                2875

AAT ACA GTT GCT GCG AAA TAT CAA GAT AAA GGT GGC AAA GTC GTT TCT      2304
Asn Thr Val Ala Ala Lys Tyr Gln Asp Lys Gly Gly Lys Val Val Ser
2880                2885                2890                2895
```

FIG.26I

```
GTA ACG GAT AAT ACT GAA GCT ACC ATA ACC AAC AAA GGT TCT GGC TAT      2352
Val Thr Asp Asn Thr Glu Ala Thr Ile Thr Asn Lys Gly Ser Gly Tyr
                2900                     2905                2910

GTA ACA GGT AAC CAA GTG GCA GAT GCG ATT GCG AAA TCA GGC TTT GAG      2400
Val Thr Gly Asn Gln Val Ala Asp Ala Ile Ala Lys Ser Gly Phe Glu
            2915                    2920                2925

CTT GGC TTG GCT GAT GAA GCT GAT GCG AAA CGG GCG TTT GAT GAT AAG      2448
Leu Gly Leu Ala Asp Glu Ala Asp Ala Lys Arg Ala Phe Asp Asp Lys
        2930                    2935                2940

ACA AAA GCC TTA TCT GCT GGT ACA ACG GAA ATT GTA AAT GCC CAC GAT      2496
Thr Lys Ala Leu Ser Ala Gly Thr Thr Glu Ile Val Asn Ala His Asp
    2945                    2950                2955

AAA GTC CGT TTT GCT AAT GGT TTA AAT ACC AAA GTG AGC GCG GCA ACG      2544
Lys Val Arg Phe Ala Asn Gly Leu Asn Thr Lys Val Ser Ala Ala Thr
2960                    2965                2970                2975

GTG GAA AGC ACC GAT GCA AAC GGC GAT AAA GTG ACC ACA ACC TTT GTG      2592
Val Glu Ser Thr Asp Ala Asn Gly Asp Lys Val Thr Thr Thr Phe Val
                2980                    2985                2990
```

FIG.26J

```
AAA ACC GAT GTG GAA TTG CCT TTA ACG CAA ATC TAC AAT ACC GAT GCA      2640
Lys Thr Asp Val Glu Leu Pro Leu Thr Gln Ile Tyr Asn Thr Asp Ala
            2995                3000                3005

AAC GGT AAG AAA ATC ACT AAA GTT GTC AAA GAT GGG CAA ACT AAA TGG      2688
Asn Gly Lys Lys Ile Thr Lys Val Val Lys Asp Gly Gln Thr Lys Trp
        3010                3015                3020

TAT GAA CTG AAT GCT GAC GGT ACG GCT GAT ATG ACC AAA GAA GTT ACC      2736
Tyr Glu Leu Asn Ala Asp Gly Thr Ala Asp Met Thr Lys Glu Val Thr
    3025                3030                3035

CTC GGT AAC GTG GAT TCA GAC GGC AAG AAA GTT GTG AAA GAC AAC GAT      2784
Leu Gly Asn Val Asp Ser Asp Gly Lys Lys Val Val Lys Asp Asn Asp
3040                3045                3050                3055

GGC AAG TGG TAT CAC GCC AAA GCT GAC GGT ACT GCG GAT AAA ACC AAA      2832
Gly Lys Trp Tyr His Ala Lys Ala Asp Gly Thr Ala Asp Lys Thr Lys
                3060                3065                3070

GGC GAA GTG AGC AAT GAT AAA GTT TCT ACC GAT GAA AAA CAC GTT GTC      2880
Gly Glu Val Ser Asn Asp Lys Val Ser Thr Asp Glu Lys His Val Val
            3075                3080                3085
```

FIG.26K

```
AGC CTT GAT CCA AAT GAT CAA TCA AAA GGT AAA GGT GTC GTG ATT GAC      2928
Ser Leu Asp Pro Asn Asp Gln Ser Lys Gly Lys Gly Val Val Ile Asp
        3090                3095                3100

AAT GTG GCT AAT GGC GAT ATT TCT GCC ACT TCC ACC GAT GCG ATT AAC      2976
Asn Val Ala Asn Gly Asp Ile Ser Ala Thr Ser Thr Asp Ala Ile Asn
    3105                3110                3115

GGA AGT CAG TTG TAT GCT GTG GCA AAA GGG GTA ACA AAC CTT GCT GGA      3024
Gly Ser Gln Leu Tyr Ala Val Ala Lys Gly Val Thr Asn Leu Ala Gly
3120                3125                3130                3135

CAA GTG AAT AAT CTT GAG GGC AAA GTG AAT AAA GTG GGC AAA CGT GCA      3072
Gln Val Asn Asn Leu Glu Gly Lys Val Asn Lys Val Gly Lys Arg Ala
            3140                3145                3150

GAT GCA GGT ACA GCA AGT GCA TTA GCG GCT TCA CAG TTA CCA CAA GCC      3120
Asp Ala Gly Thr Ala Ser Ala Leu Ala Ala Ser Gln Leu Pro Gln Ala
            3155                3160                3165

ACT ATG CCA GGT AAA TCA ATG GTT GCT ATT GCG GGA AGT AGT TAT CAA      3168
Thr Met Pro Gly Lys Ser Met Val Ala Ile Ala Gly Ser Ser Tyr Gln
        3170                3175                3180
```

FIG.26L

```
GGT CAA AAT GGT TTA GCT ATC GGG GTA TCA AGA ATT TCC GAT AAT GGC      3216
Gly Gln Asn Gly Leu Ala Ile Gly Val Ser Arg Ile Ser Asp Asn Gly
    3185                3190                3195

AAA GTG ATT ATT CGC TTG TCA GGC ACA ACC AAT AGT CAA GGT AAA ACA      3264
Lys Val Ile Ile Arg Leu Ser Gly Thr Thr Asn Ser Gln Gly Lys Thr
3200                3205                3210                3215

GGC GTT GCA GCA GGT GTT GGT TAC CAG TGG                              3294
Gly Val Ala Ala Gly Val Gly Tyr Gln Trp
                3220                3225
```

FIG.27A

Alignment of NTHi strain 12 5′ ORF with HI1733 from H. influenzae strain Rd

```
X        10        20        30        40        50        60        70
PTPAATPETAQQIHWLHQFTKARIQWRKTHSLFFKEKPDYAFVLAENGKVQEIKAEYRRIANQIVEEAMIIA
      ||||||||||||||||||||||||||||||||||||||||||||||||||||||||||||||||||
AWQPEMPETAQQIHWLHQFTKARIQWRKTHSLFFKEKPDYAFVLAENGKVQEIKAEYRRIANQIVEEAMIIA
330       340       350       360       370       380       390       400

         80        90       100       110       120       130       140
NICAAQFLHEQAKTGIFNAHSGFDKKYLENAHHFLMANLANEQNQTELAERYSVENLATLNGYCQMRHDIEP
|||||||||||||||||| ||||||| ||||| |||||||||||||||||||||||||||||||||||||||
NICAAQFLHEQAKTGIFNTHSGFDKKFLENAHNFLMANLANEQNQTELAERYSVENLATLNGYCQMRHDIEP
      410       420       430       440       450       460       470

   150       160       170       180       190       200       210
IESDYLELRLRRYLTFAEFKSELAPHFGLGLEGYATWTSPIRKYSDMVNHRLIKAVLAKQPYEKPQNDVLAR
||||||||||||||||||||||||||||||||||||||||||||||||||||||||||||||||||||||||
IESDYLELRLRRYLTFAEFKSELAPHFGLGLEGYATWTSPIRKYSDMVNHRLIKAVLAKQPYEKPQNDVLAR
    480       490       500       510       520       530       540

  220       230       240       250       260       270       280
LQESRRQNRLVERDIADWLYCRYLADKVAENVEFNAEVQDVMRAGLRVQLLENGASLFIPAATLHNNKEEIQ
||| ||||||||||||||||||||||||| | || |||||||||||||||||||||||||||||||||||||
LQEARRQNRLVERDIADWLYCRYLADKVASNAEFEAEVQDVMRAGLRVQLLENGASLFIPAATLHNNKEEIQ
   550       560       570       580       590       600       610
```

FIG.27B

```
290       300       310       320       330
LNPDELALYIKGERTYKIGDIVKVKLTEVKEATRSIVGEILQ
||||||||||||||||||| ||||||||||||||||||||
LNPDELALYIKGERTYKIGDMVKVKLTEVKEATRSIVGEILQ
620       630       640       650         X
```

```
;       ##cross-references GB:L42023; TIGR:HI1733
;       ##note          named as homolog to a protein from Escherichia coli
; SUMMARY         #length 659  #molecular-weight 75782  #checksum 8365
```

A64139

```
MFQDNPLLAQLKQQIHDSKEQVEGVVKSTDKAYGFLECDKKTYFIAPPSMKKVMHGDKIKATIEKQGDKE
QAEPEALIEPMLTRFIAKVRFNKDKKLQVLVDHPSINQPIGAQQAKSVKEELQEGDWVVANLKTHPLRDD
RFFYATINQLICRADDELAPWWVTLARHEQSRYPVRGAEPYEMLDQKTRENLTALHFVTIDSESTMDMDD
ALYIEPIAQNSTQTGWKLVVAIADPTAYIALDSQIEQEAKQRCFTNYLPGFNIPMLPRELSDELCSLIAN
ETRPALVCYIETDLTGNITAKPHFVSAYVQSKAKLAYNKVSDYLEQADNAWQPEMPETAQQIHWLHQFTK
ARIQWRKTHSLFFKEKPDYAFVLAENGKVQEIKAEYRRIANQIVEEAMIIANICAAQFLHEQAKTGIFNT
HSGFDKKFLENAHNFLMANLANEQNQTELAERYSVENLATLNGYCQMRHDIEPIESDYLELRLRRYLTFA
EFKSELAPHFGLGLEGYATWTSPIRKYSDMVNHRLIKAVLAKQPYEKPQNDVLARLQEARRQNRLVERDI
ADWLYCRYLADKVASNAEFEAEVQDVMRAGLRVQLLENGASLFIPAATLHNNKEEIQLNPDELALYIKGE
RTYKIGDMVKVKLTEVKEATRSIVGEILQ
```

FIG.28A

Alignment of *H. influenzae* Hia/Hsf and *M. catarrhalis* 200 kDa proteins

```
         10        20        30        40         50              ...
MNKIFNVIWNVMTQTWAVVSELTRAHTKRASATVAAAVLATVLSATVQA-S-----------...
...........V....V.......T...C......V.....L.......N------------...
...........V....V...........C......V.....A....AE.NN-----------...
...........V....V...........C......V.....A....AE.NN-----------...
...................................T.....L..T....TT-----------...
...........V....V.......T...C......V.....L.....E.NN-----------...
...................................T.....Q....AE.NS-----------...
.....N..........V.......T..........ET.....L.F.....NATDEDEELDPVV...
................V.......T..........ET.....L.F.....NATDEDEELDPVV...
.....K.....V....V............T.....T.............IN---------DA...
..H.YK..F.KA.G.FMA.A.YAKS.STGGGSCATGQ.GSVCTLSFARIAALAVLVIGATLS...
..H.YK..F.KA.G.FMA.A.CAKS.SGGSSSSTAGQ.GSSPVIRLTRVATLAILVIGATLN...
** ** ****  * **  *** *****  ***  *  * *                      ...
```

```
...
...-----------------------------------------------        33
...-----------------------------------------------        32
...-----------------------------------------------        29
...-----------------------------------------------        K22
...-----------------------------------------------        M4071
...-----------------------------------------------        11
...-----------------------------------------------        K9
...RTAPVLSFHSDKEGTGEKEVTENSNWGIYFDNKGVLKA--------        HSF
```

FIG.28B

```
...RTAPVLSFHSDKEGTGEKEVTENSNWGIYFHNKGVLKA--------   API
...GTFVKVQSTEDDIEDSAATKDDNKNQALKAGDTLTLKA--------   Rd
...GSAYAQKKDTKHIAIGEQNQPRRSGTAKADGDRAIAIGENANAQGG   4223
...GSAYAQN-NSK-AIFGTTGNNDN---ASASNEASIAIGSLAKAHAN   LES-1
...          *     *          *    *     *

-------------------------------------------------------------...
-------------------------------------------------------------...
-------------------------------------------------------------...
-------------------------------------------------------------...
-------------------------------------------------------------...
-------------------------------------------------------------...
-------------------------------------------------------------...
GAITLKAGDNLKIKQNTDESTNASSFTYSLKKDLTDLTSVATEKLSFGANGDKVDITSDANG...
GAITLKAGDNLKIKQ----STNASSFTYSLKKDLTDLTSVATEKLSFGANGDKVDITSDANG...
GKN-LKAKLDQGGKSVTFALAKDLDVKTAKVSDTLTIGGNTPAAGGATP---KVSITSTADG...
QAIAIGSSNKTVNG-SSLDKIGTDITGQESIAIGGDVKASGDASIAIGSDDLHLLDQHGNPK...
QAIAIGGSKPDPRNQAANQKAGSHAKGKESIAIGGDVLAEGDASIAIGSDDLYLDRNSTNSK...
   **          *                   * * * *  * * *   *          ...

...----------------------------------------------   33
...----------------------------------------------   32
...----------------------------------------------   29
...----------------------------------------------   K22
...----------------------------------------------   M4071
...----------------------------------------------   11
```

```
...---------------------------------------------     K9
...LKLAKTGNGN--VHLNGLDSTLPDAVTNTGVLSSSS-FTPNDVEKTR     HSF
...LKLAKTGNGN--VHLNGLDSTLPDAVTNTGVLSSSS-FTPNDVEKTR     API
...LKLAKGTNGDTAVHLNGLASTLPDVTTNTGASTSVT-FSPSDIEKTR     Rd
...HPKGTLINDLINGHAVLKEIRSSKDNDVKYRRTTASGHASTAVGAMS     4223
...YPNGLLSTLIQN-HTVLRQIRDSNGSQ-KYRRTAAEGHASTAVGAMA     LES-1
...   *          *                  **    **   *

------------------------------------------------------------...
------------------------------------------------------------...
------------------------------------------------------------...
------------------------------------------------------------...
------------------------------------------------------------...
------------------------------------------------------------...
------------------------------------------------------------...
AATVKDVLNAGWNIKGAKTAGGNVESVDLVSAYNNVEFITGDKNTLDVVLTAKENGKTTEVK ...
AATVKDVLNAGWNIKGAKTAGGNVESVDLVSAYNNVEFITGDKNTLDVVLTAKENGKTTEVK...
AATIKDVLNAGWNIKGAKVAGGNTESVDLVAGYDNVEFITGDKNTLDVVLTAKENGKTTEVK...
YAQGHFSNAFGTRA-TAKSAYSLAVGLAATAEGQSTIAIGSDATSSSLGAIALGAGTRAQLQ...
YAKGHFANAFGTRS-TAEGNYSKAVGLTAKAEKGYTIAIGSNAQAINYGALALGADTRVDLD...
 *        *    ***     *     *   *        ****   *       *       **  ...

...-----------------------------------------------     33
...-----------------------------------------------     32
...-----------------------------------------------     29
...-----------------------------------------------     K22
```

```
...---------------------------------------------------   M4071
...---------------------------------------------------   11
...---------------------------------------------------   K9
...FTPKT---SVIKEKD----GKLFTGKENNDTNKV--TSNTA--------    HSF
...FTPKT---SVIKEKD----GKLFTGKENNDTNKV--TSNTA--------    API
...FTPKT---SVIKDNN----GKLLTGKQLKDANTG--TATNA--------    Rd
...GSIALGQGSVVTQSD-NNSRPAYTPNTQALDPKFQ-ATNNTKAGPLSIG    4223
...YGIALGYGSQILNNNNNNNNKAYVPEGNGSNIKSSKATGNGLF---SIG    LES-1
... *      * * * *                      **  *

-----------------------------------------------------------...
-----------------------------------------------------------...
-----------------------------------------------------------...
-----------------------------------------------------------...
-----------------------------------------------------------...
-----------------------------------------------------------...
-----------------------------------------------------------...
TDNTDEGNGLVTAKAVI-DAVNKAGWTVKTTTANGQNGDFATVASGTNVTFESGDGTTASVT...
TDNTDEGNGLVTAKAVI-DAVNKAGWTVKTTTANGQNGDFATVASGTNVTFESGDGTTASVT...
TEDTDEAMA*                                                     ...
 *RYRRGNGLVTAKTVI-EAVNKSGWRVKTTTANGQNDDFATVASGTNVTFANGNGTTASVT...
SNSIKRKIINVGAGVNKTDAVNVAQLEAVVKWAKERRITFQGDDNSTDVKIGLDNTLTIKGG...
SSTIKRKIINVGAGYEDTDAVNVAQLKAVENLAK-RQITFKGDDNGTGVKKKLGETLTIKGG...
*        ***     **** *        *     * *   ** *     ** *   *...
                          ...-----------------------------------------   33
```

FIG.28E

```
...--------------------------------------------    32
...--------------------------------------------    29
...--------------------------------------------    K22
...--------------------------------------------    M4071
...--------------------------------------------    11
...--------------------------------------------    K9
...KDTNGNGITVKYD-ALVGDGLKFDSDKKIVADTTALTVTG----    HSF
...KDTNGNGITVKYD-ALVGDGLKFDSDKKIVADTTALTVTG----    API
...                                                Rd
...NSTD--GITVKYE-ALVGDGLKIDGDQKIVADTTALTVTG----    Rd
...AETNA--LTDNN- IGVVKEADNSGLKVKLAKTLNNLTEVTTTL    4223
...-ETQADKLTDNNNIGVVTD-NNTGLKVKLAKNLSGLETVSTKNL    LES-1
...  **** **   * * * **       **     *

--------------------------------------------------------------...
--------------------------------------------------------------...
--------------------------------------------------------------...
--------------------------------------------------------------...
--------------------------------------------------------------...
--------------------------------------------------------------...
--------------------------------------------------------------...
GKVAEIAKEDDKKKLVNAGDLVTALGNLSWKAKAEADTD--GALEGISKDQEVKAGETVTFK...
GKVAEIAKEDDKKKLVNAGDLVTALGNLSWKAKAEADTDTDGALEGISKDQEVKAGETVTFK...
GKVAEIAKEDDKKKLVNAGDLVTALGNLSWKAKAEADTD--GALEGTSKDQEVKAGETVTFK...
NATTTVKVGSSSSTTAELLSDSLTFTQPNTGSQSTSKTVYGVNGVKFTNNAETTAAIGTT-R...
```

FIG.28F

```
TASEKVTVGSGNN-TAELQSGGLTFT-PTTNA-STDKTVYGTDGLKFTDNSN-TALEDTT-R...
        *         *       * **     * *    *  *       * * *   *    * *...
                                   ...--------------------------------------        33
                                   ...--------------------------------------        32
                                   ...--------------------------------------        29
                                   ...--------------------------------------        K22
                                   ...--------------------------------------        M4071
                                   ...--------------------------------------        11
                                   ...--------------------------------------        K9
                                   ...AGKNLKVKQDGANFTYSLQDALTGLTSATLGGTTNGGNDA      HSF
                                   ...AGKNLKVKQDGANFTYSLQDALTGLTSATLGGTTNGGNDA      API
                                   ...AGKNLKVKQDGANFTYSLQDALTGLTSATLGGTTNGGNDA      Rd
                                   ...ITRDKIGFARD-GDVDE----------------------       4223
                                   ...ITKDKIGFSNKAGTVDENKPYLDKDKLKVGNSTLNNGGLT      LES-1
                                   ... ***       *         *         ** * *  *

                                         60          70          ...
 ------------------------------AGSTTGTNSLNVYGK-NNSNFNSANNSIA...
 -----------------------------------------------------------...
 ------------------------------NN--.SV..G..A..D---T...TT........
 ------------------------------N--.SV..G..A..D---T...TT........
 ------------------------------T.G..S..G.KA..ST..P...A.G..AT...
 ------------------------------N--.PV..K.KA..D-A.F..--T........
 ---------------------------------.ASV.CR.....D-T.TK..A.........
KTVINKDGLTITPAGNGGTTGTNTISBTKDGIK..NKAI..VASGLRAYDDA..DVL...AT...
```

FIG.28G

```
KTVINKDGLTITPAGNGGTTGTNTISBTKDGIK..NKAI..VASGLRAYDDA..DVL...AT...
KTVINKDGLTITPAGNGGTTGTNTISBTKDGIK..NKAI..VASGLRAYDDA..DVL...AT...
-----------------------------------------------------------...
-------------VNNTIGGSNKQIQVGADGIKFADVNVNVSNAAKFGTTRITEEEIGFAD....
               ** ***   * ** **** *                        * *...

                          ...80        90        100       110       120
                          ...DLNKQNDSVYDGLLNLNEKGTDKSKFLVADETTATVGNLRKL------    33
                          ...----------------------ATDENED..EELEPVQRSV.------    32
                          .....E.HVQDA.K........D.N..S.....N.A.........------    29
                          .....E.HVQDA.K........D.N..S.....N.A.........------    K22
                          .....AR.F.GA..........DAN.N-L..T.DKA.........------    M4071
                          ....AE..VQEA.K........NAS-D.L..E.N.A....D....------    11
                          ..........G.H........N.AN.-.L..D.N.A....D....------    K9
                          ......RHVEDA.K........NAN.QP-..T.S.A....D....------    HSF
                          ......RHVEDA.K........NAN.QP-..TDS.A....D....------    API
                          ......RHVEDA.K........NAN.QP-....S.A....D....------    Rd
                          ...-----KQAP.LDKKQ.KVGSVAITIDNGI.AGNKKIS..A.GSSANDA    4223
                          ....GKVDKK.P.LDKKQ.QVG.VKIT.DSGINAGDQKISNVKDATDDTDA    LES-1
                          ...*        *    **             *        *

      130        140        150        160                    ...
GWVVSTKNSTKEE-SNQVKQADEVLFEG-KDGVTVTSKSENGKHTVT---------------...
R.SFKSAKEGTG.QEGTTEV------------------------------------------...
...L.S..G.RN.K.Y.........T.-SGAA..S.S.KD....I.----------------...
...L.S..G.RN.K.Y.........T.-SGAA..S.S.KD....I.----------------...
```

FIG.28H

```
...L.S..G.RN.K.Q...H........-.................---------------...
...L.S..G.RN.K.Q...H........-.G..Q..T......I.---------------...
........GKEN.K.Q.........K.S.G..Q..T.....AI.---------------...
........G...-...........T.-AGAA...........I.VSVAETKADCGLEKD...
........G...-...........T.-AGAA...........I.VSVAETKADSGLEKD...
........G...-...........T.-AGAA...........I.VSVAETKADSGLEKD...
VTIEQL.AAKPTLNAGAGISVTPTEISVDAKSGN..APTY.IGVKT.ELNSDGTSDKFSVKG...
VTYKQL.-------------------------------------------------------...
                                  *  *** * *     *    ** **    * ...

...
...------------------------------------------------       33
...------------------------------------------------       32
...------------------------------------------------       29
...------------------------------------------------       K22
...------------------------------------------------       M4071
...------------------------------------------------       11
...------------------------------------------------       K9
...GDTIKLKVDNQNTDNVLTVGNNGTAVTKGGFETVKTGATDADRGKVT        HSF
...GDTIKLKVDNQNTDNVLTVGNNGTAVTKGGFETVKTGATDADRGKVT        API
...GDTIKLKVDNQNTDNVLTVGNNGTAVTKGGFETVKTGATDADRGKVT        Rd
...SGTNNSLVTAEHLASYLNEVNRTADSALQSF-TVKEED-DDDANAIT        4223
...-----------------QVQQDADGALQSF-SIRDEK-GQEFTISN        LES-1
...* *    * *    *   *  *    ******   *  *

---------------------------------------------------------------...
```

```
--------------------------------------------------------------...
--------------------------------------------------------------...
--------------------------------------------------------------...
--------------------------------------------------------------...
--------------------------------------------------------------...
--------------------------------------------------------------...
VKDATANDADKKVATVKDVATAINSAATFVKTENLTTSIDEDNPTDNGKDDALKAGDTLTFK...
VKDATANDADKKVATVKDVATAINSAATFVKTENLTTSIDEDNPTDNGKDDALKAGDTLTFK...
VKDATANDADKKVATVKDVATAINSAATFVKTENLTTALDEADAKDQG-DDALKAGDTLTFK...
VAKDITKNAGAVSILKLKGKNGLTVATKKD-GTVTFGLSQDSGLTIGKSTLNNDGLTVKDTN...
LYSNGNTPNTFETITFA-GENGISISNDIAKGKVKVGIDPINGLTTPKLTVGSDKDGKTQLV...
*   *                 **  *    **    *                         ...

...-------------------------------------------------     33
...-------------------------------------------------     32
...-------------------------------------------------     29
...-------------------------------------------------     K22
...-------------------------------------------------     M4071
...-------------------------------------------------     11
...-------------------------------------------------     K9
...AGKNLKVKRDGKNITFDLAKNLEVKTAKVSDTLTIGGNTPTGGTTAT--     HSF
...AGKNLKVKRDGKNITFDLAKNLEVKTAKVSDTLTIGGNTPTGGTTAT--     API
...AGKNLKVKRDGKNITFDLAKNLEVKTATFSDRLTIG-------------     Rd
...-EQIQVGANGI.FTNVNGSNPGTGIANTARITRDKIGFAGSDGAVDTNK     4223
...IEQVASGN-.T...IR---------------------------------     LES-1
...           *    * *       *          * * * **  *
```

FIG.28J

```
                                                                                      33
                                                                                      32
                                                                                      29
                                                                                      K22
                                                                                      M4071
                                                                                      11
                                                                                      K9
                                                                                      HSF
                                                                                      API
                                                                                      Rd
                                                                                      4223
                                                                                      LES-1
```

```
...........................................................................--------
...........................................................................--------
...........................................................................--------
...........................................................................--------
...........................................................................--------
...........................................................................--------
PKVNITSTADGLNFAKETADASGSKNVYLKGIATTLTEPSAGAKSSHVDLNVDATK-KSNAA...------
PKVNITSTADGLNFAKETADASGSKNVYLKGIATTLTEPSAGAKSSHVDLNVDATK-KSNAA...------
...........................................................................--------
PYLDQDKLQVGNVKITNTGINAGGKAITGLSPTLPSIADQSS-RNIELGNTI-QDKDKSNAA...------
---------------------------------GLSPTL[S]ITNAGGVRTTEQNTITSDEDKSKAA...--
 *  *    *****  * ***   *  **    *     *    **  ** **   *    ** **
...........................................................................--------
...........................................................................--------
...........................................................................--------
...........................................................................--------
...........................................................................--------
...........................................................................--------
...........................................................................--------
...SIEDVLRAGMTNQGNGNNVDYVATYDIVNFIDDSTGTTTVTVTQKADG
...SIEDVLRAGMTNQGNGNNVDYVATYDIVNFIDDSTGTTTVTVTQKADG
...........................................................................--------
...SINDILNTGFNLKNNSNSVGFVSTYNTVDFIDGNATTAKVTY-DEINQ
...SIGDILNTGFNLKNNSNSVGFVSTYNTVDFIDGNATTAKVTY-TEINQ
```

```
..*** *****   *  *  *  *******  ***    * *******   **** ***   * **

------------                                                         33
------------                                                         32
------------                                                         29
------------                                                         K22
------------                                                         M4071
------------                                                         11
------------                                                         K9
------------KGADVKIGAKTSVIKDHNGKLFTGKDLKDANNGATVSEDDGKDIGTGLVTAKTVIDAVNKSG... HSF
------------KGADVKIGAKTSVIKDHNGKLFTGKDLKDANNGATVSEDDGKDIGIGLVTAKTVIDAVNKSG... API
------------TSKVVYDVNVDDTTHLTGTDDNK-KLGVKTTKLNKTDANGNTAITNFNVNSSDEDALVNAKD... Rd
            TSKVVTYDVNVDEKTTELTGDNGKTINKIGVKTTLTTTNANGK-ATNF-STTTNDALVNAKDI
            *        *           ** **         *   **          **
```

```
                                                                     33
                                                                     32
                                                                     29
                                                                     K22
                                                                     M4071
                                                                     11
                                                                     K9
...WRVTGEGATAETGATAVNAGNAETVTSGTSVNFKMGNATTATVSKDNGNIN               HSF
...WRVTGEGATAETGATAVNAGNAETVTSGTSVNFKMGNATTATVSKDNGNIN               API
                                                                     Rd
```

FIG.28L

```
...IAENLNTLAKEIHTTKGTADTALQTFTVKKVDENNNADDANAIT-------   4223
...AENLNTLAKEIHTTKGTADTALQTFKVKK-----DGATDDETIT-------   LES-1
...     ** * *  **   *  *            *     ***

--------------------------------------------------------------...
--------------------------------------------------------------...
--------------------------------------------------------------...
--------------------------------------------------------------...
--------------------------------------------------------------...
--------------------------------------------------------------...
--------------------------------------------------------------...
VKYDVNVGDGLKIGDDKKIVADTTTLTVTGGKVSVPAGANSVNNNKKLVNAEGLATALNNLS...
VKYDVNVGDGLKIGDDKKIVADTTTLTVTGGKVSVPAGANSVNNNKKLVNAEGLATALNNLS...
--------------------------------------------------------------...
VGQKNANNQ--VNTLTLKGENGLNIKTDKNGTVTFGIN------------------------...
VGKDGTQNGKTVNTLKLKGENGLTVATNKDGTVTFGIN------------------------...
*            *   *        *   * **                            ...
...---------------------------------------------------   33
...---------------------------------------------------   32
...---------------------------------------------------   29
...---------------------------------------------------   K22
...---------------------------------------------------   M4071
...---------------------------------------------------   11
...---------------------------------------------------   K9
...WTAKADKYADGESEGETDQEVKAGDKVTF-KAGKNLKVKQSEKDFTYSLQD   HSF
```

FIG.28M

```
...WTAKADKYADGESEGETDQEVKAGDKVTF-KAGKNLKVKQSEKDFTYSLQD   API
...---------------------------------------------------   Rd
...----------------TTSGLKAGKST-LNDGGLSIKNPTGSEQIQVGADG   4223
...----------------TQSGLKAGDSTTLNKDGKSIKNPASNEQIQVGADG   LES-1
                   *   ****        *  **   *  *   * *
...

----------------------------------------------------------------...
----------------------------------------------------------------...
----------------------------------------------------------------...
----------------------------------------------------------------...
----------------------------------------------------------------...
----------------------------------------------------------------...
----------------------------------------------------------------...
TLTGLTSITLGGTANGRNDTGTVINKDGLTITLANGAAAGTDASNGNT----ISVTKDGISA...
TLTGLTSITLGGTANGRNDTGTVINKDGLTITLANGAAAGTDASNGNT----ISVTKDGISA...
----------------------------------------------------------------...
VKFAKVNNNGVVGAGIDGTTRITRDEIGFTGTNGSLDKSKPHL------------SLDGINA...
VKFAKVDK-GNSSTGIDGTSRITKDQIGFTGANGSLDTTKPHLTKDKLKVGEVEITNTGINA...
   *         **      *     *   *  *  *  *    *    *        * **   ** *...
                         ...-------------------------------     33
                         ...-------------------------------     32
                         ...-------------------------------     29
                         ...-------------------------------     K22
                         ...-------------------------------     M4071
                         ...-------------------------------     11
```

FIG.28N

```
...-------------------------------                     K9
...GNKEITNVKSA---------LKTYKDTQNTA                     HSF
...GNKEITNVKSA---------LKTYKDTQNTA                     API
...-------------------------------                     Rd
...GGKKITNIQSGEIAQNSHDAVTGGKIYDLKT                     4223
...GGKKITNIQSGDITQNSNDAVTGGRVYDLKT                     LES-1
...* * **** ******** *** *    *  *

------------------------------------------------------------...
------------------------------------------------------------...
------------------------------------------------------------...
------------------------------------------------------------...
------------------------------------------------------------...
------------------------------------------------------------...
------------------------------------------------------------...
----------------------------------------------------------DE...
GATQPAANTAEVAKQDLVDLTKPATGAAGNGADAKAPDTTAATVGDLRGLGWVLSAKKTADE...
------------------------------------------------------------...
----------------------------------------------------------EL...
----------------------------------------------------------EL...
                                                          * ...

...-------------------------------                     33
...-------------------------------                     32
...-------------------------------                     29
...-------------------------------                     K22
```

```
...------------------------------ M4071
...------------------------------ 11
...------------------------------ K9
...TQDKEFHAAVKNANEVEFVGKNGATVSAKT HSF
...TQDKEFHAAVKNANEVEFVGKNGATVSAKT SPI
...------------------------------ Rd
...ENKISSTAKTAQNSLHEFSVADEQGNNFTV 4223
...ESKINSAAKTAQNSLHEFSVADEQGNNFTV LES-1
...        *   *    **   *  *

-------------------------------------------------------------...
-------------------------------------------------------------...
---------------------------------------------------ISVTKGSFAEVKT...
---------------------------------------------------ISVTKGSFAEVKT...
-------------------------------------------------------------...
-------------------------------------------------------------...
-------------------------------------------------------------...
DNNGKHTVTIDVAEAKVGDGLEKDTDGKIKLIVDNTDGNNLLTVDATKGASVAKGEFNAVTT...
DNNGKHTVTIDVAEAKVGDGLEKDTDGKIKLIVDNTDGNNLLTVDATKGASVAKGEFNAVTT...
SNPYSSYDTSKTSDVITFAGENGITTKVNKGVVRVGIDQTKGLTTPKLTVGNNNGKGIVIDS...
SNPYSSYDTSKTSDVITFAGENGITTKVNKGVVRVGIDQTKGLTTPKLTVGNNNGKGIVIDS...
 *     *   **    * * *   * * * *         * *    *  * *...

...---------------------------------------- 33
...---------------------------------------- 32
...DATTGGQVNAD-RGKVK----AEDENGADVDKKV------- 29
```

FIG.28P

```
...DATTGGQVNAD-RGKVK----AEDENGADVDKKV-------      K22
...-----------------------------------------      M4071
...-----------------------------------------      11
...-----------------------------------------      K9
...DATTAQGTNANERGKVVVKGSNGATATETDKKKV-------      HSF
...DATTAQGTNANERGKVVVKGSNGATATETDKKKV-------      API
...QNGQNTITGLSNTLANVTNDKGSVRTTEQGNIIKDEDKTRA      Rd
...KDGQNTITGLSNTLANVTNDGAGHSLS-QGLAN-DTDKTRA      LES-1
...                           *

                                                              ...
--------------------------------------------------------------...
                             INLNTDSSGNAVGSSTITFKAGDNLKIKQSGN...
ATVKDVAKAINDAATFVKVESTDDDIENGAAGKNETTDQALKAGDTLTLKAGKNLKAKLDQN...
ATVKDVAKAINDAATFVKVESTDDDIENGAAGKNETTDQALKAGDTLTLKAGKNLKAKLDQN...
--------------------------------------------------------------...
--------------------------------------------------------------...
--------------------------------------------------------------...
ATVGDVAKAINDAATFVKVEN-DDSATIDDSPTDDGANDALKAGDTLTLKAGKNLKVKRDG-...
ATVGDVAKAINDAATFVKVEN-DDSATIDDSPTDDGANDALKAGDTLTLKAGKNLKVKRDG-...
--------------------------------------------------------------...
ASIVDVLSAGFNLQGNGEAVDFVSTYDTVNFADGNATTAKVTYDDTSKTSKVVYDVNVDDTT...
ASIGDVLNAGFNLQGNGEAVDFVSTYDTVDFIDGNATTAKVTYDDTSKTSKVVYDVNVDNKT...
*** *      *    *                   *           *
                         ...        170       180       190       200
```

FIG.28Q

```
...-----FALANDLNVKNATVSDKLSLGANGKKVDITSDANG-------      33
...D--FTYS.KKE.KNLTSVETE...F....N..........-------      32
...GKSVT....K..D.TS.K......I.KDTN..........-------      29
...GKSVT....K..D.TS.K......I.KDTN..........-------      K22
...-----.T.EK..................N.......T..-------      M4071
...-----....K..G..T.....T.TI.GGAAAGAT.TPKVNVTSTTDG      11
...-----....K..SMRT.....T.TI.GSTTTGSA.TPKVNVTSTASG      K9
...-KNIT.......S..S..........T..N..N....TK.-------      HSF
...-KNIT.......S..S..........T..N..N....TK.-------      API
...-------------------------...N.......T..-------      Rd
...IEVK-DKKLGVKTTTLTSTGTGANKFALSNQATGDALVKASDIVA--      4223
...IEVTSDKKLGVKTTTLTKTSANGNATKFSA-ADGDALVKASDIAT--      LES-1
...                  *  *        *      *

      210          220        230        240          250         ...
LKFAKQGT-NGQNGN--VHLNGIASTLDDPRVGGKTAHLTKEISDTERN--RAASVGDVLNA...
..L..T.NG....S.--..........T.TLA.T.G.VDTN.DAVNYH--......Q....S...
..L..T.NG......--..........T.TIT.MT.QASNGVAVQ-NH--......A........
..L..T.NG......--..........T.TIT.MT.QASNGVAVQ-NH--......A........
.....PS.-......--..........T.TIT.TTKSATNGVDVQNH-.--.....A........
.....DAA--.A..DTT......G...T.TK..SPAT.IDGGDQS.HYT--.....IK........
.V...GA.GANGDTT--...TN.....Q.TLLNTGVVSKLDGNGITADEKK.....Q....S...
.....DSKT-.DDA.--I.........T.TLLNSGATTNLGGNGITDNEKK.....K........
..x..DSKT-.DDA.--I.........T.TLLNSGATTNLGGNGITDNEKK.....K........
.....P..-......--................................--..............
```

FIG.28R

```
------------------...TLSGDIQTAKGASQANNSAGYVDADGNKVIYDSTDNKYYQA...
------------------...TLSGDIQTAKGASQASSSASYVDADGNKVIYDSTDNKYYQV...
*  ***      **   ***  *** *                          **      *  ...
                          ...260          270        280        290        300
                          ...GMNIRGAK--TIGG-TVDNVDFVSTYDIVEFASGANANVSVTTDDN--      33
                          .......Q.NGNNVDFVR.Y.T....N---------.........A.TAH-      32
                          .......Q.NGASVDFVNAY.T....N---------.T.T..N....TAH-      29
                          .......Q.NGASVDFVNAY.T....N---------.T.T..N....TAH-      K22
                          .......Q.NGAS---------....N.....D.VN.L.T..N....TAHN      M4071
                          .......K.V.AGSTT-GQSE.....H.......L.-.DTETTTV.V.S--      11
                          .......K.V.TGAT---.S......R.......L..SEETTL..V.S---      K9
                          ......V..V.PASANNQ-.E.I...A.....D.V..DKDTT...VES---      HSF
                          ......V..V.PASANNQ-.E.I...A.....D.V..DKDTT...VES---      API
                          ...........--....-...............................--      Rd
                          ...KNDGTVD.TKEVAKDKLVAQAQTPDGTLAQMNVKSVI.KEQVN.A.--      4223
                          ...NDKGQVD.NKEVAKDKLVAQAQTPDGTLAQMNVKSVI.KEQVN.A.--      LES-1
                          ...                                *

       310        320        330        340         350        360 ...
KKTTVRVDVTGLPVQYVTEDSKTVVKVGNEYYEAKQDGSADMDKKV-ENGKLAKTKVKLVSA...
....................G...........K..D......NQ..-...E..............
....................G......D.K...............-...E..............
....................G......D.K...............-...E..............
....................GE...........................-.................
           ..F......G.......................-K..E.V............
```

FIG.28S

```
.ENGK.TE.KIGAKTS.IKEKDGKLFT.KANK.TNKVDG.NATEDA-DE..GLV.AKDVID....
ESNGKSTK.KIGAKTSGIKEKDGKLFT.KANKDTN.VASNNAADDT-DE..GLV.AETVIN....
.DNGK.TE.KIGAKTS.IK.HNGKLFT.K.LKD.NNN.VTVTETDGKDE.NGLV.AKAVID....
.DNGK.TE.KIGAKTS.IK.HNGKLFT.K.LKD.NNN.VTVTETDGKDE.NGLV.AKAVID....
...........................................-.................
..QGINEDNAFVKGLEKAASDNKTKNAAVTVGDLNAVAQTPLTFAG-DT.TT..KLGETLTI...
..QGINEDNAFIKGLENAAKDTKTKNAAVTVGDLNAVAQTPLTFAG-DT.TT..KLGETLTI...
** *                                          *     *   ...
                      ...   370    380    390    400
                      ...NGTNPVKISNVADGTEDTDAVSFKQLKALQDKQVTLSAS      33
                      ...S...................................T.       32
                      ...S.Q.........E...EN...........E.....T..       29
                      ...S.Q.........E...EN...........E.....T..       K22
                      ..................N.....................        M4071
                      ...............E................N........       12
                      ...VNKTGWR.KTTDANGQNG.---FATVASGTNVTF---..      11
                      ...VNKAGWR.KTTGANNQAGQ---FETVTSGTNVTF---.D      K9
                      ...VNKAGWRVKTTGANGQND.---FATVASGTNVTF---.D      HSF
                      ...VNKAGWRVKTTGANGQND.---FATVASGTNVTF---.D      API
                      ........................................        Rd
                      ...KGGQTDTNKLTDNNIGVVAGTDGFTV.LAK.LTNLN.VN      4223
                      ...KGGQTDTNKLTDNNIGVVAGTDGFTV.LAK.LTNLN.VN      LESS-1
                      ...                                 *    *

    410     420     430     440     450     460  ...
```

```
NAYANGGSDADGGKATQTLGNDLNFKFKSTDSELLNIKAAGDTVTFTPKKGSVQVGDDGKAT...
.......T.N.........S.G.......S.G...K.S.T...................S...
.......N...........N.G.........G......VEN..............E........
.......N...........N.G.........G......VEN..............E........
..............GI...S.G.........G.......EN.......................
...........V..V....S.G.........G.......DK....I.---------------...
GNGTTATVTNG-TDGITVKYDAKVGDGLKLDGD-KIAADTTALTVNDGKNANNPKGKVADVA...
GNGTTAVVTGDATNGITVKYEAKVGDGLKIGNDQKITADTTALTVTGGK--------VTAPD...
GNGTTAEVTKANDGSITVKYNVKVADGLKLDGD-KIVADTTVLTVADGK--------VTAPN...
GNGTTAEVTKANDGSITVKYNVKVADGLKLDGD-KIVADTTVLTVADGK--------VTAPN...
..............G....S.G.........G.......EN.......................
AGGTKIDDKGVSF-------------------------------------------------...
AGGTRIDEKGISFVDANGQAKANTPVLSANGLDLGGKRISNIGAAVDDNDAVNFKQFNEVAK...
  *                              *                  *          ...
                           ...   470       480       490        500
                           ...IQDGAKTTTGLVEASELVDSLNKLGWKVGVGKDGTG---AT        33
                           ....SK..N..E........E..........E.V.S.---EL        32
                           .....N.T...D........E..........D...S.---EL        29
                           .....N.T...D........E..........D...S.---E.        K22
                           ..............................T.T....V.---        M4071
                           ...-----------------------------------------        12
                           ...STDEKK----..T.KG..TA..S.S.TTTAAEADG.---TL        11
                           ...ATNGKK----..N..G.A.A....S.TAK-AEADTANGGEL        K9
                           ...NGDGKK----F.D..G.A.A....S.TATA..E...---EV        HSF
                           ...NGDGKK----F.D..G.A.A....S.TATA..E...---EV        API
```

FIG.28U

```
                         ......................................---..          Rd
                         ...---------------------------------------           4223
                         ...TVNNLNNQSNSGASLPFVVTDANGKPIN.TDGKPQKAIKGA         LES-1
                         ...              *     *

      510       520       530       540       550       560 ...
DGTHTD-TLVKSGDKVTLKAGDNLKVKQEGTNFTYVLRDELTGVKSVEFKDTENGANGASTK...
...SKE-..........................A.K.............A............
..ASNE-..............E......D......A.K.............A..S.........
..ASNE-..............E......D......A.K.............A..S.........
......-.........................A.K...D.........A............
-----------------------------------------------------------------...
..NASE-QE..A.....F...K........A....S.Q.A...LT.ITLGTGN...K---.E...
...ADE-KE..A.ET..F...K........A....S.Q.A...LT.ITLGTGN...K---.E...
.PANSAGQE..A.....F.......I..S.KD...S.KK..KDLT......ANG.TGSE......
.PANSAGQE..A.....F.......I..S.KD...S.KK..KDLT......ANG.TGSE......
......-.........................................................
-----------------------------------------------------------------...
..KYYH-------------------------------------------------..ANGVP...
**                                                     * * *   ...
                         ...     570       580       590       600
                         ...ITKDGLTITPAND-ANGAAATDADKIK---VASDGISAGNKAV       33
                         ............L..G-....TV.......---.............       32
                         ............S..G-.............---.............       29
                         ............S..G-.............---.............       K22
```

FIG.28V

```
...............G-.GA.G.NT.NT.S---.TK..........    M4071
...---------R.SG-............---.............    12
....N..........G-.---G.NN.NT.S---.TK......DQS.    11
....N..........G-----G.NN.NT.S---.TK......DQS.    K9
...............G-.GA.G.NT.NT,S---.TK..........    HSF
...............G-.GA.G.NT.NT,S---.TK..........    API
..........F...G-.............---......R......    Rd
...------------------------------------------    4223
...VD...KP..D.DKL..L..HGKPLDAGHQV...L.-GNSD-.I    LES-1
...* ***  ** *   *  **          **  * * *  **

       610        620        630        640        650        660 ...
KNVVSGLKKFGDANFNPLTSSADNLTKQYDNAYKGLTNLDEKSKGKQTPTVADNTAATVGDL...
--------------------------------------------------------------...
.............................D..........GAD...L................
.............................D..........GAD...L................
...............D...............................................
.-------------------------------------------------------------...
...............D...........N.D..........GTD....V...............
.............. .............D..........GAD...L................
T...........GHTLANGTV..FE-.H.......D......GADNN-.................
T...........GHTLANGTV..FE-.H......XD......GADNN-.................
--------------------------------------------------------------...
--------------------------------------------------------------...
----------------TLTNIKSTLP.I.TPNT.NA.AGQAQSLPSLSAAQQSN..S.K.V...
```

FIG. 28W

```
                       *                  *  **  *              *    ****  **     ****....700
                     670            680            690
           ...TGLGWVISADKTTGES-KEYSAQVRNANEVKFKSGNGIN    33
           ..........................H                  32
           ............LN..N..........                  29
           ............LN..N..........H                 K22
           ............LN..N..........H                 M4071
           ..........K.LN..N..........                  12
           ...........................                  11
           ......G.-T.HD..............                  K9
           ........LD..N..............                  HSF
           ........PNQ.N..............                  API
           ........PNQ.N..............                  Rd
           ---------------------------                  4223
           ---------------------------                  LES-1

                                                              **
           ..LNV.FNLQTNHNQVDFV.A.DTVNFVNGTGADITSVRSA
              *** * **                           *
                        730           740           750           760
           VSGKTLDNGTREITFELAKDENAIAFGSGSKALRDNTVAIGTGNVVNAEKSGAFGDPNYIED...
             710           720

           ----V-..R...........Y..........
           ----V-..R...........Y..........
           ...............................
           ...............................
           ......V-..R...........G.--------
           -------------------------------
           -------------------------------
           ...............................
           ...............................
           ...............................
           ...............................
           ...............................
           ...............................
```

```
.....V-..R.........G.----------------------------------------...
......-....V.......G.----------------------------------------...
......-....V.......G.----------------------------------------...
----------------------------------------------------------------...
----------------------------------------------------------------...
DGTMSNITVNTALAATDDDGNVL.KAKD.KFYKA.DLMPN.SLKAGKSASDAKTPTGLSLVN...
 ** *       **     *  *         ** *  **     *   *      * *...
                          ...   770      780      790      800
                          ...KAGGSYAFGNDNRITSKNTFVLGNGVNAKYKANGKVDT-----   33
                          ...-----------------------------------------   32
                          ..........................................   29
                          ..........................................   K22
                          ........................S....RD...N.L.EE---   M4071
                          ...-----------------------------------------   12
                          ...-----------------------------------------   11
                          ...-----------------------------------------   K9
                          ...-----------------------------------------   HSF
                          ...-----------------------------------------   API
                          ...-----------------------------------------   Rd
                          ...-----------------------------------------   4223
                          ...PNA.KGST.DAVALNNLSKA.FKSKDGTTTTTVSSDGISIQGK   LES-1
                          ...  **  * **   *      *      *    * *

----------------------------------------------------------------...
----------------------------------------------------------------...
```

```
-----------------------------------------------------------...
-----------------------------------------------------------...
-----------------------------------------------------------...
-----------------------------------------------------------...
VVKSNEFTVKETNGKETSLVKVGDLYYSKEDIDLTTGQPKLKDGNTVAAKYQDKGGKVVS-V...
VVKSNEFTVKETNGKETSLVKVGDLYYSKEDIDPATGKPKVTNGNAVAAKYQDKDGKVVSAD...
VVKSNEFTVKNADGSETNLVKVGDLYYSKEDIDPATSKPMTGKTE----KYKVENGKVVSAN ...
VVKSNEFTVKNADGSETNLVKVGDLYYSKEDIDPATSKPMTGKTE----KYKVENGKVVSAN...
-----------------------------------------------------------...
VDSSGQAKANTPVLSANGLDLGGKVISNVGKGTKDTDAANVQQLNEVRNLLGLGNAGNDNAD...
DNSSI-------TLSKDGLNVGGKVISNVGKGTKDTDAANVQQLNEVRNLLGLGNAGNDNAD...
  * *          *   *          *       * *       *    **...
                        ...-------------------------------------      33
                        ...-------------------------------------      32
                        ...-------------------------------------      29
                        ...-------------------------------------      K22
                        ...-------------------------------------      M4071
                        ...-------------------------------------      12
                        ...TDNTEATITNKGSGYVTGNQ-----------------      11
                        ...GSSNTAVTLTNKGYGYVTGNQ----------------      K9
                        ...GSK-TEVTLTMKGSGYVTGNQ----------------      HSF
                        ...GSK-TEVTLTMKGSGYVTGNQ----------------      API
                        ...-------------------------------------      Rd
                        ...GNQVNIADIKKDPNSGSSSNRTVIKAGTVLGGKGNNDT     4223
                        ...GNQVNIADIKKDPNSGSSSNRTVIKAGTVLGGKGNNDT     LES-1
```

```
                  ...       *      ***

--------------------------------------------------------------...
-------------------------------------------------------------- ...
-------------------------------------------------------------- ...
--------------------------------------------------------------...
--------------------------------------------------------------...
--------------------------------------------------------------...
VADAIAKSGFEKGKADEADAKRAFDD--KTKALSAGTTE-IVNAHDKVRFANGLNTKVSAAT...
VADAIAKSGFEKGKADAEKAKAAFGD--ETKALSSDKLE-TVNANDKVRFANGLNTKVSAAT...
VADAIAKSGFEKGKADAAEAEKAFAESAKDKQLSKDKAE-TVNAHDKVRFANGLNTKVSAAT ...
VADAIAKSGFEKGKADAAEAEKAFAESAKDKQLSKDKAE-TVNAHDKVRFANGLNTKVSAAT...
--------------------------------------------------------------...
EKLATGGIQVGVDKDGNANGDLSNVWVKTQKDGSKKALLATYNAAGQTNYLTNNPAEAIDRI...
EKLATGGVQVGVDKDGNANGDLSNVWVKTQKDGSKKALLATYNAAGQTNYLTNNPAEAIDRI...
  * *     *       * *      * *    * **     *     *     ...
                       ...----------------------------------------     33
                       ...----------------------------------------     32
                       ...----------------------------------------     29
                       ...----------------------------------------     K22
                       ...----------------------------------------     M4071
                       ...----------------------------------------     12
                       ...VESTDANGDKVTTTFVKTDVELPLTQIYNTDANGKKITKVV   11
                       ...VESTDANGDKVTTTFVKTDVELPLTQIYNTDANGKKI---V   K9
                       ...VESTDANGDKVTTTFVKTDVELPLTQIYNTDANGNKI---V   HSF
```

FIG.28A'

```
                         ...VESTDANGDKVTTTFVKTDVELPLTQIYNTDANGNKI---V           API
                         ...-----------------------------------------           Rd
                         ...NEQGIRFFHVNDGNQEPVVQGRNGIDSSASGKHSVAIGFQ-           4223
                         ...NEQGIRFFHVNDGNQEPVVQGRNGIDSSASGKHSVAIGFQ-           LES-1
                         ...  * *     *         *  *  *  **

-----------------------------------------------------------------...
-----------------------------------------------------------------...
-----------------------------------------------------------------...
-----------------------------------------------------------------...
-----------------------------------------------------------------...
-----------------------------------------------------------------...
KDGQTKWYELNADGTADMTKEVTLGNVDSDGKKVVKDNDG---KWYHAKADGTADKTKGEVD...
KNGD-KWYYTKDDGSTDMTKEVTLGNVDSDGKKVVKEDN----KWYGVKSDGSTDKTQVVEE...
KKADGKWYELNADGTASN-KEVTLGNVDANGKKVVKVTENGADKWYYTNADGAADKTKGEVS...
KKADGKWYELNADGTASN-KEVTLGNVDANGKKVVKVTENGADKWYYTNADGAADKTKGEVS...
-----------------------------------------------------------------...
AKADGEAAVAIGRQTQAGNQSIAIGDNAQATGDQSIAIGTGNVVAGKHSGAIGDPSTVKADN...
AKADGEAAVAIGRQTQAGNQSIAIGDNAQATGDQSIAIGTGNVVTGKHSGAIGDPSTVKADN...
  **      *    *****   *       *      *  *  *                ...
                         ...---------------------------                         33
                         ...---------------------------                         32
                         ...---------------------------                         29
                         ...---------------------------                         K22
                         ...---------------------------                         M4071
```

FIG.28B'

```
                                   ...-------------------------                          12
                                   ...NDKVSTDEKHVVSLDPNDQSKGKGVV                         11
                                   ...A-KVSTDEKHVVSLDPNDQSKGKGVV                         K9
                                   ...NDKVSTDEKHVVSLDPNDQSKGKGVV                         HSF
                                   ...NDKVSTDEKHVVSLDPNDQSKGKGVV                         API
                                   ...--------------------------                         Rd
                                   ...SYSVGNNNQGTDATQTDVFGVGNNIT                         4223
                                   ...SYSVGNNNQGTDATQTDVFGVGNNIT                         LES-1
                                   ...    ** **       * *  * *  *

        810       820        830        840       850       860 ...
ETVTVKDKDGKETTVTVPKALGATVENSVYLGNKSTATKDKGKNLKSDGTAGNITTAGTTGT...
--------------------------------------------------------------...
..............................................................
..............................................................
.EKE.VG..AK.K...Q...E...........A.....................A.....
--------------------------------------------------------------...
--------------------------------------------------------------...
--------------------------------------------------------------...
--------------------------------------------------------------...
--------------------------------------------------------------...
--------------------------------------------------------------...
VTESNSVAL.SNSAISAGTHA.TQAK-------------------.......T.....A......
VTESNSVAL.SNSAISAGTHA.TQAK-------------------.......T.....A......
         *  * **      *                     ******* *********...
                                   ...     870       880       890       900
                                   ...VNGFAGATAHGAVSVGASGEERRIQNVAAGEISATSTD             33
                                   ...----------------------K.............               32
                                   ........................................              29
```

FIG.28C'

```
...........................................                              K22
...........................................                              M4071
...--------------------------.............                               12
...------------------------.D..N.D.......                                11
...------------------------.N.M.N.........                               K9
...------------------------.D..N.........                                HSF
...------------------------.D..N.........                                API
...-------------------------K............                                Rd
....K....Q..V.........A...........V.....                                 4223
....K....Q..V.........A...........V.....                                 LES-1
...* **** ** ********* **** *** *********

       910       920              930       940       950       ...
AINGSQLYAVAKGVTNLAGQVN-------KVGKRADAGTASALAASQLPQASMSGKSMVSIA...
......................NLEGKVN....................T.P...........
......................-------.....................P...........
......................-------.....................P...........
......................-------.....................P...........
......................-------.....................P...........
......................NLEGKVN....................T.P.....A.....
......................NLEGKVN....................T.P...........
......................NLEGKVN....................T.P.....A.....
......................NLEGKVN....................T.P.....A.....
......................-------.....................P...........
.V......---.ATQSI.NAT.ELDHRIHQNENK.N..IS..M.MASM...YIP.R...TGG...
.V......---.ATQGI.NAT.ELDHRIHQNENK.N..IS..M.MASM...YIP.R...TGG...
********   **   **   *            ***** ***** * ****   ****** *...
```

FIG.28D'

```
...  960       970       980       990      1000
...GSSYQGQSGLAIGVSRISDNGKVIIRLSGTTNSQGKTGVAAGVGYQW*    33
..........N.......................................*    32
..........N.......................................*    29
..........N.......................................*    K22
..................................................*    M4071
.........................L........................*    12
..........N.......................................*    11
..........N.......................................*    K9
..........N.......................................*    HSF
..........N.......................................*    API
..................................................*    Rd
...IATHN..GAV.V.L.KL....QWVFKIN.SADT..HV.A.V.A.FHF*    4223
...IATHN..GAV.V.L.KL....QWVFKIN.SADT..HV.A.V.A.FHF*    LES-1
...  ****** *************  * ** *******  * * * ** *
```

RECOMBINANT *HAEMOPHILUS INFLUENZAE* ADHESIN PROTEINS

FIELD OF INVENTION

The present invention relates to the field of molecular genetics and, in particular, to the production of recombinant *Haemophilus influenzae* adhesin (Hia) proteins.

BACKGROUND TO THE INVENTION

*Haemophilus influenzae* is the cause of several serious human diseases, such as meningitis, epiglottitis, septicemia and otitis media. There are six serotypes of *H. influenzae*, designated a to f, that are identified by their capsular polysaccharide. *H. influenzae* type b (Hib) was a major cause of bacterial meningitis until the introduction of several Hib conjugate vaccines in the 1980's (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Vaccines based upon *H. influenzae* type b capsular polysaccharide conjugated to diphtheria toxoid (ref. 2), tetanus toxoid (ref. 3 and U.S. Pat. No. 4,496,538), or *Neisseria meningitidis* outer membrane protein (ref. 4) have been effective in reducing *H. influenzae* type b-induced meningitis. The other serotypes of *H. influenzae* are associated with invasive disease at low frequencies, although there appears to be an increase in the incidence in disease caused by these strains as the incidence of Hib disease declines (ref. 5; ref. 6). Non-encapsulated or non-typeable *H. influenzae* (NTHi) are also responsible for a wide range of human diseases including otitis media, epiglottitis, pneumonia, and tracheobronchitis. The incidence of NTHi-induced disease has not been affected by the introduction of the Hib vaccines (ref. 7).

Otitis media is the most common illness of early childhood, with 60 to 70% of all children, of less than 2 years of age, experiencing between one and three ear infections (ref. 8). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection by NTHi, surface-exposed outer membrane proteins that stimulate an antibody response are potentially important targets for bactericidal and/or protective antibodies and, therefore, potential vaccine candidates. A family of high molecular weight proteins (HMW1 and HMW2) that are important in attachment of NTHi to epithelial cells has been identified in about 70 to 75% of NTHi strains (ref. 9; ref. 10). These high molecular weight adhesins have been shown to afford some protection in the chinchilla model of otitis media (ref. 11). A second family of high molecular weight adhesion proteins has been identified in about 25% of NTHi and in encapsulated *H. influenzae* strains (ref. 12; ref. 13, ref. 14). The NTHi member of this second family is termed *Haemophilus influenzae* adhesin or Hia and the homologous protein found in encapsulated strains is termed *Haemophilus influenzae* surface fibril protein or Hsf. The hia gene was originally cloned from an expression library using convalescent sera from an otitis media patient, which indicates that it is an important immunogen during disease. The prototype Hia and Hsf proteins demonstrate about 82% sequence similarity, although the Hsf protein is considerably larger. The proteins are comprised of conserved amino and carboxy termini and several repeat motifs, with Hsf containing more repeat sequences than Hia. A high molecular weight protein (200 kDa) has also been identified from Moraxella catarrhalis that has some sequence homology with the Hsf and Hia proteins (U.S. Pat. No. 5,808,024).

Since Hia or Hsf is conserved amongst encapsulated strains of *Haemophilus influenzae* and about 20 to 25% of non-encapsulated strains, and has been demonstrated to be an adhesin, the protein has utility in diagnosis of and vaccination against disease caused by *H. influenzae* or other bacterial pathogens that produce Hia or a protein capable of raising antibodies specifically reactive with Hia.

A disadvantage of Hia for use as an antigen in diagnosis, for the generation of anti-Hia antibodies useful in diagnosis and as an immunogen in vaccination is the low recovery of the native protein from *Haemophilus influenzae* species.

It would be advantageous to provide recombinant Hia protein for use as antigens, in immunogenic preparations including vaccines, carriers for other immunogens and in the generation of diagnostic reagents.

SUMMARY OF THE INVENTION

The present invention is directed towards the provision of recombinant *H. influenzae* adhesin (rHia) proteins.

In connection with the provision of such recombinant proteins, the present invention provides certain isolated and purified nucleic acid molecules. Accordingly, in one aspect thereof the present invention provides an isolated and purified nucleic acid molecule encoding a *Haemophilus influenzae* adhesin (Hia) protein of a strain of *Haemophilus influenzae* having: (a) a DNA sequence selected from the group consisting of those shown in FIGS. 18, 19, 20, 21, 22, 23, 24 and 25 (SEQ ID Nos: 23, 25, 27, 29, 31, 33, 35, 37); or (b) a DNA sequence encoding a *Haemophilus influenzae* adhesin (Hia) protein having an amino acid sequence selected from the group consisting of those shown in FIGS. 18, 19, 20, 21, 22, 23, 24 and 25 (SEQ ID Nos: 24, 26, 28, 30, 32, 34, 36, 38).

Such nucleic acid may be included in a vector, which may be a plasmid vector. In particular, the nucleic acid molecule may encode the Hia protein from strain 11 or 33 of non-typeable Haemophilus.

In another aspect of the present invention, there is provided an isolated and purified nucleic acid molecule encoding an N-truncated *Haemophilus influenzae* adhesin (Hia) protein of a strain of *Haemophilus influenzae* which is amplifiable by a pair of nucleotides which are selected from the group consisting of SEQ ID No: 7 and SEQ ID No: 15; SEQ ID No: 9 and SEQ ID No: 15; SEQ ID No: 11 and SEQ ID No: 15; SEQ ID No: 13 and SEQ ID No: 15.

Such nucleic acid may be included in a vector, which may be a plasmid vector. In particular, the nucleic acid molecule may encode an N-truncated Hia protein from strain 11 or 33 of non-typeable Haemophilus, starting at codon V38.

The plasmid vector incorporating the isolated and purified nucleic acid provided in accordance with these aspects of the invention may have the identifying characteristics of a plasmid which is selected from the group consisting of:

DS-2008-2-3 as shown in FIG. 1A

DS-2186-1-1 as shown in FIG. 5A

DS-2201-1 as shown in FIG. 5A

DS-2186-2-1 as shown in FIG. 5A

DS-2168-2-6 as shown in FIG. 5A

The vector provided herein may include the cer gene from *E. coli*. Accordingly, in another aspect of the present invention, there is provided a vector for transforming a host, comprising a nucleic acid molecule encoding a full-length or N-truncated *Haemophilus influenzae* adhesin (Hia) protein, a promoter for expression of said full-length or truncated Hia protein and, optionally, the cer gene of *E. coli*. The vector may be a plasmid vector or other non-replicating vector, which may have the identifying characteristics of a plasmid vector which is selected from the group consisting of:

BK-96-2-11 as shown in FIG. 6A

DS-2242-1 as shown in FIG. 7A

DS-2242-2 as shown in FIG. 7A

DS-2340-2-3 as shown in FIG. 8A

DS-2447-2 as shown in FIG. 9A

DS-2448-17 as shown in FIG. 9B

The vectors provided herein may comprise a replicating vector, including a vector from Salmonella, BCG, adenovirus, poxvirus, vaccinia or poliovirus.

Any of the vectors provided herein may be employed to transform a suitable host cell for expression therein of a protective *Haemophilus influenzae* adhesin (Hia) protein of a non-typeable strain of Haemophilus, which may be in full-length or truncated form. Such host conveniently may be *E. coli*. Such expression may be under the control of the T7 promoter and expression of the recombinant Hia from the transformed host may be effected by culturing in an inducing concentration of lactose or other convenient inducing agent.

The present invention further includes, in a further aspect thereof, a recombinant protective *Haemophilus influenzae* adhesin (Hia) protein of a non-typeable Haemophilus strain producible by the transformed host, particularly *E. coli*, provided herein. Such Hia protein may be provided in the form of an immunogenic fragment or adhesin-functional analog of the recombinant protein.

The recombinant Hia proteins, full-length or N-truncated, provided herein are useful as antigens in immunogenic composition, carriers for other immunogens, diagnostic agents and in the generation of diagnostic agents. The nucleic acid molecules which encode the Hia protein, full-length or N-truncated, also are useful as probes for diagnostic use and also in immunogenic compositions.

The present invention, in an additional aspect thereof, provides an immunogenic composition, comprising at least one immunologically active component which is selected from the group consisting of an isolated and purified nucleic acid molecule as provided herein and a recombinant protective Hia protein, full-length or N-truncated, of a strain of Haemophilus, as provided herein, and a pharmaceutically-acceptable carrier therefor.

The immunogenic compositions provided herein may be formulated as a vaccine for in vivo administration to a host to provide protection against disease caused by *H. influenzae*. For such purpose, the compositions may be formulated as a microparticle, capsule, ISCOM or liposome preparation. The immunogenic composition may be provided in combination with a targeting molecule for delivery to specific cells of the immune system or to mucosal surfaces.

The immunogenic compositions of the invention (including vaccines) may further comprise at least one other immunogenic or immunostimulating material and the immunostimulating material may be at least one adjuvant or at least one cytokine. Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants.

Advantageous combinations of adjuvants are described in copending U.S. patent application Ser. No. 08/261,194 filed Jun. 16, 1994 and Ser. No. 08/483,856 filed Jun. 7, 1995, assigned to the assignee hereof and the disclosure of which is incorporated herein by reference (WO 95/34308 published Nov. 21, 1995).

In accordance with another aspect of the invention, there is provided a method for generating an immune response in a host, comprising the step of administering to a susceptible host an effective amount of the immunogenic composition as recited above. The immune response may be humoral or a cell-mediated immune response. Hosts in which protection against disease may be conferred include primates, including humans.

The present invention includes, in a yet additional aspect thereof, a method for the production of a protective *Haemophilus influenzae* adhesin (Hia) protein of a non-typeable strain of *Haemophilus influenzae*, which comprises:

transforming a host, such as *E. coli*, with a vector comprising a nucleic acid molecule encoding an N-truncated form of the *Haemophilus influenzae* adhesin protein as provided herein, growing the host to express the encoded truncated Hia, and isolating and purifying the expressed Hia protein.

The encoded truncated Hia may be expressed in inclusion bodies. The isolation and purification step may be effected by disrupting the grown transformed cells to produce a supernatant and the inclusion bodies containing the Hia, solubilizing the inclusion bodies after separation from the supernatant, to produce a solution of the recombinant Hia, chromatographically purifying the solution of recombinant Hia free from cell debris, and isolating the purified recombinant Hia protein.

The vector transforming the host cell, such as *E. coli*, may include the T7 promoter and the *E. coli* or other host cell may be cultured in the presence of an inducing amount of lactose or other convenient inducing agent.

The strain of *Haemophilus influenzae* herein may be selected from the group of non-typeable strain consisting of strains 11, 33, 32, 29, M4071, K9, K22 and 12. Specific nucleic acid sequences for the gene encoding the Hia protein from such strain are provided herein and are described below.

The nucleic acid molecules provided herein are useful in diagnostic applications. Accordingly, in a further aspect of the invention, there is provided a method of determining the presence, in a sample, of nucleic acid encoding a *Haemophilus influenzae* adhesin protein, comprising the steps of:

a) contact the sample with a nucleic acid molecule as provided herein to produce duplexes comprising the nucleic acid molecule encoding the Hia protein of a strain of Haemophilus present in the sample and specifically hybridizable therewith; and b) determining the production of the duplexes.

In addition, the present invention provides a diagnostic kit for determining the presence, in a sample, of nucleic acid encoding a *Haemophilus influenzae* adhesin protein, comprising:

a) a nucleic acid molecule as provided herein;

b) means for contacting the nucleic acid molecule with the sample to produce duplexes comprising the nucleic acid molecule and any such nucleic acid molecule; and c) means for determining production of the duplexes.

The recombinantly produced truncated Hia proteins provided herein also are useful in diagnostic: applications. Accordingly, in another aspect of the invention, there is provided a method of determining the presence of antibodies specifically reactive with the Hia protein in a sample, comprising the steps of (a) contacting the sample with the recombinant Hia protein provided herein to provide complexes of the recombinant Hia protein and any such antibodies present in the sample specifically reactive therewith; and (b) determining production of the complexes.

Advantages of the present invention include:

an isolated and purified nucleic acid molecule encoding a *Haemophilus influenzae* adhesin protein or a fragment or an analog of the Hia protein;

recombinantly-produced Hia proteins, free from any other Haemophilus proteins; and diagnostic kits and immunological reagents for specific identification of Haemophilus.

BRIEF DESCRIPTION OF DRAWINGS

The present invention will be further understood from the following description with reference to the drawings, in which:

FIG. 1B shows the oligonucleotides used to PCR amplify the strain 11 hia gene. Sense Strand (5038.SL): SEQ ID No: 1, encoded amino acids SEQ ID No: 2; Antisense Strand (5039.SL): SEQ ID No: 3, complement SEQ ID No: 4, encoded amino acids SEQ ID No: 5. Restriction enzyme sites are: B, BamH I; Bg, Bgl II; H, Hind III; N, Nde I; Ps, Pst I; Sty, Sty I. Other abbreviations are: T7p, T7 promoter; ApR, ampicillin resistance.

FIG. 4 shows the sites of truncation for the strain 11 Hia protein (SEQ ID No: 6).

FIG. 5B shows the oligonucleotides used to PCR amplify the 5'-fragments for the truncated genes. E21 truncation: Sense (5524.SL): SEQ ID No: 7, encoded amino acids SEQ ID No: 8; T33 truncation: Sense (5525.SL) SEQ ID No: 9, encoded amino acids SEQ ID No: 10; V38 truncation: Sense (5526.SL): SEQ ID No: 11, encoded amino acids, SEQ ID No: 12; N52 truncation: Sense (5527.SL): SEQ ID No: 13, encoded amino acids SEQ ID No: 14; Antisense (5528.SL): SEQ ID No: 15; complement SEQ ID No: 16, encoded amino acids SEQ ID No: 17.

FIG. 6B shows the oligonucleotides used to construct the multiple cloning site and transcription terminators. "R" and "Ps" indicate termini that will overlap with EcoR I or Pst I ends, but will not regenerate the sites. Upperstrand (SEQ ID No.: 50) lower strand (SEQ ID No.: 51).

FIG. 7B shows the oligonucleotides used to generate the 5'-end of the strain 33 hia gene coding strand (SEQ ID No.: 52), complementary strand (SEQ ID No.: 53), and encoded amino acid sequence (SEQ ID No.: 54).

FIG. 8B shows the oligonucleotides used to PCR amplify the 5'-end of the truncated hia gene. Sense (6286.SL): SEQ ID No: 16, encoded amino acids SEQ ID No: 17; antisense (6287.SL) SEQ ID No: 18, complement SEQ ID No: 19, encoded amino acids SEQ ID No: 20.

FIG. 15A shows the antibody response in mice and FIG. 15B shows the response in guinea pigs.

FIG. 17 shows the oligonucleotides used to PCR amplify additional hia genes. Sense (5040.SL), SEQ ID No: 21, encoded amino acids SEQ ID No: 22; Antisense (5039.SL), SEQ ID No: 3, complement SEQ ID No: 4, encoded amino acids SEQ ID No: 5.

FIG. 18 shows the nucleotide sequence (SEQ ID No: 23) and deduced amino acid sequence (SEQ ID No: 24) of the hia gene from NTHi strain 33.

FIG. 19 shows the nucleotide sequence (SEQ ID No: 25) and deduced amino acid sequence (SEQ ID No: 26) of the hia gene from NTHI strain 32.

FIG. 20 shows the nucleotide sequence (SEQ ID No: 27) and deduced amino acid sequence (SEQ ID No: 28) of the hia gene from NTHi strain 29.

FIG. 21 shows the nucleotide sequence (SEQ ID No: 29) and deduced amino acid sequence (SEQ ID No: 30 of the hia gene from NTHi strain M4071.

FIG. 22 shows the nucleotide sequence (SEQ ID No: 31) and deduced amino acid sequence (SEQ ID No: 32) of the hia gene from NTHi strain K9.

FIG. 23 shows the nucleotide sequence (SEQ ID No: 33) and deduced amino acid sequence (SEQ ID No: 34) of the hia gene from NTHi strain K22.

FIG. 24 shows the nucleotide sequence (SEQ ID No: 35) and deduced amino acid sequence (SEQ ID No: 36) of the hia gene from type c strain API.

FIG. 25 shows the nucleotide sequence (SEQ ID No: 37) and deduced amino acid sequence (SEQ ID No: 38) of the hia locus from NTHi strain 12. The overlined or underlined sequences indicate oligonucleotides used to PCR amplify across the junction of the two orfs. Sense (6431.SL) SEQ ID No: 39, (6432.SL) SEQ ID No: 40; antisense (6295.SL) SEQ ID No: 41, (6271.SL) SEQ ID No: 42.

FIG. 26 shows the nucleotide sequence (SEQ ID No.: 43) and deduced amino acid sequence (SEQ ID No.: 44) of the hia locus from NTHi strain 11, as published in U.S. Pat. No. 5,646,259.

FIG. 27 shows the alignment of the upstream ORF from the strain 12 hia locus (SEQ ID No: 45) with part of the HI1732 protein (SEQ ID No: 46) from *H. influenzae* type b strain Rd.

FIG. 28 shows the alignment of amino acid sequences from Hia (SEQ ID Nos. 24, 26, 28, 34, 30, 44, 32), Hsf (SEQ ID No.: 47) and partial sequences from *Moraxella catarrhalis* high molecular weight proteins (200 kDa) from strains 4223 and LES-1 (SEQ ID Nos.: 48, 49). Asterisks within sequences indicate stop codons, but below the sequence they indicated sequence homology. Dots indicate identical residues. The sequence alignments were prepared by direct comparison of the amino acid sequences of the respective proteins.

GENERAL DESCRIPTION OF THE INVENTION

Figure 1A:
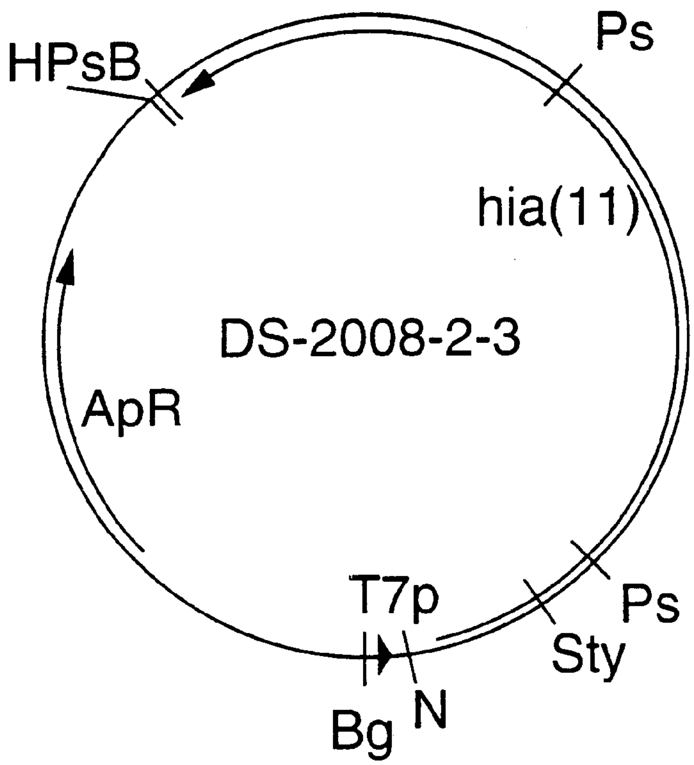
FIG. 1A shows a restriction map for plasmid DS-2008-2-3 that contains the T7 promoter and the full-length NTHi strain 11 hia gene.

Since *H. influenzae* strains produce low quantities of the Hia and Hsf proteins, the hia gene from NTHi strains was cloned into an expression vector for overproduction of the recombinant protein in *E. coli*. When the full-length recombinant Hia (rHia) protein was expressed, it was made in relatively low quantities. In order to confirm that there was expression of the recombinant protein, an immunoblot was performed using antibody raised to a *Moraxella catarrhalis* high molecular weight adhesin protein identified as 200 kDa in U.S. Pat. No. 5,808,024, assigned to the assignee and the disclosure of which is incorporated herein by reference. Antibody against the gel-purified native 200 kDa protein recognized a specific induced band in the rHia protein sample. The yield of rHia was not significantly improved by increasing the gene copy number of the T7 hia gene cassette.

The *E. coli* cer gene has been shown to stabilize plasmids containing large inserts (ref. 15), but the yield of rHia was not significantly improved by adding the *E. coli* cer gene to the expression vector. However, the *E. coli* cells were observed to clump during culture, suggesting that there was surface expression of the Hia adhesin protein. The apparent toxicity of the rHia protein might be overcome if it were made as inclusion bodies, so truncations were made at the 5'-end of the gene to delete putative signal sequences. This modification resulted in good production and recovery of truncated rHia starting from the V38 position.

The full-length and V38-truncated rHia proteins were immunogenic and the resultant anti-rHia antibodies were protective in passive infant rat models of bacteremia due to *H. influenzae* type a or type b strains. In addition, the truncated V38 rHia protein was found to be partially protective against nasopharyngeal colonization in an active challenge model in chinchillas. The protection afforded by rHia derived from an NTHi strain against disease caused by NTHi and encapsulated type a or type b strains, indicates that there may be common protective epitopes. The cloning and sequence analysis of additional hia genes may help to identify conserved regions. The full-length or N-terminal truncated rhia proteins may be used as vaccine components to protect against *Haemophilus influenzae* disease.

Any Haemophilus strains that have hia genes may be conveniently used to provide the purified and isolated nucleic acid molecules (which may be in the form of DNA molecules), comprising at least a portion coding for a Hia protein as typified by embodiments of the present invention. Such strains are generally available from clinical sources and from bacterial culture collections, such as American Type Culture Collection. Appropriate strains of Haemophilus include:

Non-typeable Haemophilus strain 11;
Non-typeable Haemophilus strain 33;
Non-typeable Haemophilus strain 32;
Non-typeable Haemophilus strain 29;
Non-typeable Haemophilus strain M4071;

Non-typeable Haemophilus strain K9;

Non-typeable Haemophilus strain K22;

Non-typeable Haemophilus strain 12;

Type C Haemophilus strain API.

In this application, the term "Hia" protein is used to define a family of Hia proteins that includes those having naturally occurring variations in their amino acid sequences as found in various strains of Haemophilus.

Referring to FIG. 1A, there is illustrated a restriction map of plasmid DS-2008-2-3 that contains a full-length hia gene from non-typeable *Haemophilus influenzae* strain 11, under the influence of the T7 promoter. The nucleic acid (SEQ ID No.: 43) and deduced amino acid sequence (SEQ ID No.: 44) of the hia gene from strain 11, are described in the aforementioned U.S. Pat. No. 5,646,259 (and identified as "HA1"). The oligonucleotides used to PCR amplify the hia gene from the ATG start codon of the gene of strain 11 are shown in FIG. 1B.

Figure 2:
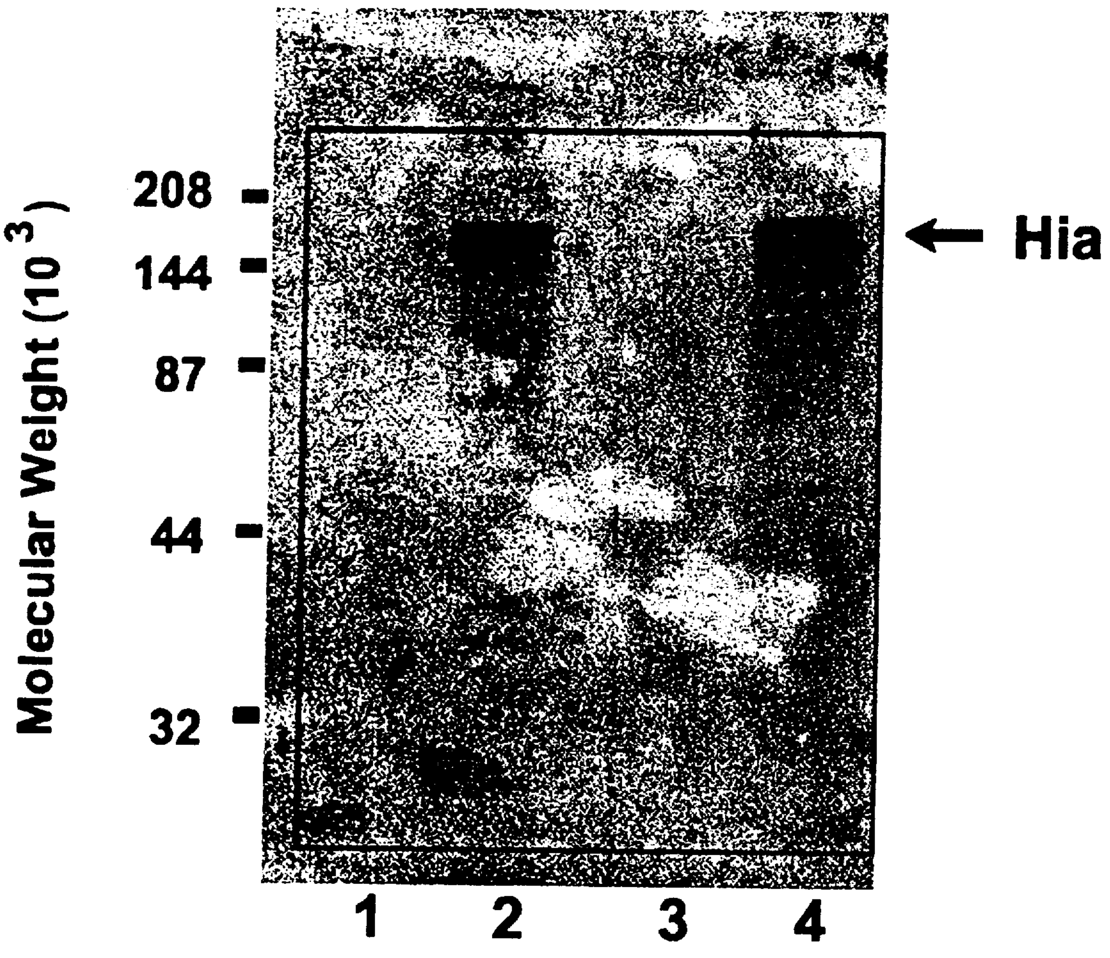
FIG. 2 shows an immunoblot of the recognition of full-length rhia protein by anti-native *Moraxella catarrhalis* high molecular weight adhesin antibody. Lane 1, DS-2043-1 uninduced; lane 2, DS-2043-1, induced for 4h; lane 3, DS-2043-2 uninduced; lane 4, DS-2043-2, induced for 4 h; lane 5, molecular weight markers. DS-2043-1 and DS-2043-2 are independent clones of pT7 hia (11) in BL21 (DE3).

Referring to FIG. 2, there is illustrated an immunoblot demonstrating the recognition of the rHia (11) protein by anti-native *Moraxella catarrhalis* high molecular weight adhesin antibody. The *M. catarrhalis* high molecular weight adhesin or 200 kDa protein described in the aforementioned U.S. Pat. No. 5,808,024 has some sequence homology with the Hia and Hsf proteins, especially at the carboxy terminus (FIG. 28).

Figure 3:
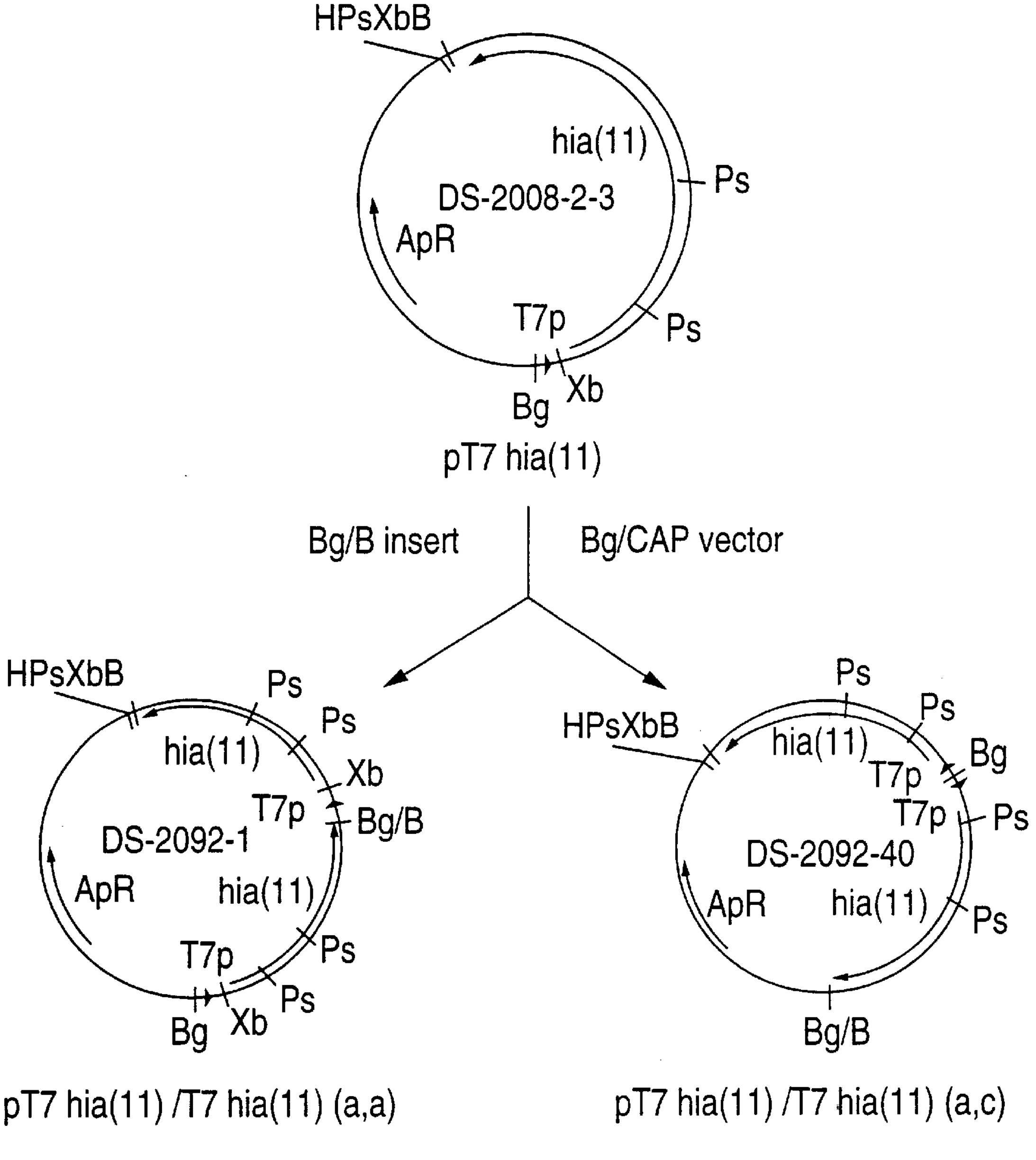
FIG. 3 shows the construction of plasmids DS-2092-1 and DS-2092-40 that contain tandem copies of the T7 hia gene cassette for the strain 11 hia gene. Restriction enzyme sites are: B, BamH I; Bg, Bgl II; H, Hind III; Ps, Pst I; Xb, Xba I. Other abbreviations are: CAP, calf alkaline phosphatase; T7p, T7 promoter; ApR, ampicillin resistance.

Referring to FIG. 3, there is illustrated a construction scheme for plasmids DS-2092-1 and DS-2092-40 that contain tandem copies of T7 hia gene cassettes comprising the full-length hia gene from NTHi strain 11. Such plasmids that contain increased copy numbers of genes often have enhanced production levels for recombinant proteins. However, as seen below, the low yield of recombinant Hia was not significantly improved by increasing the gene copy number.

Referring to FIG. 4, there is illustrated the N-terminal sequence of the NTHi strain 11 protein and the position of four N-terminally truncated rHia proteins. The N-terminal truncation up to position E21 deletes a long hydrophobic region that may constitute part of a signal sequence for Hia. The deletion up to position T33 includes a long hydrophobic region and follows a potential Ala-X-Ala signal cleavage site. The deletion up to position V38 includes a long hydrophobic region and follows a potential Ala-X-Ala signal cleavage site. The recombinant Hia protein starting at position N52 mimics the approximate start of the related high molecular weight (200 kDa) adhesin from *Moraxella catarrhalis* described in the aforementioned U.S. Pat. No. 5,808,024, which recombinant protein is over-produced if truncated at its N-terminus to start at V56.

Figure 5A:
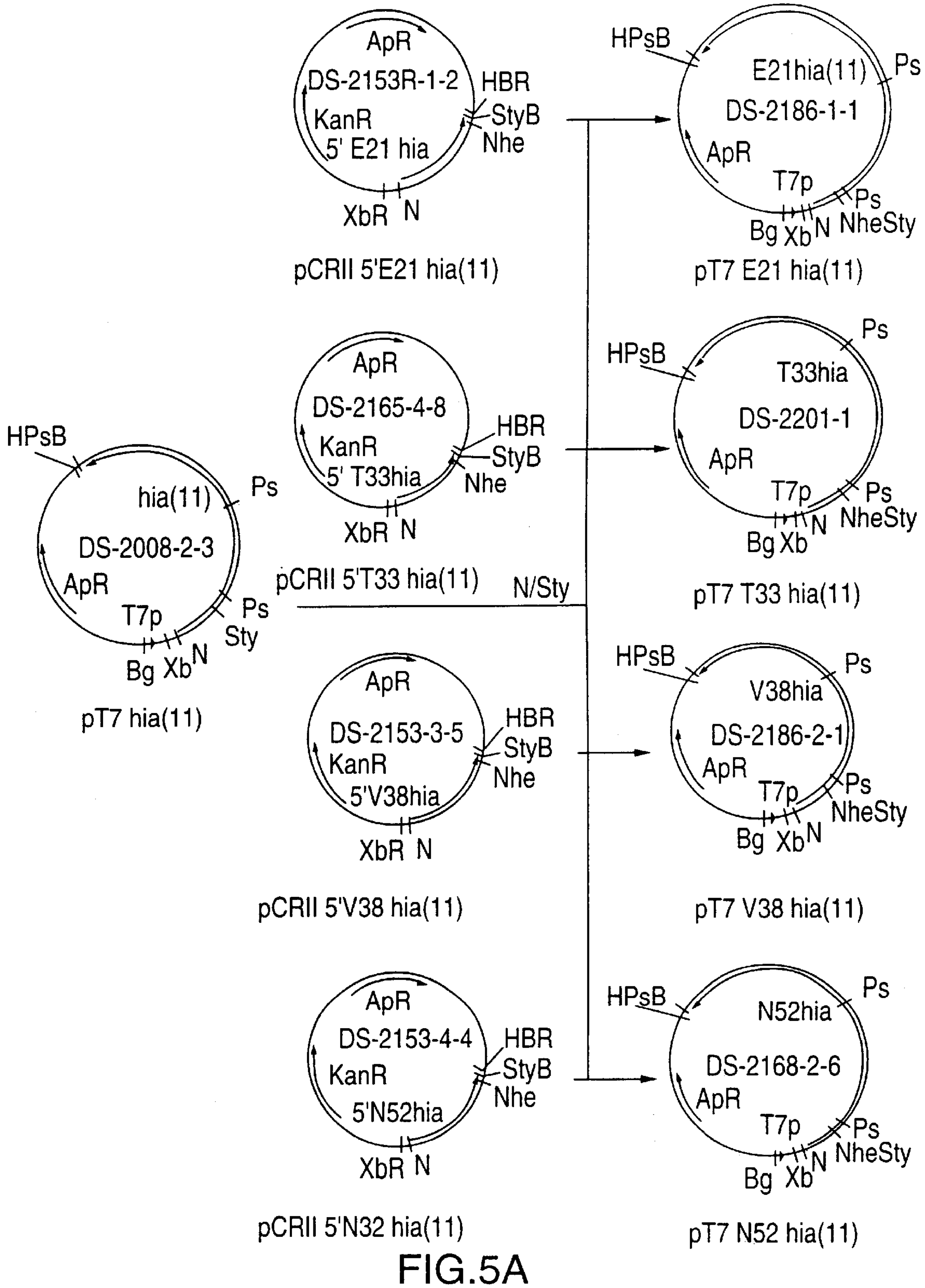
FIG. 5A shows the construction of plasmids expressing truncated hia genes from strain 11. Restriction enzyme sites are: B, BamH I; Bg, Bgl II; H, Hind III; N, Nde I; Nhe, Nhe I; Ps, Pst I; R, EcoR I; Sty, Sty I; Xb, Xba I. Other abbreviations are: T7p, T7 promoter; ApR, ampicillin resistance; KanR, kanamycin resistance.

Referring to FIG. 5A, there is illustrated the construction scheme for the generation of plasmids DS-2186-1-1, DS-2201-1, DS-2186-2-1, and DS-2168-2-6 producing the N-terminal truncated rHia proteins. The oligonucleotides used to PCR amplify the 5'-fragments are shown in FIG. 5B.

Figure 6A:
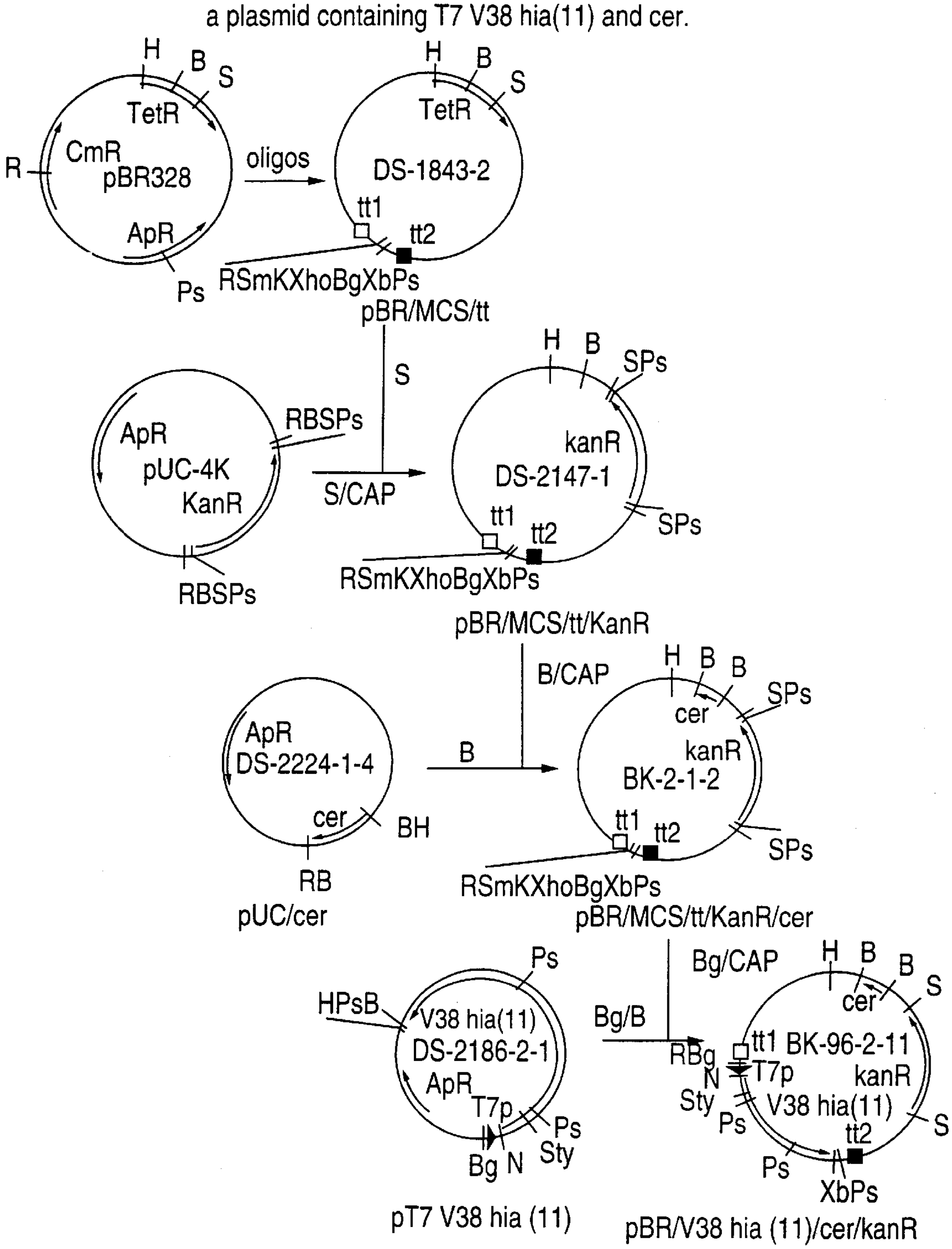
FIG. 6A shows the construction of plasmid BK-96-2-11 that contains the V38 hia gene from NTHi strain 11 and the *E. coli* cer gene. Restriction enzyme sites are: B, BamH I; Bg, Bgl II; K, Kpn I; N, Nde I; P, Pst I; R, EcoR I; S, Sal I; Sm, Sma I; Sty, Sty I; Xb, Xba I; Xho, Xho I. Other abbreviations are: T7p, T7 promoter; ApR, ampicillin resistance; KanR, kanamycin resistance; CAP, calf alkaline phosphatase; tt1 transcription terminator 1 from trpA; tt2, transcription terminator 2 from T7 gene 10.

Referring to FIG. 6A, there is illustrated a construction scheme for the generation of plasmid BK-96-2-11 that contains the V38 hia gene from NTHi strain 11 as well as the *E. coli* cer gene that has been shown to stabilize plasmids. The introduction of the cer gene into plasmids producing toxic proteins, was predicted to enhance protein production. There was an observed change in the morphology of the *E. coli* cells producing full-length rHia in the presence of the cer gene, in that they clumped. This suggests that there was enhanced expression of the adhesin at the surface of the cells that caused the clumping. The expression plasmid BK-96-2-11 also contains transcription terminators upstream and downstream of the T7 V38 hia gene cassette that were predicted to enhance the gene stability. The oligonucleotides used to generate the multiple cloning site and transcription terminators are shown in FIG. 6B.

Figure 7A:
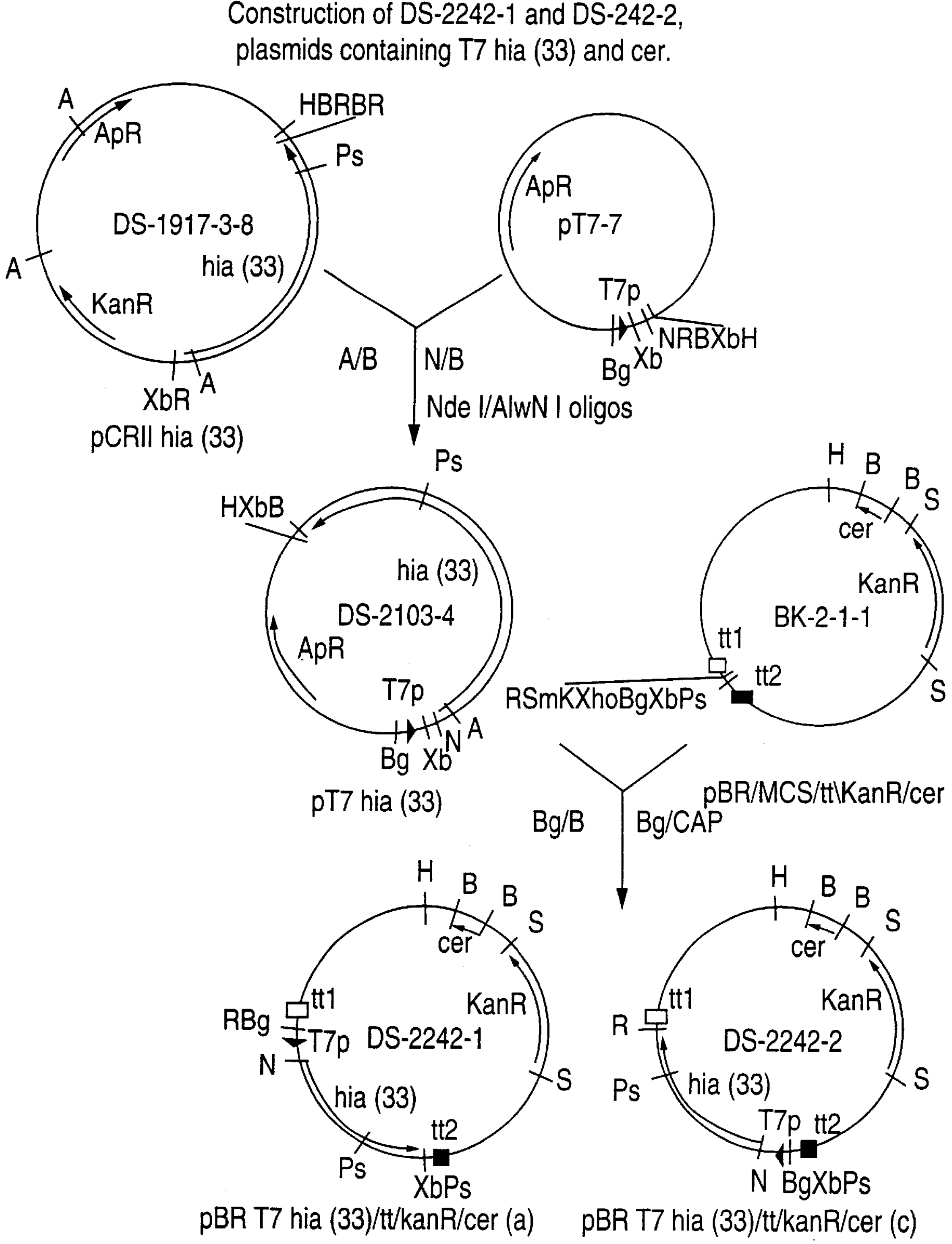
FIG. 7A shows the construction of plasmids DS-2242-1 and DS-2242-2 that contain the T7 promoter and full-length NTHi strain 33 hia gene, the *E. coli* cer gene and the kanamycin resistance gene. Restriction enzyme sites are: A, AlwN I; B, BamH I; Bg, Bgl II; H, Hind III; K, Kpn I; N, Nde I; Ps, Pst I; R, EcoR I; S, Sal I; Sm, Sma I; Xb, Xba I; Xho, Xho I. Other abbreviations are: T7p, T7 promoter; ApR, ampicillin resistance; KanR, kanamycin resistance; tt1, transcription terminator 1 from trpA; tt2, transcription terminator 2 from T7 gene 10.

Referring to FIG. 7A, there is illustrated a construction scheme for plasmids DS-2242-1 and DS-2242-2 that contain a full-length hia gene from non-typeable *Haemophilus influenzae* strain 33, under the influence of the T7 promoter. The expression plasmids also contain the *E. coli* cer gene and transcription terminators upstream and downstream of the T7 hia (33) gene cassette. DS-2242-1 has the terminators coded on the same strand as the T7 hia (33) gene. However, there was no observable difference in the expression of rHia from the two plasmids. The oligonucleotides used to construct the authentic 5'-end of the NTHi strain 33 gene are shown in FIG. 7B.

Figure 8A:
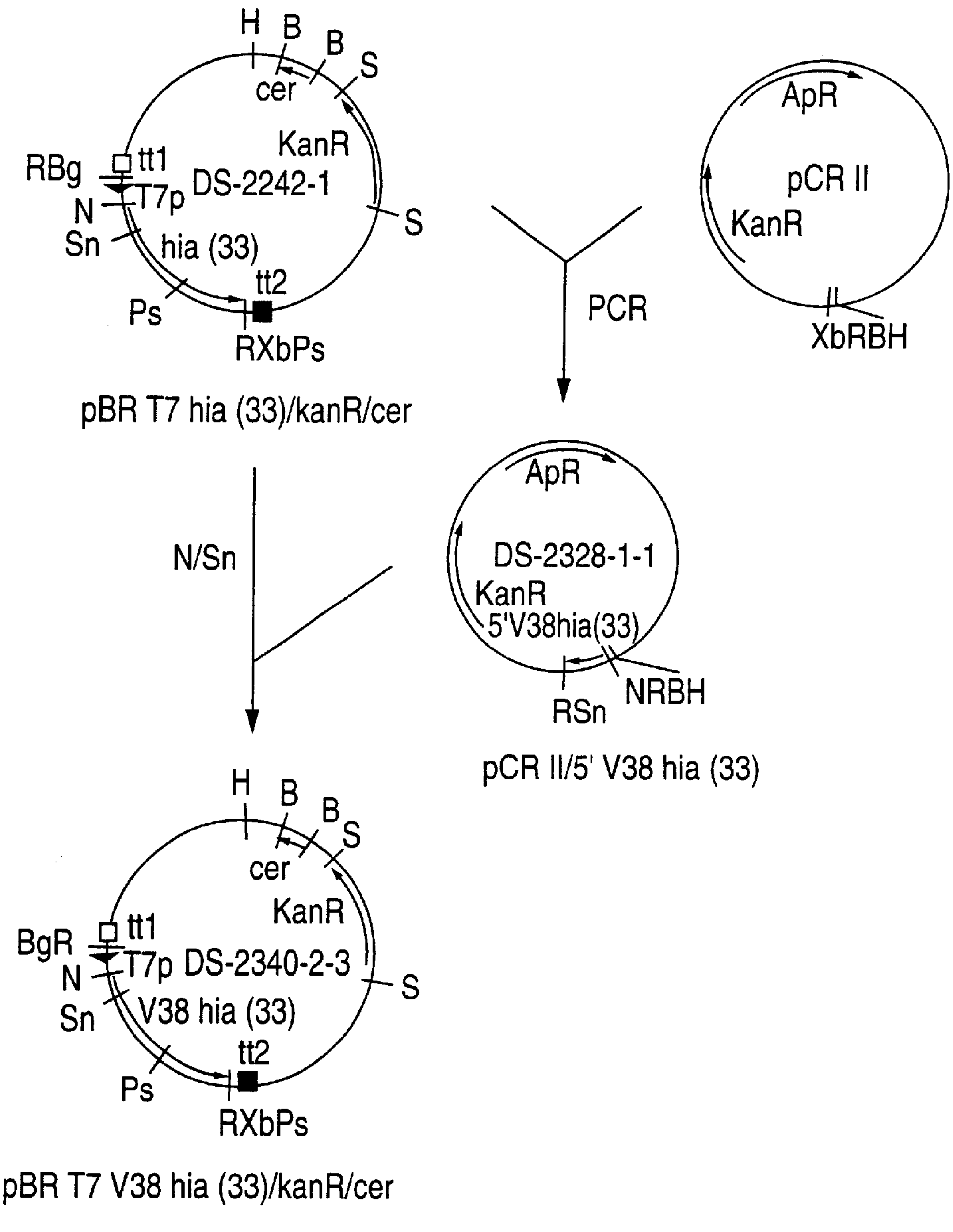
FIG. 8A shows the construction of plasmid DS-2340-2-3 that contains the T7 promoter and the V38 hia gene from strain 33, the *E. coli* cer gene and the kanamycin resistance gene. Restriction enzyme sites are: B, BamH I; Bg, Bgl II; H, Hind III; N, Nde I; Ps; Pst I; R, EcoR I; S, Sal I; Sn, SnaB I; Xb, Xba I. Other abbreviations are: T7p, T7 promoter; ApR, ampicillin resistance; KanR, kanamycin resistance; tt1, transcription terminator 1 from trpA; tt2, transcription terminator 2 from T7 gene 10.

Referring to FIG. 8A, there is illustrated a construction scheme for plasmid DS-2340-2-3 that contains the V38 hia gene from NTHi strain 33 as well as the *E. coli* cer gene. There are also transcription terminators located upstream and downstream of the T7 V38 hia gene cassette, on the same strand. The oligonucleotides used to PCR amplify the NTHi strain 33 hia gene from the V38 codon, are shown in FIG. 8B.

Referring to FIG. 9, there is shown the construction of plasmids DS-2447-2 and DS-2448-17 that contain tandem copies of the T7 V38 hia (11) or T7 V38 hia (33) gene cassettes, respectively.

Figure 10:
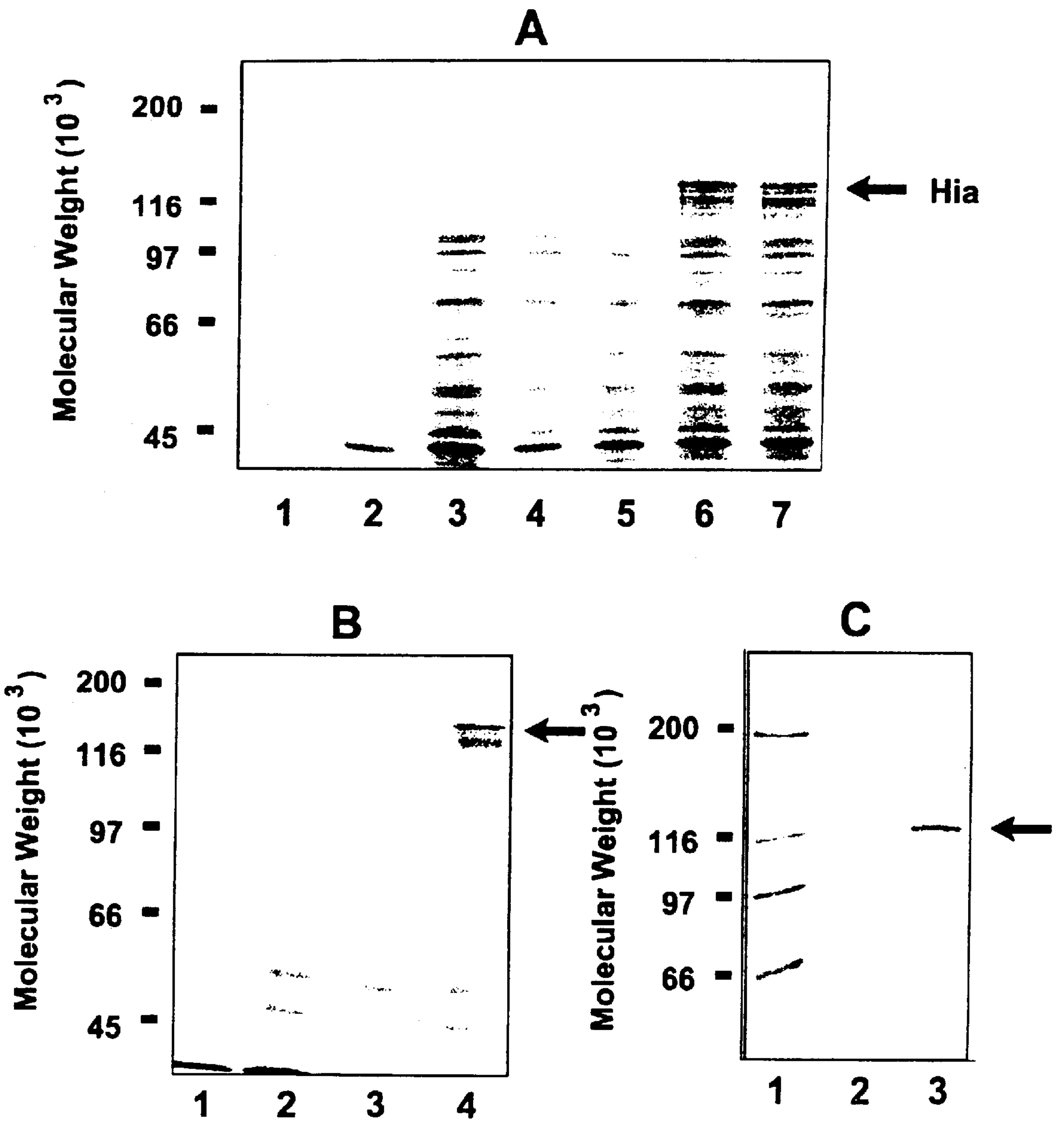
FIGS. 10A–10C shows the expression of rHia. Panel A: lane 1, full-length rHia (11) no induction; lane 2, full-length rhia (11); lane 3, E21 rHia (11); lane 4, T33 rhia (11); lane 5, V38 rHia (11); lane 6, N52 rHia (11). Panel B: lane 1, V38 rHia (11) no induction; lane 2, V38 rHia (11); lane 3, V38 rHia (11)/cer.

Referring to FIG. 10, panel A, there is illustrated the production of rHia proteins from plasmids encoding full-length or truncated hia genes from NTHi strain 11. The production of the full-length rHia (11) protein was very low. There was also low expression observed for the E21 and T33 truncated rHia proteins. However, the V38 and N52 truncated rHia proteins have significantly improved expression levels. As shown in FIG. 10, panel B, the production of V38 rHia (11) appears to be enhanced when the *E. coli* cer gene is added to the expression plasmid.

Figure 11:
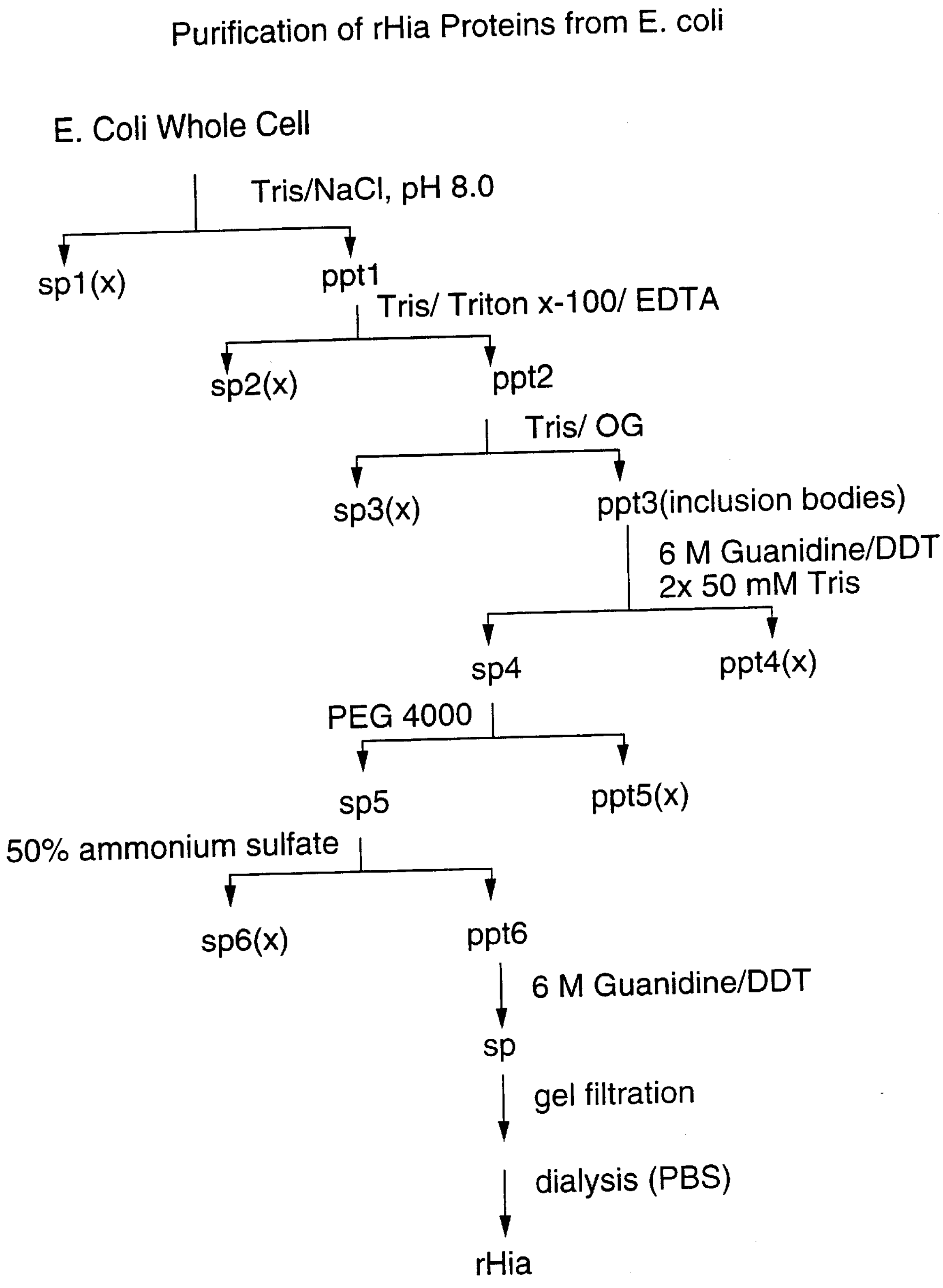
FIG. 11 shows a purification scheme for rHia proteins. Abbreviations are: SP, supernatant; PPT, precipitate; DTT, dithiothreitol; OG, octyl glucoside; (x) means discarded.

Referring to FIG. 11, there is illustrated a purification scheme for rHia proteins, produced as inclusion bodies. Cells were lysed by sonication and the inclusion bodies purified by serial extractions. The inclusion bodies were solubilized in guanidinium chloride and impurities precipitated by the addition of polyethlyene glycol (PEG). Addition of $(NH_4)_2SO_4$ resulted in precipitation of rHia and the crude rHia was further purified by gel filtration.

Figure 12:
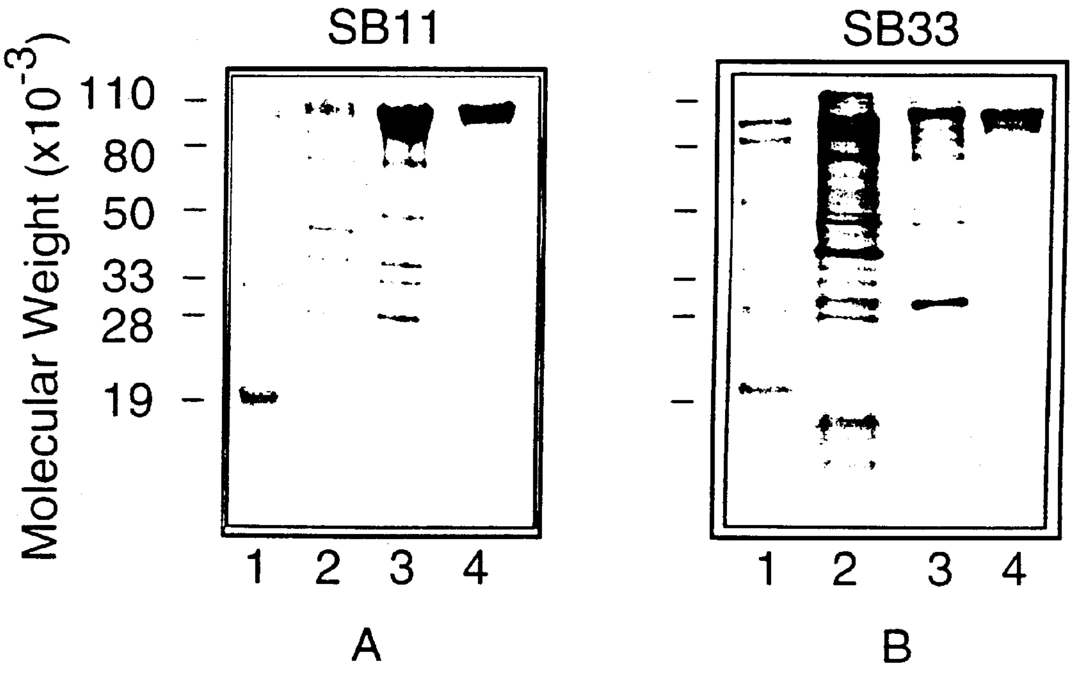
FIGS. 12A–B, having panels A and B, shows the SDS-PAGE analysis of purified rHia. Panel A shows purified V38 rHia protein from strain 11 and panel B shows purified V38 rHia protein from strain 33. Lane 1, molecular weight markers; lane 2, whole-cell lysate; lane 3, crude extract; lane 4, purified rHia protein.

Referring to FIG. 12, there is illustrated the purified V38 rHia proteins from strains 11 and 33. The inclusion bodies are shown in lane 3 and the final purified protein in lane 4. The estimated purity of the purified protein is greater than about 90% as determined by SDS-PAGE densitometry.

Figure 13A:
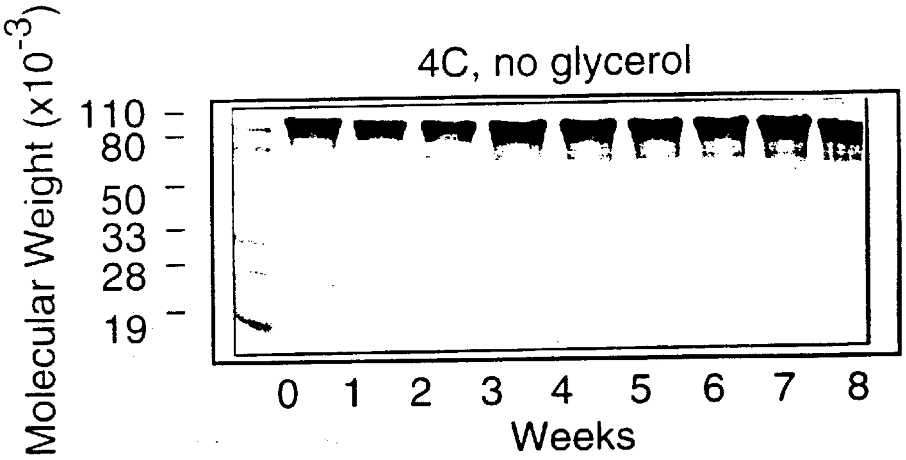
FIGS. 13A–C, having panels A, B and C, shows the stability of V38 rHia (11). Panel A shows samples stored at 4° C. without glycerol. Panel B shows samples stored at 4° C., in the presence of 20% glycerol. Panel C shows samples stored at −20° C. in the presence of 20% glycerol. Lane 0 indicates $t_0$; lanes 1 to 8 indicate samples stored for 1 to 8 weeks.
Figure 13B:
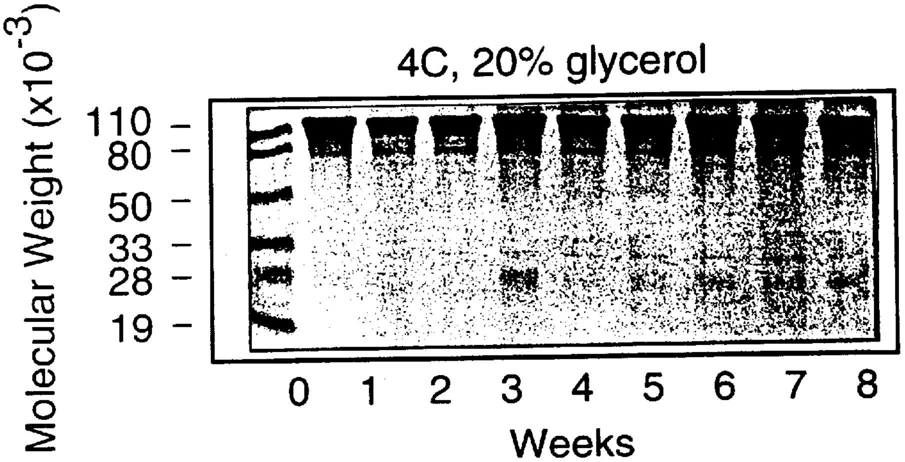
Figure 13C:
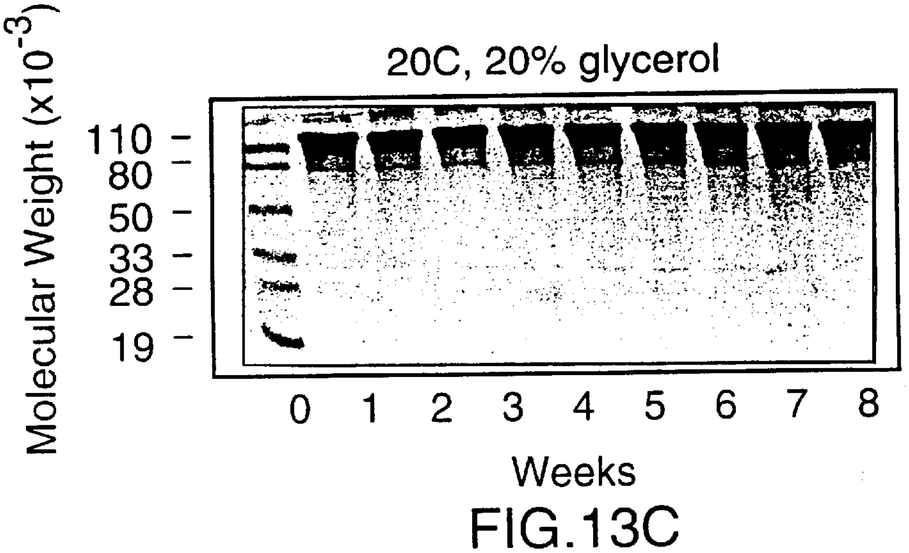

Referring to FIG. 13, there is shown the SDS-PAGE analysis of the stability of rHia proteins produced as described herein during 8 weeks of storage with or without glycerol at 4° C. and with glycerol at −20° C. The protein is stable under any of these conditions.

Figure 14A:
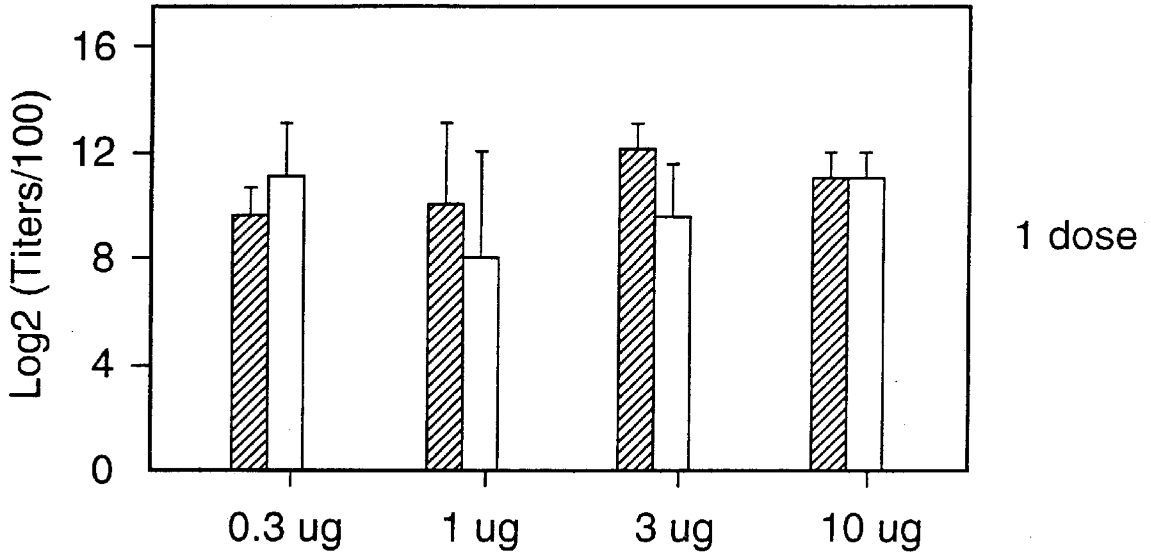
FIGS. 14A–B, having panels A and B, shows the immunogenicity of V38 rHia (11) or V38 rHia (33) in CD-1 mice. Panel A shows the response after a single immunization and panel B shows the response of a prime/boost immunization.
Figure 14B:
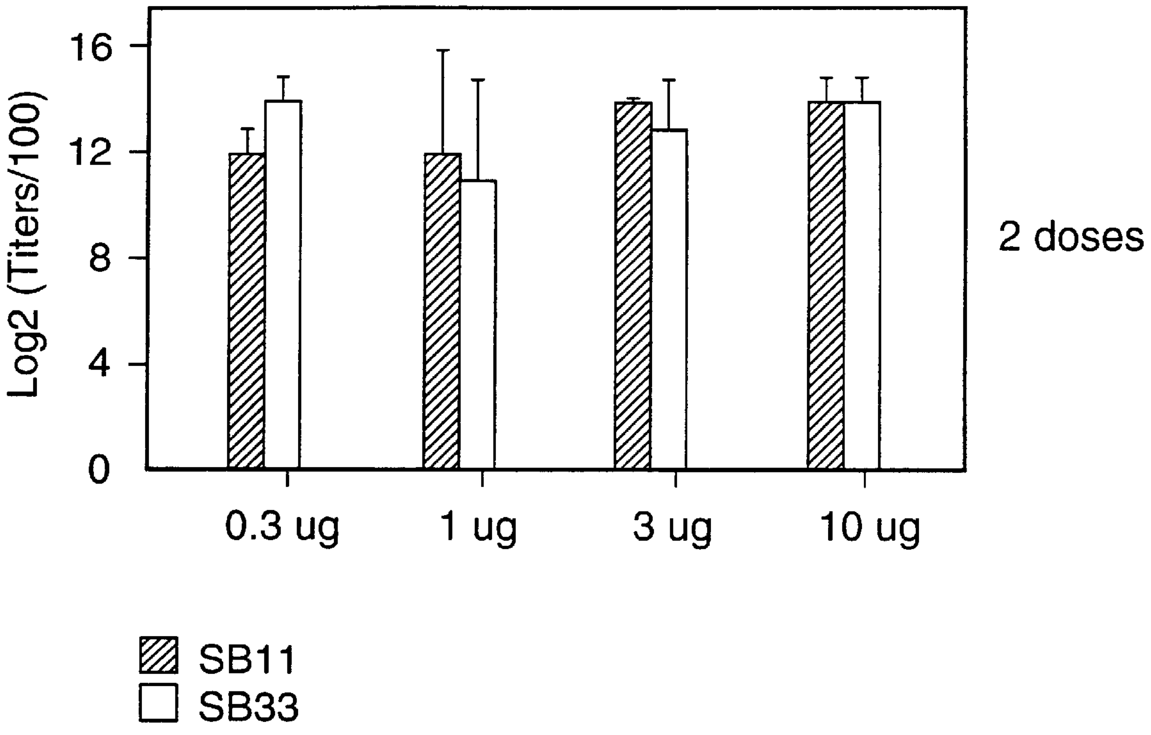
Figure 15A:
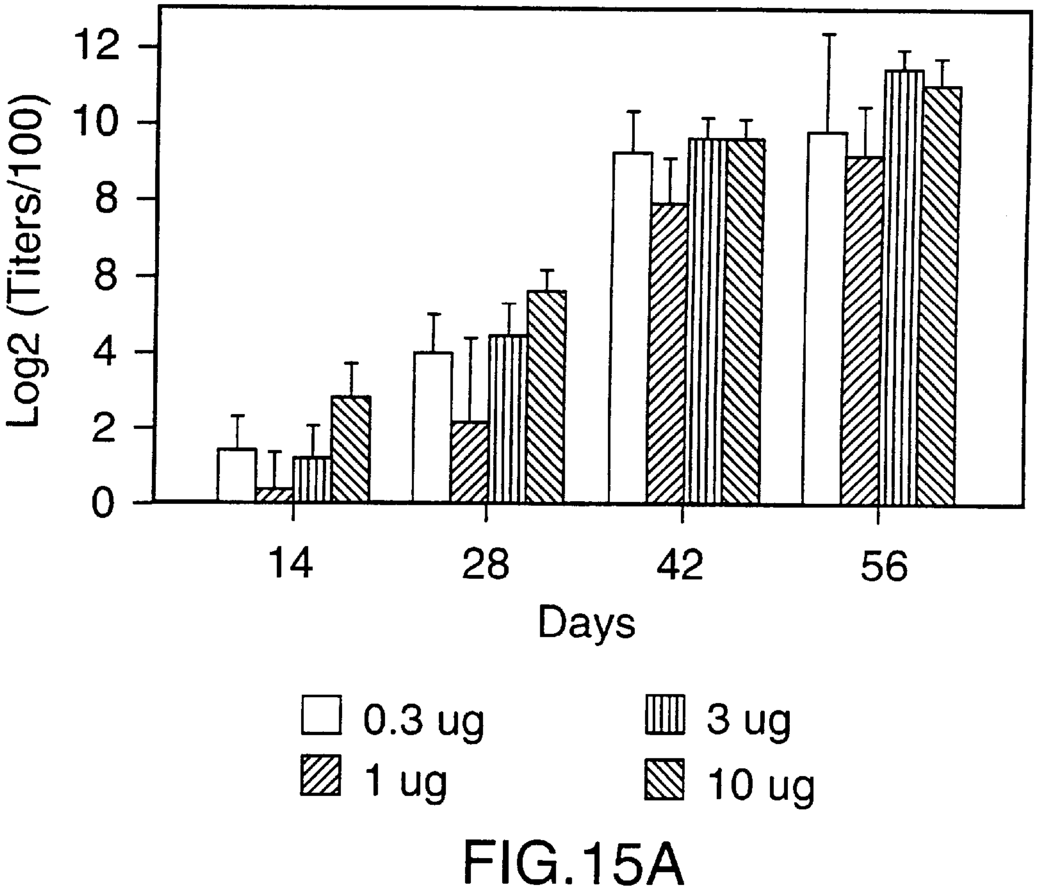
FIGS. 15A and 15B show the immunogenicity of V38 rHia (11) in BALB/c mice and guinea pigs.
Figure 15B:
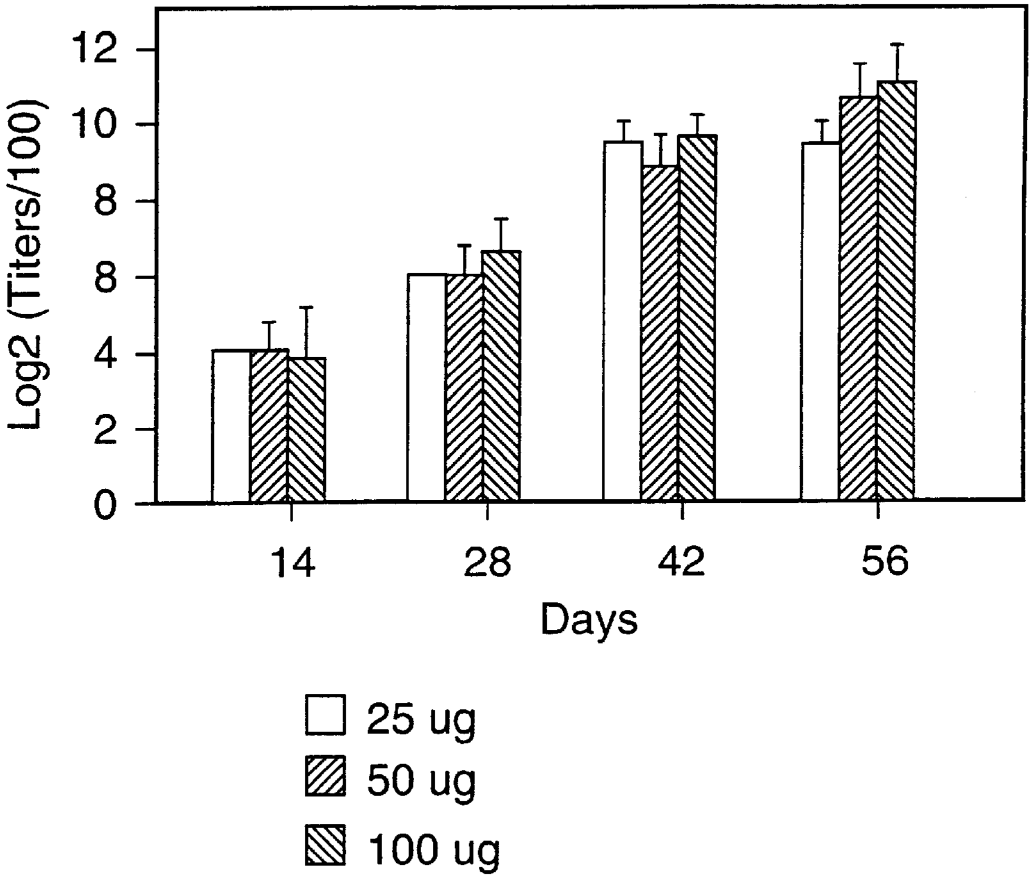

Referring to FIG. 14, there is illustrated the immunogenicity of V38 rHia proteins from strains 11 and 33 in CD-1 mice. At doses from 0.3 to 10 $\mu$g, there is a strong immune response after one or two doses with either protein. There is no obvious dose response at these levels. Similar results were observed in BALB/c mice (FIG. 15A) and in guinea pigs (FIG. 15B), indicating that rHia was very immunogenic, even at 0.3 $\mu$g per dose.

Figure 16:
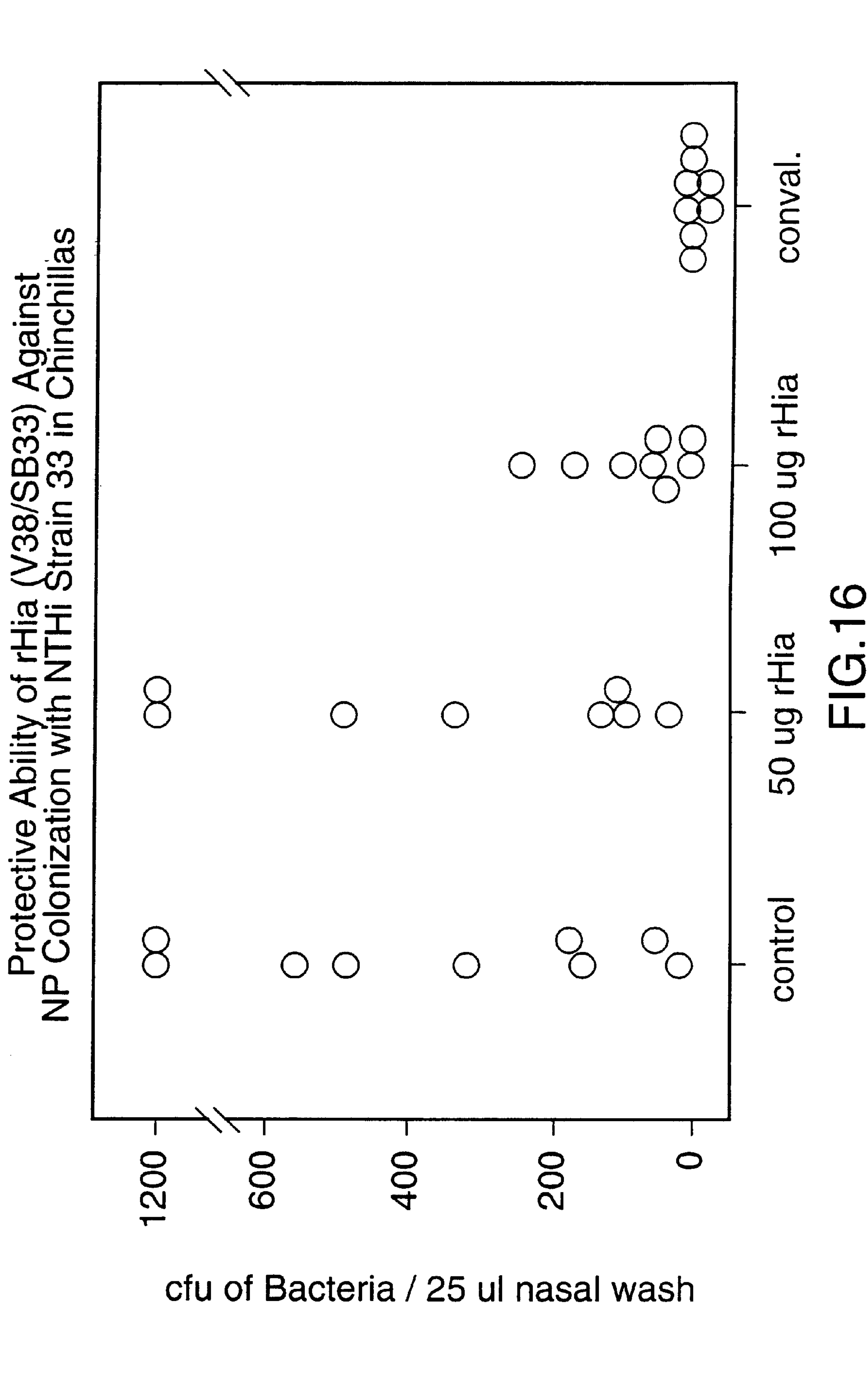
FIG. 16 illustrates the protective ability of V38 rHia (33) against nasopharyngeal colonization in a chinchilla model.

Referring to FIG. 16, there is illustrated the protection afforded by V38 rHia (33) against colonization by NTHi strain 33. As described by Yang et al (ref. 20), a chinchilla nasopharyngeal colonization model has been developed to assess protection against this earliest stage of disease. The model was initially established for NTHi strains that express hmw genes and had to be adapted for NTHi strains expressing hia genes. For the prototype hmw-expressing strain (NTHi 12), $10^2$ to $10^8$ cfu could be used to establish infection, but $5\times10^8$ cfu of NTHi strain 33 was required, and even at this high level no infection could be established with the prototype hia-expressing strain 11. At a 100 μg dose, it is evident that there is partial protection in the immunized cohort, although there is no protection at a 50 μg dose. Such protection against the early stages of disease illustrates the utility of the rHia adhesins as vaccine antigens.

Referring to FIG. 17, there is illustrated the oligonucleotides used to PCR amplify additional *Haemophilus influenzae* hia genes. The sequences are based upon the conserved amino and carboxy terminal sequences of the Hia and Hsf proteins.

Referring to FIG. 18, there is illustrated the complete nucleotide sequence and deduced amino acid sequence of the NTHi strain 33 hia gene. Referring to FIG. 19, there is illustrated the complete nucleotide sequence and deduced amino acid sequence of the NTHi strain 32 hia gene. Referring to FIG. 20, there is illustrated the complete nucleotide sequence and deduced amino acid sequence of the NTHi strain 29 hia gene. Referring to FIG. 21, there is illustrated the complete nucleotide sequence and deduced amino acid sequence of the NTHi strain M4071 hia gene. Referring to FIG. 22, there is illustrated the complete nucleotide sequence and deduced amino acid sequence of the NTHi strain K9 hia gene. Referring to FIG. 23, there is illustrated the complete nucleotide sequence and deduced amino acid sequence of the NTHi strain K22 hia gene. Referring to FIG. 24, there is illustrated the complete nucleotide sequence and deduced amino acid sequence of the *Haemophilus influenzae* type c strain API hia gene. Referring to FIG. 25, there is illustrated the complete nucleotide sequence and deduced amino acid sequence of the hia locus from NTHi strain 12. The PCR amplified fragment contains the 3'-end of a gene related to HI1733 gene of the *Haemophilus influenzae* type d strain Rd genome joined to the 3'-end of an hia gene. An alignment of the upstream ORF with the HI1733 protein is shown in FIG. 27.

FIG. 26 shows the complete nucleotide sequence and the deduced amino acid sequence of the Hia gene from NTHi strain 11, as published in the aforementioned U.S. Pat. No. 5,646,259.

Referring to FIG. 28, there is illustrated an alignment of the deduced protein sequences from Hsf, Hia, and partial sequences of the *M. catarrhalis* 200 kDa protein.

It is clearly apparent to one skilled in the art, that the various embodiments of the present invention have use in applications in the fields of vaccination, diagnosis, treatment of Haemophilus infection and the generation of immunological agents. A further non-limiting discussion of such uses is further presented below.

Vaccine Preparation and Use

Immunogenic compositions, suitable to be used as vaccines, may be prepared from immunogenic recombinant *Haemophilus influenzae* adhesin (rHia) proteins of non-typeable Haemophilus strains, immunogenic analogs and fragments thereof and/or immunogenic peptides as disclosed herein. The vaccine elicits an immune response which produces antibodies, including anti-rHia antibodies and antibodies that are opsonizing or bactericidal.

Immunogenic compositions, including vaccines, may be prepared as injectables, as liquid solutions or emulsions. The rHia protein, immunogenic analogs and fragments thereof and/or immunogenic peptides may be mixed with pharmaceutically acceptable excipients which are compatible with the rHia protein, immunogenic fragments analogs or immunogenic peptides. Such excipients may include, water, saline, dextrose, glycerol, ethanol and combinations thereof.

The immunogenic compositions and vaccines may further contain auxiliary substances such as wetting or emulsifying agents, pH buffering agents, or adjuvants to enhance the effectiveness of the vaccines.

Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes.

The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al).

Alternatively, other modes of administration including suppositories and oral formulations may be desirable. For suppositories, binders and carriers may include, for example polyalkalene glycols or triglycerides. Oral formulations may include normally employed incipients such as, for example pharmaceutical grades of saccharine, cellulose and magnesium carbonate. These compositions take the form of solutions, suspensions, tablets, pills, capsules, sustained release formulations or powders and contain about 1 to 95% of the rHia protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the rHia, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the rHia proteins of non-typeable Haemophilus may also be used directly for immunization by administration of the DNA directly, for example by injection for genetic immunization or by constructing a live vector, such as Salmonella, BCG, adenovirus, poxvirus, vaccinia or poliovirus, containing the nucleic acid molecule. A discussion of some live vectors that have been used to carry heterologous antigens to the immune system is contained in, for example, O'Hagan (1992) (ref. 16). Processes for the direct injection of DNA into test subjects for genetic immunization are described in, for example, Ulmer et al., 1993 (ref. 17).

Immunogenicity can be significantly improved if the antigens are co-administered with adjuvants, commonly used as an 0.05 to 1.0 percent solution in phosphate— buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to antigens. These include the specific adjuvants detailed above as well as saponins complexed to membrane protein antigens (immune stimulating complexes), pluronic polymers with mineral oil, killed mycobacteria and mineral oil, Freund's complete adjuvants, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 18) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990 (ref. 19), reported that octadecyl esters of aromatic amino acids complexed with a recombinant hepatitis B surface antigen, enhanced the host immune responses against hepatitis B virus.

Immunoassays

The rHia protein of a non-typeable strain of Haemophilus, analogs and fragments thereof produced according to the present invention are useful as immunogens, as antigens in immunoassays including enzyme-linked immunosorbent assay (ELISA), RIAs and other non-enzyme linked antibody binding assays or procedures known in the art for the detection of anti-bacterial, Haemophilus, and/or Hia antibodies. In ELISA assays, the Hia protein, analogs and fragments are immobilized onto a selected surface, for example a surface capable of binding proteins or peptides, such as the wells of a polystyrene microtiter plate. After washing to remove incompletely adsorbed Hia protein, analogs and/or fragments, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to about 4 hours, at temperature such as of the order of about 25° to about 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound Hia protein, analogs and/or fragments, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity, that will generate, for example, a color development, upon incubating with an appropriate chromogenic substrate. Quantification may then achieved by measuring the degree of color generation using, for example, a visible spectra spectrophotometer.

Use of Sequences as Hybridization Probes

The nucleotide sequences of the present invention, comprising the newly-isolated and characterized sequences of the hia genes, allow for the identification and cloning of the hia genes from other non-typeable strains of Haemophilus.

The nucleotide sequences comprising the sequence of hia genes of the present invention are useful for their ability to selectively form duplex molecules with complementary stretches of other hia genes. Depending on the application, a variety of hybridization conditions may be employed to achieve varying degrees of selectivity of the probe toward the other hia genes in other strains of non-typeable Haemophilus. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between 20° C. to 55° C. Hybridization conditions can also be rendered more stringent by the addition of increasing amount of formamide, to destabilize the hybrid duplex. Thus, particular hybridization conditions can be readily manipulated, and will generally be a method of choice depending on the desired results. In general, convenient hybridization temperatures in the presence of 50% formamide and 0.15 M NaCl are: 42° C. for an hia gene which is about 95 to 100% homologous to the target nucleic acid fragment, 37° C. for about 90 to 95 homology and 32° C. for about 8 to 90% homology.

In a clinical diagnostic embodiment, the nucleic acid sequences of the hia genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing Hia genes sequences.

The nucleic acid sequences of Hia genes of the present invention are useful as hybridization probes in solution hybridizations and in embodiments employing solid-phase procedures. In embodiments involving solid-phase procedures the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hia genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Haemophilus. The selected probe may be at least 18 bp in length and may be in the range of 30 bp to 90 bp long.

Expression of the *Haemphilus influenzae* adhesin Genes

Plasmid vectors containing replicon and control sequences which are derived from species compatible with the host cell may be used for the expression of the hia genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system employed herein in preferred embodiments (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the Hia protein and immunological fragments or analogs thereof include *E. coli*, Bordetella species, Bacillus species, Haemophilus, fungi, yeast or the baculovirus expression system may be used. *E. coli* is the preferred host used herein.

In accordance with this invention, it is preferred to produce the Hia proteins by recombinant methods, particularly when the naturally occurring Hia protein as purified from a culture of a species of Haemophilus may include trace amounts of toxic materials or other contaminants. This problem can be avoided by using recombinantly produced Hia protein in heterologous systems which can be isolated from the host in a manner to minimize contaminants in the purified materials, specifically employing the constructs described herein.

Biological Deposits

A vector that contains nucleic acid coding for a high molecular weight protein of a non-typeable strain of Haemophilus that is described and referred to herein has been deposited with the America Type Culture Collection (ATCC) located at 10801 University Boulevard, Manassas, Va. 20110-2209, USA, pursuant the Budapest Treaty and prior to the filing of this application. Samples of the deposited vector will become available to the public and all restrictions imposed or access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

| Deposit Summary | | |
|---|---|---|
| Plasmid | ATCC | Deposit Date |
| BK-96-2-11 | 203771 | February 11, 1999 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the construction of plasmid DS-2008-2-3 that expresses full-length rHia proteins from NTHi strain 11.

Chromosomal DNA was purified from NTHi strain 11 and the full-length hia gene was PCR amplified using the oligonucleotides (5038.SL and 5039.SL) described in FIG. 1B. An Nde I site was engineered at the 5'-end of the gene and a BamH I site was engineered at the 3'-end for cloning into the pT7-7 expression vector (ref. 21). The amplified fragment was digested with Nde I/BamH I and cloned into pT7-7 that had been digested with the same enzymes. Plasmid DS-2008-2-3 contains a 3.4 kb strain 11 hia gene downstream of the T7 promoter (FIG. 1A). The plasmid was used to express recombinant Hia (Example 9 below).

Example 2

This Example illustrates the recognition of rHia by anti-native *Moraxella catarrhalis* high molecular weight adhesin antibody.

There is some sequence conservation observed between the *Haemophilus influenzae* Hia proteins and a *Moraxella catarrhalis* high molecular weight adhesin identified as the *M. catarrhalis* 200 kDa protein in aforementioned U.S. Pat. No. 5,808,024 (FIG. 28). The native *M. catarrhalis* 200 kDa protein was gel purified as described in U.S. Pat. No. 5,808,024 and guinea pig anti-native 200 kDa antibody was generated. The T7 hia gene was expressed from plasmid DS-2008-2-3 and the cell culture containing the rHia protein was electroblotted to nitrocellulose membrane. Immunoblot analysis using anti-native 200 kDa antibody showed that. the antibody recognized the rHia protein, as seen in FIG. 2.

Example 3

This Example describes the construction of plasmids DS-2092-1 and DS-2092-40 that contain tandem copies of T7 hia (11) gene cassettes.

In order to improve the production of full-length recombinant Hia protein, tandem copies of the T7 hia gene cassette containing the strain 11 hia gene (Example 1) were inserted into a single vector. Plasmid DS-2008-2-3 was linearized with Bgl II and dephosphorylated. Plasmid DS-2008-2-3 was also digested with Bgl II and BamH I to excise the T7 hia gene cassette. The T7 hia fragment was ligated into the linearized vector to generate plasmid DS-2092-1 that contains two copies of the T7 hia gene in the anti-clockwise orientation (a,a) and plasmid DS-2092-40 that contains tandem copies in opposite orientations (a,c) (FIG. 3). There was no obvious improvement in expression of rHia from either construct (see Example 9 below).

Example 4

This Example describes the construction of plasmids expressing truncated strain 11 hia genes.

The production of the rhia protein from single or tandem copies of the T7 hia gene cassette was very low and the protein seemed to be toxic to *E. coli* (as described below in Example 9). Since *H. influenzae* Hia is a surface-exposed adhesin molecule, it must either utilize a signal sequence or accessory protein(s) for secretion, but there are no known accessory genes involved. If the signal sequence were removed for expression of the recombinant protein in *E. coli*, the rHia might be expressed as inclusion bodies and the toxic effect reduced. A putative signal sequence and cleavage sites were identified and four constructs expressing N-terminally truncated rHia proteins were designed (FIG. 4). There is a unique Sty I site in the strain 11 hia gene about 500 bp from the start codon. Plasmid DS-2008-2-3 was digested with Nde I and Sty I and the 5.7 kb vector fragment purified (FIG. 5A). PCR primers were designed to amplify from the truncation site to the Sty I site and a unique Nhe I site was introduced into the antisense primer for screening truncated clones (FIG. 5B). The amplified fragments were subcloned into pCRII for easier manipulation, generating plasmids DS-2153R-1-2 (E21), DS-2165-4-8 (T33), DS-2153-3-5 (V38), and DS-2153-4-4 (N52). The pCRII hia plasmids were digested with Nde I and Sty I and the fragments ligated with the vector piece from DS-2008-2-3. Plasmids DS-2186-1-1 (E21), DS-2201-1 (T33), DS-2186-2-1 (V38), and DS-2168-2-6 (N52) were generated that contained the T7 promoter and truncated hia genes as indicated in parentheses. These plasmids were used to express recombinant Hia (see Example 9 below).

Example 5

This Example describes the construction of plasmid BK-96-2-11 that contains the T7 V38 hia (11) cassette, the *E. coli* cer gene, and the kanamycin resistance gene.

Plasmid DS-1843-2 is a pBR328-based plasmid in which a multiple cloning site and two transcription terminators have been introduced on oligonucleotides, between the EcoR I and Pst I sites, thus destroying both the chloramphenicol and ampicillin resistance genes (FIG. 6B). The kanamycin resistance gene from pUC-4K was inserted at the Sal I site, to generate plasmid DS-2147-1 that is kanamycin resistant and tetracycline sensitive. Plasmid DS-2224-1-4 is a pUC plasmid containing a synthetic *E. coli* cer gene (ref. 15) constructed from oligonucleotides and flanked by BamH I sites. The 290 bp BamH I fragment of the cer gene was inserted into the BamH I site of DS-2147-1 creating plasmid BK-2-1-2. This pBR-based plasmid thus contains a multiple cloning site, the kanamycin resistance gene and the cer gene. Plasmid BK-2-1-2 was linearized with Bgl II and dephosphorylated. Plasmid DS-2186-2-1 was digested with Bgl II and BamH I and the 3.6 kb T7 V38 hia fragment was inserted into BK-2-1-2, creating plasmid BK-96-2-11 (FIG. 6A).

Example 6

This Example describes the construction of plasmids DS-2242-1 and DS-2242-2 that express the full-length NTHi strain 33 hia gene in the presence of the *E. coli* cer gene.

Chromosomal DNA was purified from NTHi strain 33 and PCR amplification was performed using oligonucleotides 5039.SL and 5040.SL (FIG. 17). The sense primer (5040.SL) was designed based upon the 5'-flanking sequence of strain 11 hia and the conserved amino terminal sequences of the NTHi Hia and Hib Hsf proteins. The antisense primer (5039.SL) was the same as that described in Example 1 and was based upon the conserved carboxy terminal sequences of the Hia and Hsf proteins. The 3 kb strain 33 hia PCR fragment was cloned into pCR II, generating plasmid DS-1917-3-8.

In order to express the full-length strain 33 hia gene, approximately 106 bp of the 5'-end of the gene was synthesized from oligonucleotides, from the start codon to an AlwN I site (FIG. 7B). Plasmid DS-1917-3-8 was digested with AlwN I and BamH I and the approximately 2.9 kb fragment containing the hia gene was purified. Plasmid pT7-7 was digested with Nde I and BamH I. The Nde I - AlwN I oligonucleotides and AlwN I-BamH I hia fragment were ligated into the pT7-7 vector, generating plasmid DS-2103-4.

In order to include the *E. coli* cer gene and utilize kanamycin selection, the Bgl II-BamH I fragment containing the T7 hia (33) gene cassette was excised from DS-2103-4 and cloned into BK-2-1-1 that had been digested with Bgl II and dephosphorylated. Plasmids DS-2242-1 and DS-2242-2 contain single copies of the T7 hia (33) gene cassette in opposite orientations, the *E. coli* cer gene, and the kanamycin resistance gene (FIG. 7A).

Example 7

This Example describes the construction of plasmid DS-2340-2-3 that contains a T7 hia gene cassette with a truncated V38 strain 33 hia gene, the *E. coli* cer gene, and the kanamycin resistance gene.

PCR primers were designed to amplify a 250 bp fragment of the 5'-end of the NTHi strain 33 hia gene from a V38 start codon up to an internal SnaB I site. An Nde I site was added at the 5'-end for cloning purposes and the fragment was amplified using plasmid DS-2242-1 as template. The construction scheme is shown in FIG. 8A and the PCR primers are shown in FIG. 8B. The fragment was cloned into pCR II generating plasmid DS-2328-1-1. DS-2242-1 was digested with Nde I and SnaB I and the 8.5 kb vector fragment purified. DS-2328-1-1 was digested with Nde I and SnaB I and the 0.25 kb 5' hia fragment was ligated with the 8.5 kb vector fragment from DS-2242-1, to generate plasmid DS-2340-2-3.

Example 8

This Example illustrates the construction of plasmids DS-2447-2 and DS-2448-17 that contain tandem copies of T7 V38 hia (11) or T7 V38 hia (33) gene cassettes, respectively, the *E. coli* cer gene, and a kanamycin resistance gene.

Figure 9A:
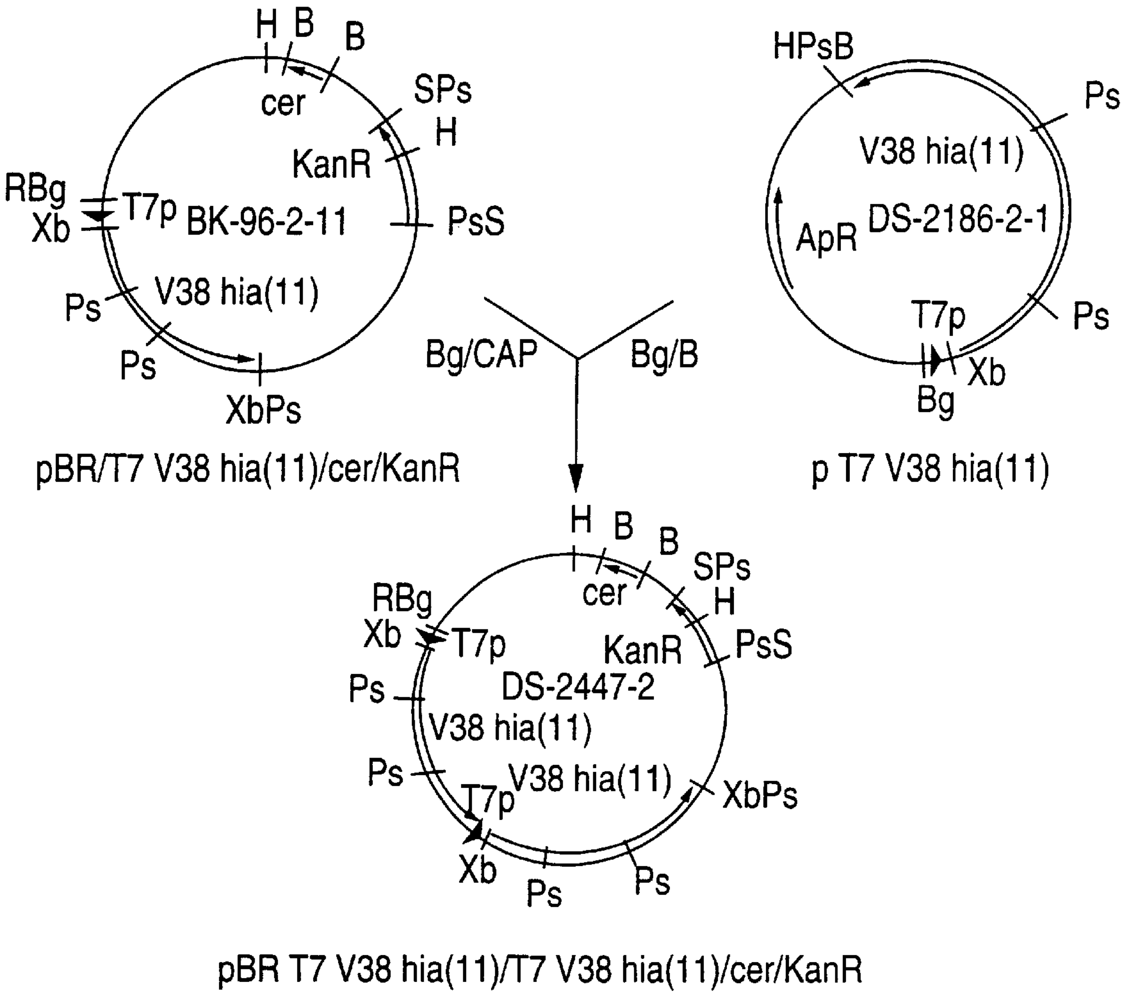
FIGS. 9A and 9B show the construction of plasmids DS-2447-2 and DS-2448-17, that contain tandem copies of the T7 V38 hia (11) and T7 V38 hia (33) genes, respectively. Restriction enzyme sites are: B, BamH I; Bg, Bgl II; H, Hind III; Ps; Pst I; R, EcoR I; S, Sal I; Xb, Xba I. Other abbreviations are: T7p, T7 promoter; ApR, ampicillin resistance; KanR, kanamycin resistance; CAP, calf alkaline phosphatase; tt1, transcription terminator 1 from trpA; tt2, transcription terminator 2 from T7 gene 10.

Plasmid BK-96-2-11, that contains a T7 V38 hia (11) gene cassette, was linearized with Bgl II and dephosphorylated. The Bgl II-BamH I T7 V38 hia (11) gene cassette from DS-2186-2-1 was ligated into BK-96-2-11, generating plasmid DS-2447-2 that contains tandem copies of the T7 V38 hia (11) gene in the same orientation (FIG. 9A).

Figure 9B:
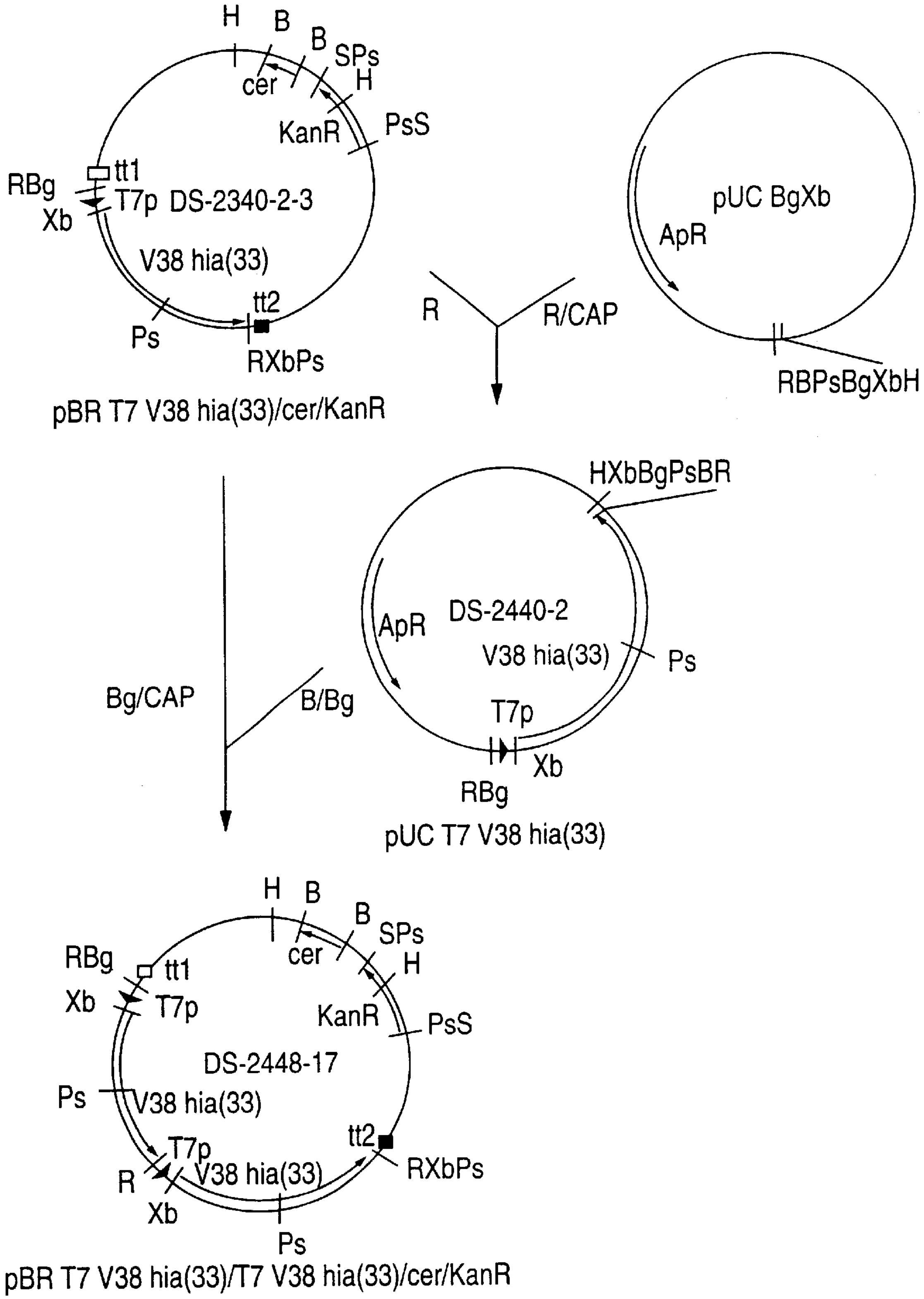

Plasmid DS-2340-2-3 was digested with EcoR I and the T7 V38 hia (33) gene cassette was subcloned into pUC-BgXb that had been digested with EcoR I and dephosphorylated. The resultant plasmid, DS-2440-2 was digested with Bgl II and BamH I to release the T7 V38 hia (33) cassette that was ligated with DS-2340-2-3 that had been linearized with Bgl II and dephosphorylated. Plasmid DS-2448-17 contains tandem T7 V38 hia(33) genes in the same orientation (FIG. 9B).

Example 9

This Example illustrates the expression of full-length and truncated recombinant hia genes.

DNA from expression plasmids prepared as described in the preceding Examples, was introduced into electrocompetent *E. coli* BL21 (DE3) cells using a BioRad electroporator. Cells were grown at 37° C. in NZCYM medium using the appropriate antibiotic selection to A 578 of 0.3 before the addition of lactose to 1.0% for 4 hours. Samples were adjusted to 0.2 OD/$\mu$l with SDS-PAGE lysis + loading buffer and the same amount of each protein sample was loaded onto SDS-PAGE gels (ref. 22). FIG. 10 illustrates the relative production of rHia (11) proteins from various constructs. As seen in panel A, there is an increase in production with decreased size of rHia. V38-(lane 5) and N52-truncated rHia (lane 6) have significantly higher expression levels than their longer counterparts (lanes 2, 3, 4). In addition, panel B demonstrates that the production of V38 rHia is apparently increased in the presence of the cer gene.

Example 10

This Example illustrates the purification of rHia proteins.

All the recombinant Hia proteins were expressed as inclusion bodies in *E. coli* and were purified by the same procedure (FIG. 11). *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet ($PPT_1$) was further extracted, in 50 ml of 50 mM Tris-HCl, pH 8.0 containing 0.5% Triton X-100 and 10 mM EDTA, then centrifuged at 20,000 g for 30 min, and the supernatant was discarded. The pellet ($PPT_2$) was further extracted in 50 ml of 50 mM Tris-HCl, pH 8.0, containing 1% octylglucoside, then centrifuged at 20,000 g for 30 min, and the supernatant was discarded.

The resultant pellet ($PPT_3$) obtained after the above extractions contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant ($SUP_4$) was precipitated with polyethylene glycol (PEG) 4000 at a final concentration of 7%. The resultant pellet ($PPT_5$) was removed by centrifugation at 20,000 g for 30 min and the supernatant was precipitated by $(NH_4)_2SO_4$ at 50% saturation. The $(NH_4)_2SO_4$ precipitate was collected by centrifugation at 20,000 g for 30 min. The resultant pellet ($PPT_6$) was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rhia were pooled and dialysed overnight at 4° C. against PBS, then centrifuged at 20,000 g for 30 min. The protein remained soluble under these conditions and glycerol was added to the rHia preparation at a final concentration of 20% for storage at −20° C. SDS-PAGE analysis of purified V38 rHia (11) and V38 rHia (33) is illustrated in FIG. 12. The average yield of the purified V38 rHia proteins is about 10 mg $L^{-1}$ culture.

In order to study the stability of rHia, the purified V38 rhia (11) protein was stored at 4° C. with or without glycerol and at −20° C. with glycerol. The protein was found to be stable under all three conditions and remained intact for at least eight weeks with repeated freezing and thawing (FIG. 13).

Example 11

This Example illustrates the immunogenicity of V38 rHia (11) and V38 rHia (33) proteins.

Hyperimmune antisera against rHia proteins were produced by immunizing two guinea pigs (Charles River) intramuscularly (i.m.) with 5 μg doses of antigen emulsified in complete Freund's adjuvant (CFA, Difco) on day 1. Animals were boosted on days 14 and 28 with 5 μg doses of protein in incomplete Freund's adjuvant (IFA) and sera were collected on day 42. Anti-Hib strain MinnA and anti-Haemophilus type a strain ATCC 9006 antisera were generated using the same protocol, except that a heat-inactivated bacterial preparation was used as the immunogen ($1\times10^8$ cfu per dose).

To study the immunogenicity of the V38 rHia proteins, groups of five CD-1 mice (Charles River, Quebec) were immunized s.c. on days 1 and 28 with 0.3, 1, 3, and 10 μg of antigen, in the presence of $AlPO_4$ (alum) (1.5 mg per dose). Blood samples were collected on days 1, 28 and 42. Mice generated significant anti-V38 rhia antibody responses even with a single injection of 0.3 μg antigen (FIG. 14, panel A), suggesting that both proteins had retained immunogenicity after inclusion body extraction and solubilization. No statistically significant difference was found in the antibody titers induced by the V38 rHia proteins derived from strains 11 or 33.

To study the immunogenicity of the V38 rHia (11) protein in BALB/c mice, groups of five animals (Charles River, Quebec) were immunized s.c. on days 1, 28 and 42 with 0.3, 1, 3, and 10 μg of antigen, in the presence of $AlPO_4$ (1.5 mg per dose). Blood samples were collected on days 1, 14, 28, 42 and 56. High antibody titers were observed in all groups, indicating that the protein is very immunogenic even at 0.3 μg per dose (FIG. 15, panel A).

To study the immunogenicity of the V38 rHia (11) protein in guinea pigs, groups of five animals (Charles River, Quebec) were immunized s.c. on days 1, 28 and 42 with 0.3, 1, 3, and 10 μg of antigen, in the presence of $AlPO_4$ (1.5 mg per dose). Blood samples were collected on days 1, 14, 28, 42 and 56. High antibody titers were observed in all groups, indicating that the protein is also very immunogenic in guinea pigs (FIG. 15, panel B).

Example 12

This Example illustrates the analysis of the protection afforded by anti-rHia antibodies in passive infant rat models of bacteremia.

Pregnant Wistar rats were purchased from Charles River. In the *H. influenzae* type b bacteremia model, groups of 6 to 10 five-day old infant rats were injected s.c. in the dorsal region with 0.1 ml of guinea pig anti-rHia or anti-strain MinnA antiserum. The control animals received injections with pre-immune sera only. Twenty hours later, the animals were challenged intraperitoneally (i.p.) with 200 to 240 colony-forming units (cfu) of freshly grown Hib strain MinnA (0.1 ml). Blood samples were collected 20 h post-challenge, via cardiac puncture under isoflurane anesthesia and plated on chocolate agar plates. Colonies were counted after one day and the results were statistically analyzed by Fisher's Exact test.

In the *H. influenzae* type a bacteremia model (ref. 23), groups of 9 to 10 five-day old infant rats were injected s.c. in the dorsal region with 0.1 ml of guinea pig anti-rhia or anti-strain ATCC 9006 antiserum. The animals in the control group were injected with guinea pig pre-immune serum. Twenty hours later, the animals were challenged i.p. with 100,000 cfu of freshly grown *H. influenzae* type a strain ATCC 9006 (0.1 ml). Blood samples were collected 20 h post-challenge and analysed as described above.

As shown in Tables 1 and 2 below, the infant rats that were passively immunized with either guinea pig anti-rHia (11) or anti-V38 rHia (11) antisera, were all significantly protected against type a or type b *H. influenzae* caused bacteremia. These results demonstrate that antibodies raised to the slightly truncated Hia protein (V38 rHia) are as efficacious as those raised to the full-length protein at protecting animals against bacteremia caused by type a or type b *H. influenzae*. Such protection afforded by an NTHi-derived recombinant protein against invasive disease caused by encapsulated bacteria, illustrates the utility of the rHia proteins as vaccine antigens.

Example 13

This Example illustrates the protection afforded by immunization with V38 rHia protein in a chinchilla model of nasopharyngeal colonization.

A nasopharyngeal colonization model has been described by Yang et al (ref. 20). The model works well for those NTHi strains that produce the HMW adhesins, but reproducible colonization could not be established with Hia-producing strains under the same conditions. Repeated attempts to colonize with the prototype Hia-producing NTHi strain 11, were unsuccessful. Colonization was achieved with NTHi strain 33 at $5\times10^8$ cfu per inoculum, compared with only $10^8$ cfu required for the prototype HMW-producing NTHi strain 12. Under these conditions, partial protection was observed in animals immunized with 100 μg of V38 rHia (33) and challenged with the homologous NTHi strain 33.

Example 14

This Example illustrates the cloning and sequence analysis of additional hia genes from *H. influenzae* strains.

Oligonucleotides (5040.SL and 5039.SL) for PCR amplification were designed based upon the conserved promoter, N-terminal and C-terminal sequences of the hia and hsf genes and proteins (FIG. 17). The strains chosen for PCR amplification were chosen based upon their reactivity with anti-rHia (11) antisera.

Chromosomal DNA was prepared from NTHi strains 12, 29, 32, M4071, K9 and, K22 and Haemophilus type c strain API. PCR amplification was performed as follows: each reaction mixture contained 5 to 100 ng of DNA, 1 μg of each primer, 5 units of taq+ or tsg+ (Sangon) or taq plus long (Stratagene), 2 mM dNTPs, 20 mM Tris-HCl (pH 8.8), 10 mM KCl, 10 mM $(NH_4)_2SO_4$, 2 mM $MgSO_4$, 0.1% Triton X-100, BSA. Cycling conditions were: 95° C. for 1 min, followed by 25 cycles of 95° C. for 30 sec, 45° C. for 1 min, 72° C. for 2 min; then 72° C. for 10 min.

The nucleotide and deduced amino acid sequences of the hia gene from strain 33 are shown in FIG. 18. The predicted Hia protein from strain 33 has a molecular weight of 103.6 kDa and a pI of 9.47. The nucleotide and deduced amino acid sequences of the hia gene from strain 32 are shown in FIG. 19. The predicted Hia protein from strain 32 has a molecular weight of 70.4 kDa and a pI of 5.67. There is a KDEL sequence present between residues 493 and 496. Such sequences have been associated with anchoring proteins to the endoplasmic reticulum. The deduced strain 32 Hia protein is significantly smaller and has a significantly different pI, however it does contain many of the motifs present in other Hia molecules.

The nucleotide and deduced amino acid sequences of the hia gene from strain 29 are shown in FIG. 20. The predicted Hia protein from strain 29 has a molecular weight of 114.4 kDa and a pI of 7.58. The nucleotide and deduced amino acid sequences of the hia gene from strain K22 are shown in FIG. 23. The predicted Hia protein from strain K22 has a molecular weight of 114.4 kDa and a pI of 7.58. The deduced Hia sequences from NTHI strains 29 and K22 were found to be identical. Strain 29 was isolated from a 7-month old child with otitis media in Cleveland, Ohio, while strain K22 was isolated from an aborigine near Kimberly, Australia.

The nucleotide and deduced amino acid sequences of the hia gene from strain 4071 are shown in FIG. 21. The predicted Hia protein from strain M4071 has a molecular weight of 103.4 kDa and a pI of 9.49. There is a KDEL sequence present between residues 534 and 537.

The nucleotide and deduced amino acid sequences of the hia gene from strain K9 are shown in FIG. 22. The predicted Hia protein from K9 has a molecular weight of 113.8 kDa and a pI of 6.45.

The nucleotide and deduced amino acid sequences of the hia gene from strain type c Haemophilus API are shown in FIG. 24. The predicted Hia protein from API has a molecular weight of 249.4 kDa and a pI of 5.34. The deduced Hia/Hsf sequence from the type c strain API is nearly identical to the published type b Hsf sequence except for a 60 residue insert. Since the NTHi-based Hia protein provided herein protects in passive models of type a and type b infection, it is likely that it will also protect against type c disease due to sequence similarity between the type b and type c proteins.

The nucleotide and deduced amino acid sequences of the hia locus from strain 12 are shown in FIG. 25. NTHi strain 12 does not produce Hia. However, part of the hia gene can be PCR amplified, there is inconsistent positive reactivity of SB12 cell lysates with anti-rHia antibody, and there is reactivity with a DNA probe derived from the 3'-end of the strain 11 hia gene, on Southern blots. Analysis of the PCR amplified DNA, revealed a 1.8 kb fragment that contains 1 kb of the 3'-end of the upstream HI1732-related gene and 0.8 kb of the 3'-end of the hia gene.

PCR amplification using primers that would amplify across the putative junction of these two genes in strain 12, confirmed the genetic composition of the locus. Thus it would appear that strain 12 does not produce Hia because it has suffered a deletion of the 5'-end of the hia gene. FIG. 27 shows a sequence comparison between the upstream orf of strain 12 and the Rd genome deduced HI1733 protein. Over the region of homology, the two proteins are 95% identical.

An alignment of the deduced Hia sequences from NTHi strains 33, 32, 29, K22, M4071, 11 and K9 and type c strain API compared with *H. influenzae* type b Hsf, the aida-like (Hsf/Hia) HI1732 gene from the Rd genome, and the *M. catarrhalis* 200 kDa protein from strains 4223 and LES-1 is shown in FIG. 28. There is a frame shift in the Rd genome sequence resulting in premature truncation of the HI1732 protein. Additional downstream sequence related to hia, is included here. The asterisks below the sequence indicate conserved residues. The N-terminal (approximately 50 residues) and C-terminal sequences (approximately 150 residues) are highly conserved amongst the Haemophilus strains, while some similarity is evident with the *M. catarrhalis* counterpart. Sequence analysis reveals that there are two potential gene families of Hia proteins, one related to the prototype strain 11 and the other more closely related to strain 33. The strains 11 and K9 proteins appear to be more like the Hsf proteins from the type b, type c or type d Haemophilus strains while the strains 33, 32, 29, K22 and M4071 proteins appear to form a second family.

SUMMARY OF THE DISCLOSURE

In summary of this disclosure, the present invention provides novel isolated and purified nucleic acid molecules encoding full-length and N-terminal truncated *Haemophilus influenzae* adhesin (Hia) proteins from Haemophilus which enable protective Hia proteins to be produced recombinantly. Modifications are possible within the scope of this invention.

REFERENCES

1. Barbour, M. L., R. T. Mayon-White, C. Coles, D. W. M. Crook, and E. R. Moxon. 1995. The impact of conjugate vaccine on carriage of *Haemophilus influenzae* type b. J. Infect. Dis. 171:93–98.
2. Berkowitz et al. 1987. J. Pediatr. 110:509.
3. Claesson et al. 1989. J. Pediatr. 114:97.
4. Black, S. B., H. R. Shinefield, B. Fireman, R. Hiatt, M. Polen, E . Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
5. Nitta, D. M., M. A. Jackson, V. F. Burry, and L. C. Olson. 1995. Invasive *Haemophilus influenzae* type f disease. Pediatr. Infect. Dis. J. 14:157–160.
6. Waggoner-Fountain, L. A., J. O. Hendley, E. J. Cody, V. A. Perriello, and L. G. Donowitz. 1995. The emergence of *Haemophilus influenzae* types e and f as significant pathogens. Clin. Infect. Dis. 21:1322–1324.
7. Madore, D. V. 1996. Impact of immunization on *Haemophilus influenzae* type b disease. Infectious Agents and Disease 5:8–20.
8. Bluestone, C. D. 1982. Current concepts in otolaryngology. Otitis media in children: to treat or not to treat? N. Engl. J. Med. 306:1399–1404.
9. Barenkamp, S. J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302–1313.
10. St. Geme III, J. W., S. Falkow, and S. J. Barenkamp. 1993. High-molecular-weight proteins of nontypeable *Haemophilus influenzae* mediate attachment to human epithelial cells. Proc. Natl. Acad. Sci. USA 90:2875–2879.
11. Barenkamp, S. J. 1996. Immunization with high-molecular-weight adhesion proteins of nontypeable *Hae-*

*mophilus influenzae* modifies experimental otitis media in chinchillas. Infect. Immun. 64:1246–1251.

12. St. Geme, J. W. and D. Cutter. 1995. Evidence that surface fibrils expressed by *Haemophilus influenzae* type b promote attachment to human epithelial cells. Molec. Microbiol. 15:77–85.
13. Barenkamp, S. J. and J. W. St. Geme. 1996. Identification of a second family of high-molecular-weight adhesion proteins expressed by non-typable *Haemophilus influenzae*. Molec. Microbiol. 19:1215–1223.
14. St. Geme, J. W., D. Cutter, and S. J. Barenkamp. 1996. Characterization of the genetic locus encoding *Haemophilus influenzae* type b surface fibrils. J. Bact. 178:6281–6287.
15. Patient, M. E., and D. K. Summers. 1993. ColE1 multimer formation triggers inhibition of *Escherichia coli* cell division. Molec. Microbiol. 9:1089–1095.
16. O'Hagan, D T. 1992. Oral delivery of vaccines. Formulation and clinical pharmaco kinetic considerations. Clin. Pharmacokinet 22(t): 1–10.
17. Ulmer et al. 1993. Curr. Opinion Invest. Drugs 2:983–989.
18. Lockhoff, O., 1991. Glycolipids as immunomodulators: Synthesis and properties.
19. Nixon-George A., et al., 1990. The adjuvant effect of stearyl tyrosine on a recombinant subunit hepatitis B surface antigen. J. Immunol 144 (12):4798–4802.
20. Yang, Y-P., S. M. Loosmore, B. J. Underdown, and M. H. Klein. 1998. Nasopharyngeal colonization with non-typeable *Haemophilus influenzae* in chinchillas. Infect. Immun. 66:1973–1980.
21. Tabor, S., and C. C. Richardson. 1985. A bacteriophage T7 RNA polymerase/promoter system for controlled exclusive expression of specific genes. Proc. Natl. Acad. Sci. USA 82:1074–1078.
22. Laemmli, U.K. 1970. Cleavage of structural proteins during the assembly of the head of bacteriophage T4. Nature 227:680–685.
23. Loosmore, S. M., Y-P. Yang, D. C. Coleman, J. M. Shortreed, D. M. England, and M. H. Klein. 1997. Outer membrane protein D15 is conserved among *Haemophilus influenzae* species and may represent a universal protective antigen against invasive disease. Infect. Immun. 65:3701–3707.
24. Needleman, S. B. and Wunsch, C. D. 1970, J. Mol. Biol. 48:443–453.
25. Sellers, P. H. 1974 On the theory and computation of evolutionary distances. J. Appl. Math(Siam) 26:787–793.
26. Waterman, M. S., Smith, T. F. and Beyer, W. A. 1976. Advan. Math. 20:367–387.
27. Smith, T. F. and Waterman, M. S. 1981 Identification of common molecular subsequences. J. Mol. Biol. 147:195–197.
28. Sobel, E. and Martinez, H. M. 1985 A multiple Sequence Alignment Program. Nucleic Acid Res. 14:363–374.

TABLE 1

Protective effect of guinea pig anti-rHia (full-length) antiserum against type a or b *H. influenzae* in the infant rat model of bacteremia

| Group (#) | Guinea pig serum | Anti-rHia antibody titers | No. bacteremic/ No. challenged | Mean cfu/ 100 μl blood |
|---|---|---|---|---|
| 1 | Anti-type a | nd | 0/10* | 0** |
| 2 | Anti-rHia | 204,800 | 1/10* | 0** |
| 3 | Preimmune | <100 | 7/10 | 88 |

TABLE 1-continued

Protective effect of guinea pig anti-rHia (full-length) antiserum against type a or b *H. influenzae* in the infant rat model of bacteremia

| Group (#) | Guinea pig serum | anti-rHia antibody titers | No. bacteremic/ No. challenged | Mean cfu/ 2.5 μl blood |
|---|---|---|---|---|
| 4 | Anti-MinnA | nd | 0/10* | 0** |
| 5 | Anti-rHia | 204,800 | 1/10* | 2** |
| 6 | Preimmune | <100 | 10/10 | 600 |

Five-day old infant rats were passively immunized s.c. with 0.1 ml of indicated guinea pig antiserum or preimmune serum. Twenty hours later, infant rats were challenged i.p. with either freshly grown *H. influenzae* type a strain ATCC 9006 ($10^5$ cfu, 0.1 ml) for groups #1 to 3; or with freshly grown Hib strain MinnA (240 cfu, 0.1 ml) for groups #4 to 6. Infected animals are defined as >20 cfu recovered from 100 μl of blood for groups #1 to 3; or >30 cfu recovered from 2.5 μl of blood for groups #4 to 6.

Fisher exact test. Statistical significance compared to animals in group 3 or 6 was found (P<0.05)

Student's unpaired t test. Statistical significance compared to animals in group 3 or 6 was found (P<0.05).

nd: not determined.

TABLE 2

Protective effect of guinea pig anti-V38 rHia (SB11) antiserum against type a or b *H. influenzae* in the infant rat model of bacteremia

| Group (#) | Guinea pig serum | Anti-rHia antibody titers | No. bacteremic/ No. challenged | Mean cfu/ 20 μl blood |
|---|---|---|---|---|
| 1 | Anti-type a | nd | 0/6* | 0** |
| 2 | Anti-rHia | 204,800 | 1/9* | 5** |
| 3 | Preimmune | <100 | 5/8 | 165 |
| **Group (#)** | **Guinea pig serum** | **anti-rHia antibody titers** | **No. bacteremic/ No. challenged** | **Mean cfu/ 2 μl blood** |
| 4 | Anti-MinnA | nd | 0/6* | 0** |
| 5 | Anti-rHia | 204,800 | 1/9* | 2** |
| 6 | Preimmune | <100 | 10/10 | 820 |

Five-day old infant rats were passively immunized s.c. with 0.1 ml of indicated guinea pig antiserum or preimmune serum. Twenty hours later, infant rats were challenged i.p. with either freshly grown *H. influenzae* type a strain ATCC 9006 ($10^5$ cfu, 0.1 ml) for groups #1 to 3; or with freshly grown Hib strain MinnA (190 cfu, 0.1 ml) for groups #4 to 6. Infected animals is defined as >20 cfu recovered from 20 μl of blood for groups #1 to 3; or >30 cfu recovered from 2 μl of blood for groups #4 to 6.

Fisher exact test. Statistical significance compared to animals in group 3 or 6 was found (P<0.05)

Student's unpaired t test. Statistical significance compared to animals in group 3 or 6 was found (P<0.05).

nd: Not determined.

What we claim is:

1. An isolated and purified nucleic acid molecule encoding a *Haemophilus influenzae* adhesin (Hia) protein of a strain of *Haemophilus influenzae* consisting of:

(a) a DNA sequence selected from the group consisting of SEQ ID Nos: 23, 27, 29, 31, 33, 35 and 37; or (b) a DNA sequence encoding a *Haemophilus influenzae* adhesin (Hia) protein having an amino acid sequence selected from the group consisting of SEQ ID Nos: 24, 28, 30, 32, 34, 36 and 38.

2. An isolated and purified nucleic acid molecule encoding an N-truncated *Haemophilus influenzae* adhesin (Hia) protein of a strain of *Haemophilus influenzae*, said Hia protein having the ability to bind to human epithelial cells, said nucleic acid molecule being amplifiable by a pair of nucleotides which are selected from the group consisting of:

SEQ ID No: 7 and SEQ ID No: 15
SEQ ID No: 9 and SEQ ID No: 15
SEQ ID No: 11 and SEQ ID No: 15
SEQ ID No: 13 and SEQ ID No: 15
SEQ ID No: 16 and SEQ ID No: 18.

3. An isolated and purified nucleic acid encoding a truncated *Haemophilus influenzae* adhesin (Hia) protein of a strain of *Haemophilus influenzae* expressible as inclusion bodies and selected from the group consisting of the E21, T33, V38 and N52 truncation of *Haemophilus influenzae* strain 11 and V38 truncation of *Haemophilus influenzae* strain 33.

4. A vector for transforming a host comprising the nucleic acid molecule of claim 1.

5. A vector for transforming a host comprising the nucleic acid molecule of claim 2 or 3.

6. The vector of claim 5 which is a plasmid vector.

7. The vector of claim 6 wherein said plasmid vector has the identifying characteristics of a plasmid which is selected from the group consisting of:

DS-2008-2-3 as shown in FIG. 1A

DS-2186-1-1 as shown in FIG. 5A

DS-2201-1 as shown in FIG. 5A

DS-2186-2-1 as shown in FIG. 5A

DS-2168-2-6 as shown in FIG. 5A.

8. A vector for transforming a host, comprising a nucleic acid molecule encoding a full-length *Haemophilus influenzae* adhesin (Hia) protein as claimed in claim 1 and a promoter operatively coupled to said nucleic acid molecule for expression of said full-length Hia protein.

9. The vector of claim 8 further comprising the cer gene of *E. coli.*

10. The vector of claim 8 which is a plasmid vector.

11. The vector of claim 10 wherein said plasmid vector has the identifying characteristics of a plasmid vector which is selected from the group consisting of:

BK-96-2-11 as shown in FIG. 6A

DS-2242-1 as shown in FIG. 7A

DS-2242-2 as shown in FIG. 7A

DS-2340-2-3 as shown in FIG. 8A

DS-2447-2 as shown in FIG. 9A

DS-2448-17 as shown in FIG. 9B.

12. A host cell transformed by a vector as claimed in claim 8 and expressing a protective *Haemophilus influenzae* adhesin (Hia) protein of a non-typeable strain of Haemophilus.

13. The host cell of claim 12 which is a strain of *E. coli.*

14. A method for the production of a protective *Haemophilus influenzae* adhesin (Hia) protein of a non-typeable strain of *Haemophilus influenzae*, which comprises:

transforming a host with a vector as claimed in claim 5, growing the host cell to express the encoded truncated Hia, and isolating and purifying the expressed Hia protein.

15. The method of claim 14 wherein the host cell is *E. coli.*

16. The method of claim 14 wherein said encoded truncated Hia is expressed in inclusion bodies.

17. The method of claim 16 wherein said isolation and purification of the expressed Hia is effected by:

disrupting the grown transformed cells to produce a supernatant and the inclusion bodies, solubilizing the inclusion bodies to produce a solution of the recombinant Hia, chromatographically purifying the solution of recombinant Hia free from cell debris, and isolating the purified recombinant Hia protein.

18. The method of claim 14 wherein said non-typeable strain of Haemophilus is selected from the group consisting of strains 11, 33, 32, 29, M4071, K9, K22 and 12.

19. The method of claim 14 wherein said vector includes the T7 promoter and said *E. coli* is cultured in the presence of an inducing amount of lactose.

20. The vector of claim 4 which is a plasmid vector.

21. A host cell transformed by a vector as claimed in claim 4 and expressing a protective *Haemophilus influenzae* adhesin (Hia) protein of a non-typeable strain of Haemophilus.

22. A host cell transformed by a vector as claimed in claim 5 and expressing a protective *Haemophilus influenzae* adhesin (Hia) protein of a non-typeable strain of Haemophilus.

23. A vector for transforming a host, comprising a nucleic acid molecule encoding a N-truncated *Haemophilus influenzae* adhesin (Hia) protein as claimed in claim 2 and a promoter operatively coupled to said nucleic acid molecule for expression of said truncated Hia protein.

24. A vector for transforming a host, comprising a nucleic acid molecule encoding a N-truncated *Haemophilus influenzae* adhesin (Hia) protein as claimed in claim 3 and a promoter operatively coupled to said nucleic acid molecule for expression of said truncated Hia protein.

* * * * *

SEQUENCE LISTING

<160> NUMBER OF SEQ ID NOS: 54

<210> SEQ ID NO 1
<211> LENGTH: 40
<212> TYPE: DNA
<213> ORGANISM: Haemophilus influenzae

<400> SEQUENCE: 1
gcgaattcat atgaacaaaa tttttaacgt tatttggaat 40

<210> SEQ ID NO 2
<211> LENGTH: 10
<212> TYPE: PRT
<213> ORGANISM: Haemophilus influenzae

<400> SEQUENCE: 2

```
Met Asn Lys Ile Phe Asn Val Ile Trp Asn
  1               5                  10
```

<210> SEQ ID NO 3
<211> LENGTH: 56
<212> TYPE: DNA
<213> ORGANISM: Haemophilus influenzae

<400> SEQUENCE: 3
ttttgtccgc aacgtcgtcc acaaccaatg gtcaccatta tcttaaggcc taggcg 56

<210> SEQ ID NO 4
<211> LENGTH: 42
<212> TYPE: DNA
<213> ORGANISM: Haemophilus influenzae

<400> SEQUENCE: 4
aaaacaggcg ttgcagcagg tgttggttac cagtggtaat ag 42

<210> SEQ ID NO 5
<211> LENGTH: 12
<212> TYPE: PRT
<213> ORGANISM: Haemophilus influenzae

<400> SEQUENCE: 5

```
Lys Thr Gly Val Ala Ala Gly Val Gly Tyr Gln Trp
  1               5                  10
```

<210> SEQ ID NO 6
<211> LENGTH: 64
<212> TYPE: PRT
<213> ORGANISM: Haemophilus influenzae

<400> SEQUENCE: 6

```
Met Asn Lys Ile Phe Asn Val Ile Trp Asn Val Val Thr Gln Thr Trp
  1               5                  10                  15

Val Val Val Ser Glu Leu Thr Arg Thr His Thr Leu Cys Ala Ser Ala
             20                  25                  30

Thr Val Ala Val Ala Val Leu Ala Thr Leu Leu Ser Ala Thr Val Glu
         35                  40                  45

Ala Asn Ala Asn Thr Pro Val Thr Asn Lys Leu Lys Ala Tyr Gly Asp
     50                  55                  60
```

<210> SEQ ID NO 7
<211> LENGTH: 43

-continued

<212> TYPE: DNA
<213> ORGANISM: Haemophilus influenzae

<400> SEQUENCE: 7
gggaattcat atggaactca ctcgcaccca caccaaatgg gcc 43

<210> SEQ ID NO 8
<211> LENGTH: 11
<212> TYPE: PRT
<213> ORGANISM: Haemophilus influenzae

<400> SEQUENCE: 8

Met Glu Leu Thr Arg Thr His Thr Lys Cys Ala
1 5 10

<210> SEQ ID NO 9
<211> LENGTH: 43
<212> TYPE: DNA
<213> ORGANISM: Haemophilus influenzae

<400> SEQUENCE: 9
gggaattcat atgaccgtgg cggttgccgt attggcaacc ctg 43

<210> SEQ ID NO 10
<211> LENGTH: 11
<212> TYPE: PRT
<213> ORGANISM: Haemophilus influenzae

<400> SEQUENCE: 10

Met Thr Val Ala Val Ala Val Leu Ala Thr Leu
1 5 10

<210> SEQ ID NO 11
<211> LENGTH: 40
<212> TYPE: DNA
<213> ORGANISM: Haemophilus influenzae

<400> SEQUENCE: 11
gggaattcat atggtattgg caaccctgtt gtccgcaacg 40

<210> SEQ ID NO 12
<211> LENGTH: 10
<212> TYPE: PRT
<213> ORGANISM: Haemophilus influenzae

<400> SEQUENCE: 12

Met Val Leu Ala Thr Leu Leu Ser Ala Thr
1 5 10

<210> SEQ ID NO 13
<211> LENGTH: 43
<212> TYPE: DNA
<213> ORGANISM: Haemophilus influenzae

<400> SEQUENCE: 13
gggaattcat atgaatactc ctgttacgaa taagttgaag gct 43

<210> SEQ ID NO 14
<211> LENGTH: 11
<212> TYPE: PRT
<213> ORGANISM: Haemophilus influenzae

<400> SEQUENCE: 14

Met Asn Thr Pro Val Thr Asn Lys Leu Lys Ala

-continued

```
  1               5                   10


<210> SEQ ID NO 15
<211> LENGTH: 45
<212> TYPE: DNA
<213> ORGANISM: Haemophilus influenzae

<400> SEQUENCE: 15

gtgtggtaat ggaaacgcga tcgctttctg gaaccaccct agggc                    45


<210> SEQ ID NO 16
<211> LENGTH: 38
<212> TYPE: DNA
<213> ORGANISM: Haemophilus influenzae

<400> SEQUENCE: 16

cacaccatta cctttgcgct agcgaaagac cttggtgg                            38


<210> SEQ ID NO 17
<211> LENGTH: 12
<212> TYPE: PRT
<213> ORGANISM: Haemophilus influenzae

<400> SEQUENCE: 17

His Thr Ile Thr Phe Ala Leu Ala Lys Asp Leu Gly
  1               5                   10


<210> SEQ ID NO 18
<211> LENGTH: 47
<212> TYPE: DNA
<213> ORGANISM: Haemophilus influenzae

<400> SEQUENCE: 18

ctgctttggt ggcgttggca tccgttaaat gcatttaact tcgaagc                  47


<210> SEQ ID NO 19
<211> LENGTH: 47
<212> TYPE: DNA
<213> ORGANISM: Haemophilus influenzae

<400> SEQUENCE: 19

gacgaaacca ccgcaaccgt aggcaattta cgtaaattga agcttcg                  47


<210> SEQ ID NO 20
<211> LENGTH: 13
<212> TYPE: PRT
<213> ORGANISM: Haemophilus influenzae

<400> SEQUENCE: 20

Asp Glu Thr Thr Ala Thr Val Gly Asn Leu Arg Lys Leu
  1               5                   10


<210> SEQ ID NO 21
<211> LENGTH: 42
<212> TYPE: DNA
<213> ORGANISM: Haemophilus influenzae

<400> SEQUENCE: 21

ttaaatataa ggtaaataaa aatgaacaaa atttttaacg tt                       42


<210> SEQ ID NO 22
<211> LENGTH: 7
<212> TYPE: PRT
<213> ORGANISM: Haemophilus influenzae
```

-continued

<400> SEQUENCE: 22

Met Asn Lys Ile Phe Asn Val
1 5

<210> SEQ ID NO 23
<211> LENGTH: 3036
<212> TYPE: DNA
<213> ORGANISM: Haemophilus influenzae

<400> SEQUENCE: 23
gaattcggct taaataaaaa tgaacaaaat ttttaacgtt atttggaatg ttatgactca 60
aacttgggct gtcgtatctg aactcactcg cgcccacacc aaacgtgcct ccgcaaccgt 120
ggcagccgct gtattggcga ccgtattgtc tgcaacggtt caggcgagtg caggcagtac 180
gacaggtaca aatagtttga atgtttatgg aaagaataat tcgaatttca attcagccaa 240
taattcaata gcagatttaa ataaacaaaa tgatagtgtt tacgatggtt tattaaatct 300
gaatgaaaaa ggtacggata agtcaaaatt cctggttgct gacgaaacca ccgcaaccgt 360
aggcaattta cgtaaattgg gttgggtagt atcaaccaaa aacagtacga aagaagaaag 420
caatcaagtc aaacaggcgg atgaagtgtt gtttgaaggc aaagacggtg taacggttac 480
ttccaaatct gaaaacggca aacacaccgt tacttttgcc cttgcgaatg accttaatgt 540
aaaaaacgca accgttagcg ataaattatc gcttggtgca aacggcaaga aagtcgatat 600
taccagtgat gcaaacggct tgaaatttgc gaaacagggt acgaatggtc aaaacggtaa 660
tgttcactta aacggtattg cttcgacttt agatgatcct cgtgtgggtg gaaaaacagc 720
acaccttaca aaagaaatca gcgatacaga acgtaaccgt gctgcgagcg tgggcgatgt 780
attgaatgcg ggttggaata ttcgtggcgc aaaaacgatt ggcggtacag tggataatgt 840
tgattttgtt tcaacttatg acactgttga atttgccagc ggcgcaaacg caaatgtgag 900
cgttacgact gatgataaca aaaaaacaac cgtccgtgtg gatgtaacag gcttgccggt 960
ccaatatgtt acggaagaca gcaaaaccgt tgtgaaagtg ggcaatgagt attacgaagc 1020
caagcaagac ggttcggcgg atatggataa aaaagtcgaa aatggcaagc tggcgaaaac 1080
taaagtgaaa ttggtatcgg caaacggtac aaatccggtg aaaatcagca atgttgcgga 1140
cggcacggaa gataccgatg cggtcagctt taagcagttg aaagccttgc aagataaaca 1200
ggttacgtta agtgcgagca atgcttatgc caatggcggt agcgatgccg acggcggcaa 1260
ggcaactcaa actttaggca atgatttgaa ttttaaattt aaatccacag acagcgagtt 1320
gttgaacatc aaagcagcag gtgacacggt tacctttacg ccgaaaaaag gttcggtgca 1380
ggttggcgat gatggtaagg ctacgattca agacggcgcg aaaacaacta ccggtttggt 1440
tgaggcttct gaattggttg acagcctgaa caaattgggc tggaaagtgg gcgttggtaa 1500
agacggcaca ggagcgaccg atggcacgca taccgacact ttagtgaagt cgggcgataa 1560
agtaactttg aaagccggcg ataatctgaa ggtcaaacaa gagggtacaa acttcactta 1620
cgtgctcaga gatgaattga cgggcgtaaa gagcgtggag tttaaagaca cggagaatgg 1680
tgcaaacggt gcaagcacga agattaccaa agacggcttg accattacgc cggcaaacga 1740
tgcgaatggt gcggcggcga ctgatgctga caagattaaa gtggcttcag acggcattag 1800
tgcgggtaat aaagcagtta aaaacgttgt gagcggactg aagaaatttg gtgatgcgaa 1860
tttcaatccg ctgactagct cagccgacaa cttaacgaaa caatatgaca atgcctataa 1920
aggcttgacc aatctggatg aaaaaagtaa aggcaagcaa actccgaccg ttgctgacaa 1980

-continued

```
taccgctgca accgtgggcg atttgcgcgg tttgggctgg gtcatttctg cagacaaaac   2040

cacaggcgag tcaaaggaat atagcgcgca agtgcgtaac gccaatgaag tgaaattcaa   2100

gagcggcaac ggtatcaatg tttccggtaa aacattggat aacggtacgc gcgaaattac   2160

ttttgaattg gctaaagacg aaaatgccat tgctttcggt tctggctcaa aagccttgcg   2220

cgataacacg gtggcgattg gtacgggcaa cgttgtgaat gcggaaaaat ctggtgcatt   2280

cggcgatccg aactacatcg aagataaagc cggtggcagc tacgctttcg gtaacgataa   2340

ccgtattact tctaaaaaca cttttgtgtt gggtaatgga gttaatgcga aatataaagc   2400

caatggagat gttgatacgg aaaccgtaac tgttaaggac aaagacggta aagagactac   2460

cgttactgtt cctaaagcgt taggggctac ggttgaaaac tccgtttatt tgggtaataa   2520

atcgactgcg acaaaagata agggtaaaaa tctgaaatct gatggtacgg cgggtaacac   2580

tacaactgct ggtacaacgg gtacggtaaa cggctttgcc ggtgcaacgg cgcacggtgc   2640

ggtttctgtc ggcgcaagcg gcgaagaaag acgtatccaa aacgttgcgg caggcgaaat   2700

ttccgctact tccaccgatg cgattaacgg cagccagttg tatgccgtgg caaaaggggt   2760

aacaaacctt gctggacaag tgaataaagt gggcaaacgt gcagatgcag gtacagcaag   2820

tgcattagcg gcttcacagt taccacaagc ctctatgtca ggtaaatcaa tggtttctat   2880

tgcgggaagt agttatcaag gtcaaagtgg tttagctatc ggggtatcaa gaatttccga   2940

taatggcaaa gtgattattc gcttgtcagg cacaaccaat agccaaggta aaacaggcgt   3000

tgcagcaggt gttggttacc agtggtaata gaattc                             3036
```

<210> SEQ ID NO 24
<211> LENGTH: 1002
<212> TYPE: PRT
<213> ORGANISM: Haemophilus influenzae

<400> SEQUENCE: 24

```
Met Asn Lys Ile Phe Asn Val Ile Trp Asn Val Met Thr Gln Thr Trp
  1               5                  10                  15

Ala Val Val Ser Glu Leu Thr Arg Ala His Thr Lys Arg Ala Ser Ala
             20                  25                  30

Thr Val Ala Ala Ala Val Leu Ala Thr Val Leu Ser Ala Thr Val Gln
         35                  40                  45

Ala Ser Ala Gly Ser Thr Thr Gly Thr Asn Ser Leu Asn Val Tyr Gly
     50                  55                  60

Lys Asn Asn Ser Asn Phe Asn Ser Ala Asn Asn Ser Ile Ala Asp Leu
 65                  70                  75                  80

Asn Lys Gln Asn Asp Ser Val Tyr Asp Gly Leu Leu Asn Leu Asn Glu
                 85                  90                  95

Lys Gly Thr Asp Lys Ser Lys Phe Leu Val Ala Asp Glu Thr Thr Ala
            100                 105                 110

Thr Val Gly Asn Leu Arg Lys Leu Gly Trp Val Val Ser Thr Lys Asn
        115                 120                 125

Ser Thr Lys Glu Glu Ser Asn Gln Val Lys Gln Ala Asp Glu Val Leu
    130                 135                 140

Phe Glu Gly Lys Asp Gly Val Thr Val Thr Ser Lys Ser Glu Asn Gly
145                 150                 155                 160

Lys His Thr Val Thr Phe Ala Leu Ala Asn Asp Leu Asn Val Lys Asn
                165                 170                 175

Ala Thr Val Ser Asp Lys Leu Ser Leu Gly Ala Asn Gly Lys Lys Val
```

-continued

```
            180                 185                 190

Asp Ile Thr Ser Asp Ala Asn Gly Leu Lys Phe Ala Lys Gln Gly Thr
        195                 200                 205

Asn Gly Gln Asn Gly Asn Val His Leu Asn Gly Ile Ala Ser Thr Leu
    210                 215                 220

Asp Asp Pro Arg Val Gly Gly Lys Thr Ala His Leu Thr Lys Glu Ile
225                 230                 235                 240

Ser Asp Thr Glu Arg Asn Arg Ala Ala Ser Val Gly Asp Val Leu Asn
                245                 250                 255

Ala Gly Trp Asn Ile Arg Gly Ala Lys Thr Ile Gly Gly Thr Val Asp
            260                 265                 270

Asn Val Asp Phe Val Ser Thr Tyr Asp Thr Val Glu Phe Ala Ser Gly
        275                 280                 285

Ala Asn Ala Asn Val Ser Val Thr Thr Asp Asp Asn Lys Lys Thr Thr
    290                 295                 300

Val Arg Val Asp Val Thr Gly Leu Pro Val Gln Tyr Val Thr Glu Asp
305                 310                 315                 320

Ser Lys Thr Val Val Lys Val Gly Asn Glu Tyr Tyr Glu Ala Lys Gln
                325                 330                 335

Asp Gly Ser Ala Asp Met Asp Lys Lys Val Glu Asn Gly Lys Leu Ala
            340                 345                 350

Lys Thr Lys Val Lys Leu Val Ser Ala Asn Gly Thr Asn Pro Val Lys
        355                 360                 365

Ile Ser Asn Val Ala Asp Gly Thr Glu Asp Thr Asp Ala Val Ser Phe
    370                 375                 380

Lys Gln Leu Lys Ala Leu Gln Asp Lys Gln Val Thr Leu Ser Ala Ser
385                 390                 395                 400

Asn Ala Tyr Ala Asn Gly Gly Ser Asp Ala Asp Gly Gly Lys Ala Thr
                405                 410                 415

Gln Thr Leu Gly Asn Asp Leu Asn Phe Lys Phe Lys Ser Thr Asp Ser
            420                 425                 430

Glu Leu Leu Asn Ile Lys Ala Ala Gly Asp Thr Val Thr Phe Thr Pro
        435                 440                 445

Lys Lys Gly Ser Val Gln Val Gly Asp Asp Gly Lys Ala Thr Ile Gln
    450                 455                 460

Asp Gly Ala Lys Thr Thr Thr Gly Leu Val Glu Ala Ser Glu Leu Val
465                 470                 475                 480

Asp Ser Leu Asn Lys Leu Gly Trp Lys Val Gly Val Gly Lys Asp Gly
                485                 490                 495

Thr Gly Ala Thr Asp Gly Thr His Thr Asp Thr Leu Val Lys Ser Gly
            500                 505                 510

Asp Lys Val Thr Leu Lys Ala Gly Asp Asn Leu Lys Val Lys Gln Glu
        515                 520                 525

Gly Thr Asn Phe Thr Tyr Val Leu Arg Asp Glu Leu Thr Gly Val Lys
    530                 535                 540

Ser Val Glu Phe Lys Asp Thr Glu Asn Gly Ala Asn Gly Ala Ser Thr
545                 550                 555                 560

Lys Ile Thr Lys Asp Gly Leu Thr Ile Thr Pro Ala Asn Asp Ala Asn
                565                 570                 575

Gly Ala Ala Ala Thr Asp Ala Asp Lys Ile Lys Val Ala Ser Asp Gly
            580                 585                 590

Ile Ser Ala Gly Asn Lys Ala Val Lys Asn Val Val Ser Gly Leu Lys
        595                 600                 605
```

-continued

```
Lys Phe Gly Asp Ala Asn Phe Asn Pro Leu Thr Ser Ser Ala Asp Asn
    610                 615                 620

Leu Thr Lys Gln Tyr Asp Asn Ala Tyr Lys Gly Leu Thr Asn Leu Asp
625                 630                 635                 640

Glu Lys Ser Lys Gly Lys Gln Thr Pro Thr Val Ala Asp Asn Thr Ala
                645                 650                 655

Ala Thr Val Gly Asp Leu Arg Gly Leu Gly Trp Val Ile Ser Ala Asp
            660                 665                 670

Lys Thr Thr Gly Glu Ser Lys Glu Tyr Ser Ala Gln Val Arg Asn Ala
        675                 680                 685

Asn Glu Val Lys Phe Lys Ser Gly Asn Gly Ile Asn Val Ser Gly Lys
    690                 695                 700

Thr Leu Asp Asn Gly Thr Arg Glu Ile Thr Phe Glu Leu Ala Lys Asp
705                 710                 715                 720

Glu Asn Ala Ile Ala Phe Gly Ser Gly Ser Lys Ala Leu Arg Asp Asn
                725                 730                 735

Thr Val Ala Ile Gly Thr Gly Asn Val Val Asn Ala Glu Lys Ser Gly
            740                 745                 750

Ala Phe Gly Asp Pro Asn Tyr Ile Glu Asp Lys Ala Gly Gly Ser Tyr
        755                 760                 765

Ala Phe Gly Asn Asp Asn Arg Ile Thr Ser Lys Asn Thr Phe Val Leu
    770                 775                 780

Gly Asn Gly Val Asn Ala Lys Tyr Lys Ala Asn Gly Asp Val Asp Thr
785                 790                 795                 800

Glu Thr Val Thr Val Lys Asp Lys Asp Gly Lys Glu Thr Thr Val Thr
                805                 810                 815

Val Pro Lys Ala Leu Gly Ala Thr Val Glu Asn Ser Val Tyr Leu Gly
            820                 825                 830

Asn Lys Ser Thr Ala Thr Lys Asp Lys Gly Lys Asn Leu Lys Ser Asp
        835                 840                 845

Gly Thr Ala Gly Asn Thr Thr Thr Ala Gly Thr Thr Gly Thr Val Asn
    850                 855                 860

Gly Phe Ala Gly Ala Thr Ala His Gly Ala Val Ser Val Gly Ala Ser
865                 870                 875                 880

Gly Glu Glu Arg Arg Ile Gln Asn Val Ala Ala Gly Glu Ile Ser Ala
                885                 890                 895

Thr Ser Thr Asp Ala Ile Asn Gly Ser Gln Leu Tyr Ala Val Ala Lys
            900                 905                 910

Gly Val Thr Asn Leu Ala Gly Gln Val Asn Lys Val Gly Lys Arg Ala
        915                 920                 925

Asp Ala Gly Thr Ala Ser Ala Leu Ala Ala Ser Gln Leu Pro Gln Ala
    930                 935                 940

Ser Met Ser Gly Lys Ser Met Val Ser Ile Ala Gly Ser Ser Tyr Gln
945                 950                 955                 960

Gly Gln Ser Gly Leu Ala Ile Gly Val Ser Arg Ile Ser Asp Asn Gly
                965                 970                 975

Lys Val Ile Ile Arg Leu Ser Gly Thr Thr Asn Ser Gln Gly Lys Thr
            980                 985                 990

Gly Val Ala Ala Gly Val Gly Tyr Gln Trp
        995                 1000
```

<210> SEQ ID NO 25
<211> LENGTH: 2079

-continued

<212> TYPE: DNA
<213> ORGANISM: Haemophilus influenzae

<400> SEQUENCE: 25

```
gaattcggct ttaaatataa ggtaaataaa aatgaacaaa atttttaacg ttatttggaa     60
tgttgtgact caaacttggg ttgtcgtatc tgaactcact cgcacccaca ccaaatgcgc    120
ctccgccacc gtggcagttg ccgtattggc aaccctgttg tccgcaacgg ttcaggcgaa    180
tgctaccgat gaaaacgaag atgatgaaga agagttagaa cccgtacaac gctctgtttt    240
aaggtggagc ttcaaatccg ctaaggaagg cactggagaa caagagggaa caacagaggt    300
aataaatttg aacacagatt catcaggaaa tgcagtagga agcagcacaa tcaccttcaa    360
agccggcgac aacctgaaaa tcaaacaaag cggcaatgac ttcacctact cgctgaaaaa    420
agagctgaaa aacctgacca gtgttgaaac tgaaaaatta tcgtttggcg caaacggcaa    480
taaagttgat attaccagtg atgcaaatgg cttgaaattg gcgaaaacag gtaacggaaa    540
tggtcaaaac agtaatgttc acttaaacgg tattgcttcg actttgaccg atacgcttgc    600
cggtggcaca acaggacacg ttgacaccaa cattgatgcg gttaattatc atcgcgctgc    660
aagcgtacaa gatgtgttaa acagcggttg gaatatccaa ggcaatggaa acaatgtcga    720
ttttgtccgt acttacgaca ccgtggactt tgtcaatggc gcgaatgcca atgtgagcgt    780
tacggctgat acggctcaca aaaagacaac tgtccgtgtg gatgtaacag gcttgccggt    840
tcaatatgtt acggaagacg gcaaaaccgt tgtgaaagtg ggcaatgagt attacaaagc    900
caaagatgac ggttcggcgg atatgaatca aaaagtcgaa aacggcgagc tggcgaaaac    960
caaagtgaaa ttggtatcgg caagcggtac aaatccggtg aaaattagca atgttgcaga   1020
cggcacggaa gacaccgatg cggtcagctt taagcaatta aaagccttgc aagacaaaca   1080
ggttacgttg agcacgagca atgcttatgc caatggcggt acagataacg acggcggcaa   1140
ggcaactcaa actttaagca atggtttgaa ttttaaattt aaatctagcg atggcgagtt   1200
gttgaaaatt agcgcgaccg gcgatacggt tacttttacg ccgaaaaaag gttcggtaca   1260
ggttggcgat gatggcaagg cttcaatttc aaaaggtgca aatacaactg aaggtttggt   1320
tgaggcttct gaattggttg aaagcctgaa caaactgggt tggaaagtag ggggttgagaa  1380
agtcggcagc ggcgagcttg atggtacatc caaggaaact ttagtgaagt cgggcgataa   1440
agtaactttg aaagccggcg acaatctgaa ggtcaaacaa gagggcacaa acttcactta   1500
cgcgctcaaa gatgaattga cgggcgtgaa gagcgtggag tttaaagaca cggcgaatgg   1560
tgcaaacggt gcaagcacga agattaccaa agacggcttg accattacgc tggcaaacgg   1620
tgcgaatggt gcgacggtga ctgatgccga caagattaaa gttgcttcgg acggcattag   1680
cgcgggtaat aaagcagtta aaaacgtcgc ggcaggcgaa atttctgcca cttccaccga   1740
tgcgattaac ggaagccagt tgtatgccgt ggcaaaaggg gtaacaaacc ttgctggaca   1800
agtgaataat cttgagggca aagtgaataa agtgggcaaa cgtgcagatg caggtactgc   1860
aagtgcatta gcggcttcac agttaccaca agccactatg ccaggtaaat caatggtttc   1920
tattgcggga agtagttatc aaggtcaaaa tggtttagct atcggggtat caagaatttc   1980
cgataatggc aaagtgatta ttcgcttgtc aggcacaacc aatagtcaag gtaaaacagg   2040
cgttgcagca ggtgttggtt accagtggta atagaattc                         2079
```

<210> SEQ ID NO 26
<211> LENGTH: 679
<212> TYPE: PRT

-continued

<213> ORGANISM: Haemophilus influenzae

<400> SEQUENCE: 26

```
Met Asn Lys Ile Phe Asn Val Ile Trp Asn Val Val Thr Gln Thr Trp
  1               5                  10                  15

Val Val Val Ser Glu Leu Thr Arg Thr His Thr Lys Cys Ala Ser Ala
             20                  25                  30

Thr Val Ala Val Ala Val Leu Ala Thr Leu Leu Ser Ala Thr Val Gln
         35                  40                  45

Ala Asn Ala Thr Asp Glu Asn Glu Asp Asp Glu Glu Glu Leu Glu Pro
     50                  55                  60

Val Gln Arg Ser Val Leu Arg Trp Ser Phe Lys Ser Ala Lys Glu Gly
 65                  70                  75                  80

Thr Gly Glu Gln Glu Gly Thr Thr Glu Val Ile Asn Leu Asn Thr Asp
                 85                  90                  95

Ser Ser Gly Asn Ala Val Gly Ser Ser Thr Ile Thr Phe Lys Ala Gly
            100                 105                 110

Asp Asn Leu Lys Ile Lys Gln Ser Gly Asn Asp Phe Thr Tyr Ser Leu
        115                 120                 125

Lys Lys Glu Leu Lys Asn Leu Thr Ser Val Glu Thr Glu Lys Leu Ser
    130                 135                 140

Phe Gly Ala Asn Gly Asn Lys Val Asp Ile Thr Ser Asp Ala Asn Gly
145                 150                 155                 160

Leu Lys Leu Ala Lys Thr Gly Asn Gly Asn Gly Gln Asn Ser Asn Val
                165                 170                 175

His Leu Asn Gly Ile Ala Ser Thr Leu Thr Asp Thr Leu Ala Gly Gly
            180                 185                 190

Thr Thr Gly His Val Asp Thr Asn Ile Asp Ala Val Asn Tyr His Arg
        195                 200                 205

Ala Ala Ser Val Gln Asp Val Leu Asn Ser Gly Trp Asn Ile Gln Gly
    210                 215                 220

Asn Gly Asn Asn Val Asp Phe Val Arg Thr Tyr Asp Thr Val Asp Phe
225                 230                 235                 240

Val Asn Gly Ala Asn Ala Asn Val Ser Val Thr Ala Asp Thr Ala His
                245                 250                 255

Lys Lys Thr Thr Val Arg Val Asp Val Thr Gly Leu Pro Val Gln Tyr
            260                 265                 270

Val Thr Glu Asp Gly Lys Thr Val Val Lys Val Gly Asn Glu Tyr Tyr
        275                 280                 285

Lys Ala Lys Asp Asp Gly Ser Ala Asp Met Asn Gln Lys Val Glu Asn
    290                 295                 300

Gly Glu Leu Ala Lys Thr Lys Val Lys Leu Val Ser Ala Ser Gly Thr
305                 310                 315                 320

Asn Pro Val Lys Ile Ser Asn Val Ala Asp Gly Thr Glu Asp Thr Asp
                325                 330                 335

Ala Val Ser Phe Lys Gln Leu Lys Ala Leu Gln Asp Lys Gln Val Thr
            340                 345                 350

Leu Ser Thr Ser Asn Ala Tyr Ala Asn Gly Gly Thr Asp Asn Asp Gly
        355                 360                 365

Gly Lys Ala Thr Gln Thr Leu Ser Asn Gly Leu Asn Phe Lys Phe Lys
    370                 375                 380

Ser Ser Asp Gly Glu Leu Leu Lys Ile Ser Ala Thr Gly Asp Thr Val
385                 390                 395                 400
```

-continued

```
Thr Phe Thr Pro Lys Lys Gly Ser Val Gln Val Gly Asp Asp Gly Lys
                405                 410                 415

Ala Ser Ile Ser Lys Gly Ala Asn Thr Thr Glu Gly Leu Val Glu Ala
            420                 425                 430

Ser Glu Leu Val Glu Ser Leu Asn Lys Leu Gly Trp Lys Val Gly Val
        435                 440                 445

Glu Lys Val Gly Ser Gly Glu Leu Asp Gly Thr Ser Lys Glu Thr Leu
    450                 455                 460

Val Lys Ser Gly Asp Lys Val Thr Leu Lys Ala Gly Asp Asn Leu Lys
465                 470                 475                 480

Val Lys Gln Glu Gly Thr Asn Phe Thr Tyr Ala Leu Lys Asp Glu Leu
                485                 490                 495

Thr Gly Val Lys Ser Val Glu Phe Lys Asp Thr Ala Asn Gly Ala Asn
            500                 505                 510

Gly Ala Ser Thr Lys Ile Thr Lys Asp Gly Leu Thr Ile Thr Leu Ala
        515                 520                 525

Asn Gly Ala Asn Gly Ala Thr Val Thr Asp Ala Asp Lys Ile Lys Val
    530                 535                 540

Ala Ser Asp Gly Ile Ser Ala Gly Asn Lys Ala Val Lys Asn Val Ala
545                 550                 555                 560

Ala Gly Glu Ile Ser Ala Thr Ser Thr Asp Ala Ile Asn Gly Ser Gln
                565                 570                 575

Leu Tyr Ala Val Ala Lys Gly Val Thr Asn Leu Ala Gly Gln Val Asn
            580                 585                 590

Asn Leu Glu Gly Lys Val Asn Lys Val Gly Lys Arg Ala Asp Ala Gly
        595                 600                 605

Thr Ala Ser Ala Leu Ala Ala Ser Gln Leu Pro Gln Ala Thr Met Pro
    610                 615                 620

Gly Lys Ser Met Val Ser Ile Ala Gly Ser Ser Tyr Gln Gly Gln Asn
625                 630                 635                 640

Gly Leu Ala Ile Gly Val Ser Arg Ile Ser Asp Asn Gly Lys Val Ile
                645                 650                 655

Ile Arg Leu Ser Gly Thr Thr Asn Ser Gln Gly Lys Thr Gly Val Ala
            660                 665                 670

Ala Gly Val Gly Tyr Gln Trp
        675
```

<210> SEQ ID NO 27
<211> LENGTH: 6706
<212> TYPE: DNA
<213> ORGANISM: Haemophilus influenzae

<400> SEQUENCE: 27

```
ttaaatataa ggtaaataaa aatgaacaaa atttttaacg ttatttggaa tgttgtgact     60

aatttatatt ccatttattt ttacttgttt taaaaattgc aataaacctt acaacactga    120

caaacttggg ttgtcgtatc tgaactcact cgcgcccaca ccaaatgcgc ctccgccacc    180

gtttgaaccc aacagcatag acttgagtga gcgcgggtgt ggtttacgcg gaggcggtgg    240

gtggcggttg ccgtattggc aactgcgttg tctgcaacgg ctgaagcgaa caacaatact    300

caccgccaac ggcataaccg ttgacgcaac agacgttgcc gacttcgctt gttgttatga    360

tctgttacga atgggttgaa tgcttatggc gatactaatt ttaatacaac caataattcg    420

agacaatgct tacccaactt acgaataccg ctatgattaa aattatgttg gttattaagc    480

atagcagatt tggaaaaaca cgttcaagat gcttataaag gcttattaaa tctgaatgaa    540
```

-continued

```
tatcgtctaa accttttttgt gcaagttcta cgaatatttc cgaataattt agacttactt    600
aaagatacaa ataagtcaag tttcttggtt gccgacaata ccgccgcaac cgtaggcaat    660
tttctatgtt tattcagttc aaagaaccaa cggctgttat ggcggcgttg gcatccgtta    720
ttgcgtaaat tgggctgggt attgtctagc aaaaacggca caaggaacga gaaaagctat    780
aacgcattta acccgaccca taacagatcg tttttgccgt gttccttgct cttttcgata    840
caagtaaaac aagctgatga agttctcttt actggatctg gtgctgcaac ggttagttcc    900
gttcattttg ttcgactact tcaagagaaa tgacctagac cacgacgttg ccaatcaagg    960
agctctaaag acggtaaaca taccattacc atttctgtta ccaaaggtag ttttgctgag   1020
tcgagatttc tgccatttgt atggtaatgg taaagacaat ggtttccatc aaaacgactc   1080
gtaaaaactg atgcaactac tggaggtcaa gtaaacgccg accgtggtaa agtgaaagct   1140
catttttgac tacgttgatg acctccagtt catttgcggc tggcaccatt tcactttcga   1200
gaggacgaga atggagctga tgttgataag aaagttgcaa ctgtaaaaga tgttgctaag   1260
ctcctgctct tacctcgact acaactattc tttcaacgtt gacattttct acaacgattc   1320
gcgattaacg atgccgcaac tttcgtgaaa gtggaaagca cagatgatga cattgaaaat   1380
cgctaattgc tacggcgttg aaagcacttt cacctttcgt gtctactact gtaactttta   1440
ggtgctgcag gcaaaaatga aactacagac caagctctca aagcaggcga caccttaacc   1500
ccacgacgtc cgtttttact ttgatgtctg gttcgagagt ttcgtccgct gtggaattgg   1560
ttaaaagcgg gtaaaaactt aaaagctaag ttagaccaaa atggtaaatc agtaaccttt   1620
aattttcgcc catttttgaa ttttcgattc aatctggttt taccatttag tcattggaaa   1680
gctttagcga aagaccttga tgtgacctct gcgaaagtga gtgataagtt gtctattggt   1740
cgaaatcgct ttctggaact acactggaga cgctttcact cactattcaa cagataacca   1800
aaagatacga ataaagttga tattaccagt gatgcaaatg gcttgaaatt ggcgaaaaca   1860
tttctatgct tatttcaact ataatggtca ctacgtttac cgaactttaa ccgcttttgt   1920
ggtaacggaa atggtcaaaa cggtaatgtc cacttaaatg gtattgcttc gactttgacc   1980
ccattgcctt taccagtttt gccattacag gtgaatttac cataacgaag ctgaaactgg   2040
gataccatta caggtatgac aacacaagca agcaatggcg tggctgtgca gaatcataat   2100
ctatggtaat gtccatactg ttgtgttcgt tcgttaccgc accgacacgt cttagtatta   2160
cgtgctgcga gtgtggctga tgtattaaat gcaggctgga atattcaagg caacggagcg   2220
gcacgacgct cacaccgact acataattta cgtccgacct tataagttcc gttgcctcgc   2280
agcgttgatt ttgtcaatgc ttacgacaca gtagattttg tcaatggtac aaacaccaat   2340
tcgcaactaa aacagttacg aatgctgtgt catctaaaac agttaccatg tttgtggtta   2400
gtgaacgtta cgactgatac ggctcacaaa aagacaaccg tccgtgtgga tgtaacaggc   2460
cacttgcaat gctgactatg ccgagtgttt ttctgttggc aggcacacct acattgtccg   2520
ttgccggttc aatatgttac ggaagacggc aaaaccgttg tgaaagtgga caataagtat   2580
aacggccaag ttatacaatg ccttctgccg ttttggcaac actttcacct gttattcata   2640
tacgaagcta agcaagacgg ttcggcggat atggataaaa aagtcgaaaa tggcgagctg   2700
atgcttcgat tcgttctgcc aagccgccta tacctatttt ttcagctttt accgctcgac   2760
gcgaaaacca aagtgaaatt ggtgtcggca agcggtcaaa atccggtgaa aatcagcaat   2820
cgcttttggt ttcactttaa ccacagccgt tcgccagttt taggccactt ttagtcgtta   2880
```

-continued

```
gttgcggaag gcacggaaga aaacgatgcg gtcagcttta agcaattgaa agccttgcaa   2940
caacgccttc cgtgccttct tttgctacgc cagtcgaaat tcgttaactt tcggaacgtt   3000
gagaaacagg ttactttaac tgcgagcaat gcttatgcca atggtggtaa cgatgccgac   3060
ctctttgtcc aatgaaattg acgctcgtta cgaatacggt taccaccatt gctacggctg   3120
ggcggcaagg caactcaaac tttaaacaat ggtttgaatt ttaaatttaa atccacagac   3180
ccgccgttcc gttgagtttg aaatttgtta ccaaacttaa aatttaaatt taggtgtctg   3240
ggcgagttgt tgaacatcaa agtagaaaat gacacagtta cctttacgcc gaaaaaaggt   3300
ccgctcaaca acttgtagtt tcatctttta ctgtgtcaat ggaaatgcgg ctttttttcca   3360
tcggtacagg ttggcgaaga cggtaaggct acgattcaaa atggtacgaa aacaaccgac   3420
agccatgtcc aaccgcttct gccattccga tgctaagttt taccatgctt ttgttggctg   3480
ggtttggttg aagcttccga attggttgaa agcctgaaca aactgggctg gaaagtgggc   3540
ccaaaccaac ttcgaaggct taaccaactt tcggacttgt ttgacccgac ctttcacccg   3600
gttgataaag acggcagcgg cgagcttgat ggtgcatcca atgaaacttt agtgaagtcg   3660
caactatttc tgccgtcgcc gctcgaacta ccacgtaggt tactttgaaa tcacttcagc   3720
ggcgataaag taactttgaa agccggcgag aatctgaagg tcaaacaaga cggcacaaac   3780
ccgctatttc attgaaactt tcggccgctc ttagacttcc agtttgttct gccgtgtttg   3840
ttcacttacg cgctcaaaga tgaattgacg ggcgtgaaga gcgtggagtt taaagacacg   3900
aagtgaatgc gcgagtttct acttaactgc ccgcacttct cgcacctcaa atttctgtgc   3960
gcgaatggtt caaacggtgc aagcacgaag attaccaaag acggcttgac cattacgtcg   4020
cgcttaccaa gtttgccacg ttcgtgcttc taatggtttc tgccgaactg gtaatgcagc   4080
gcaaacggtg cgaatggtgc ggcggcgact gatgcggaca agattaaagt ggcttcagac   4140
cgtttgccac gcttaccacg ccgccgctga ctacgcctgt tctaatttca ccgaagtctg   4200
ggcatcagtg cgggtaataa agcggttaaa aacgttgtga gcggactgaa gaaatttggt   4260
ccgtagtcac gcccattatt tcgccaattt ttgcaacact cgcctgactt ctttaaacca   4320
gatgcgaatt tcaatccact gaccagttcc gccgacaact taacgaaaca atatgacgat   4380
ctacgcttaa agttaggtga ctggtcaagg cggctgttga attgctttgt tatactgcta   4440
gcctataaag gcttgaccaa tttggatgaa aaaggtgcgg acaagcaaac tctgactgtt   4500
cggatatttc cgaactggtt aaacctactt tttccacgcc tgttcgtttg agactgacaa   4560
gccgacaata ctgccgcaac cgtgggcgat ttgcgcggct tgggctgggt catttctgcg   4620
cggctgttat gacggcgttg gcacccgcta aacgcgccga acccgaccca gtaaagacgc   4680
gacaaaacca caggcgaact caataaggaa tacaacgcgc aagtgcgtaa cgccaatgaa   4740
ctgttttggt gtccgcttga gttattcctt atgttgcgcg ttcacgcatt gcggttactt   4800
gtgaaattca agagcggcaa cggtatccat gtttccggta aaacggtcaa cggtaggcgc   4860
cactttaagt tctcgccgtt gccataggta caaaggccat tttgccagtt gccatccgcg   4920
gaaattactt ttgaattggc taaagacgaa aatgccattg ctttcggtta tggctcaaaa   4980
ctttaatgaa aacttaaccg atttctgctt ttacggtaac gaaagccaat accgagtttt   5040
gccttgcgcg ataacacggt ggcaattggt acgggcaacg ttgtgaatgc ggaaaaatct   5100
cggaacgcgc tattgtgcca ccgttaacca tgcccgttgc aacacttacg cctttttaga   5160
ggtgcattcg gcgatccgaa ctacatcgaa gataaagccg gtggcagcta cgctttcggt   5220
ccacgtaagc cgctaggctt gatgtagctt ctatttcggc caccgtcgat gcgaaagcca   5280
```

-continued

```
aacgataacc gtattacttc taaaaacact tttgtgttgg gtaatggagt taatgcgaaa   5340
ttgctattgg cataatgaag atttttgtga aaacacaacc cattacctca attacgcttt   5400
tataaagcca atggagatgt tgatacggaa accgtaaccg ttaaggacaa agacggtaaa   5460
atatttcggt tacctctaca actatgcctt tggcattggc aattcctgtt tctgccattt   5520
gagactaccg ttactgttcc taaagcgtta ggggctacgg ttgaaaactc cgtttatttg   5580
ctctgatggc aatgacaagg atttcgcaat ccccgatgcc aacttttgag gcaaataaac   5640
ggtaataaat cgactgcgac aaaagataag ggtaaaaacc tgaaatctga tggtacggcg   5700
ccattattta gctgacgctg ttttctattc ccatttttgg actttagact accatgccgc   5760
ggtaacacta caactgctgg cacaacgggt acggtaaacg gctttgccgg tgcaacggcg   5820
ccattgtgat gttgacgacc gtgttgccca tgccatttgc cgaaacggcc acgttgccgc   5880
cacggtgcgg tttctgtcgg cgcaagcggc gaagaaagac gtatccaaaa cgtcgcggca   5940
gtgccacgcc aaagacagcc gcgttcgccg cttctttctg cataggtttt gcagcgccgt   6000
ggcgaaattt ccgccacttc caccgatgcg attaacggca gccagttgta tgctgtggca   6060
ccgctttaaa ggcggtgaag gtggctacgc taattgccgt cggtcaacat acgacaccgt   6120
aaaggggtaa caaatcttgc tggacaagtg aataaagtgg gcaaacgtgc agatgcaggt   6180
tttccccatt gtttagaacg acctgttcac ttatttcacc cgtttgcacg tctacgtcca   6240
acagcaagtg cattagcagc ttcacagtta ccacaagcct ctatgccagg taaatcaatg   6300
tgtcgttcac gtaatcgtcg aagtgtcaat ggtgttcgga gatacggtcc atttagttac   6360
gtttctattg cgggaagtag ttatcaaggt caaaatggtt tagctatcgg ggtatcacga   6420
caaagataac gcccttcatc aatagttcca gttttaccaa atcgatagcc ccatagtgct   6480
atttccgata atggcaaagt gattattcgc ttgtcaggca caaccaatag ccaaggtaaa   6540
taaaggctat taccgtttca ctaataagcg aacagtccgt gttggttatc ggttccattt   6600
acaggcgttg cagcaggtgt tggttaccag tggtaataga attccggatc cgctgtccgc   6660
aacgtcgtcc acaaccaatg gtcaccatta tcttaaggcc taggcg                  6706
```

<210> SEQ ID NO 28
<211> LENGTH: 1104
<212> TYPE: PRT
<213> ORGANISM: Haemophilus influenzae

<400> SEQUENCE: 28

```
Met Asn Lys Ile Phe Asn Val Ile Trp Asn Val Val Thr Gln Thr Trp
  1               5                  10                  15

Val Val Val Ser Glu Leu Thr Arg Ala His Thr Lys Cys Ala Ser Ala
             20                  25                  30

Thr Val Ala Val Ala Val Leu Ala Thr Ala Leu Ser Ala Thr Ala Glu
         35                  40                  45

Ala Asn Asn Asn Thr Ser Val Thr Asn Gly Leu Asn Ala Tyr Gly Asp
     50                  55                  60

Thr Asn Phe Asn Thr Thr Asn Asn Ser Ile Ala Asp Leu Glu Lys His
 65                  70                  75                  80

Val Gln Asp Ala Tyr Lys Gly Leu Leu Asn Leu Asn Glu Lys Asp Thr
                 85                  90                  95

Asn Lys Ser Ser Phe Leu Val Ala Asp Asn Thr Ala Ala Thr Val Gly
            100                 105                 110

Asn Leu Arg Lys Leu Gly Trp Val Leu Ser Ser Lys Asn Gly Thr Arg
```

-continued

```
        115                 120                 125

Asn Glu Lys Ser Tyr Gln Val Lys Gln Ala Asp Glu Val Leu Phe Thr
    130                 135                 140

Gly Ser Gly Ala Ala Thr Val Ser Ser Ser Ser Lys Asp Gly Lys His
145                 150                 155                 160

Thr Ile Thr Ile Ser Val Thr Lys Gly Ser Phe Ala Glu Val Lys Thr
                165                 170                 175

Asp Ala Thr Thr Gly Gly Gln Val Asn Ala Asp Arg Gly Lys Val Lys
            180                 185                 190

Ala Glu Asp Glu Asn Gly Ala Asp Val Asp Lys Lys Val Ala Thr Val
        195                 200                 205

Lys Asp Val Ala Lys Ala Ile Asn Asp Ala Ala Thr Phe Val Lys Val
    210                 215                 220

Glu Ser Thr Asp Asp Asp Ile Glu Asn Gly Ala Ala Gly Lys Asn Glu
225                 230                 235                 240

Thr Thr Asp Gln Ala Leu Lys Ala Gly Asp Thr Leu Thr Leu Lys Ala
                245                 250                 255

Gly Lys Asn Leu Lys Ala Lys Leu Asp Gln Asn Gly Lys Ser Val Thr
            260                 265                 270

Phe Ala Leu Ala Lys Asp Leu Asp Val Thr Ser Ala Lys Val Ser Asp
        275                 280                 285

Lys Leu Ser Ile Gly Lys Asp Thr Asn Lys Val Asp Ile Thr Ser Asp
    290                 295                 300

Ala Asn Gly Leu Lys Leu Ala Lys Thr Gly Asn Gly Asn Gly Gln Asn
305                 310                 315                 320

Gly Asn Val His Leu Asn Gly Ile Ala Ser Thr Leu Thr Asp Thr Ile
                325                 330                 335

Thr Gly Met Thr Thr Gln Ala Ser Asn Gly Val Ala Val Gln Asn His
            340                 345                 350

Asn Arg Ala Ala Ser Val Ala Asp Val Leu Asn Ala Gly Trp Asn Ile
        355                 360                 365

Gln Gly Asn Gly Ala Ser Val Asp Phe Val Asn Ala Tyr Asp Thr Val
    370                 375                 380

Asp Phe Val Asn Gly Thr Asn Thr Asn Val Asn Val Thr Thr Asp Thr
385                 390                 395                 400

Ala His Lys Lys Thr Thr Val Arg Val Asp Val Thr Gly Leu Pro Val
                405                 410                 415

Gln Tyr Val Thr Glu Asp Gly Lys Thr Val Val Lys Val Asp Asn Lys
            420                 425                 430

Tyr Tyr Glu Ala Lys Gln Asp Gly Ser Ala Asp Met Asp Lys Lys Val
        435                 440                 445

Glu Asn Gly Glu Leu Ala Lys Thr Lys Val Lys Leu Val Ser Ala Ser
    450                 455                 460

Gly Gln Asn Pro Val Lys Ile Ser Asn Val Ala Glu Gly Thr Glu Glu
465                 470                 475                 480

Asn Asp Ala Val Ser Phe Lys Gln Leu Lys Ala Leu Gln Glu Lys Gln
                485                 490                 495

Val Thr Leu Thr Ala Ser Asn Ala Tyr Ala Asn Gly Gly Asn Asp Ala
            500                 505                 510

Asp Gly Gly Lys Ala Thr Gln Thr Leu Asn Asn Gly Leu Asn Phe Lys
        515                 520                 525

Phe Lys Ser Thr Asp Gly Glu Leu Leu Asn Ile Lys Val Glu Asn Asp
    530                 535                 540
```

-continued

```
Thr Val Thr Phe Thr Pro Lys Lys Gly Ser Val Gln Val Gly Glu Asp
545                 550                 555                 560

Gly Lys Ala Thr Ile Gln Asn Gly Thr Lys Thr Thr Asp Gly Leu Val
                565                 570                 575

Glu Ala Ser Glu Leu Val Glu Ser Leu Asn Lys Leu Gly Trp Lys Val
            580                 585                 590

Gly Val Asp Lys Asp Gly Ser Gly Glu Leu Asp Gly Ala Ser Asn Glu
        595                 600                 605

Thr Leu Val Lys Ser Gly Asp Lys Val Thr Leu Lys Ala Gly Glu Asn
    610                 615                 620

Leu Lys Val Lys Gln Asp Gly Thr Asn Phe Thr Tyr Ala Leu Lys Asp
625                 630                 635                 640

Glu Leu Thr Gly Val Lys Ser Val Glu Phe Lys Asp Thr Ala Asn Gly
                645                 650                 655

Ser Asn Gly Ala Ser Thr Lys Ile Thr Lys Asp Gly Leu Thr Ile Thr
            660                 665                 670

Ser Ala Asn Gly Ala Asn Gly Ala Ala Ala Thr Asp Ala Asp Lys Ile
        675                 680                 685

Lys Val Ala Ser Asp Gly Ile Ser Ala Gly Asn Lys Ala Val Lys Asn
    690                 695                 700

Val Val Ser Gly Leu Lys Lys Phe Gly Asp Ala Asn Phe Asn Pro Leu
705                 710                 715                 720

Thr Ser Ser Ala Asp Asn Leu Thr Lys Gln Tyr Asp Asp Ala Tyr Lys
                725                 730                 735

Gly Leu Thr Asn Leu Asp Glu Lys Gly Ala Asp Lys Gln Thr Leu Thr
            740                 745                 750

Val Ala Asp Asn Thr Ala Ala Thr Val Gly Asp Leu Arg Gly Leu Gly
        755                 760                 765

Trp Val Ile Ser Ala Asp Lys Thr Thr Gly Glu Leu Asn Lys Glu Tyr
    770                 775                 780

Asn Ala Gln Val Arg Asn Ala Asn Glu Val Lys Phe Lys Ser Gly Asn
785                 790                 795                 800

Gly Ile His Val Ser Gly Lys Thr Val Asn Gly Arg Arg Glu Ile Thr
                805                 810                 815

Phe Glu Leu Ala Lys Asp Glu Asn Ala Ile Ala Phe Gly Tyr Gly Ser
            820                 825                 830

Lys Ala Leu Arg Asp Asn Thr Val Ala Ile Gly Thr Gly Asn Val Val
        835                 840                 845

Asn Ala Glu Lys Ser Gly Ala Phe Gly Asp Pro Asn Tyr Ile Glu Asp
    850                 855                 860

Lys Ala Gly Gly Ser Tyr Ala Phe Gly Asn Asp Asn Arg Ile Thr Ser
865                 870                 875                 880

Lys Asn Thr Phe Val Leu Gly Asn Gly Val Asn Ala Lys Tyr Lys Ala
                885                 890                 895

Asn Gly Asp Val Asp Thr Glu Thr Val Thr Val Lys Asp Lys Asp Gly
            900                 905                 910

Lys Glu Thr Thr Val Thr Val Pro Lys Ala Leu Gly Ala Thr Val Glu
        915                 920                 925

Asn Ser Val Tyr Leu Gly Asn Lys Ser Thr Ala Thr Lys Asp Lys Gly
    930                 935                 940

Lys Asn Leu Lys Ser Asp Gly Thr Ala Gly Asn Thr Thr Thr Ala Gly
945                 950                 955                 960
```

-continued

```
Thr Thr Gly Thr Val Asn Gly Phe Ala Gly Ala Thr Ala His Gly Ala
                965                 970                 975

Val Ser Val Gly Ala Ser Gly Glu Glu Arg Arg Ile Gln Asn Val Ala
            980                 985                 990

Ala Gly Glu Ile Ser Ala Thr Ser Thr Asp Ala Ile Asn Gly Ser Gln
        995                 1000                1005

Leu Tyr Ala Val Ala Lys Gly Val Thr Asn Leu Ala Gly Gln Val Asn
    1010                1015                1020

Lys Val Gly Lys Arg Ala Asp Ala Gly Thr Ala Ser Ala Leu Ala Ala
1025                1030                1035                1040

Ser Gln Leu Pro Gln Ala Ser Met Pro Gly Lys Ser Met Val Ser Ile
                1045                1050                1055

Ala Gly Ser Ser Tyr Gln Gly Gln Asn Gly Leu Ala Ile Gly Val Ser
            1060                1065                1070

Arg Ile Ser Asp Asn Gly Lys Val Ile Ile Arg Leu Ser Gly Thr Thr
        1075                1080                1085

Asn Ser Gln Gly Lys Thr Gly Val Ala Ala Gly Val Gly Tyr Gln Trp
    1090                1095                1100


<210> SEQ ID NO 29
<211> LENGTH: 3030
<212> TYPE: DNA
<213> ORGANISM: Haemophilus influenzae

<400> SEQUENCE: 29

gcgaattcat atgaacaaaa tttttaacgt tatttggaat gttatgactc aaacttgggc     60

tgtcgtatct gaactcactc gcgcccacac caaacgtgcc tccgcaaccg tggcaaccgc    120

cgtattggcg acgttgttgt ctacaacagt tcaggcgaca actactggcg gtacgacaag    180

tacaaacggt ttgaaagctt atggaagtac gaataatccg aatttcaatg ctgcaggtaa    240

ctctgcaact gatttagcta gacagtttga tggtgcttat gacggtttat taaatctaaa    300

tgaaaaagat gcgaataaaa atctgttggt gactgatgat aaggcggcga ccgtaggcaa    360

tttgcgtaaa ttgggttggg tattgtctag taaaaacggc acaaggaacg agaaaagcca    420

acaagtcaaa cacgcggatg aagtgttgtt tgaaggcaaa gacggtgtaa cggttacttc    480

caaatctgaa aacggtaaac acaccgttac ttttaccctt gagaaagacc ttaatgtaaa    540

aaacgcaacc gttagcgata aattatcgct tggtgcaaac ggcaataaag tcgatattac    600

cagtgataca aacggcttga aatttgcgaa accaagtacg aatggtcaaa acggtaatgt    660

tcacttaaac ggtattgcct ctaccttaac tgacacaatt acaggtacaa caaaatctgc    720

aactaatggt gtagatgtgc agaatcataa tcgtgctgcg agtgtagctg atgtattgaa    780

tgcaggctgg aatattcaag gcaacggagc gagcgttgat tttgtcaata cttacgacac    840

agtagatttt gtcaatggtt taaataccaa tgtgaacgtt acgactgata cggctcacaa    900

caaaaagaca accgtccgtg tggatgtaac gggcttgccg gtccaatatg ttacggaaga    960

cggcgaaacc gttgtgaaag tgggcaatga gtattacgaa gccaagcaag acggttcggc   1020

ggatatggat aaaaaagtcg aaaatggcaa gctggcgaaa actaaagtta aattggtatc   1080

ggcaaacggt acaaatccgg tgaaaatcag caatgttgcg gacggcacgg aaaataccga   1140

tgcggtcagc tttaagcagt tgaaagcctt gcaagacaaa caggttacgt taagtgcgag   1200

caatgcttat gccaatggcg gtagcgatgc cgacggcggc aagggaattc aaactttaag   1260

caatggtttg aattttaaat ttaaatccac agacggcgag ttgttgaata tcaaagcaga   1320
```

-continued

```
aaatgacacg gttaccttta cgccgaaaaa aggttcggtg caggttggcg atgatggtaa   1380

ggctacgatt caagacggcg caaaaacaac taccggtttg gttgaggctt ctgaattggt   1440

tgacagcctg aacaaattgg gttggaaagt gggcaccggc actgacggca caggagtgac   1500

cgatggcacg cataccgaca ctttagtgaa gtcgggcgat aaagtaactt tgaaagccgg   1560

cgacaatctg aaggtcaaac aagagggtac aaacttcact tatgcgctca aagatgaatt   1620

gacggacgtg aagagcgtgg agtttaaaga cacggcgaat ggtgcaaacg gtgcaagcac   1680

gaagattacc aaagacggct tgaccattac gccggcaaac ggtgcgggtg cggcaggtgc   1740

aaacactgca aacaccatta gcgtaaccaa agacggcatt agcgcgggta ataaagcagt   1800

taaaaacgtt gtgagcggac tgaagaaatt tggtgatgcg aatttcgatc cgctgactag   1860

ctcagccgac aacttaacga aacaatatga caatgcctat aaaggcttga ccaatctgga   1920

tgaaaaaagt aaaggcaagc aaactccgac cgttgctgac aataccgctg caaccgtggg   1980

cgatttgcgc ggcttgggct gggtcatttc tgcagacaaa accaaaggcg aactcaataa   2040

ggaatacaac gcacaagtgc gtaacgctaa tgaagtgaaa ttcaagagcg gcaacggtat   2100

caatgtttcc ggtaaaacat tggataacgg tacgcgcgaa attacttttg aattggctaa   2160

agacgaaaat gccattgctt tcggttctgg ctcaaaagcc ttgcgcgata acacggtggc   2220

aattggtacg ggcaacgttg tgaatgcgga aaaatctggt gcattcggcg atccgaacta   2280

catcgaagat aaagccggtg gcagctacgc tttcggtaac gataaccgta ttacttctaa   2340

aaacactttt gtgttgggta atagtgttaa tgcgaaacgt gatgcaaatg gcaatgtact   2400

gaccgaagaa aaagaagtgg ttggaaaaga cggtgcgaag acgaaagtaa ccgtgccgca   2460

agccttaggc gaaaccgtag aaaattctgt ttatctcggt aatgcttcaa ctgcgacaaa   2520

agataagggt aaaaacctga aatctgatgg tacggcgggt aacactacaa ctgctggcgc   2580

aacgggtacg gtaaacggct ttgccggtgc aacggcgcac ggtgcggttt ctgtcggcgc   2640

aagtggcgaa gaaagacgta tccaaaacgt cgcggcaggc gaaatttccg ctacttccac   2700

agatgcgatt aacggtagcc agttgtatgc tgtggcaaaa ggggtaacaa accttgctgg   2760

acaagtgaat aaagtgggca aacgtgcaga tgcaggtaca gcaagtgcat tagcggcttc   2820

acagttacca caagcctcta tgccaggtaa atcaatggtt tctattgcgg gaagtagtta   2880

tcaaggtcaa agtggtttag ctatcggggt atcaagaatt tccgataatg gcaaagtgat   2940

tattcgcttg tcaggcacaa ccaatagcca aggtaaaaca ggcgttgcag caggtgttgg   3000

ttaccagtgg taatagaatt ccggatccgc                                    3030
```

<210> SEQ ID NO 30
<211> LENGTH: 1004
<212> TYPE: PRT
<213> ORGANISM: Haemophilus influenzae

<400> SEQUENCE: 30

```
Met Asn Lys Ile Phe Asn Val Ile Trp Asn Val Met Thr Gln Thr Trp
  1               5                  10                  15

Ala Val Val Ser Glu Leu Thr Arg Ala His Thr Lys Arg Ala Ser Ala
             20                  25                  30

Thr Val Ala Thr Ala Val Leu Ala Thr Leu Leu Ser Thr Thr Val Gln
         35                  40                  45

Ala Thr Thr Thr Gly Gly Thr Thr Ser Thr Asn Gly Leu Lys Ala Tyr
     50                  55                  60

Gly Ser Thr Asn Asn Pro Asn Phe Asn Ala Ala Gly Asn Ser Ala Thr
```

-continued

```
65                  70                  75                  80

Asp Leu Ala Arg Gln Phe Asp Gly Ala Tyr Asp Gly Leu Leu Asn Leu
                85                  90                  95

Asn Glu Lys Asp Ala Asn Lys Asn Leu Leu Val Thr Asp Asp Lys Ala
            100                 105                 110

Ala Thr Val Gly Asn Leu Arg Lys Leu Gly Trp Val Leu Ser Ser Lys
        115                 120                 125

Asn Gly Thr Arg Asn Glu Lys Ser Gln Gln Val Lys His Ala Asp Glu
    130                 135                 140

Val Leu Phe Glu Gly Lys Asp Gly Val Thr Val Thr Ser Lys Ser Glu
145                 150                 155                 160

Asn Gly Lys His Thr Val Thr Phe Thr Leu Glu Lys Asp Leu Asn Val
                165                 170                 175

Lys Asn Ala Thr Val Ser Asp Lys Leu Ser Leu Gly Ala Asn Gly Asn
            180                 185                 190

Lys Val Asp Ile Thr Ser Asp Thr Asn Gly Leu Lys Phe Ala Lys Pro
        195                 200                 205

Ser Thr Asn Gly Gln Asn Gly Asn Val His Leu Asn Gly Ile Ala Ser
    210                 215                 220

Thr Leu Thr Asp Thr Ile Thr Gly Thr Thr Lys Ser Ala Thr Asn Gly
225                 230                 235                 240

Val Asp Val Gln Asn His Asn Arg Ala Ala Ser Val Ala Asp Val Leu
                245                 250                 255

Asn Ala Gly Trp Asn Ile Gln Gly Asn Gly Ala Ser Val Asp Phe Val
            260                 265                 270

Asn Thr Tyr Asp Thr Val Asp Phe Val Asn Gly Leu Asn Thr Asn Val
        275                 280                 285

Asn Val Thr Thr Asp Thr Ala His Asn Lys Lys Thr Thr Val Arg Val
    290                 295                 300

Asp Val Thr Gly Leu Pro Val Gln Tyr Val Thr Glu Asp Gly Glu Thr
305                 310                 315                 320

Val Val Lys Val Gly Asn Glu Tyr Tyr Glu Ala Lys Gln Asp Gly Ser
                325                 330                 335

Ala Asp Met Asp Lys Lys Val Glu Asn Gly Lys Leu Ala Lys Thr Lys
            340                 345                 350

Val Lys Leu Val Ser Ala Asn Gly Thr Asn Pro Val Lys Ile Ser Asn
        355                 360                 365

Val Ala Asp Gly Thr Glu Asn Thr Asp Ala Val Ser Phe Lys Gln Leu
    370                 375                 380

Lys Ala Leu Gln Asp Lys Gln Val Thr Leu Ser Ala Ser Asn Ala Tyr
385                 390                 395                 400

Ala Asn Gly Gly Ser Asp Ala Asp Gly Gly Lys Gly Ile Gln Thr Leu
                405                 410                 415

Ser Asn Gly Leu Asn Phe Lys Phe Lys Ser Thr Asp Gly Glu Leu Leu
            420                 425                 430

Asn Ile Lys Ala Glu Asn Asp Thr Val Thr Phe Thr Pro Lys Lys Gly
        435                 440                 445

Ser Val Gln Val Gly Asp Asp Gly Lys Ala Thr Ile Gln Asp Gly Ala
    450                 455                 460

Lys Thr Thr Thr Gly Leu Val Glu Ala Ser Glu Leu Val Asp Ser Leu
465                 470                 475                 480

Asn Lys Leu Gly Trp Lys Val Gly Thr Gly Thr Asp Gly Thr Gly Val
                485                 490                 495
```

-continued

```
Thr Asp Gly Thr His Thr Asp Thr Leu Val Lys Ser Gly Asp Lys Val
            500                 505                 510

Thr Leu Lys Ala Gly Asp Asn Leu Lys Val Lys Gln Glu Gly Thr Asn
        515                 520                 525

Phe Thr Tyr Ala Leu Lys Asp Glu Leu Thr Asp Val Lys Ser Val Glu
    530                 535                 540

Phe Lys Asp Thr Ala Asn Gly Ala Asn Gly Ala Ser Thr Lys Ile Thr
545                 550                 555                 560

Lys Asp Gly Leu Thr Ile Thr Pro Ala Asn Gly Ala Gly Ala Ala Gly
                565                 570                 575

Ala Asn Thr Ala Asn Thr Ile Ser Val Thr Lys Asp Gly Ile Ser Ala
            580                 585                 590

Gly Asn Lys Ala Val Lys Asn Val Val Ser Gly Leu Lys Lys Phe Gly
        595                 600                 605

Asp Ala Asn Phe Asp Pro Leu Thr Ser Ser Ala Asp Asn Leu Thr Lys
    610                 615                 620

Gln Tyr Asp Asn Ala Tyr Lys Gly Leu Thr Asn Leu Asp Glu Lys Ser
625                 630                 635                 640

Lys Gly Lys Gln Thr Pro Thr Val Ala Asp Asn Thr Ala Ala Thr Val
                645                 650                 655

Gly Asp Leu Arg Gly Leu Gly Trp Val Ile Ser Ala Asp Lys Thr Lys
            660                 665                 670

Gly Glu Leu Asn Lys Glu Tyr Asn Ala Gln Val Arg Asn Ala Asn Glu
        675                 680                 685

Val Lys Phe Lys Ser Gly Asn Gly Ile Asn Val Ser Gly Lys Thr Leu
    690                 695                 700

Asp Asn Gly Thr Arg Glu Ile Thr Phe Glu Leu Ala Lys Asp Glu Asn
705                 710                 715                 720

Ala Ile Ala Phe Gly Ser Gly Ser Lys Ala Leu Arg Asp Asn Thr Val
                725                 730                 735

Ala Ile Gly Thr Gly Asn Val Val Asn Ala Glu Lys Ser Gly Ala Phe
            740                 745                 750

Gly Asp Pro Asn Tyr Ile Glu Asp Lys Ala Gly Gly Ser Tyr Ala Phe
        755                 760                 765

Gly Asn Asp Asn Arg Ile Thr Ser Lys Asn Thr Phe Val Leu Gly Asn
    770                 775                 780

Ser Val Asn Ala Lys Arg Asp Ala Asn Gly Asn Val Leu Thr Glu Glu
785                 790                 795                 800

Lys Glu Val Val Gly Lys Asp Gly Ala Lys Thr Lys Val Thr Val Pro
                805                 810                 815

Gln Ala Leu Gly Glu Thr Val Glu Asn Ser Val Tyr Leu Gly Asn Ala
            820                 825                 830

Ser Thr Ala Thr Lys Asp Lys Gly Lys Asn Leu Lys Ser Asp Gly Thr
        835                 840                 845

Ala Gly Asn Thr Thr Thr Ala Gly Ala Thr Gly Thr Val Asn Gly Phe
    850                 855                 860

Ala Gly Ala Thr Ala His Gly Ala Val Ser Val Gly Ala Ser Gly Glu
865                 870                 875                 880

Glu Arg Arg Ile Gln Asn Val Ala Ala Gly Glu Ile Ser Ala Thr Ser
                885                 890                 895

Thr Asp Ala Ile Asn Gly Ser Gln Leu Tyr Ala Val Ala Lys Gly Val
            900                 905                 910
```

-continued

```
Thr Asn Leu Ala Gly Gln Val Asn Lys Val Gly Lys Arg Ala Asp Ala
        915                 920                 925

Gly Thr Ala Ser Ala Leu Ala Ala Ser Gln Leu Pro Gln Ala Ser Met
    930                 935                 940

Pro Gly Lys Ser Met Val Ser Ile Ala Gly Ser Ser Tyr Gln Gly Gln
945                 950                 955                 960

Ser Gly Leu Ala Ile Gly Val Ser Arg Ile Ser Asp Asn Gly Lys Val
                965                 970                 975

Ile Ile Arg Leu Ser Gly Thr Thr Asn Ser Gln Gly Lys Thr Gly Val
            980                 985                 990

Ala Ala Gly Val Gly Tyr Gln Trp Asn Ser Gly Ser
        995                 1000
```

<210> SEQ ID NO 31
<211> LENGTH: 3300
<212> TYPE: DNA
<213> ORGANISM: Haemophilus influenzae

<400> SEQUENCE: 31

```
atgaacaaaa tttttaacgt tatttggaat gttatgactc aaacttgggc tgtcgtatct     60

gaactcactc gcgcccacac caaacgtgcc tccgcaaccg tggcgaccgc cgtattggcg    120

acgcagttgt ctgcaacggc tgaagcgaac agtagtgctt ctgttacgag taggttgaat    180

gtttatggcg atacgaatac taaattcaat gcagccaata attcaatagc agatttaaat    240

aaacaaaatg atggtgttca cgatggttta ttaaatctga atgaaaacgg tgcgaataaa    300

aagctgttgg tggatgacaa tactgcggcg accgtaggcg atttacgtaa attgggctgg    360

gtcgtatcaa ccaaaaatgg caaggaaaat gagaaaagcc aacaagtcaa acaggcggat    420

gaagtgttgt ttaaaggcag caaaggcggt gtgcaggtta cttccacctc tgaaaacggc    480

aaacacgcca ttacctttgc tttagcgaaa gaccttgata tgagaactgc gactgtgagt    540

gataccttaa cgattggcgg tagtactact acaggtagtg caacaacacc aaaagtgaat    600

gtgactagca cggcaagcgg cttgaacttt gcgaaaggcg ctacaggtgc taatggcgat    660

actacggttc acttgactaa tattgcttca actttgcaag atactctatt gaatactggg    720

gttgtgagta aattagatgg taatggtatt actgctgacg agaaaaaacg tgcggcaagc    780

gttcaagatg ttttaaatag tggttggaat atcaagggtg ttaaaacagg tgcgacgact    840

tctgataacg ttgattttgt ccgtacttac gacacagttg agtttttgag cggaagtgaa    900

gaaactacac tggttacagt ggatagtgaa agtaatggaa aatctactaa agttaaaatc    960

ggtgcgaaga cctctgttat caaagaaaaa gacggtaagt tatttactgg aaaagctaat   1020

aaagacacaa atcaagtcgc aagtaataat gcagctgatg atacggatga gggcaaaggc   1080

ttagtcactg cagagactgt tatcaatgca gtaaacaagg ctggttggag aattaaaaca   1140

acgggtgcta ataatcaagc tggtcagttt gaaactgtca catcaggcac aaatgtaacc   1200

tttgctgatg gcaatggtac aactgcagtc gtaactggcg atgctaccaa tggtattact   1260

gttaaatacg aagcgaaagt tggcgacggc ttgaagattg gtaacgacca aaaaatcact   1320

gcagatacga ccgcacttac tgtgacgggc ggtaaagtta ctgcccctga tgcaaccaat   1380

ggtaagaaac ttgttaatgc aagtggttta gctgatgcgt taaacaaatt aagttggact   1440

gcaaaagctg aagcagatac tgctaatggc ggcgagcttg atggaactgc agatgaaaaa   1500

gaagttaaag caggcgaaac ggtaaccttt aaagcgggca agaacttaaa agtgaaacaa   1560

gatggtgcga actttactta ttcactgcaa gatgctttaa caggcttaac gagcattact   1620
```

-continued

```
ttaggtacag gaaataatgg tgcgaaaact gaaatcaaca aagacggctt aaccatcaca   1680
ccagcaaatg gtgcgggtgc aaataatgca aacaccatca gcgtaaccaa agacggcatt   1740
agtgcgggcg gtcagtcggt taaaaacgtt gtgagcggac tgaagaaatt tggtgatgcg   1800
aatttcgatc cgctgactag ctccgccgac aacttaacga aacaatatga cgatgcctat   1860
aaaggcttga ccaatttgga tgaaaaaggt gcggacaagc aaactctgac tgttgccgac   1920
aatactgccg caaccgtggg cgatttgcgc ggcttgggct gggtcatttc tgcggacaaa   1980
accacaggcg aactcgataa ggaatacaac gcgcaagtgc gtaacgccaa tgaagtgaaa   2040
ttcaaaagcg gcaacggtat caatgtttcc ggtaaaactg tcaacggtag gcgtgaaatt   2100
acttttgaat tggctaaagg cgaagtggtt aaatcgaatg aatttactgt caaagaaacc   2160
aatggcaagg aaacgagcct ggttaaagtt ggcgataaat attacagcaa agaggatatt   2220
gacccagcaa ccggtaaacc gaaagttaca aatggcaatg cagttgctgc gaaatatcaa   2280
gataaagatg gcaaagtcgt ttctgctgac ggcagcagca ataccgctgt taccctaacc   2340
aacaaaggtt atggctatgt aacaggtaac caagtggcag atgcgattgc gaaatcaggc   2400
tttgagcttg gtttggctga tgcagaaaaa gcgaaagctg cgtttggcga tgaaacaaaa   2460
gccttgtctt ctgataaatt ggaaaccgta aatgccaacg acaaagtccg ttttgctaat   2520
ggtttaaata ccaaagtgag cgcggcaacg gtggaaagca tcgatgcaaa cggcgataaa   2580
gtgactacaa cctttgtgaa aaccgatgtg gaattgcctt taacgcaaat ctacaatacc   2640
gatgcaaacg gtaagaaaat cgttaaaaat ggcgataaat ggtattacac gaaagatgac   2700
ggctcaactg atatgactaa agaagttacc cttggcaatg tggattcaga cggcaagaaa   2760
gttgtgaaag aagacaacaa gtggtatcac gttaaatctg atggttctac ggataaaaca   2820
caggtggtcg aagaagctaa agtttctacc gatgaaaaac acgttgtcag ccttgatcca   2880
aatgatcaat caaaaggtaa aggcgtggtc attaacaata tggctaatgg cgaaatttct   2940
gccacttcca ccgatgcgat taacggaagt cagttgtatg ccgtggcaaa aggggtaaca   3000
aaccttgctg gacaagtgaa taatcttgag ggcaaagtga ataaagtggg caaacgtgca   3060
gatgcaggta ctgcaagtgc attagcggct tcacagttac cacaagccac tatgccaggt   3120
aaatcaatgg tttctattgc gggaagtagt tatcaaggtc aaaatggttt agctatcggg   3180
gtatcaagaa tttccgataa tggcaaagtg attattcgct tgtcaggcac aaccaatagt   3240
caaggtaaaa caggcgttgc agcaggtgtt ggttaccagt ggtaatagaa ttccggatcc   3300
```

<210> SEQ ID NO 32
<211> LENGTH: 1094
<212> TYPE: PRT
<213> ORGANISM: Haemophilus influenzae

<400> SEQUENCE: 32

```
Met Asn Lys Ile Phe Asn Val Ile Trp Asn Val Met Thr Gln Thr Trp
  1               5                  10                  15

Ala Val Val Ser Glu Leu Thr Arg Ala His Thr Lys Arg Ala Ser Ala
             20                  25                  30

Thr Val Ala Thr Ala Val Leu Ala Thr Gln Leu Ser Ala Thr Ala Glu
         35                  40                  45

Ala Asn Ser Ser Ala Ser Val Thr Ser Arg Leu Asn Val Tyr Gly Asp
     50                  55                  60

Thr Asn Thr Lys Phe Asn Ala Ala Asn Asn Ser Ile Ala Asp Leu Asn
 65                  70                  75                  80
```

-continued

```
Lys Gln Asn Asp Gly Val His Asp Gly Leu Leu Asn Leu Asn Glu Asn
                85                  90                  95

Gly Ala Asn Lys Lys Leu Leu Val Asp Asp Asn Thr Ala Ala Thr Val
            100                 105                 110

Gly Asp Leu Arg Lys Leu Gly Trp Val Val Ser Thr Lys Asn Gly Lys
        115                 120                 125

Glu Asn Glu Lys Ser Gln Gln Val Lys Gln Ala Asp Glu Val Leu Phe
    130                 135                 140

Lys Gly Ser Lys Gly Gly Val Gln Val Thr Ser Thr Ser Glu Asn Gly
145                 150                 155                 160

Lys His Ala Ile Thr Phe Ala Leu Ala Lys Asp Leu Asp Met Arg Thr
                165                 170                 175

Ala Thr Val Ser Asp Thr Leu Thr Ile Gly Gly Ser Thr Thr Thr Gly
            180                 185                 190

Ser Ala Thr Thr Pro Lys Val Asn Val Thr Ser Thr Ala Ser Gly Leu
        195                 200                 205

Asn Phe Ala Lys Gly Ala Thr Gly Ala Asn Gly Asp Thr Thr Val His
    210                 215                 220

Leu Thr Asn Ile Ala Ser Thr Leu Gln Asp Thr Leu Leu Asn Thr Gly
225                 230                 235                 240

Val Val Ser Lys Leu Asp Gly Asn Gly Ile Thr Ala Asp Glu Lys Lys
                245                 250                 255

Arg Ala Ala Ser Val Gln Asp Val Leu Asn Ser Gly Trp Asn Ile Lys
            260                 265                 270

Gly Val Lys Thr Gly Ala Thr Thr Ser Asp Asn Val Asp Phe Val Arg
        275                 280                 285

Thr Tyr Asp Thr Val Glu Phe Leu Ser Gly Ser Glu Glu Thr Thr Leu
    290                 295                 300

Val Thr Val Asp Ser Glu Ser Asn Gly Lys Ser Thr Lys Val Lys Ile
305                 310                 315                 320

Gly Ala Lys Thr Ser Val Ile Lys Glu Lys Asp Gly Lys Leu Phe Thr
                325                 330                 335

Gly Lys Ala Asn Lys Asp Thr Asn Gln Val Ala Ser Asn Asn Ala Ala
            340                 345                 350

Asp Asp Thr Asp Glu Gly Lys Gly Leu Val Thr Ala Glu Thr Val Ile
        355                 360                 365

Asn Ala Val Asn Lys Ala Gly Trp Arg Ile Lys Thr Thr Gly Ala Asn
    370                 375                 380

Asn Gln Ala Gly Gln Phe Glu Thr Val Thr Ser Gly Thr Asn Val Thr
385                 390                 395                 400

Phe Ala Asp Gly Asn Gly Thr Thr Ala Val Val Thr Gly Asp Ala Thr
                405                 410                 415

Asn Gly Ile Thr Val Lys Tyr Glu Ala Lys Val Gly Asp Gly Leu Lys
            420                 425                 430

Ile Gly Asn Asp Gln Lys Ile Thr Ala Asp Thr Thr Ala Leu Thr Val
        435                 440                 445

Thr Gly Gly Lys Val Thr Ala Pro Asp Ala Thr Asn Gly Lys Lys Leu
    450                 455                 460

Val Asn Ala Ser Gly Leu Ala Asp Ala Leu Asn Lys Leu Ser Trp Thr
465                 470                 475                 480

Ala Lys Ala Glu Ala Asp Thr Ala Asn Gly Gly Glu Leu Asp Gly Thr
                485                 490                 495
```

-continued

```
Ala Asp Glu Lys Glu Val Lys Ala Gly Glu Thr Val Thr Phe Lys Ala
            500                 505                 510

Gly Lys Asn Leu Lys Val Lys Gln Asp Gly Ala Asn Phe Thr Tyr Ser
        515                 520                 525

Leu Gln Asp Ala Leu Thr Gly Leu Thr Ser Ile Thr Leu Gly Thr Gly
    530                 535                 540

Asn Asn Gly Ala Lys Thr Glu Ile Asn Lys Asp Gly Leu Thr Ile Thr
545                 550                 555                 560

Pro Ala Asn Gly Ala Gly Ala Asn Asn Ala Asn Thr Ile Ser Val Thr
                565                 570                 575

Lys Asp Gly Ile Ser Ala Gly Gly Gln Ser Val Lys Asn Val Val Ser
            580                 585                 590

Gly Leu Lys Lys Phe Gly Asp Ala Asn Phe Asp Pro Leu Thr Ser Ser
        595                 600                 605

Ala Asp Asn Leu Thr Lys Gln Tyr Asp Asp Ala Tyr Lys Gly Leu Thr
    610                 615                 620

Asn Leu Asp Glu Lys Gly Ala Asp Lys Gln Thr Leu Thr Val Ala Asp
625                 630                 635                 640

Asn Thr Ala Ala Thr Val Gly Asp Leu Arg Gly Leu Gly Trp Val Ile
                645                 650                 655

Ser Ala Asp Lys Thr Thr Gly Glu Leu Asp Lys Glu Tyr Asn Ala Gln
            660                 665                 670

Val Arg Asn Ala Asn Glu Val Lys Phe Lys Ser Gly Asn Gly Ile Asn
        675                 680                 685

Val Ser Gly Lys Thr Val Asn Gly Arg Arg Glu Ile Thr Phe Glu Leu
    690                 695                 700

Ala Lys Gly Glu Val Val Lys Ser Asn Glu Phe Thr Val Lys Glu Thr
705                 710                 715                 720

Asn Gly Lys Glu Thr Ser Leu Val Lys Val Gly Asp Lys Tyr Tyr Ser
                725                 730                 735

Lys Glu Asp Ile Asp Pro Ala Thr Gly Lys Pro Lys Val Thr Asn Gly
            740                 745                 750

Asn Ala Val Ala Ala Lys Tyr Gln Asp Lys Asp Gly Lys Val Val Ser
        755                 760                 765

Ala Asp Gly Ser Ser Asn Thr Ala Val Thr Leu Thr Asn Lys Gly Tyr
    770                 775                 780

Gly Tyr Val Thr Gly Asn Gln Val Ala Asp Ala Ile Ala Lys Ser Gly
785                 790                 795                 800

Phe Glu Leu Gly Leu Ala Asp Ala Glu Lys Ala Lys Ala Ala Phe Gly
                805                 810                 815

Asp Glu Thr Lys Ala Leu Ser Ser Asp Lys Leu Glu Thr Val Asn Ala
            820                 825                 830

Asn Asp Lys Val Arg Phe Ala Asn Gly Leu Asn Thr Lys Val Ser Ala
        835                 840                 845

Ala Thr Val Glu Ser Ile Asp Ala Asn Gly Asp Lys Val Thr Thr Thr
    850                 855                 860

Phe Val Lys Thr Asp Val Glu Leu Pro Leu Thr Gln Ile Tyr Asn Thr
865                 870                 875                 880

Asp Ala Asn Gly Lys Lys Ile Val Lys Asn Gly Asp Lys Trp Tyr Tyr
                885                 890                 895

Thr Lys Asp Asp Gly Ser Thr Asp Met Thr Lys Glu Val Thr Leu Gly
            900                 905                 910

Asn Val Asp Ser Asp Gly Lys Lys Val Val Lys Glu Asp Asn Lys Trp
```

-continued

```
        915                 920                 925

Tyr His Val Lys Ser Asp Gly Ser Thr Asp Lys Thr Gln Val Val Glu
    930                 935                 940

Glu Ala Lys Val Ser Thr Asp Glu Lys His Val Val Ser Leu Asp Pro
945                 950                 955                 960

Asn Asp Gln Ser Lys Gly Lys Gly Val Val Ile Asn Asn Met Ala Asn
                965                 970                 975

Gly Glu Ile Ser Ala Thr Ser Thr Asp Ala Ile Asn Gly Ser Gln Leu
            980                 985                 990

Tyr Ala Val Ala Lys Gly Val Thr Asn Leu Ala Gly Gln Val Asn Asn
        995                 1000                1005

Leu Glu Gly Lys Val Asn Lys Val Gly Lys Arg Ala Asp Ala Gly Thr
    1010                1015                1020

Ala Ser Ala Leu Ala Ala Ser Gln Leu Pro Gln Ala Thr Met Pro Gly
1025                1030                1035                1040

Lys Ser Met Val Ser Ile Ala Gly Ser Ser Tyr Gln Gly Gln Asn Gly
                1045                1050                1055

Leu Ala Ile Gly Val Ser Arg Ile Ser Asp Asn Gly Lys Val Ile Ile
            1060                1065                1070

Arg Leu Ser Gly Thr Thr Asn Ser Gln Gly Lys Thr Gly Val Ala Ala
        1075                1080                1085

Gly Val Gly Tyr Gln Trp
    1090


<210> SEQ ID NO 33
<211> LENGTH: 6678
<212> TYPE: DNA
<213> ORGANISM: Haemophilus influenzae

<400> SEQUENCE: 33

gcgaattcat atgaacaaaa tttttaacgt tatttggaat gttgtgactc aaacttgggt     60

cgcttaagta tacttgtttt aaaaattgca ataaacctta caacactgag tttgaaccca    120

tgtcgtatct gaactcactc gcgcccacac caaatgcgcc tccgccaccg tggcggttgc    180

acagcataga cttgagtgag cgcgggtgtg gtttacgcgg aggcggtggc accgccaacg    240

cgtattggca actgcgttgt ctgcaacggc tgaagcgaac aacaatactt ctgttacgaa    300

gcataaccgt tgacgcaaca gacgttgccg acttcgcttg ttgttatgaa gacaatgctt    360

tgggttgaat gcttatggcg atactaattt taatacaacc aataattcga tagcagattt    420

acccaactta cgaataccgc tatgattaaa attatgttgg ttattaagct atcgtctaaa    480

ggaaaaacac gttcaagatg cttataaagg cttattaaat ctgaatgaaa aagatacaaa    540

ccttttttgtg caagttctac gaatatttcc gaataattta gacttacttt ttctatgttt    600

taagtcaagt ttcttggttg ccgacaatac cgccgcaacc gtaggcaatt tgcgtaaatt    660

attcagttca aagaaccaac ggctgttatg gcggcgttgg catccgttaa acgcatttaa    720

gggctgggta ttgtctagca aaaacggcac aaggaacgag aaaagctatc aagtaaaaca    780

cccgacccat aacagatcgt tttgccgtg ttccttgctc ttttcgatag ttcattttgt    840

agctgatgaa gttctcttta ctggatctgg tgctgcaacg gttagttcca gctctaaaga    900

tcgactactt caagagaaat gacctagacc acgacgttgc caatcaaggt cgagatttct    960

cggtaaacat accattacca tttctgttac caaaggtagt tttgctgagg taaaaactga   1020

gccatttgta tggtaatggt aaagacaatg gtttccatca aacgactcc atttttgact   1080
```

-continued

```
tgcaactact ggaggtcaag taaacgccga ccgtggtaaa gtgaaagctg aggacgagaa   1140
acgttgatga cctccagttc atttgcggct ggcaccattt cactttcgac tcctgctctt   1200
tggagctgat gttgataaga aagttgcaac tgtaaaagat gttgctaagg cgattaacga   1260
acctcgacta caactattct ttcaacgttg acattttcta caacgattcc gctaattgct   1320
tgccgcaact ttcgtgaaag tggaaagcac agatgatgac attgaaaatg gtgctgcagg   1380
acggcgttga aagcactttc acctttcgtg tctactactg taacttttac cacgacgtcc   1440
caaaaatgaa actacagacc aagctctcaa agcaggcgac accttaacct taaaagcggg   1500
gtttttactt tgatgtctgg ttcgagagtt tcgtccgctg tggaattgga attttcgccc   1560
taaaaactta aaagctaagt tagaccaaaa tggtaaatca gtaacctttg ctttagcgaa   1620
atttttgaat tttcgattca atctggtttt accatttagt cattggaaac gaaatcgctt   1680
agaccttgat gtgacctctg cgaaagtgag tgataagttg tctattggta aagatacgaa   1740
tctggaacta cactggagac gctttcactc actattcaac agataaccat ttctatgctt   1800
taaagttgat attaccagtg atgcaaatgg cttgaaattg gcgaaaacag gtaacggaaa   1860
atttcaacta taatggtcac tacgtttacc gaactttaac cgcttttgtc cattgccttt   1920
tggtcaaaac ggtaatgtcc acttaaatgg tattgcttcg actttgaccg ataccattac   1980
accagttttg ccattacagg tgaatttacc ataacgaagc tgaaactggc tatggtaatg   2040
aggtatgaca acacaagcaa gcaatggcgt ggctgtgcag aatcataatc gtgctgcgag   2100
tccatactgt tgtgttcgtt cgttaccgca ccgacacgtc ttagtattag cacgacgctc   2160
tgtggctgat gtattaaatg caggctggaa tattcaaggc aacggagcga gcgttgattt   2220
acaccgacta cataatttac gtccgacctt ataagttccg ttgcctcgct cgcaactaaa   2280
tgtcaatgct tacgacacag tagattttgt caatggtaca aacaccaatg tgaacgttac   2340
acagttacga atgctgtgtc atctaaaaca gttaccatgt ttgtggttac acttgcaatg   2400
gactgatacg gctcacaaaa agacaaccgt ccgtgtggat gtaacaggct tgccggttca   2460
ctgactatgc cgagtgtttt tctgttggca ggcacaccta cattgtccga acggccaagt   2520
atatgttacg gaagacggca aaaccgttgt gaaagtggac aataagtatt acgaagctaa   2580
tatacaatgc cttctgccgt tttggcaaca ctttcacctg ttattcataa tgcttcgatt   2640
gcaagacggt tcggcggata tggataaaaa agtcgaaaat ggcgagctgg cgaaaaccaa   2700
cgttctgcca agccgcctat acctattttt tcagctttta ccgctcgacc gcttttggtt   2760
agtgaaattg gtgtcggcaa gcggtcaaaa tccggtgaaa atcagcaatg ttgcggaagg   2820
tcactttaac cacagccgtt cgccagtttt aggccacttt tagtcgttac aacgccttcc   2880
cacggaagaa aacgatgcgg tcagctttaa gcaattgaaa gccttgcaag agaaacaggt   2940
gtgccttctt ttgctacgcc agtcgaaatt cgttaacttt cggaacgttc tctttgtcca   3000
tactttaact gcgagcaatg cttatgccaa tggtggtaac gatgccgacg gcggcaaggc   3060
atgaaattga cgctcgttac gaatacggtt accaccattg ctacggctgc cgccgttccg   3120
aactcaaact ttaaacaatg gtttgaattt taaatttaaa tccacagacg gcgagttgtt   3180
ttgagtttga aatttgttac caaacttaaa atttaaattt aggtgtctgc cgctcaacaa   3240
gaacatcaaa gtagaaaatg acacagttac ctttacgccg aaaaaaggtt cggtacaggt   3300
cttgtagttt catcttttac tgtgtcaatg gaaatgcggc tttttccaa gccatgtcca   3360
tggcgaagac ggtaaggcta cgattcaaaa tggtacgaaa acaaccgacg gtttggttga   3420
accgcttctg ccattccgat gctaagtttt accatgcttt tgttggctgc caaaccaact   3480
```

-continued

```
agcttccgaa ttggttgaaa gcctgaacaa actgggctgg aaagtgggcg ttgataaaga   3540
tcgaaggctt aaccaacttt cggacttgtt tgacccgacc tttcacccgc aactatttct   3600
cggcagcggc gagcttgatg gtgcatccaa tgaaacttta gtgaagtcgg gcgataaagt   3660
gccgtcgccg ctcgaactac cacgtaggtt actttgaaat cacttcagcc cgctatttca   3720
aactttgaaa gccggcgaga atctgaaggt caaacaagac ggcacaaact tcacttacgc   3780
ttgaaacttt cggccgctct tagacttcca gtttgttctg ccgtgtttga agtgaatgcg   3840
gctcaaagat gaattgacgg gcgtgaagag cgtggagttt aaagacacgg cgaatggttc   3900
cgagtttcta cttaactgcc cgcacttctc gcacctcaaa tttctgtgcc gcttaccaag   3960
aaacggtgca agcacgaaga ttaccaaaga cggcttgacc attacgtcgg caaacggtgc   4020
tttgccacgt tcgtgcttct aatggtttct gccgaactgg taatgcagcc gtttgccacg   4080
gaatggtgcg gcggcgactg atgcggacaa gattaaagtg gcttcagacg gcatcagtgc   4140
cttaccacgc cgccgctgac tacgcctgtt ctaatttcac cgaagtctgc cgtagtcacg   4200
gggtaataaa gcggttaaaa acgttgtgag cggactgaag aaatttggtg atgcgaattt   4260
cccattattt cgccaatttt tgcaacactc gcctgacttc tttaaaccac tacgcttaaa   4320
caatccactg accagttccg ccgacaactt aacgaaacaa tatgacgatg cctataaagg   4380
gttaggtgac tggtcaaggc ggctgttgaa ttgctttgtt atactgctac ggatatttcc   4440
cttgaccaat ttggatgaaa aaggtgcgga caagcaaact ctgactgttg ccgacaatac   4500
gaactggtta aacctacttt ttccacgcct gttcgtttga gactgacaac ggctgttatg   4560
tgccgcaacc gtgggcgatt tgcgcggctt gggctgggtc atttctgcgg acaaaaccac   4620
acggcgttgg cacccgctaa acgcgccgaa cccgacccag taaagacgcc tgttttggtg   4680
aggcgaactc aataaggaat acaacgcgca agtgcgtaac gccaatgaag tgaaattcaa   4740
tccgcttgag ttattcctta tgttgcgcgt tcacgcattg cggttacttc actttaagtt   4800
gagcggcaac ggtatccatg tttccggtaa aacggtcaac ggtaggcgcg aaattacttt   4860
ctcgccgttg ccataggtac aaaggccatt ttgccagttg ccatccgcgc tttaatgaaa   4920
tgaattggct aaagacgaaa atgccattgc tttcggttat ggctcaaaag ccttgcgcga   4980
acttaaccga tttctgcttt tacggtaacg aaagccaata ccgagttttc ggaacgcgct   5040
taacacggtg gcaattggta cgggcaacgt tgtgaatgcg gaaaaatctg gtgcattcgg   5100
attgtgccac cgttaaccat gcccgttgca acacttacgc ctttttagac cacgtaagcc   5160
cgatccgaac tacatcgaag ataaagccgg tggcagctac gctttcggta acgataaccg   5220
gctaggcttg atgtagcttc tatttcggcc accgtcgatg cgaaagccat tgctattggc   5280
tattacttct aaaaacactt ttgtgttggg taatggagtt aatgcgaaat ataaagccaa   5340
ataatgaaga tttttgtgaa aacacaaccc attacctcaa ttacgcttta tatttcggtt   5400
tggagatgtt gatacggaaa ccgtaaccgt taaggacaaa gacggtaaag agactaccgt   5460
acctctacaa ctatgccttt ggcattggca attcctgttt ctgccatttc tctgatggca   5520
tactgttcct aaagcgttag gggctacggt tgaaaactcc gtttatttgg gtaataaatc   5580
atgacaagga tttcgcaatc cccgatgcca acttttgagg caaataaacc cattatttag   5640
gactgcgaca aaagataagg gtaaaaacct gaaatctgat ggtacggcgg gtaacactac   5700
ctgacgctgt tttctattcc catttttgga ctttagacta ccatgccgcc cattgtgatg   5760
aactgctggc acaacgggta cggtaaacgg ctttgccggt gcaacggcgc acggtgcggt   5820
```

-continued ttgacgaccg tgttgcccat gccatttgcc gaaacggcca cgttgccgcg tgccacgcca 5880
ttctgtcggc gcaagcggcg aagaaagacg tatccaaaac gtcgcggcag gcgaaatttc 5940
aagacagccg cgttcgccgc ttctttctgc ataggttttg cagcgccgtc cgctttaaag 6000
cgccacttcc accgatgcga ttaacggcag ccagttgtat gctgtggcaa aaggggtaac 6060
gcggtgaagg tggctacgct aattgccgtc ggtcaacata cgacaccgtt ttccccattg 6120
aaatcttgct ggacaagtga ataaagtggg caaacgtgca gatgcaggta cagcaagtgc 6180
tttagaacga cctgttcact tatttcaccc gtttgcacgt ctacgtccat gtcgttcacg 6240
attagcagct tcacagttac cacaagcctc tatgccaggt aaatcaatgg tttctattgc 6300
taatcgtcga agtgtcaatg gtgttcggag atacggtcca tttagttacc aaagataacg 6360
gggaagtagt tatcaaggtc aaaatggttt agctatcggg gtatcacgaa tttccgataa 6420
cccttcatca atagttccag ttttaccaaa tcgatagccc catagtgctt aaaggctatt 6480
tggcaaagtg attattcgct tgtcaggcac aaccaatagc caaggtaaaa caggcgttgc 6540
accgtttcac taataagcga acagtccgtg ttggttatcg gttccatttt gtccgcaacg 6600
agcaggtgtt ggttaccagt ggtaatagaa ttgatccgct cgtccacaac caatggtcac 6660
cattatctta actaggcg 6678

<210> SEQ ID NO 34
<211> LENGTH: 1104
<212> TYPE: PRT
<213> ORGANISM: Haemophilus influenzae

<400> SEQUENCE: 34

Met Asn Lys Ile Phe Asn Val Ile Trp Asn Val Val Thr Gln Thr Trp
1 5 10 15

Val Val Val Ser Glu Leu Thr Arg Ala His Thr Lys Cys Ala Ser Ala
20 25 30

Thr Val Ala Val Ala Val Leu Ala Thr Ala Leu Ser Ala Thr Ala Glu
35 40 45

Ala Asn Asn Asn Thr Ser Val Thr Asn Gly Leu Asn Ala Tyr Gly Asp
50 55 60

Thr Asn Phe Asn Thr Thr Asn Asn Ser Ile Ala Asp Leu Glu Lys His
65 70 75 80

Val Gln Asp Ala Tyr Lys Gly Leu Leu Asn Leu Asn Glu Lys Asp Thr
85 90 95

Asn Lys Ser Ser Phe Leu Val Ala Asp Asn Thr Ala Ala Thr Val Gly
100 105 110

Asn Leu Arg Lys Leu Gly Trp Val Leu Ser Ser Lys Asn Gly Thr Arg
115 120 125

Asn Glu Lys Ser Tyr Gln Val Lys Gln Ala Asp Glu Val Leu Phe Thr
130 135 140

Gly Ser Gly Ala Ala Thr Val Ser Ser Ser Ser Lys Asp Gly Lys His
145 150 155 160

Thr Ile Thr Ile Ser Val Thr Lys Gly Ser Phe Ala Glu Val Lys Thr
165 170 175

Asp Ala Thr Thr Gly Gly Gln Val Asn Ala Asp Arg Gly Lys Val Lys
180 185 190

Ala Glu Asp Glu Asn Gly Ala Asp Val Asp Lys Lys Val Ala Thr Val
195 200 205

Lys Asp Val Ala Lys Ala Ile Asn Asp Ala Ala Thr Phe Val Lys Val
210 215 220

-continued

```
Glu Ser Thr Asp Asp Asp Ile Glu Asn Gly Ala Ala Gly Lys Asn Glu
225                 230                 235                 240

Thr Thr Asp Gln Ala Leu Lys Ala Gly Asp Thr Leu Thr Leu Lys Ala
                245                 250                 255

Gly Lys Asn Leu Lys Ala Lys Leu Asp Gln Asn Gly Lys Ser Val Thr
            260                 265                 270

Phe Ala Leu Ala Lys Asp Leu Asp Val Thr Ser Ala Lys Val Ser Asp
        275                 280                 285

Lys Leu Ser Ile Gly Lys Asp Thr Asn Lys Val Asp Ile Thr Ser Asp
    290                 295                 300

Ala Asn Gly Leu Lys Leu Ala Lys Thr Gly Asn Gly Asn Gly Gln Asn
305                 310                 315                 320

Gly Asn Val His Leu Asn Gly Ile Ala Ser Thr Leu Thr Asp Thr Ile
                325                 330                 335

Thr Gly Met Thr Thr Gln Ala Ser Asn Gly Val Ala Val Gln Asn His
            340                 345                 350

Asn Arg Ala Ala Ser Val Ala Asp Val Leu Asn Ala Gly Trp Asn Ile
        355                 360                 365

Gln Gly Asn Gly Ala Ser Val Asp Phe Val Asn Ala Tyr Asp Thr Val
    370                 375                 380

Asp Phe Val Asn Gly Thr Asn Thr Asn Val Asn Val Thr Thr Asp Thr
385                 390                 395                 400

Ala His Lys Lys Thr Thr Val Arg Val Asp Val Thr Gly Leu Pro Val
                405                 410                 415

Gln Tyr Val Thr Glu Asp Gly Lys Thr Val Val Lys Val Asp Asn Lys
            420                 425                 430

Tyr Tyr Glu Ala Lys Gln Asp Gly Ser Ala Asp Met Asp Lys Lys Val
        435                 440                 445

Glu Asn Gly Glu Leu Ala Lys Thr Lys Val Lys Leu Val Ser Ala Ser
    450                 455                 460

Gly Gln Asn Pro Val Lys Ile Ser Asn Val Ala Glu Gly Thr Glu Glu
465                 470                 475                 480

Asn Asp Ala Val Ser Phe Lys Gln Leu Lys Ala Leu Gln Glu Lys Gln
                485                 490                 495

Val Thr Leu Thr Ala Ser Asn Ala Tyr Ala Asn Gly Gly Asn Asp Ala
            500                 505                 510

Asp Gly Gly Lys Ala Thr Gln Thr Leu Asn Asn Gly Leu Asn Phe Lys
        515                 520                 525

Phe Lys Ser Thr Asp Gly Glu Leu Leu Asn Ile Lys Val Glu Asn Asp
    530                 535                 540

Thr Val Thr Phe Thr Pro Lys Lys Gly Ser Val Gln Val Gly Glu Asp
545                 550                 555                 560

Gly Lys Ala Thr Ile Gln Asn Gly Thr Lys Thr Thr Asp Gly Leu Val
                565                 570                 575

Glu Ala Ser Glu Leu Val Glu Ser Leu Asn Lys Leu Gly Trp Lys Val
            580                 585                 590

Gly Val Asp Lys Asp Gly Ser Gly Glu Leu Asp Gly Ala Ser Asn Glu
        595                 600                 605

Thr Leu Val Lys Ser Gly Asp Lys Val Thr Leu Lys Ala Gly Glu Asn
    610                 615                 620

Leu Lys Val Lys Gln Asp Gly Thr Asn Phe Thr Tyr Ala Leu Lys Asp
625                 630                 635                 640
```

-continued

```
Glu Leu Thr Gly Val Lys Ser Val Glu Phe Lys Asp Thr Ala Asn Gly
                645                 650                 655

Ser Asn Gly Ala Ser Thr Lys Ile Thr Lys Asp Gly Leu Thr Ile Thr
            660                 665                 670

Ser Ala Asn Gly Ala Asn Gly Ala Ala Ala Thr Asp Ala Asp Lys Ile
        675                 680                 685

Lys Val Ala Ser Asp Gly Ile Ser Ala Gly Asn Lys Ala Val Lys Asn
    690                 695                 700

Val Val Ser Gly Leu Lys Lys Phe Gly Asp Ala Asn Phe Asn Pro Leu
705                 710                 715                 720

Thr Ser Ser Ala Asp Asn Leu Thr Lys Gln Tyr Asp Asp Ala Tyr Lys
                725                 730                 735

Gly Leu Thr Asn Leu Asp Glu Lys Gly Ala Asp Lys Gln Thr Leu Thr
            740                 745                 750

Val Ala Asp Asn Thr Ala Ala Thr Val Gly Asp Leu Arg Gly Leu Gly
        755                 760                 765

Trp Val Ile Ser Ala Asp Lys Thr Thr Gly Glu Leu Asn Lys Glu Tyr
    770                 775                 780

Asn Ala Gln Val Arg Asn Ala Asn Glu Val Lys Phe Lys Ser Gly Asn
785                 790                 795                 800

Gly Ile His Val Ser Gly Lys Thr Val Asn Gly Arg Arg Glu Ile Thr
                805                 810                 815

Phe Glu Leu Ala Lys Asp Glu Asn Ala Ile Ala Phe Gly Tyr Gly Ser
            820                 825                 830

Lys Ala Leu Arg Asp Asn Thr Val Ala Ile Gly Thr Gly Asn Val Val
        835                 840                 845

Asn Ala Glu Lys Ser Gly Ala Phe Gly Asp Pro Asn Tyr Ile Glu Asp
    850                 855                 860

Lys Ala Gly Gly Ser Tyr Ala Phe Gly Asn Asp Asn Arg Ile Thr Ser
865                 870                 875                 880

Lys Asn Thr Phe Val Leu Gly Asn Gly Val Asn Ala Lys Tyr Lys Ala
                885                 890                 895

Asn Gly Asp Val Asp Thr Glu Thr Val Thr Val Lys Asp Lys Asp Gly
            900                 905                 910

Lys Glu Thr Thr Val Thr Val Pro Lys Ala Leu Gly Ala Thr Val Glu
        915                 920                 925

Asn Ser Val Tyr Leu Gly Asn Lys Ser Thr Ala Thr Lys Asp Lys Gly
    930                 935                 940

Lys Asn Leu Lys Ser Asp Gly Thr Ala Gly Asn Thr Thr Thr Ala Gly
945                 950                 955                 960

Thr Thr Gly Thr Val Asn Gly Phe Ala Gly Ala Thr Ala His Gly Ala
                965                 970                 975

Val Ser Val Gly Ala Ser Gly Glu Glu Arg Arg Ile Gln Asn Val Ala
            980                 985                 990

Ala Gly Glu Ile Ser Ala Thr Ser Thr Asp Ala Ile Asn Gly Ser Gln
        995                 1000                1005

Leu Tyr Ala Val Ala Lys Gly Val Thr Asn Leu Ala Gly Gln Val Asn
    1010                1015                1020

Lys Val Gly Lys Arg Ala Asp Ala Gly Thr Ala Ser Ala Leu Ala Ala
1025                1030                1035                1040

Ser Gln Leu Pro Gln Ala Ser Met Pro Gly Lys Ser Met Val Ser Ile
                1045                1050                1055

Ala Gly Ser Ser Tyr Gln Gly Gln Asn Gly Leu Ala Ile Gly Val Ser
```

-continued

```
            1060                1065                1070

Arg Ile Ser Asp Asn Gly Lys Val Ile Ile Arg Leu Ser Gly Thr Thr
        1075                1080                1085

Asn Ser Gln Gly Lys Thr Gly Val Ala Ala Gly Val Gly Tyr Gln Trp
    1090                1095                1100
```

<210> SEQ ID NO 35
<211> LENGTH: 7253
<212> TYPE: DNA
<213> ORGANISM: Haemophilus influenzae

<400> SEQUENCE: 35

```
atgaacaaaa tttttaacgt tatttggaat gttatgactc aaacttgggt tgtcgtatct     60

gaactcactc gcacccacac caaacgcgcc tccgcaaccg tggagaccgc cgtattggcg    120

acactgttgt ttgcaacggt tcaggcgaat gctaccgatg aagatgaaga gttagacccc    180

gtagtacgca ctgctcccgt gttgagcttc cattccgata aagaaggcac gggagaaaaa    240

gaagttacag aaaattcaaa ttggggaata tatttccaca ataaaggagt actaaaagcc    300

ggagcaatca ccctcaaagc cggcgacaac ctgaaaatca aacaaagcac caatgccagt    360

agcttcacct actcgctgaa aaaagacctc acagatctga ccagtgttgc aactgaaaaa    420

ttatcgtttg gcgcaaacgg cgataaagtt gatattacca gtgatgcaaa tggcttgaaa    480

ttggcgaaaa caggtaacgg aaatgttcat ttgaatggtt tggattcaac tttgcctgat    540

gcggtaacga atacaggtgt gttaagttca tcaagtttta cacctaatga tgttgaaaaa    600

acaagagctg caactgttaa agatgtttta aatgcaggtt ggaacattaa aggtgctaaa    660

actgctggag gtaatgttga gagtgttgat ttagtgtccg cttataataa tgttgaattt    720

attacaggcg ataaaaacac gcttgatgtt gtattaacag ctaaagaaaa cggtaaaaca    780

accgaagtga aattcacacc gaaaacctct gttatcaaag aaaaagacgg taagttattt    840

actggaaaag agaataacga cacaaataaa gttacaagta acacggcgac tgataataca    900

gatgagggta atggcttagt cactgcaaaa gctgtgattg atgctgtgaa caaggctggt    960

tggagagtta aaacaactac tgctaatggt caaaatggcg acttcgcaac tgttgcgtca   1020

ggcacaaatg taacctttga aagtggcgat ggtacaacag cgtcagtaac taaagatact   1080

aacggcaatg gcatcactgt taagtacgac gcgaaagttg gcgacggctt gaaatttgat   1140

agcgataaaa aaatcgttgc agatacgacc gcacttactg tgacaggtgg taaggtagct   1200

gaaattgcta aagaagatga caagaaaaaa cttgttaatg caggcgattt ggtaacagct   1260

ttaggtaatc taagttggaa agcaaaagct gaggctgata ctgatactga tggtgcgctt   1320

gaggggattt caaaagacca agaagtcaaa gcaggcgaaa cggtaacctt taaagcgggc   1380

aagaacttaa aagtgaaaca ggatggtgcg aactttactt attcactgca agatgcttta   1440

acgggtttaa cgagcattac tttaggtggt acaactaatg gcggaaatga tgcgaaaacc   1500

gtcatcaaca aagacggttt aaccatcacg ccagcaggta atggcggtac gacaggtaca   1560

aacaccatca gcgtaaccaa agatggcatt aaagcaggta ataaagctat tactaatgtt   1620

gcgagtggtt taagagctta tgacgatgcg aattttgatg ttttaaataa ctctgcaact   1680

gatttaaata gacacgttga agatgcttat aaaggtttat taaatctaaa tgaaaaaaat   1740

gcaaataaac aaccgttggt gactgacagc acggcggcga ctgtaggcga tttacgtaaa   1800

ttgggttggg tagtatcaac caaaaacggt acgaaagaag aaagcaatca agttaaacaa   1860

gctgatgaag tcctctttac cggagccggt gctgctacgg ttacttccaa atctgaaaac   1920
```

-continued

```
ggtaaacata cgattaccgt tagtgtggct gaaactaaag cggatagcgg tcttgaaaaa   1980
gatggcgata ctattaagct caaagtggat aatcaaaaca ctgataatgt tttaactgtt   2040
ggtaataatg gtactgctgt cactaaaggt ggctttgaaa ctgttaaaac tggagcgact   2100
gatgcagatc gcggtaaagt aactgtaaaa gatgctactg ctaatgacgc tgataagaaa   2160
gtcgcaactg taaaagatgt tgcaaccgca attaatagtg cggcgacttt tgtgaaaaca   2220
gagaatttaa ctacctctat tgatgaagat aatcctacag ataacggcaa agatgacgca   2280
cttaaagcgg gcgatacctt aacctttaaa gcaggtaaaa acctgaaagt taaacgtgat   2340
ggaaaaaata ttacttttga cttggcgaaa aaccttgagg tgaaaactgc gaaagtgagt   2400
gatactttaa cgattggcgg gaatacacct acaggtggca ctactgcgac gccaaaagtg   2460
aatattacta gcacggctga tggtttgaat tttgcaaaag aaacagccga tgcctcgggt   2520
tctaagaatg tttatttgaa aggtattgcg acaactttaa ctgagccaaag cgcgggagcg   2580
aagtcttcac acgttgattt aaatgtggat gcgacgaaaa aatccaatgc agcaagtatt   2640
gaagatgtat tgcgcgcagg ttggaatatt caaggtaatg gtaataatgt tgattatgta   2700
gcgacgtatg acacagtaaa ctttaccgat gacagcacag gtacaacaac ggtaaccgta   2760
acccaaaaag cagatggcaa aggtgctgac gttaaaatcg gtgcgaaaac ttctgttatc   2820
aaagaccaca acggcaaact gtttacaggc aaagacctga aagatgcgaa taatggtgca   2880
accgttagtg aagatgatgg caaagacacc ggcacaggct tagttactgc aaaaactgtg   2940
attgatgcag taaataaaag cggttggagg gtaaccggtg agggcgcgac tgccgaaacc   3000
ggtgcaaccg ccgtgaatgc gggtaacgct gaaaccgtta catcaggcac gagcgtgaac   3060
ttcaaaaacg gcaatgcgac cacagcgacc gtaagcaaag ataatggcaa catcaatgtc   3120
aaatacgatg taaatgttgg tgacggcttg aagattggcg atgacaaaaa aatcgttgca   3180
gacacgacca cacttactgt aacaggtggt aaggtgtctg ttcctgctgg tgctaatagt   3240
gttaataaca ataagaaact tgttaatgca gagggtttag cgactgcttt aaacaaccta   3300
agctggacgg caaaagccga taaatatgca gatggcgagt cagagggcga aaccgaccaa   3360
gaagtcaaag caggcgacaa agtaaccttt aaagcaggca agaacttaaa agtgaaacag   3420
tctgaaaaag actttactta ttcactgcaa gacactttaa caggcttaac gagcattact   3480
ttaggtggta cagctaatgg cagaaatgat acgggaaccg tcatcaacaa agacggctta   3540
accatcacgc tggcaaatgg tgctgcggca ggcacagatg cgtctaacgg aaacaccatc   3600
agtgtaacca aagacggcat tagtgcgggt aataaagaaa ttaccaatgt taagagtgct   3660
ttaaaaacct ataaagatac tcaaaacact gcaggtgcaa ctcaacctgc ggctaataca   3720
gctgaagtag ccaaacaaga cttggttgat ttaactaaac ctgcgacagg tgcagctgga   3780
aatggtgcag atgcaaaagc tcccgatacc acagctgcaa ccgtaggcga cttgcgtggt   3840
ttgggctggg tgctttcagc taagaaaact gcagatgaaa cacaagataa agagttccac   3900
gccgccgtta aaaacgcaaa tgaagttgag ttcgtgggta aaaacggtgc aaccgtgtct   3960
gcaaaaactg ataacaacgg aaaacatact gtaacgattg atgttgcaga agccaaagtt   4020
ggtgatggtc ttgaaaaaga tactgacggc aagattaaac tcaaagtaga taatacagat   4080
gggaataatc tattaaccgt tgatgcaaca aaaggtgcat ccgttgccaa gggcgagttt   4140
aatgccgtaa caacagatgc aactacagcc caaggcacaa atgccaatga gcgcggtaaa   4200
gtggttgtca agggttcaaa tggtgcaact gctaccgaaa ctgacaagaa aaaagtggca   4260
```

-continued

```
actgttggcg acgttgctaa agcgattaac gacgcagcaa ctttcgtgaa agtggaaaat   4320
gacgacagtg ctacgattga tgatagccca acagatgatg gcgcaaatga tgctctcaaa   4380
gcaggcgaca ccttgacctt aaaagcgggt aaaaacttaa aagttaaacg tgatggtaaa   4440
aatattactt ttgcccttgc gaacgacctt agtgtaaaaa gcgcaaccgt tagcgataaa   4500
ttatcgcttg gtacaaacgg caataaagtc aatatcacaa gcgacaccaa aggcttgaac   4560
ttcgctaaag atagtaagac aggcgatgat gctaatattc acttaaatgg cattgcttca   4620
actttaactg atacattgtt aaatagtggt gcgacaacca atttaggtgg taatggtatt   4680
actgataacg agaaaaaacg cgcggcgagc gttaaagatg tcttgaatgc gggttggaat   4740
gttcgtggtg ttaaaccggc atctgcaaat aatcaagtgg agaatatcga ctttgtagca   4800
acctacgaca cagtggactt tgttagtgga gataaagaca ccacgagtgt aactgttgaa   4860
agtaaagata atggcaagag aaccgaagtt aaaatcggtg cgaagacttc tgttatcaaa   4920
gaccacaacg gcaaactgtt tacaggcaaa gagctgaagg atgctaacaa taatggcgta   4980
actgttaccg aaaccgacgg caaagacgag ggtaatggtt tagtgactgc aaaagctgtg   5040
attgatgccg tgaataaggc tggttggaga gttaaaacaa caggtgctaa tggtcagaat   5100
gatgacttcg caactgttgc gtcaggcaca aatgtaacct ttgctgatgg taatggcaca   5160
actgccgaag taactaaagc aaacgacggt agtattactg ttaaatacaa tgttaaagtg   5220
gctgatggct taaaactaga cggcgataaa atcgttgcag acacgaccgt acttactgtg   5280
gcagatggta aagttacagc tccgaataat ggcgatggta agaaatttgt tgatgcaagt   5340
ggtttagcgg atgcgttaaa taaattaagc tggacggcaa ctgctggtaa agaaggcact   5400
ggtgaagttg atcctgcaaa ttcagcaggg caagaagtca aagcgggcga caaagtaacc   5460
tttaaagccg gcgacaacct gaaaatcaaa caaagcggca aagactttac ctactcgctg   5520
aaaaaagagc tgaaagacct gaccagcgta gagttcaaag acgcaaacgg cggtacaggc   5580
agtgaaagca ccaagattac caaagacggc ttgaccatta cgccggcaaa cggtgcgggt   5640
gcggcaggtg caaacactgc aaacaccatt agcgtaacca aagatggcat tagcgcgggt   5700
aataaagcag ttacaaacgt tgtgagcgga ctgaagaaat ttggtgatgg tcatacgttg   5760
gcaaatggca ctgttgctga ttttgaaaag cattatgaca atgcctataa agacttgacc   5820
aatttggatg aaaaaggcgc ggataataat ccgactgttg ccgacaatac cgctgcaacc   5880
gtgggcgatt tgcgcggctt gggctgggtc atttctgcgg acaaaaccac aggcgaaccc   5940
aatcaggaat acaacgcgca agtgcgtaac gccaatgaag tgaaattcaa gagcggcaac   6000
ggtatcaatg tttccggtaa aacattgaac ggtacgcgcg tgattacctt tgaattggct   6060
aaaggcgaag tggttaaatc gaatgaattt accgttaaga atgccgatgg ttcggaaacg   6120
aacttggtta aagttggcga tatgtattac agcaaagagg atattgaccc ggcaaccagt   6180
aaaccgatga caggtaaaac tgaaaaatat aaggttgaaa acggcaaagt cgtttctgct   6240
aacggcagca agaccgaagt taccctaacc aacaaaggtt ccggctatgt aacaggtaac   6300
caagtggctg atgcgattgc gaaatcaggc tttgagcttg gtttggctga tgcggcagaa   6360
gctgaaaaag cctttgcaga aagcgcaaaa gacaagcaat tgtctaaaga taaagcggaa   6420
actgtaaatg cccacgataa agtccgtttt gctaatggtt taaataccaa agtgagcgcg   6480
gcaacggtgg aaagcactga tgcaaacggc gataaagtga ccacaacctt tgtgaaaacc   6540
gatgtggaat tgcctttaac gcaaatctac aataccgatg caaacggtaa taagatcgtt   6600
aaaaaagctg acggaaaatg gtatgaactg aatgctgatg gtacggcgag taacaaagaa   6660
```

-continued

```
gtgacacttg gtaacgtgga tgcaaacggt aagaaagttg tgaaagtaac cgaaaatggt   6720

gcggataagt ggtattacac caatgctgac ggtgctgcgg ataaaaccaa aggcgaagtg   6780

agcaatgata aagtttctac cgatgaaaaa cacgttgtcc gccttgatcc gaacaatcaa   6840

tcgaacggca aaggcgtggt cattgacaat gtggctaatg gcgaaatttc tgccacttcc   6900

accgatgcga ttaacggaag tcagttgtat gccgtggcaa aaggggtaac aaaccttgct   6960

ggacaagtga ataatcttga gggcaaagtg aataaagtgg gcaaacgtgc agatgcaggt   7020

acagcaagtg cattagcggc ttcacagtta ccacaagcca ctatgccagg taaatcaatg   7080

gttgctattg cgggaagtag ttatcaaggt caaaatggtt tagctatcgg ggtatcaaga   7140

atttccgata atggcaaagt gattattcgc ttgtcaggca caaccaatag tcaaggtaaa   7200

acaggcgttg cagcaggtgt tggttaccag tggtaataga attccggatc cgc          7253
```

<210> SEQ ID NO 36
<211> LENGTH: 2411
<212> TYPE: PRT
<213> ORGANISM: Haemophilus influenzae

<400> SEQUENCE: 36

```
Met Asn Lys Ile Phe Asn Val Ile Trp Asn Val Met Thr Gln Thr Trp
  1               5                  10                  15

Val Val Val Ser Glu Leu Thr Arg Thr His Thr Lys Arg Ala Ser Ala
             20                  25                  30

Thr Val Glu Thr Ala Val Leu Ala Thr Leu Leu Phe Ala Thr Val Gln
         35                  40                  45

Ala Asn Ala Thr Asp Glu Asp Glu Glu Leu Asp Pro Val Val Arg Thr
     50                  55                  60

Ala Pro Val Leu Ser Phe His Ser Asp Lys Glu Gly Thr Gly Glu Lys
 65                  70                  75                  80

Glu Val Thr Glu Asn Ser Asn Trp Gly Ile Tyr Phe His Asn Lys Gly
                 85                  90                  95

Val Leu Lys Ala Gly Ala Ile Thr Leu Lys Ala Gly Asp Asn Leu Lys
            100                 105                 110

Ile Lys Gln Ser Thr Asn Ala Ser Ser Phe Thr Tyr Ser Leu Lys Lys
        115                 120                 125

Asp Leu Thr Asp Leu Thr Ser Val Ala Thr Glu Lys Leu Ser Phe Gly
    130                 135                 140

Ala Asn Gly Asp Lys Val Asp Ile Thr Ser Asp Ala Asn Gly Leu Lys
145                 150                 155                 160

Leu Ala Lys Thr Gly Asn Gly Asn Val His Leu Asn Gly Leu Asp Ser
                165                 170                 175

Thr Leu Pro Asp Ala Val Thr Asn Thr Gly Val Leu Ser Ser Ser Ser
            180                 185                 190

Phe Thr Pro Asn Asp Val Glu Lys Thr Arg Ala Ala Thr Val Lys Asp
        195                 200                 205

Val Leu Asn Ala Gly Trp Asn Ile Lys Gly Ala Lys Thr Ala Gly Gly
    210                 215                 220

Asn Val Glu Ser Val Asp Leu Val Ser Ala Tyr Asn Asn Val Glu Phe
225                 230                 235                 240

Ile Thr Gly Asp Lys Asn Thr Leu Asp Val Val Leu Thr Ala Lys Glu
                245                 250                 255

Asn Gly Lys Thr Thr Glu Val Lys Phe Thr Pro Lys Thr Ser Val Ile
            260                 265                 270
```

-continued

```
Lys Glu Lys Asp Gly Lys Leu Phe Thr Gly Lys Glu Asn Asn Asp Thr
        275                 280                 285

Asn Lys Val Thr Ser Asn Thr Ala Thr Asp Asn Thr Asp Glu Gly Asn
    290                 295                 300

Gly Leu Val Thr Ala Lys Ala Val Ile Asp Ala Val Asn Lys Ala Gly
305                 310                 315                 320

Trp Arg Val Lys Thr Thr Thr Ala Asn Gly Gln Asn Gly Asp Phe Ala
                325                 330                 335

Thr Val Ala Ser Gly Thr Asn Val Thr Phe Glu Ser Gly Asp Gly Thr
            340                 345                 350

Thr Ala Ser Val Thr Lys Asp Thr Asn Gly Asn Gly Ile Thr Val Lys
        355                 360                 365

Tyr Asp Ala Lys Val Gly Asp Gly Leu Lys Phe Asp Ser Asp Lys Lys
    370                 375                 380

Ile Val Ala Asp Thr Thr Ala Leu Thr Val Thr Gly Gly Lys Val Ala
385                 390                 395                 400

Glu Ile Ala Lys Glu Asp Asp Lys Lys Lys Leu Val Asn Ala Gly Asp
                405                 410                 415

Leu Val Thr Ala Leu Gly Asn Leu Ser Trp Lys Ala Lys Ala Glu Ala
            420                 425                 430

Asp Thr Asp Thr Asp Gly Ala Leu Glu Gly Ile Ser Lys Asp Gln Glu
        435                 440                 445

Val Lys Ala Gly Glu Thr Val Thr Phe Lys Ala Gly Lys Asn Leu Lys
    450                 455                 460

Val Lys Gln Asp Gly Ala Asn Phe Thr Tyr Ser Leu Gln Asp Ala Leu
465                 470                 475                 480

Thr Gly Leu Thr Ser Ile Thr Leu Gly Gly Thr Thr Asn Gly Gly Asn
                485                 490                 495

Asp Ala Lys Thr Val Ile Asn Lys Asp Gly Leu Thr Ile Thr Pro Ala
            500                 505                 510

Gly Asn Gly Gly Thr Thr Gly Thr Asn Thr Ile Ser Val Thr Lys Asp
        515                 520                 525

Gly Ile Lys Ala Gly Asn Lys Ala Ile Thr Asn Val Ala Ser Gly Leu
    530                 535                 540

Arg Ala Tyr Asp Asp Ala Asn Phe Asp Val Leu Asn Asn Ser Ala Thr
545                 550                 555                 560

Asp Leu Asn Arg His Val Glu Asp Ala Tyr Lys Gly Leu Leu Asn Leu
                565                 570                 575

Asn Glu Lys Asn Ala Asn Lys Gln Pro Leu Val Thr Asp Ser Thr Ala
            580                 585                 590

Ala Thr Val Gly Asp Leu Arg Lys Leu Gly Trp Val Val Ser Thr Lys
        595                 600                 605

Asn Gly Thr Lys Glu Glu Ser Asn Gln Val Lys Gln Ala Asp Glu Val
    610                 615                 620

Leu Phe Thr Gly Ala Gly Ala Ala Thr Val Thr Ser Lys Ser Glu Asn
625                 630                 635                 640

Gly Lys His Thr Ile Thr Val Ser Val Ala Glu Thr Lys Ala Asp Ser
                645                 650                 655

Gly Leu Glu Lys Asp Gly Asp Thr Ile Lys Leu Lys Val Asp Asn Gln
            660                 665                 670

Asn Thr Asp Asn Val Leu Thr Val Gly Asn Asn Gly Thr Ala Val Thr
        675                 680                 685
```

-continued

```
Lys Gly Gly Phe Glu Thr Val Lys Thr Gly Ala Thr Asp Ala Asp Arg
    690                 695                 700

Gly Lys Val Thr Val Lys Asp Ala Thr Ala Asn Asp Ala Asp Lys Lys
705                 710                 715                 720

Val Ala Thr Val Lys Asp Val Ala Thr Ala Ile Asn Ser Ala Ala Thr
                725                 730                 735

Phe Val Lys Thr Glu Asn Leu Thr Thr Ser Ile Asp Glu Asp Asn Pro
            740                 745                 750

Thr Asp Asn Gly Lys Asp Asp Ala Leu Lys Ala Gly Asp Thr Leu Thr
        755                 760                 765

Phe Lys Ala Gly Lys Asn Leu Lys Val Lys Arg Asp Gly Lys Asn Ile
    770                 775                 780

Thr Phe Asp Leu Ala Lys Asn Leu Glu Val Lys Thr Ala Lys Val Ser
785                 790                 795                 800

Asp Thr Leu Thr Ile Gly Gly Asn Thr Pro Thr Gly Gly Thr Thr Ala
                805                 810                 815

Thr Pro Lys Val Asn Ile Thr Ser Thr Ala Asp Gly Leu Asn Phe Ala
            820                 825                 830

Lys Glu Thr Ala Asp Ala Ser Gly Ser Lys Asn Val Tyr Leu Lys Gly
        835                 840                 845

Ile Ala Thr Thr Leu Thr Glu Pro Ser Ala Gly Ala Lys Ser Ser His
    850                 855                 860

Val Asp Leu Asn Val Asp Ala Thr Lys Lys Ser Asn Ala Ala Ser Ile
865                 870                 875                 880

Glu Asp Val Leu Arg Ala Gly Trp Asn Ile Gln Gly Asn Gly Asn Asn
                885                 890                 895

Val Asp Tyr Val Ala Thr Tyr Asp Thr Val Asn Phe Thr Asp Asp Ser
            900                 905                 910

Thr Gly Thr Thr Thr Val Thr Val Thr Gln Lys Ala Asp Gly Lys Gly
        915                 920                 925

Ala Asp Val Lys Ile Gly Ala Lys Thr Ser Val Ile Lys Asp His Asn
    930                 935                 940

Gly Lys Leu Phe Thr Gly Lys Asp Leu Lys Asp Ala Asn Asn Gly Ala
945                 950                 955                 960

Thr Val Ser Glu Asp Asp Gly Lys Asp Thr Gly Thr Gly Leu Val Thr
                965                 970                 975

Ala Lys Thr Val Ile Asp Ala Val Asn Lys Ser Gly Trp Arg Val Thr
            980                 985                 990

Gly Glu Gly Ala Thr Ala Glu Thr Gly Ala Thr Ala Val Asn Ala Gly
        995                 1000                1005

Asn Ala Glu Thr Val Thr Ser Gly Thr Ser Val Asn Phe Lys Asn Gly
    1010                1015                1020

Asn Ala Thr Thr Ala Thr Val Ser Lys Asp Asn Gly Asn Ile Asn Val
1025                1030                1035                1040

Lys Tyr Asp Val Asn Val Gly Asp Gly Leu Lys Ile Gly Asp Asp Lys
                1045                1050                1055

Lys Ile Val Ala Asp Thr Thr Thr Leu Thr Val Thr Gly Gly Lys Val
            1060                1065                1070

Ser Val Pro Ala Gly Ala Asn Ser Val Asn Asn Asn Lys Lys Leu Val
        1075                1080                1085

Asn Ala Glu Gly Leu Ala Thr Ala Leu Asn Asn Leu Ser Trp Thr Ala
    1090                1095                1100

Lys Ala Asp Lys Tyr Ala Asp Gly Glu Ser Glu Gly Glu Thr Asp Gln
```

-continued

```
1105                1110                1115                1120

Glu Val Lys Ala Gly Asp Lys Val Thr Phe Lys Ala Gly Lys Asn Leu
                1125                1130                1135

Lys Val Lys Gln Ser Glu Lys Asp Phe Thr Tyr Ser Leu Gln Asp Thr
            1140                1145                1150

Leu Thr Gly Leu Thr Ser Ile Thr Leu Gly Gly Thr Ala Asn Gly Arg
        1155                1160                1165

Asn Asp Thr Gly Thr Val Ile Asn Lys Asp Gly Leu Thr Ile Thr Leu
    1170                1175                1180

Ala Asn Gly Ala Ala Ala Gly Thr Asp Ala Ser Asn Gly Asn Thr Ile
1185                1190                1195                1200

Ser Val Thr Lys Asp Gly Ile Ser Ala Gly Asn Lys Glu Ile Thr Asn
                1205                1210                1215

Val Lys Ser Ala Leu Lys Thr Tyr Lys Asp Thr Gln Asn Thr Ala Gly
            1220                1225                1230

Ala Thr Gln Pro Ala Ala Asn Thr Ala Glu Val Ala Lys Gln Asp Leu
        1235                1240                1245

Val Asp Leu Thr Lys Pro Ala Thr Gly Ala Ala Gly Asn Gly Ala Asp
    1250                1255                1260

Ala Lys Ala Pro Asp Thr Thr Ala Ala Thr Val Gly Asp Leu Arg Gly
1265                1270                1275                1280

Leu Gly Trp Val Leu Ser Ala Lys Lys Thr Ala Asp Glu Thr Gln Asp
                1285                1290                1295

Lys Glu Phe His Ala Ala Val Lys Asn Ala Asn Glu Val Glu Phe Val
            1300                1305                1310

Gly Lys Asn Gly Ala Thr Val Ser Ala Lys Thr Asp Asn Asn Gly Lys
        1315                1320                1325

His Thr Val Thr Ile Asp Val Ala Glu Ala Lys Val Gly Asp Gly Leu
    1330                1335                1340

Glu Lys Asp Thr Asp Gly Lys Ile Lys Leu Lys Val Asp Asn Thr Asp
1345                1350                1355                1360

Gly Asn Asn Leu Leu Thr Val Asp Ala Thr Lys Gly Ala Ser Val Ala
                1365                1370                1375

Lys Gly Glu Phe Asn Ala Val Thr Thr Asp Ala Thr Thr Ala Gln Gly
            1380                1385                1390

Thr Asn Ala Asn Glu Arg Gly Lys Val Val Val Lys Gly Ser Asn Gly
        1395                1400                1405

Ala Thr Ala Thr Glu Thr Asp Lys Lys Lys Val Ala Thr Val Gly Asp
    1410                1415                1420

Val Ala Lys Ala Ile Asn Asp Ala Ala Thr Phe Val Lys Val Glu Asn
1425                1430                1435                1440

Asp Asp Ser Ala Thr Ile Asp Asp Ser Pro Thr Asp Asp Gly Ala Asn
                1445                1450                1455

Asp Ala Leu Lys Ala Gly Asp Thr Leu Thr Leu Lys Ala Gly Lys Asn
            1460                1465                1470

Leu Lys Val Lys Arg Asp Gly Lys Asn Ile Thr Phe Ala Leu Ala Asn
        1475                1480                1485

Asp Leu Ser Val Lys Ser Ala Thr Val Ser Asp Lys Leu Ser Leu Gly
    1490                1495                1500

Thr Asn Gly Asn Lys Val Asn Ile Thr Ser Asp Thr Lys Gly Leu Asn
1505                1510                1515                1520

Phe Ala Lys Asp Ser Lys Thr Gly Asp Asp Ala Asn Ile His Leu Asn
                1525                1530                1535
```

-continued

```
Gly Ile Ala Ser Thr Leu Thr Asp Thr Leu Leu Asn Ser Gly Ala Thr
            1540                1545                1550

Thr Asn Leu Gly Gly Asn Gly Ile Thr Asp Asn Glu Lys Lys Arg Ala
        1555                1560                1565

Ala Ser Val Lys Asp Val Leu Asn Ala Gly Trp Asn Val Arg Gly Val
    1570                1575                1580

Lys Pro Ala Ser Ala Asn Asn Gln Val Glu Asn Ile Asp Phe Val Ala
1585                1590                1595                1600

Thr Tyr Asp Thr Val Asp Phe Val Ser Gly Asp Lys Asp Thr Thr Ser
                1605                1610                1615

Val Thr Val Glu Ser Lys Asp Asn Gly Lys Arg Thr Glu Val Lys Ile
            1620                1625                1630

Gly Ala Lys Thr Ser Val Ile Lys Asp His Asn Gly Lys Leu Phe Thr
        1635                1640                1645

Gly Lys Glu Leu Lys Asp Ala Asn Asn Asn Gly Val Thr Val Thr Glu
    1650                1655                1660

Thr Asp Gly Lys Asp Glu Gly Asn Gly Leu Val Thr Ala Lys Ala Val
1665                1670                1675                1680

Ile Asp Ala Val Asn Lys Ala Gly Trp Arg Val Lys Thr Thr Gly Ala
                1685                1690                1695

Asn Gly Gln Asn Asp Asp Phe Ala Thr Val Ala Ser Gly Thr Asn Val
            1700                1705                1710

Thr Phe Ala Asp Gly Asn Gly Thr Thr Ala Glu Val Thr Lys Ala Asn
        1715                1720                1725

Asp Gly Ser Ile Thr Val Lys Tyr Asn Val Lys Val Ala Asp Gly Leu
    1730                1735                1740

Lys Leu Asp Gly Asp Lys Ile Val Ala Asp Thr Thr Val Leu Thr Val
1745                1750                1755                1760

Ala Asp Gly Lys Val Thr Ala Pro Asn Asn Gly Asp Gly Lys Lys Phe
                1765                1770                1775

Val Asp Ala Ser Gly Leu Ala Asp Ala Leu Asn Lys Leu Ser Trp Thr
            1780                1785                1790

Ala Thr Ala Gly Lys Glu Gly Thr Gly Glu Val Asp Pro Ala Asn Ser
        1795                1800                1805

Ala Gly Gln Glu Val Lys Ala Gly Asp Lys Val Thr Phe Lys Ala Gly
    1810                1815                1820

Asp Asn Leu Lys Ile Lys Gln Ser Gly Lys Asp Phe Thr Tyr Ser Leu
1825                1830                1835                1840

Lys Lys Glu Leu Lys Asp Leu Thr Ser Val Glu Phe Lys Asp Ala Asn
                1845                1850                1855

Gly Gly Thr Gly Ser Glu Ser Thr Lys Ile Thr Lys Asp Gly Leu Thr
            1860                1865                1870

Ile Thr Pro Ala Asn Gly Ala Gly Ala Ala Gly Ala Asn Thr Ala Asn
        1875                1880                1885

Thr Ile Ser Val Thr Lys Asp Gly Ile Ser Ala Gly Asn Lys Ala Val
    1890                1895                1900

Thr Asn Val Val Ser Gly Leu Lys Lys Phe Gly Asp Gly His Thr Leu
1905                1910                1915                1920

Ala Asn Gly Thr Val Ala Asp Phe Glu Lys His Tyr Asp Asn Ala Tyr
                1925                1930                1935

Lys Asp Leu Thr Asn Leu Asp Glu Lys Gly Ala Asp Asn Asn Pro Thr
            1940                1945                1950
```

-continued

```
Val Ala Asp Asn Thr Ala Ala Thr Val Gly Asp Leu Arg Gly Leu Gly
        1955                1960                1965

Trp Val Ile Ser Ala Asp Lys Thr Thr Gly Glu Pro Asn Gln Glu Tyr
    1970                1975                1980

Asn Ala Gln Val Arg Asn Ala Asn Glu Val Lys Phe Lys Ser Gly Asn
1985                1990                1995                2000

Gly Ile Asn Val Ser Gly Lys Thr Leu Asn Gly Thr Arg Val Ile Thr
                2005                2010                2015

Phe Glu Leu Ala Lys Gly Glu Val Val Lys Ser Asn Glu Phe Thr Val
            2020                2025                2030

Lys Asn Ala Asp Gly Ser Glu Thr Asn Leu Val Lys Val Gly Asp Met
        2035                2040                2045

Tyr Tyr Ser Lys Glu Asp Ile Asp Pro Ala Thr Ser Lys Pro Met Thr
    2050                2055                2060

Gly Lys Thr Glu Lys Tyr Lys Val Glu Asn Gly Lys Val Val Ser Ala
2065                2070                2075                2080

Asn Gly Ser Lys Thr Glu Val Thr Leu Thr Asn Lys Gly Ser Gly Tyr
                2085                2090                2095

Val Thr Gly Asn Gln Val Ala Asp Ala Ile Ala Lys Ser Gly Phe Glu
            2100                2105                2110

Leu Gly Leu Ala Asp Ala Ala Glu Ala Glu Lys Ala Phe Ala Glu Ser
        2115                2120                2125

Ala Lys Asp Lys Gln Leu Ser Lys Asp Lys Ala Glu Thr Val Asn Ala
    2130                2135                2140

His Asp Lys Val Arg Phe Ala Asn Gly Leu Asn Thr Lys Val Ser Ala
2145                2150                2155                2160

Ala Thr Val Glu Ser Thr Asp Ala Asn Gly Asp Lys Val Thr Thr Thr
                2165                2170                2175

Phe Val Lys Thr Asp Val Glu Leu Pro Leu Thr Gln Ile Tyr Asn Thr
            2180                2185                2190

Asp Ala Asn Gly Asn Lys Ile Val Lys Lys Ala Asp Gly Lys Trp Tyr
        2195                2200                2205

Glu Leu Asn Ala Asp Gly Thr Ala Ser Asn Lys Glu Val Thr Leu Gly
    2210                2215                2220

Asn Val Asp Ala Asn Gly Lys Lys Val Val Lys Val Thr Glu Asn Gly
2225                2230                2235                2240

Ala Asp Lys Trp Tyr Tyr Thr Asn Ala Asp Gly Ala Ala Asp Lys Thr
                2245                2250                2255

Lys Gly Glu Val Ser Asn Asp Lys Val Ser Thr Asp Glu Lys His Val
            2260                2265                2270

Val Arg Leu Asp Pro Asn Asn Gln Ser Asn Gly Lys Gly Val Val Ile
        2275                2280                2285

Asp Asn Val Ala Asn Gly Glu Ile Ser Ala Thr Ser Thr Asp Ala Ile
    2290                2295                2300

Asn Gly Ser Gln Leu Tyr Ala Val Ala Lys Gly Val Thr Asn Leu Ala
2305                2310                2315                2320

Gly Gln Val Asn Asn Leu Glu Gly Lys Val Asn Lys Val Gly Lys Arg
                2325                2330                2335

Ala Asp Ala Gly Thr Ala Ser Ala Leu Ala Ala Ser Gln Leu Pro Gln
            2340                2345                2350

Ala Thr Met Pro Gly Lys Ser Met Val Ala Ile Ala Gly Ser Ser Tyr
        2355                2360                2365

Gln Gly Gln Asn Gly Leu Ala Ile Gly Val Ser Arg Ile Ser Asp Asn
```

-continued

```
    2370                2375                2380

Gly Lys Val Ile Ile Arg Leu Ser Gly Thr Thr Asn Ser Gln Gly Lys
2385                2390                2395                2400

Thr Gly Val Ala Ala Gly Val Gly Tyr Gln Trp
                2405                2410
```

```
<210> SEQ ID NO 37
<211> LENGTH: 1812
<212> TYPE: DNA
<213> ORGANISM: Haemophilus influenzae

<400> SEQUENCE: 37

gaattctatt accactggta accaacacct gctgcaacgc cagaaacagc acaacaaatt     60

cactggctac atcaatttac caaagctcgc attcaatggc gcaaaaccca ttccttattc    120

tttaaagaaa aacccgatta tgcctttgtg ctggcagaaa acggcaaagt gcaagaaatc    180

aaagcagaat atcgccgcat tgccaatcaa attgtggaag aagcaatgat tattgccaac    240

atctgcgccg cccaattttt acacgaacag gcaaaaacag gcattttcaa cgcccacagc    300

gaacaaaatc aaactgaact ggcagaacgt tattcagtag aaaacttagc aaccttaaac    360

ggctattgcc aaatgcgtca cgatattgaa cccatcgaaa gcgattattt agaactgcgt    420

ttacgccgtt atttaacttt cgccgaattt aaatcagaat tagcaccgca ctttggtctt    480

ggtttagaag gctatgccac ttggacatcg cccatccgca aatattcaga tatggttaat    540

catcgcttaa tcaaagccgt gctggcaaaa cagccttatg aaaaaccaca aaatgacgtg    600

ttggcacgtt tgcaagagtc tcgccgccaa aatcgcctag tggaacgtga tattgccgat    660

tggctatatt gccgttatct tgctgacaaa gtggctgaaa atgtggaatt taatgcagaa    720

gtgcaagatg taatgcgtgc aggcttacgc gtacaactgc tcgaaaatgg tgcatcgcta    780

tttattcctg ccgccacgtt gcacaacaac aaagaagaaa tacagctaaa ccctgacgaa    840

ctcgccctct atataaaagg cgaacgcact tacaaaatag gcgacattgt gaaagtgaaa    900

ctcacagaag tgaaagaagc aactcgcagt attgtgggcg aaatacttca ataaattgcc    960

gttccaatat gttacggaag acggcaaaac cgttgtgaaa gtgggcaatg agtattacga   1020

agccaagcaa gacggttcgg cggatatgga taaaaaagtc aaaaatggcg agctggtgaa   1080

aactaaagtg aaattggtat cggcaaacgg tacaaatccg gtgaaaatca gcaatgttgc   1140

ggaaggcacg gaagataccg atgcggtcag ctttaagcag ttgaaagcct tgcaaaacaa   1200

acaggttacg ttaagcgcga gcaatgctta tgccaatggc ggtagcgatg ccgacgtcgg   1260

caaggtaact caaactttaa gcaatggttt gaattttaaa tttaaatcca cagacggcga   1320

gttgttgaac atcaaagcag acaaggacac ggttaccatt acgcgggcaa gcggtgcgaa   1380

tggtgcggcg gcgactgatg ccgacaagat taaagtggct tcagacggca ttagcgcggg   1440

taataaagca gttaaaaacg tcgcggcagg cgaaatttcc gccacttcca ccgatgcgat   1500

taacggcagt cagttgtatg ccgtggcaaa gggggtaaca aaccttgctg gacaagtgaa   1560

taaagtgggc aaacgtgcag atgcaggtac agcaagtgca ttagcggctt cacagttacc   1620

acaagcctct atgccgggta aatcaatggt ttctattgcg ggaagtagtt atcaaggtca   1680

aagtggttta gctatcgggg tatcaagaat ttccgataat ggcaaattga ttattcgctt   1740

gtcaggcaca accaatagcc aaggtaaaac aggcgttgca gcaggtgttg gttaccagtg   1800

gtaatagaat tc                                                       1812
```

-continued

<210> SEQ ID NO 38
<211> LENGTH: 616
<212> TYPE: PRT
<213> ORGANISM: Haemophilus influenzae

<400> SEQUENCE: 38

```
Tyr Tyr His Trp Pro Thr Pro Ala Ala Thr Pro Glu Thr Ala Gln Gln
  1               5                  10                  15

Ile His Trp Leu His Gln Phe Thr Lys Ala Arg Ile Gln Trp Arg Lys
             20                  25                  30

Thr His Ser Leu Phe Phe Lys Glu Lys Pro Asp Tyr Ala Phe Val Leu
         35                  40                  45

Ala Glu Asn Gly Lys Val Gln Glu Ile Lys Ala Glu Tyr Arg Arg Ile
     50                  55                  60

Ala Asn Gln Ile Val Glu Glu Ala Met Ile Ile Ala Asn Ile Cys Ala
 65                  70                  75                  80

Ala Gln Phe Leu His Glu Gln Ala Lys Thr Gly Ile Phe Asn Ala His
                 85                  90                  95

Ser Gly Phe Asp Lys Lys Tyr Leu Glu Asn Ala His His Phe Leu Met
            100                 105                 110

Ala Asn Leu Ala Asn Glu Gln Asn Gln Thr Glu Leu Ala Glu Arg Tyr
        115                 120                 125

Ser Val Glu Asn Leu Ala Thr Leu Asn Gly Tyr Cys Gln Met Arg His
    130                 135                 140

Asp Ile Glu Pro Ile Glu Ser Asp Tyr Leu Glu Leu Arg Leu Arg Arg
145                 150                 155                 160

Tyr Leu Thr Phe Ala Glu Phe Lys Ser Glu Leu Ala Pro His Phe Gly
                165                 170                 175

Leu Gly Leu Glu Gly Tyr Ala Thr Trp Thr Ser Pro Ile Arg Lys Tyr
            180                 185                 190

Ser Asp Met Val Asn His Arg Leu Ile Lys Ala Val Leu Ala Lys Gln
        195                 200                 205

Pro Tyr Glu Lys Pro Gln Asn Asp Val Leu Ala Arg Leu Gln Glu Ser
    210                 215                 220

Arg Arg Gln Asn Arg Leu Val Glu Arg Asp Ile Ala Asp Trp Leu Tyr
225                 230                 235                 240

Cys Arg Tyr Leu Ala Asp Lys Val Ala Glu Asn Val Glu Phe Asn Ala
                245                 250                 255

Glu Val Gln Asp Val Met Arg Ala Gly Leu Arg Val Gln Leu Leu Glu
            260                 265                 270

Asn Gly Ala Ser Leu Phe Ile Pro Ala Ala Thr Leu His Asn Asn Lys
        275                 280                 285

Glu Glu Ile Gln Leu Asn Pro Asp Glu Leu Ala Leu Tyr Ile Lys Gly
    290                 295                 300

Glu Arg Thr Tyr Lys Ile Gly Asp Ile Val Lys Val Lys Leu Thr Glu
305                 310                 315                 320

Val Lys Glu Ala Thr Arg Ser Ile Val Gly Glu Ile Leu Gln Leu Pro
                325                 330                 335

Phe Gln Tyr Val Thr Glu Asp Gly Lys Thr Val Val Lys Val Gly Asn
            340                 345                 350

Glu Tyr Tyr Glu Ala Lys Gln Asp Gly Ser Ala Asp Met Asp Lys Lys
        355                 360                 365

Val Lys Asn Gly Glu Leu Val Lys Thr Lys Val Lys Leu Val Ser Ala
    370                 375                 380
```

-continued

```
Asn Gly Thr Asn Pro Val Lys Ile Ser Asn Val Ala Glu Gly Thr Glu
385                 390                 395                 400

Asp Thr Asp Ala Val Ser Phe Lys Gln Leu Lys Ala Leu Gln Asn Lys
                405                 410                 415

Gln Val Thr Leu Ser Ala Ser Asn Ala Tyr Ala Asn Gly Gly Ser Asp
            420                 425                 430

Ala Asp Val Gly Lys Val Thr Gln Thr Leu Ser Asn Gly Leu Asn Phe
        435                 440                 445

Lys Phe Lys Ser Thr Asp Gly Glu Leu Leu Asn Ile Lys Ala Asp Lys
    450                 455                 460

Asp Thr Val Thr Ile Thr Arg Ala Ser Gly Ala Asn Gly Ala Ala Ala
465                 470                 475                 480

Thr Asp Ala Asp Lys Ile Lys Val Ala Ser Asp Gly Ile Ser Ala Gly
                485                 490                 495

Asn Lys Ala Val Lys Asn Val Ala Ala Gly Glu Ile Ser Ala Thr Ser
            500                 505                 510

Thr Asp Ala Ile Asn Gly Ser Gln Leu Tyr Ala Val Ala Lys Gly Val
        515                 520                 525

Thr Asn Leu Ala Gly Gln Val Asn Lys Val Gly Lys Arg Ala Asp Ala
    530                 535                 540

Gly Thr Ala Ser Ala Leu Ala Ala Ser Gln Leu Pro Gln Ala Ser Met
545                 550                 555                 560

Pro Gly Lys Ser Met Val Ser Ile Ala Gly Ser Ser Tyr Gln Gly Gln
                565                 570                 575

Ser Gly Leu Ala Ile Gly Val Ser Arg Ile Ser Asp Asn Gly Lys Leu
            580                 585                 590

Ile Ile Arg Leu Ser Gly Thr Thr Asn Ser Gln Gly Lys Thr Gly Val
        595                 600                 605

Ala Ala Gly Val Gly Tyr Gln Trp
    610                 615
```

<210> SEQ ID NO 39
<211> LENGTH: 24
<212> TYPE: DNA
<213> ORGANISM: Haemophilus influenzae

<400> SEQUENCE: 39
tgcgcaccat ttcttaatgg caaa 24

<210> SEQ ID NO 40
<211> LENGTH: 27
<212> TYPE: DNA
<213> ORGANISM: Haemophilus influenzae

<400> SEQUENCE: 40
gacgtgttgg cacgtttgca agagtct 27

<210> SEQ ID NO 41
<211> LENGTH: 23
<212> TYPE: DNA
<213> ORGANISM: Haemophilus influenzae

<400> SEQUENCE: 41
gcaagacggt tcggcggata tgg 23

<210> SEQ ID NO 42
<211> LENGTH: 22
<212> TYPE: DNA

<213> ORGANISM: Haemophilus influenzae

<400> SEQUENCE: 42
ccgccacttc caccgatgcg at 22

<210> SEQ ID NO 43
<211> LENGTH: 3294
<212> TYPE: DNA
<213> ORGANISM: Haemophilus influenzae

<400> SEQUENCE: 43
atgaacaaaa tttttaacgt tatttggaat gttgtgactc aaacttgggt tgtcgtatct 60
gaactcactc gcacccacac caaatgcgcc tccgccaccg tggcggttgc cgtattggca 120
accctgttgt ccgcaacggt tgaggcgaac aacaatactc ctgttacgaa taagttgaag 180
gcttatggcg atgcgaattt taatttcact aataattcga tagcagatgc agaaaaacaa 240
gttcaagagg cttataaagg tttattaaat ctaaatgaaa aaaatgcgag tgataaactg 300
ttggtggagg acaatactgc ggcgaccgta ggcaatttgc gtaaattggg ctgggtattg 360
tctagcaaaa acggcacaag gaacgagaaa agccaacaag tcaaacatgc ggatgaagtg 420
ttgtttgaag gcaaaggcgg tgtgcaggtt acttccacct ctgaaaacgg caaacacacc 480
attacctttg ctttagcgaa agaccttggt gtgaaaactg cgactgtgag tgatacctta 540
acgattggcg gtggtgctgc tgcaggtgct acaacaacac cgaaagtgaa tgtaactagt 600
acaactgatg gcttgaagtt cgctaaagat gctgcgggtg ctaatggcga tactacggtt 660
cacttgaatg gtattggttc aaccttgaca gacacgcttg tgggttctcc tgctactcat 720
attgacggag gagatcaaag tacgcattac actcgtgcag caagtatcaa ggatgtcttg 780
aatgcgggtt ggaatatcaa gggtgttaaa gctggctcaa caactggtca atcagaaaat 840
gtcgattttg ttcatactta cgatactgtt gagttcttga gtgcggatac agagaccacg 900
actgttactg tagatagcaa agaaaacggt aagagaaccg aagttaaaat cggtgcgaag 960
acttctgtta tcaaagaaaa agacggtaag ttatttactg gaaaagctaa caaagagaca 1020
aataaagttg atggtgctaa cgcgactgaa gatgcagacg aaggcaaagg cttagtgact 1080
gcgaaagatg tgattgacgc agtgaataag actggttgga gaattaaaac aaccgatgct 1140
aatggtcaaa atggcgactt cgcaactgtt gcatcaggca caaatgtaac ctttgctagt 1200
ggtaatggta caactgcgac tgtaactaat ggcaccgatg gtattaccgt taagtatgat 1260
gcgaaagttg gcgacggctt aaaactagat ggcgataaaa tcgctgcaga tacgaccgca 1320
cttactgtga atgatggtaa gaacgctaat aatccgaaag gtaaagtggc tgatgttgct 1380
tcaactgacg agaagaaatt ggttacagca aaaggtttag taacagcctt aaacagtcta 1440
agctggacta caactgctgc tgaggcggac ggtggtacgc ttgatggaaa tgcaagtgag 1500
caagaagtta aagcgggcga taaagtaacc tttaaagcag gcaagaactt aaaagtgaaa 1560
caagagggtg cgaactttac ttattcactg caagatgctt taacaggctt aacgagcatt 1620
actttaggta caggaaataa tggtgcgaaa actgaaatca acaaagacgg cttaaccatc 1680
acaccagcaa atggtgcggg tgcaaataat gcaaacacca tcagcgtaac caaagacggc 1740
attagtgcgg gcggtcagtc ggttaaaaac gttgtgagcg gactgaagaa atttggtgat 1800
gcgaatttcg atccgctgac tagctccgcc gacaacttaa cgaaacaaaa tgacgatgcc 1860
tataaaggct tgaccaattt ggatgaaaaa ggtacagaca agcaaactcc agttgttgcc 1920
gacaataccg ccgcaaccgt gggcgatttg cgcggcttgg gctgggtcat ttctgcggac 1980

-continued

```
aaaaccacag gcggctcaac ggaatatcac gatcaagttc ggaatgcgaa cgaagtgaaa   2040

ttcaaaagcg gcaacggtat caatgtttcc ggtaaaacgg tcaacggtag gcgtgaaatt   2100

acttttgaat tggctaaagg tgaagtggtt aaatcgaatg aatttaccgt caaagaaacc   2160

aatggaaagg aaacgagcct ggttaaagtt ggcgataaat attacagcaa agaggatatt   2220

gacttaacaa caggtcagcc taaattaaaa gatggcaata cagttgctgc gaaatatcaa   2280

gataaaggtg gcaaagtcgt ttctgtaacg gataatactg aagctaccat aaccaacaaa   2340

ggttctggct atgtaacagg taaccaagtg gcagatgcga ttgcgaaatc aggctttgag   2400

cttggcttgg ctgatgaagc tgatgcgaaa cgggcgtttg atgataagac aaaagcctta   2460

tctgctggta caacggaaat tgtaaatgcc cacgataaag tccgttttgc taatggttta   2520

aataccaaag tgagcgcggc aacggtggaa agcaccgatg caaacggcga taaagtgacc   2580

acaacctttg tgaaaaccga tgtggaattg cctttaacgc aaatctacaa taccgatgca   2640

aacggtaaga aaatcactaa agttgtcaaa gatgggcaaa ctaaatggta tgaactgaat   2700

gctgacggta cggctgatat gaccaaagaa gttaccctcg gtaacgtgga ttcagacggc   2760

aagaaagttg tgaaagacaa cgatggcaag tggtatcacg ccaaagctga cggtactgcg   2820

gataaaacca aaggcgaagt gagcaatgat aaagtttcta ccgatgaaaa acacgttgtc   2880

agccttgatc caaatgatca atcaaaaggt aaaggtgtcg tgattgacaa tgtggctaat   2940

ggcgatattt ctgccacttc caccgatgcg attaacggaa gtcagttgta tgctgtggca   3000

aaaggggtaa caaaccttgc tggacaagtg aataatcttg agggcaaagt gaataaagtg   3060

ggcaaacgtg cagatgcagg tacagcaagt gcattagcgg cttcacagtt accacaagcc   3120

actatgccag gtaaatcaat ggttgctatt gcgggaagta gttatcaagg tcaaaatggt   3180

ttagctatcg ggtatcaag aatttccgat aatggcaaag tgattattcg cttgtcaggc   3240

acaaccaata gtcaaggtaa aacaggcgtt gcagcaggtg ttggttacca gtgg         3294
```

<210> SEQ ID NO 44
<211> LENGTH: 1098
<212> TYPE: PRT
<213> ORGANISM: Haemophilus influenzae

<400> SEQUENCE: 44

```
Met Asn Lys Ile Phe Asn Val Ile Trp Asn Val Val Thr Gln Thr Trp
  1               5                  10                  15

Val Val Val Ser Glu Leu Thr Arg Thr His Thr Lys Cys Ala Ser Ala
             20                  25                  30

Thr Val Ala Val Ala Val Leu Ala Thr Leu Leu Ser Ala Thr Val Glu
         35                  40                  45

Ala Asn Asn Asn Thr Pro Val Thr Asn Lys Leu Lys Ala Tyr Gly Asp
     50                  55                  60

Ala Asn Phe Asn Phe Thr Asn Asn Ser Ile Ala Asp Ala Glu Lys Gln
 65                  70                  75                  80

Val Gln Glu Ala Tyr Lys Gly Leu Leu Asn Leu Asn Glu Lys Asn Ala
                 85                  90                  95

Ser Asp Lys Leu Leu Val Glu Asp Asn Thr Ala Ala Thr Val Gly Asn
            100                 105                 110

Leu Arg Lys Leu Gly Trp Val Leu Ser Ser Lys Asn Gly Thr Arg Asn
        115                 120                 125

Glu Lys Ser Gln Gln Val Lys His Ala Asp Glu Val Leu Phe Glu Gly
    130                 135                 140
```

-continued

```
Lys Gly Gly Val Gln Val Thr Ser Thr Ser Glu Asn Gly Lys His Thr
145                 150                 155                 160

Ile Thr Phe Ala Leu Ala Lys Asp Leu Gly Val Lys Thr Ala Thr Val
                165                 170                 175

Ser Asp Thr Leu Thr Ile Gly Gly Gly Ala Ala Ala Gly Ala Thr Thr
            180                 185                 190

Thr Pro Lys Val Asn Val Thr Ser Thr Thr Asp Gly Leu Lys Phe Ala
        195                 200                 205

Lys Asp Ala Ala Gly Ala Asn Gly Asp Thr Thr Val His Leu Asn Gly
    210                 215                 220

Ile Gly Ser Thr Leu Thr Asp Thr Leu Val Gly Ser Pro Ala Thr His
225                 230                 235                 240

Ile Asp Gly Gly Asp Gln Ser Thr His Tyr Thr Arg Ala Ala Ser Ile
                245                 250                 255

Lys Asp Val Leu Asn Ala Gly Trp Asn Ile Lys Gly Val Lys Ala Gly
            260                 265                 270

Ser Thr Thr Gly Gln Ser Glu Asn Val Asp Phe Val His Thr Tyr Asp
        275                 280                 285

Thr Val Glu Phe Leu Ser Ala Asp Thr Glu Thr Thr Thr Val Thr Val
    290                 295                 300

Asp Ser Lys Glu Asn Gly Lys Arg Thr Glu Val Lys Ile Gly Ala Lys
305                 310                 315                 320

Thr Ser Val Ile Lys Glu Lys Asp Gly Lys Leu Phe Thr Gly Lys Ala
                325                 330                 335

Asn Lys Glu Thr Asn Lys Val Asp Gly Ala Asn Ala Thr Glu Asp Ala
            340                 345                 350

Asp Glu Gly Lys Gly Leu Val Thr Ala Lys Asp Val Ile Asp Ala Val
        355                 360                 365

Asn Lys Thr Gly Trp Arg Ile Lys Thr Thr Asp Ala Asn Gly Gln Asn
    370                 375                 380

Gly Asp Phe Ala Thr Val Ala Ser Gly Thr Asn Val Thr Phe Ala Ser
385                 390                 395                 400

Gly Asn Gly Thr Thr Ala Thr Val Thr Asn Gly Thr Asp Gly Ile Thr
                405                 410                 415

Val Lys Tyr Asp Ala Lys Val Gly Asp Gly Leu Lys Leu Asp Gly Asp
            420                 425                 430

Lys Ile Ala Ala Asp Thr Thr Ala Leu Thr Val Asn Asp Gly Lys Asn
        435                 440                 445

Ala Asn Asn Pro Lys Gly Lys Val Ala Asp Val Ala Ser Thr Asp Glu
    450                 455                 460

Lys Lys Leu Val Thr Ala Lys Gly Leu Val Thr Ala Leu Asn Ser Leu
465                 470                 475                 480

Ser Trp Thr Thr Thr Ala Ala Glu Ala Asp Gly Gly Thr Leu Asp Gly
                485                 490                 495

Asn Ala Ser Glu Gln Glu Val Lys Ala Gly Asp Lys Val Thr Phe Lys
            500                 505                 510

Ala Gly Lys Asn Leu Lys Val Lys Gln Glu Gly Ala Asn Phe Thr Tyr
        515                 520                 525

Ser Leu Gln Asp Ala Leu Thr Gly Leu Thr Ser Ile Thr Leu Gly Thr
    530                 535                 540

Gly Asn Asn Gly Ala Lys Thr Glu Ile Asn Lys Asp Gly Leu Thr Ile
545                 550                 555                 560
```

-continued

```
Thr Pro Ala Asn Gly Ala Gly Ala Asn Asn Ala Asn Thr Ile Ser Val
                565                 570                 575

Thr Lys Asp Gly Ile Ser Ala Gly Gly Gln Ser Val Lys Asn Val Val
            580                 585                 590

Ser Gly Leu Lys Lys Phe Gly Asp Ala Asn Phe Asp Pro Leu Thr Ser
        595                 600                 605

Ser Ala Asp Asn Leu Thr Lys Gln Asn Asp Asp Ala Tyr Lys Gly Leu
    610                 615                 620

Thr Asn Leu Asp Glu Lys Gly Thr Asp Lys Gln Thr Pro Val Val Ala
625                 630                 635                 640

Asp Asn Thr Ala Ala Thr Val Gly Asp Leu Arg Gly Leu Gly Trp Val
                645                 650                 655

Ile Ser Ala Asp Lys Thr Thr Gly Gly Ser Thr Glu Tyr His Asp Gln
            660                 665                 670

Val Arg Asn Ala Asn Glu Val Lys Phe Lys Ser Gly Asn Gly Ile Asn
        675                 680                 685

Val Ser Gly Lys Thr Val Asn Gly Arg Arg Glu Ile Thr Phe Glu Leu
    690                 695                 700

Ala Lys Gly Glu Val Val Lys Ser Asn Glu Phe Thr Val Lys Glu Thr
705                 710                 715                 720

Asn Gly Lys Glu Thr Ser Leu Val Lys Val Gly Asp Lys Tyr Tyr Ser
                725                 730                 735

Lys Glu Asp Ile Asp Leu Thr Thr Gly Gln Pro Lys Leu Lys Asp Gly
            740                 745                 750

Asn Thr Val Ala Ala Lys Tyr Gln Asp Lys Gly Gly Lys Val Val Ser
        755                 760                 765

Val Thr Asp Asn Thr Glu Ala Thr Ile Thr Asn Lys Gly Ser Gly Tyr
    770                 775                 780

Val Thr Gly Asn Gln Val Ala Asp Ala Ile Ala Lys Ser Gly Phe Glu
785                 790                 795                 800

Leu Gly Leu Ala Asp Glu Ala Asp Ala Lys Arg Ala Phe Asp Asp Lys
                805                 810                 815

Thr Lys Ala Leu Ser Ala Gly Thr Thr Glu Ile Val Asn Ala His Asp
            820                 825                 830

Lys Val Arg Phe Ala Asn Gly Leu Asn Thr Lys Val Ser Ala Ala Thr
        835                 840                 845

Val Glu Ser Thr Asp Ala Asn Gly Asp Lys Val Thr Thr Thr Phe Val
    850                 855                 860

Lys Thr Asp Val Glu Leu Pro Leu Thr Gln Ile Tyr Asn Thr Asp Ala
865                 870                 875                 880

Asn Gly Lys Lys Ile Thr Lys Val Val Lys Asp Gly Gln Thr Lys Trp
                885                 890                 895

Tyr Glu Leu Asn Ala Asp Gly Thr Ala Asp Met Thr Lys Glu Val Thr
            900                 905                 910

Leu Gly Asn Val Asp Ser Asp Gly Lys Lys Val Val Lys Asp Asn Asp
        915                 920                 925

Gly Lys Trp Tyr His Ala Lys Ala Asp Gly Thr Ala Asp Lys Thr Lys
    930                 935                 940

Gly Glu Val Ser Asn Asp Lys Val Ser Thr Asp Glu Lys His Val Val
945                 950                 955                 960

Ser Leu Asp Pro Asn Asp Gln Ser Lys Gly Lys Gly Val Val Ile Asp
                965                 970                 975

Asn Val Ala Asn Gly Asp Ile Ser Ala Thr Ser Thr Asp Ala Ile Asn
```

-continued

```
        980                 985                 990

Gly Ser Gln Leu Tyr Ala Val Ala Lys Gly Val Thr Asn Leu Ala Gly
        995                 1000                1005

Gln Val Asn Asn Leu Glu Gly Lys Val Asn Lys Val Gly Lys Arg Ala
    1010                1015                1020

Asp Ala Gly Thr Ala Ser Ala Leu Ala Ala Ser Gln Leu Pro Gln Ala
1025                1030                1035                1040

Thr Met Pro Gly Lys Ser Met Val Ala Ile Ala Gly Ser Ser Tyr Gln
                1045                1050                1055

Gly Gln Asn Gly Leu Ala Ile Gly Val Ser Arg Ile Ser Asp Asn Gly
            1060                1065                1070

Lys Val Ile Ile Arg Leu Ser Gly Thr Thr Asn Ser Gln Gly Lys Thr
        1075                1080                1085

Gly Val Ala Ala Gly Val Gly Tyr Gln Trp
    1090                1095


<210> SEQ ID NO 45
<211> LENGTH: 660
<212> TYPE: PRT
<213> ORGANISM: Haemophilus influenzae

<400> SEQUENCE: 45

Pro Thr Pro Ala Ala Thr Pro Glu Thr Ala Gln Gln Ile His Trp Leu
  1               5                  10                  15

His Gln Phe Thr Lys Ala Arg Ile Gln Trp Arg Lys Thr His Ser Leu
            20                  25                  30

Phe Phe Lys Glu Lys Pro Asp Tyr Ala Phe Val Leu Ala Glu Asn Gly
        35                  40                  45

Lys Val Gln Glu Ile Lys Ala Glu Tyr Arg Arg Ile Ala Asn Gln Ile
     50                  55                  60

Val Glu Glu Ala Met Ile Ile Ala Ala Trp Gln Pro Glu Met Pro Glu
 65                  70                  75                  80

Thr Ala Gln Gln Ile His Trp Leu His Gln Phe Thr Lys Ala Arg Ile
                 85                  90                  95

Gln Trp Arg Lys Thr His Ser Leu Phe Phe Lys Glu Lys Pro Asp Tyr
            100                 105                 110

Ala Phe Val Leu Ala Glu Asn Gly Lys Val Gln Glu Ile Lys Ala Glu
        115                 120                 125

Tyr Arg Arg Ile Ala Asn Gln Ile Val Glu Glu Ala Met Ile Ile Ala
    130                 135                 140

Asn Ile Cys Ala Ala Gln Phe Leu His Glu Gln Ala Lys Thr Gly Ile
145                 150                 155                 160

Phe Asn Ala His Ser Gly Phe Asp Lys Lys Tyr Leu Glu Asn Ala His
                165                 170                 175

His Phe Leu Met Ala Asn Leu Ala Asn Glu Gln Asn Gln Thr Glu Leu
            180                 185                 190

Ala Glu Arg Tyr Ser Val Glu Asn Leu Ala Thr Leu Asn Gly Tyr Cys
        195                 200                 205

Gln Met Arg His Asp Ile Glu Pro Asn Ile Cys Ala Ala Gln Phe Leu
    210                 215                 220

His Glu Gln Ala Lys Thr Gly Ile Phe Asn Thr His Ser Gly Phe Asp
225                 230                 235                 240

Lys Lys Phe Leu Glu Asn Ala His Asn Phe Leu Met Ala Asn Leu Ala
                245                 250                 255
```

-continued

```
Asn Glu Gln Asn Gln Thr Glu Leu Ala Glu Arg Tyr Ser Val Glu Asn
            260                 265                 270

Leu Ala Thr Leu Asn Gly Tyr Cys Gln Met Arg His Asp Ile Glu Pro
        275                 280                 285

Ile Glu Ser Asp Tyr Leu Glu Leu Arg Leu Arg Arg Tyr Leu Thr Phe
    290                 295                 300

Ala Glu Phe Lys Ser Glu Leu Ala Pro His Phe Gly Leu Gly Leu Glu
305                 310                 315                 320

Gly Tyr Ala Thr Trp Thr Ser Pro Ile Arg Lys Tyr Ser Asp Met Val
                325                 330                 335

Asn His Arg Leu Ile Lys Ala Val Leu Ala Lys Gln Pro Tyr Glu Lys
            340                 345                 350

Pro Gln Asn Asp Val Leu Ala Arg Ile Glu Ser Asp Tyr Leu Glu Leu
        355                 360                 365

Arg Leu Arg Arg Tyr Leu Thr Phe Ala Glu Phe Lys Ser Glu Leu Ala
    370                 375                 380

Pro His Phe Gly Leu Gly Leu Glu Gly Tyr Ala Thr Trp Thr Ser Pro
385                 390                 395                 400

Ile Arg Lys Tyr Ser Asp Met Val Asn His Arg Leu Ile Lys Ala Val
                405                 410                 415

Leu Ala Lys Gln Pro Tyr Glu Lys Pro Gln Asn Asp Val Leu Ala Arg
            420                 425                 430

Leu Gln Glu Ser Arg Arg Gln Asn Arg Leu Val Glu Arg Asp Ile Ala
        435                 440                 445

Asp Trp Leu Tyr Cys Arg Tyr Leu Ala Asp Lys Val Ala Glu Asn Val
    450                 455                 460

Glu Phe Asn Ala Glu Val Gln Asp Val Met Arg Ala Gly Leu Arg Val
465                 470                 475                 480

Gln Leu Leu Glu Asn Gly Ala Ser Leu Phe Ile Pro Ala Ala Thr Leu
                485                 490                 495

His Asn Asn Lys Glu Glu Ile Gln Leu Gln Glu Ala Arg Arg Gln Asn
            500                 505                 510

Arg Leu Val Glu Arg Asp Ile Ala Asp Trp Leu Tyr Cys Arg Tyr Leu
        515                 520                 525

Ala Asp Lys Val Ala Ser Asn Ala Glu Phe Glu Ala Glu Val Gln Asp
    530                 535                 540

Val Met Arg Ala Gly Leu Arg Val Gln Leu Leu Glu Asn Gly Ala Ser
545                 550                 555                 560

Leu Phe Ile Pro Ala Ala Thr Leu His Asn Asn Lys Glu Glu Ile Gln
                565                 570                 575

Leu Asn Pro Asp Glu Leu Ala Leu Tyr Ile Lys Gly Glu Arg Thr Tyr
            580                 585                 590

Lys Ile Gly Asp Ile Val Lys Val Lys Leu Thr Glu Val Lys Glu Ala
        595                 600                 605

Thr Arg Ser Ile Val Gly Glu Ile Leu Gln Leu Asn Pro Asp Glu Leu
    610                 615                 620

Ala Leu Tyr Ile Lys Gly Glu Arg Thr Tyr Lys Ile Gly Asp Met Val
625                 630                 635                 640

Lys Val Lys Leu Thr Glu Val Lys Glu Ala Thr Arg Ser Ile Val Gly
                645                 650                 655

Glu Ile Leu Gln
            660
```

-continued

<210> SEQ ID NO 46
<211> LENGTH: 659
<212> TYPE: PRT
<213> ORGANISM: Haemophilus influenzae

<400> SEQUENCE: 46

```
Met Phe Gln Asp Asn Pro Leu Leu Ala Gln Leu Lys Gln Gln Ile His
  1               5                  10                  15

Asp Ser Lys Glu Gln Val Glu Gly Val Val Lys Ser Thr Asp Lys Ala
             20                  25                  30

Tyr Gly Phe Leu Glu Cys Asp Lys Lys Thr Tyr Phe Ile Ala Pro Pro
         35                  40                  45

Ser Met Lys Lys Val Met His Gly Asp Lys Ile Lys Ala Thr Ile Glu
     50                  55                  60

Lys Gln Gly Asp Lys Glu Gln Ala Glu Pro Glu Ala Leu Ile Glu Pro
 65                  70                  75                  80

Met Leu Thr Arg Phe Ile Ala Lys Val Arg Phe Asn Lys Asp Lys Lys
                 85                  90                  95

Leu Gln Val Leu Val Asp His Pro Ser Ile Asn Gln Pro Ile Gly Ala
            100                 105                 110

Gln Gln Ala Lys Ser Val Lys Glu Glu Leu Gln Glu Gly Asp Trp Val
        115                 120                 125

Val Ala Asn Leu Lys Thr His Pro Leu Arg Asp Asp Arg Phe Phe Tyr
    130                 135                 140

Ala Thr Ile Asn Gln Leu Ile Cys Arg Ala Asp Asp Glu Leu Ala Pro
145                 150                 155                 160

Trp Trp Val Thr Leu Ala Arg His Glu Gln Ser Arg Tyr Pro Val Arg
                165                 170                 175

Gly Ala Glu Pro Tyr Glu Met Leu Asp Gln Lys Thr Arg Glu Asn Leu
            180                 185                 190

Thr Ala Leu His Phe Val Thr Ile Asp Ser Glu Ser Thr Met Asp Met
        195                 200                 205

Asp Asp Ala Leu Tyr Ile Glu Pro Ile Ala Gln Asn Ser Thr Gln Thr
    210                 215                 220

Gly Trp Lys Leu Val Val Ala Ile Ala Asp Pro Thr Ala Tyr Ile Ala
225                 230                 235                 240

Leu Asp Ser Gln Ile Glu Gln Glu Ala Lys Gln Arg Cys Phe Thr Asn
                245                 250                 255

Tyr Leu Pro Gly Phe Asn Ile Pro Met Leu Pro Arg Glu Leu Ser Asp
            260                 265                 270

Glu Leu Cys Ser Leu Ile Ala Asn Glu Thr Arg Pro Ala Leu Val Cys
        275                 280                 285

Tyr Ile Glu Thr Asp Leu Thr Gly Asn Ile Thr Ala Lys Pro His Phe
    290                 295                 300

Val Ser Ala Tyr Val Gln Ser Lys Ala Lys Leu Ala Tyr Asn Lys Val
305                 310                 315                 320

Ser Asp Tyr Leu Glu Gln Ala Asp Asn Ala Trp Gln Pro Glu Met Pro
                325                 330                 335

Glu Thr Ala Gln Gln Ile His Trp Leu His Gln Phe Thr Lys Ala Arg
            340                 345                 350

Ile Gln Trp Arg Lys Thr His Ser Leu Phe Phe Lys Glu Lys Pro Asp
        355                 360                 365

Tyr Ala Phe Val Leu Ala Glu Asn Gly Lys Val Gln Glu Ile Lys Ala
    370                 375                 380
```

-continued

Glu Tyr Arg Arg Ile Ala Asn Gln Ile Val Glu Glu Ala Met Ile Ile
385 390 395 400

Ala Asn Ile Cys Ala Ala Gln Phe Leu His Glu Gln Ala Lys Thr Gly
405 410 415

Ile Phe Asn Thr His Ser Gly Phe Asp Lys Lys Phe Leu Glu Asn Ala
420 425 430

His Asn Phe Leu Met Ala Asn Leu Ala Asn Glu Gln Asn Gln Thr Glu
435 440 445

Leu Ala Glu Arg Tyr Ser Val Glu Asn Leu Ala Thr Leu Asn Gly Tyr
450 455 460

Cys Gln Met Arg His Asp Ile Glu Pro Ile Glu Ser Asp Tyr Leu Glu
465 470 475 480

Leu Arg Leu Arg Arg Tyr Leu Thr Phe Ala Glu Phe Lys Ser Glu Leu
485 490 495

Ala Pro His Phe Gly Leu Gly Leu Glu Gly Tyr Ala Thr Trp Thr Ser
500 505 510

Pro Ile Arg Lys Tyr Ser Asp Met Val Asn His Arg Leu Ile Lys Ala
515 520 525

Val Leu Ala Lys Gln Pro Tyr Glu Lys Pro Gln Asn Asp Val Leu Ala
530 535 540

Arg Leu Gln Glu Ala Arg Arg Gln Asn Arg Leu Val Glu Arg Asp Ile
545 550 555 560

Ala Asp Trp Leu Tyr Cys Arg Tyr Leu Ala Asp Lys Val Ala Ser Asn
565 570 575

Ala Glu Phe Glu Ala Glu Val Gln Asp Val Met Arg Ala Gly Leu Arg
580 585 590

Val Gln Leu Leu Glu Asn Gly Ala Ser Leu Phe Ile Pro Ala Ala Thr
595 600 605

Leu His Asn Asn Lys Glu Glu Ile Gln Leu Asn Pro Asp Glu Leu Ala
610 615 620

Leu Tyr Ile Lys Gly Glu Arg Thr Tyr Lys Ile Gly Asp Met Val Lys
625 630 635 640

Val Lys Leu Thr Glu Val Lys Glu Ala Thr Arg Ser Ile Val Gly Glu
645 650 655

Ile Leu Gln

<210> SEQ ID NO 47
<211> LENGTH: 2354
<212> TYPE: PRT
<213> ORGANISM: Haemophilus influenzae

<400> SEQUENCE: 47

Met Asn Lys Ile Phe Asn Val Ile Trp Asn Val Met Thr Gln Thr Trp
1 5 10 15

Val Val Val Ser Glu Leu Thr Arg Thr His Thr Lys Arg Ala Ser Ala
20 25 30

Thr Val Glu Thr Ala Val Leu Ala Thr Leu Leu Phe Ala Thr Val Gln
35 40 45

Ala Asn Ala Thr Asp Glu Asp Glu Glu Leu Asp Pro Val Val Arg Thr
50 55 60

Ala Pro Val Leu Ser Phe His Ser Asp Lys Glu Gly Thr Gly Glu Lys
65 70 75 80

Glu Val Thr Glu Asn Ser Asn Trp Gly Ile Tyr Phe Asp Asn Lys Gly
85 90 95

-continued

```
Val Leu Lys Ala Gly Ala Ile Thr Leu Lys Ala Gly Asp Asn Leu Lys
            100                 105                 110

Ile Lys Gln Asn Thr Asp Glu Ser Thr Asn Ala Ser Ser Phe Thr Tyr
        115                 120                 125

Ser Leu Lys Lys Asp Leu Thr Asp Leu Thr Ser Val Ala Thr Glu Lys
    130                 135                 140

Leu Ser Phe Gly Ala Asn Gly Asp Lys Val Lys Ile Thr Ser Asp Ala
145                 150                 155                 160

Asn Gly Leu Lys Leu Ala Lys Thr Gly Asn Gly Asn Val His Leu Asn
                165                 170                 175

Gly Leu Asp Ser Thr Leu Pro Asp Ala Val Thr Asn Thr Gly Val Leu
            180                 185                 190

Ser Ser Ser Ser Phe Thr Pro Asn Asp Val Glu Lys Thr Arg Ala Ala
        195                 200                 205

Thr Val Lys Asp Val Leu Asn Ala Gly Trp Asn Ile Lys Gly Ala Lys
    210                 215                 220

Thr Ala Gly Gly Asn Val Glu Ser Val Asp Leu Val Ser Ala Tyr Asn
225                 230                 235                 240

Asn Val Glu Phe Ile Thr Gly Asp Lys Asn Thr Leu Asp Val Val Leu
                245                 250                 255

Thr Ala Lys Glu Asn Gly Lys Thr Thr Glu Val Lys Phe Thr Pro Lys
            260                 265                 270

Thr Ser Val Ile Lys Glu Lys Asp Gly Lys Leu Phe Thr Gly Lys Glu
        275                 280                 285

Asn Asn Asp Thr Asn Lys Val Thr Ser Asn Thr Ala Thr Asp Asn Thr
    290                 295                 300

Asp Glu Gly Asn Gly Leu Val Thr Ala Lys Ala Val Ile Asp Ala Val
305                 310                 315                 320

Asn Lys Ala Gly Trp Arg Val Lys Thr Thr Thr Ala Asn Gly Gln Asn
                325                 330                 335

Gly Asp Phe Ala Thr Val Ala Ser Gly Thr Asn Val Thr Phe Glu Ser
            340                 345                 350

Gly Asp Gly Thr Thr Ala Ser Val Thr Lys Asp Thr Asn Gly Asn Gly
        355                 360                 365

Ile Thr Val Lys Tyr Asp Ala Lys Val Gly Asp Gly Leu Lys Phe Asp
    370                 375                 380

Ser Asp Lys Lys Ile Val Ala Asp Thr Thr Ala Leu Thr Val Thr Gly
385                 390                 395                 400

Gly Lys Val Ala Glu Ile Ala Lys Glu Asp Asp Lys Lys Lys Leu Val
                405                 410                 415

Asn Ala Gly Asp Leu Val Thr Ala Leu Gly Asn Leu Ser Trp Lys Ala
            420                 425                 430

Lys Ala Glu Ala Asp Thr Asp Gly Ala Leu Glu Gly Ile Ser Lys Asp
        435                 440                 445

Gln Glu Val Lys Ala Gly Glu Thr Val Thr Phe Lys Ala Gly Lys Asn
    450                 455                 460

Leu Lys Val Lys Gln Asp Gly Ala Asn Phe Thr Tyr Ser Leu Gln Asp
465                 470                 475                 480

Ala Leu Thr Gly Leu Thr Ser Ile Thr Leu Gly Gly Thr Thr Asn Gly
                485                 490                 495

Gly Asn Asp Ala Lys Thr Val Ile Asn Lys Asp Gly Leu Thr Ile Thr
            500                 505                 510

Pro Ala Gly Asn Gly Gly Thr Thr Gly Thr Asn Thr Ile Ser Val Thr
```

-continued

```
        515                 520                 525

Lys Asp Gly Ile Lys Ala Gly Asn Lys Ala Ile Thr Asn Val Ala Ser
    530                 535                 540

Gly Leu Arg Ala Tyr Asp Asp Ala Asn Phe Asp Val Leu Asn Asn Ser
545                 550                 555                 560

Ala Thr Asp Leu Asn Arg His Val Glu Asp Ala Tyr Lys Gly Leu Leu
                565                 570                 575

Asn Leu Asn Glu Lys Asn Ala Asn Lys Gln Pro Leu Val Thr Asp Ser
            580                 585                 590

Thr Ala Ala Thr Val Gly Asp Leu Arg Lys Leu Gly Trp Val Val Ser
        595                 600                 605

Thr Lys Asn Gly Thr Lys Glu Glu Ser Asn Gln Val Lys Gln Ala Asp
    610                 615                 620

Glu Val Leu Phe Thr Gly Ala Gly Ala Ala Thr Val Thr Ser Lys Ser
625                 630                 635                 640

Glu Asn Gly Lys His Thr Ile Thr Val Ser Val Ala Glu Thr Lys Ala
                645                 650                 655

Asp Cys Gly Leu Glu Lys Asp Gly Asp Thr Ile Lys Leu Lys Val Asp
            660                 665                 670

Asn Gln Asn Thr Asp Asn Val Leu Thr Val Gly Asn Asn Gly Thr Ala
        675                 680                 685

Val Thr Lys Gly Gly Phe Glu Thr Val Lys Thr Gly Ala Thr Asp Ala
    690                 695                 700

Asp Arg Gly Lys Val Thr Val Lys Asp Ala Thr Ala Asn Asp Ala Asp
705                 710                 715                 720

Lys Lys Val Ala Thr Val Lys Asp Val Ala Thr Ala Ile Asn Ser Ala
                725                 730                 735

Ala Thr Phe Val Lys Thr Glu Asn Leu Thr Thr Ser Ile Asp Glu Asp
            740                 745                 750

Asn Pro Thr Asp Asn Gly Lys Asp Asp Ala Leu Lys Ala Gly Asp Thr
        755                 760                 765

Leu Thr Phe Lys Ala Gly Lys Asn Leu Lys Val Lys Arg Asp Gly Lys
    770                 775                 780

Asn Ile Thr Phe Asp Leu Ala Lys Asn Leu Glu Val Lys Thr Ala Lys
785                 790                 795                 800

Val Ser Asp Thr Leu Thr Ile Gly Gly Asn Thr Pro Thr Gly Gly Thr
                805                 810                 815

Thr Ala Thr Pro Lys Val Asn Ile Thr Ser Thr Ala Asp Gly Leu Asn
            820                 825                 830

Phe Ala Lys Glu Thr Ala Asp Ala Ser Gly Ser Lys Asn Val Tyr Leu
        835                 840                 845

Lys Gly Ile Ala Thr Thr Leu Thr Glu Pro Ser Ala Gly Ala Lys Ser
    850                 855                 860

Ser His Val Asp Leu Asn Val Asp Ala Thr Lys Lys Ser Asn Ala Ala
865                 870                 875                 880

Ser Ile Glu Asp Val Leu Arg Ala Gly Trp Asn Ile Gln Gly Asn Gly
                885                 890                 895

Asn Asn Val Asp Tyr Val Ala Thr Tyr Asp Thr Val Asn Phe Thr Asp
            900                 905                 910

Asp Ser Thr Gly Thr Thr Thr Val Thr Val Thr Gln Lys Ala Asp Gly
        915                 920                 925

Lys Gly Ala Asp Val Lys Ile Gly Ala Lys Thr Ser Val Ile Lys Asp
    930                 935                 940
```

-continued

```
His Asn Gly Lys Leu Phe Thr Gly Lys Asp Leu Lys Asp Ala Asn Asn
945                 950                 955                 960

Gly Ala Thr Val Ser Glu Asp Asp Gly Lys Asp Thr Gly Thr Gly Leu
                965                 970                 975

Val Thr Ala Lys Thr Val Ile Asp Ala Val Asn Lys Ser Gly Trp Arg
            980                 985                 990

Val Thr Gly Glu Gly Ala Thr Ala Glu Thr Gly Ala Thr Ala Val Asn
        995                 1000                1005

Ala Gly Asn Ala Glu Thr Val Thr Ser Gly Thr Ser Val Asn Phe Lys
    1010                1015                1020

Asn Gly Asn Ala Thr Thr Ala Thr Val Ser Lys Asp Asn Gly Asn Ile
1025                1030                1035                1040

Asn Val Lys Tyr Asp Val Asn Val Gly Asp Gly Leu Lys Ile Gly Asp
                1045                1050                1055

Asp Lys Lys Ile Val Ala Asp Thr Thr Thr Leu Thr Val Thr Gly Gly
            1060                1065                1070

Lys Val Ser Val Pro Ala Gly Ala Asn Ser Val Asn Asn Asn Lys Lys
        1075                1080                1085

Leu Val Asn Ala Glu Gly Leu Ala Thr Ala Leu Asn Asn Leu Ser Trp
    1090                1095                1100

Thr Ala Lys Ala Asp Lys Tyr Ala Asp Gly Glu Ser Glu Gly Glu Thr
1105                1110                1115                1120

Asp Gln Glu Val Lys Ala Gly Asp Lys Val Thr Phe Lys Ala Gly Lys
                1125                1130                1135

Asn Leu Lys Val Lys Gln Ser Glu Lys Asp Phe Thr Tyr Ser Leu Gln
            1140                1145                1150

Asp Thr Leu Thr Gly Leu Thr Ser Ile Thr Leu Gly Gly Thr Ala Asn
        1155                1160                1165

Gly Arg Asn Asp Thr Gly Thr Val Ile Asn Lys Asp Gly Leu Thr Ile
    1170                1175                1180

Thr Leu Ala Asn Gly Ala Ala Ala Gly Thr Asp Ala Ser Asn Gly Asn
1185                1190                1195                1200

Thr Ile Ser Val Thr Lys Asp Gly Ile Ser Ala Gly Asn Lys Glu Ile
                1205                1210                1215

Thr Asn Val Lys Ser Ala Leu Lys Thr Tyr Lys Asp Thr Gln Asn Thr
            1220                1225                1230

Ala Asp Glu Thr Gln Asp Lys Glu Phe His Ala Ala Val Lys Asn Ala
        1235                1240                1245

Asn Glu Val Glu Phe Val Gly Lys Asn Gly Ala Thr Val Ser Ala Lys
    1250                1255                1260

Thr Asp Asn Asn Gly Lys His Thr Val Thr Ile Asp Val Ala Glu Ala
1265                1270                1275                1280

Lys Val Gly Asp Gly Leu Glu Lys Asp Thr Asp Gly Lys Ile Lys Leu
                1285                1290                1295

Lys Val Asp Asn Thr Asp Gly Asn Asn Leu Leu Thr Val Asp Ala Thr
            1300                1305                1310

Lys Gly Ala Ser Val Ala Lys Gly Glu Phe Asn Ala Val Thr Thr Asp
        1315                1320                1325

Ala Thr Thr Ala Gln Gly Thr Asn Ala Asn Glu Arg Gly Lys Val Val
    1330                1335                1340

Val Lys Gly Ser Asn Gly Ala Thr Ala Thr Glu Thr Asp Lys Lys Lys
1345                1350                1355                1360
```

-continued

```
Val Ala Thr Val Gly Asp Val Ala Lys Ala Ile Asn Asp Ala Ala Thr
            1365                1370                1375

Phe Val Lys Val Glu Asn Asp Asp Ser Ala Thr Ile Asp Asp Ser Pro
        1380                1385                1390

Thr Asp Asp Gly Ala Asn Asp Ala Leu Lys Ala Gly Asp Thr Leu Thr
    1395                1400                1405

Leu Lys Ala Gly Lys Asn Leu Lys Val Lys Arg Asp Gly Lys Asn Ile
    1410                1415                1420

Thr Phe Ala Leu Ala Asn Asp Leu Ser Val Lys Ser Ala Thr Val Ser
1425                1430                1435                1440

Asp Lys Leu Ser Leu Gly Thr Asn Gly Asn Lys Val Asn Ile Thr Ser
            1445                1450                1455

Asp Thr Lys Gly Leu Lys Phe Ala Lys Asp Ser Lys Thr Gly Asp Asp
        1460                1465                1470

Ala Asn Ile His Leu Asn Gly Ile Ala Ser Thr Leu Thr Asp Thr Leu
    1475                1480                1485

Leu Asn Ser Gly Ala Thr Thr Asn Leu Gly Gly Asn Gly Ile Thr Asp
    1490                1495                1500

Asn Glu Lys Lys Arg Ala Ala Ser Val Lys Asp Val Leu Asn Ala Gly
1505                1510                1515                1520

Trp Asn Val Arg Gly Val Lys Pro Ala Ser Ala Asn Asn Gln Val Glu
            1525                1530                1535

Asn Ile Asp Phe Val Ala Thr Tyr Asp Thr Val Asp Phe Val Ser Gly
        1540                1545                1550

Asp Lys Asp Thr Thr Ser Val Thr Val Glu Ser Lys Asp Asn Gly Lys
    1555                1560                1565

Arg Thr Glu Val Lys Ile Gly Ala Lys Thr Ser Val Ile Lys Asp His
    1570                1575                1580

Asn Gly Lys Leu Phe Thr Gly Lys Glu Leu Lys Asp Ala Asn Asn Asn
1585                1590                1595                1600

Gly Val Thr Val Thr Glu Thr Asp Gly Lys Asp Glu Gly Asn Gly Leu
            1605                1610                1615

Val Thr Ala Lys Ala Val Ile Asp Ala Val Asn Lys Ala Gly Trp Arg
        1620                1625                1630

Val Lys Thr Thr Gly Ala Asn Gly Gln Asn Asp Asp Phe Ala Thr Val
    1635                1640                1645

Ala Ser Gly Thr Asn Val Thr Phe Ala Asp Gly Asn Gly Thr Thr Ala
    1650                1655                1660

Glu Val Thr Lys Ala Asn Asp Gly Ser Ile Thr Val Lys Tyr Asn Val
1665                1670                1675                1680

Lys Val Ala Asp Gly Leu Lys Leu Asp Gly Asp Lys Ile Val Ala Asp
            1685                1690                1695

Thr Thr Val Leu Thr Val Ala Asp Gly Lys Val Thr Ala Pro Asn Asn
        1700                1705                1710

Gly Asp Gly Lys Lys Phe Val Asp Ala Ser Gly Leu Ala Asp Ala Leu
    1715                1720                1725

Asn Lys Leu Ser Trp Thr Ala Thr Ala Gly Lys Glu Gly Thr Gly Glu
    1730                1735                1740

Val Asp Pro Ala Asn Ser Ala Gly Gln Glu Val Lys Ala Gly Asp Lys
1745                1750                1755                1760

Val Thr Phe Lys Ala Gly Asp Asn Leu Lys Ile Lys Gln Ser Gly Lys
            1765                1770                1775

Asp Phe Thr Tyr Ser Leu Lys Lys Glu Leu Lys Asp Leu Thr Ser Val
```

-continued

```
            1780                1785                1790

Glu Phe Lys Asp Ala Asn Gly Gly Thr Gly Ser Glu Ser Thr Lys Ile
        1795                1800                1805

Thr Lys Asp Gly Leu Thr Ile Thr Pro Ala Asn Gly Ala Gly Ala Ala
    1810                1815                1820

Gly Ala Asn Thr Ala Asn Thr Ile Ser Val Thr Lys Asp Gly Ile Ser
1825                1830                1835                1840

Ala Gly Asn Lys Ala Val Thr Asn Val Val Ser Gly Leu Lys Lys Phe
                1845                1850                1855

Gly Asp Gly His Thr Leu Ala Asn Gly Thr Val Ala Asp Phe Glu Lys
            1860                1865                1870

His Tyr Asp Asn Ala Tyr Lys Asp Leu Thr Asn Leu Asp Glu Lys Gly
        1875                1880                1885

Ala Asp Asn Asn Pro Thr Val Ala Asp Asn Thr Ala Ala Thr Val Gly
    1890                1895                1900

Asp Leu Arg Gly Leu Gly Trp Val Ile Ser Ala Asp Lys Thr Thr Gly
1905                1910                1915                1920

Glu Pro Asn Gln Glu Tyr Asn Ala Gln Val Arg Asn Ala Asn Glu Val
                1925                1930                1935

Lys Phe Lys Ser Gly Asn Gly Ile Asn Val Ser Gly Lys Thr Leu Asp
            1940                1945                1950

Asn Gly Thr Arg Val Ile Thr Phe Glu Leu Ala Lys Gly Glu Val Val
        1955                1960                1965

Lys Ser Asn Glu Phe Thr Val Lys Asn Ala Asp Gly Ser Glu Thr Asn
    1970                1975                1980

Leu Val Lys Val Gly Asp Met Tyr Tyr Ser Lys Glu Asp Ile Asp Pro
1985                1990                1995                2000

Ala Thr Ser Lys Pro Met Thr Gly Lys Thr Glu Lys Tyr Lys Val Glu
                2005                2010                2015

Asn Gly Lys Val Val Ser Ala Asn Gly Ser Lys Thr Glu Val Thr Leu
            2020                2025                2030

Thr Asn Lys Gly Ser Gly Tyr Val Thr Gly Asn Gln Val Ala Asp Ala
        2035                2040                2045

Ile Ala Lys Ser Gly Phe Glu Leu Gly Leu Ala Asp Ala Ala Glu Ala
    2050                2055                2060

Glu Lys Ala Phe Ala Glu Ser Ala Lys Asp Lys Gln Leu Ser Lys Asp
2065                2070                2075                2080

Lys Ala Glu Thr Val Asn Ala His Asp Lys Val Arg Phe Ala Asn Gly
                2085                2090                2095

Leu Asn Thr Lys Val Ser Ala Ala Thr Val Glu Ser Thr Asp Ala Asn
            2100                2105                2110

Gly Asp Lys Val Thr Thr Thr Phe Val Lys Thr Asp Val Glu Leu Pro
        2115                2120                2125

Leu Thr Gln Ile Tyr Asn Thr Asp Ala Asn Gly Asn Lys Ile Val Lys
    2130                2135                2140

Lys Ala Asp Gly Lys Trp Tyr Glu Leu Asn Ala Asp Gly Thr Ala Ser
2145                2150                2155                2160

Asn Lys Glu Val Thr Leu Gly Asn Val Asp Ala Asn Gly Lys Lys Val
                2165                2170                2175

Val Lys Val Thr Glu Asn Gly Ala Asp Lys Trp Tyr Tyr Thr Asn Ala
            2180                2185                2190

Asp Gly Ala Ala Asp Lys Thr Lys Gly Glu Val Ser Asn Asp Lys Val
        2195                2200                2205
```

-continued

Ser Thr Asp Glu Lys His Val Val Arg Leu Asp Pro Asn Asn Gln Ser
    2210                2215                2220

Asn Gly Lys Gly Val Val Ile Asp Asn Val Ala Asn Gly Glu Ile Ser
2225                2230                2235                2240

Ala Thr Ser Thr Asp Ala Ile Asn Gly Ser Ala Leu Tyr Ala Val Ala
                2245                2250                2255

Lys Gly Val Thr Asn Leu Ala Gly Gln Val Asn Asn Leu Glu Gly Lys
            2260                2265                2270

Val Asn Lys Val Gly Lys Arg Ala Asp Ala Gly Thr Ala Ser Ala Leu
        2275                2280                2285

Ala Ala Ser Gln Leu Pro Gln Ala Thr Met Pro Gly Lys Ser Met Val
    2290                2295                2300

Ala Ile Ala Gly Ser Ser Tyr Gln Gly Gln Asn Gly Leu Ala Ile Gly
2305                2310                2315                2320

Val Ser Arg Ile Ser Asp Asn Gly Lys Val Ile Ile Arg Leu Ser Gly
                2325                2330                2335

Thr Thr Asn Ser Gln Gly Lys Thr Gly Val Ala Ala Gly Val Gly Tyr
            2340                2345                2350

Gln Trp

<210> SEQ ID NO 48
<211> LENGTH: 2048
<212> TYPE: PRT
<213> ORGANISM: Haemophilus influenzae

<400> SEQUENCE: 48

Met Asn His Ile Tyr Lys Val Ile Phe Asn Lys Ala Thr Gly Thr Phe
  1               5                  10                  15

Met Ala Val Ala Glu Tyr Ala Lys Ser His Ser Thr Gly Gly Gly Ser
            20                  25                  30

Cys Ala Thr Gly Gln Val Gly Ser Val Cys Thr Leu Ser Phe Ala Arg
        35                  40                  45

Ile Ala Ala Leu Ala Val Leu Val Ile Gly Ala Thr Leu Ser Gly Ser
     50                  55                  60

Ala Tyr Ala Gln Lys Lys Asp Thr Lys His Ile Ala Ile Gly Glu Gln
 65                  70                  75                  80

Asn Gln Pro Arg Arg Ser Gly Thr Ala Lys Ala Asp Gly Asp Arg Ala
                 85                  90                  95

Ile Ala Ile Gly Glu Asn Ala Asn Ala Gln Gly Gly Gln Ala Ile Ala
            100                 105                 110

Ile Gly Ser Ser Asn Lys Thr Val Asn Gly Ser Ser Leu Asp Lys Ile
        115                 120                 125

Gly Thr Asp Ala Thr Gly Gln Glu Ser Ile Ala Ile Gly Gly Asp Val
    130                 135                 140

Lys Ala Ser Gly Asp Ala Ser Ile Ala Ile Gly Ser Asp Asp Leu His
145                 150                 155                 160

Leu Leu Asp Gln His Gly Asn Pro Lys His Pro Lys Gly Thr Leu Ile
                165                 170                 175

Asn Asp Leu Ile Asn Gly His Ala Val Leu Lys Glu Ile Arg Ser Ser
            180                 185                 190

Lys Asp Asn Asp Val Lys Tyr Arg Arg Thr Thr Ala Ser Gly His Ala
        195                 200                 205

Ser Thr Ala Val Gly Ala Met Ser Tyr Ala Gln Gly His Phe Ser Asn
    210                 215                 220

-continued

```
Ala Phe Gly Thr Arg Ala Thr Ala Lys Ser Ala Tyr Ser Leu Ala Val
225                 230                 235                 240

Gly Leu Ala Ala Thr Ala Glu Gly Gln Ser Thr Ile Ala Ile Gly Ser
                245                 250                 255

Asp Ala Thr Ser Ser Ser Leu Gly Ala Ile Ala Leu Gly Ala Gly Thr
            260                 265                 270

Arg Ala Gln Leu Gln Gly Ser Ile Ala Leu Gly Gln Gly Ser Val Val
        275                 280                 285

Thr Gln Ser Asp Asn Asn Ser Arg Pro Ala Tyr Thr Pro Asn Thr Gln
    290                 295                 300

Ala Leu Asp Pro Lys Phe Gln Ala Thr Asn Asn Thr Lys Ala Gly Pro
305                 310                 315                 320

Leu Ser Ile Gly Ser Asn Ser Ile Lys Arg Lys Ile Ile Asn Val Gly
                325                 330                 335

Ala Gly Val Asn Lys Thr Asp Ala Val Asn Val Ala Gln Leu Glu Ala
            340                 345                 350

Val Val Lys Trp Ala Lys Glu Arg Arg Ile Thr Phe Gln Gly Asp Asp
        355                 360                 365

Asn Ser Thr Asp Val Lys Ile Gly Leu Asp Asn Thr Leu Thr Ile Lys
    370                 375                 380

Gly Gly Ala Glu Thr Asn Ala Leu Thr Asp Asn Asn Ile Gly Val Val
385                 390                 395                 400

Lys Glu Ala Asp Asn Ser Gly Leu Lys Val Lys Leu Ala Lys Thr Leu
                405                 410                 415

Asn Asn Leu Thr Glu Val Asn Thr Thr Thr Leu Asn Ala Thr Thr Thr
            420                 425                 430

Val Lys Val Gly Ser Ser Ser Ser Thr Thr Ala Glu Leu Leu Ser Asp
        435                 440                 445

Ser Leu Thr Phe Thr Gln Pro Asn Thr Gly Ser Gln Ser Thr Ser Lys
    450                 455                 460

Thr Val Tyr Gly Val Asn Gly Val Lys Phe Thr Asn Asn Ala Glu Thr
465                 470                 475                 480

Thr Ala Ala Ile Gly Thr Thr Arg Ile Thr Arg Asp Lys Ile Gly Phe
                485                 490                 495

Ala Arg Asp Gly Asp Val Asp Glu Lys Gln Ala Pro Tyr Leu Asp Lys
            500                 505                 510

Lys Gln Leu Lys Val Gly Ser Val Ala Ile Thr Ile Asp Asn Gly Ile
        515                 520                 525

Asp Ala Gly Asn Lys Lys Ile Ser Asn Leu Ala Lys Gly Ser Ser Ala
    530                 535                 540

Asn Asp Ala Val Thr Ile Glu Gln Leu Lys Ala Ala Lys Pro Thr Leu
545                 550                 555                 560

Asn Ala Gly Ala Gly Ile Ser Val Thr Pro Thr Glu Ile Ser Val Asp
                565                 570                 575

Ala Lys Ser Gly Asn Val Thr Ala Pro Thr Tyr Asn Ile Gly Val Lys
            580                 585                 590

Thr Thr Glu Leu Asn Ser Asp Gly Thr Ser Asp Lys Phe Ser Val Lys
        595                 600                 605

Gly Ser Gly Thr Asn Asn Ser Leu Val Thr Ala Glu His Leu Ala Ser
    610                 615                 620

Tyr Leu Asn Glu Val Asn Arg Thr Ala Asp Ser Ala Leu Gln Ser Phe
625                 630                 635                 640
```

-continued

```
Thr Val Lys Glu Glu Asp Asp Asp Asp Ala Asn Ala Ile Thr Val Ala
                645                 650                 655

Lys Asp Thr Thr Lys Asn Ala Gly Ala Val Ser Ile Leu Lys Leu Lys
            660                 665                 670

Gly Lys Asn Gly Leu Thr Val Ala Thr Lys Lys Asp Gly Thr Val Thr
        675                 680                 685

Phe Gly Leu Ser Gln Asp Ser Gly Leu Thr Ile Gly Lys Ser Thr Leu
    690                 695                 700

Asn Asn Asp Gly Leu Thr Val Lys Asp Thr Asn Glu Gln Ile Gln Val
705                 710                 715                 720

Gly Ala Asn Gly Ile Lys Phe Thr Asn Val Asn Gly Ser Asn Pro Gly
                725                 730                 735

Thr Gly Ile Ala Asn Thr Ala Arg Ile Thr Arg Asp Lys Ile Gly Phe
            740                 745                 750

Ala Gly Ser Asp Gly Ala Val Asp Thr Asn Lys Pro Tyr Leu Asp Gln
        755                 760                 765

Asp Lys Leu Gln Val Gly Asn Val Lys Ile Thr Asn Thr Gly Ile Asn
    770                 775                 780

Ala Gly Gly Lys Ala Ile Thr Gly Leu Ser Pro Thr Leu Pro Ser Ile
785                 790                 795                 800

Ala Asp Gln Ser Ser Arg Asn Ile Glu Leu Gly Asn Thr Ile Gln Asp
                805                 810                 815

Lys Asp Lys Ser Asn Ala Ala Ser Ile Asn Asp Ile Leu Asn Thr Gly
            820                 825                 830

Phe Asn Leu Lys Asn Asn Asn Asn Pro Ile Asp Phe Val Ser Thr Tyr
        835                 840                 845

Asp Ile Val Asp Phe Ala Asn Gly Asn Ala Thr Thr Ala Thr Val Thr
    850                 855                 860

His Asp Thr Ala Asn Lys Thr Ser Lys Val Val Tyr Asp Val Asn Val
865                 870                 875                 880

Asp Asp Thr Thr Ile His Leu Thr Gly Thr Asp Asp Asn Lys Lys Leu
                885                 890                 895

Gly Val Lys Thr Thr Lys Leu Asn Lys Thr Ser Ala Asn Gly Asn Thr
            900                 905                 910

Ala Thr Asn Phe Asn Val Asn Ser Ser Asp Glu Asp Ala Leu Val Asn
        915                 920                 925

Ala Lys Asp Ile Ala Glu Asn Leu Asn Thr Leu Ala Lys Glu Ile His
    930                 935                 940

Thr Thr Lys Gly Thr Ala Asp Thr Ala Leu Gln Thr Phe Thr Val Lys
945                 950                 955                 960

Lys Val Asp Glu Asn Asn Asn Ala Asp Asp Ala Asn Ala Ile Thr Val
                965                 970                 975

Gly Gln Lys Asn Ala Asn Asn Gln Val Asn Thr Leu Thr Leu Lys Gly
            980                 985                 990

Glu Asn Gly Leu Asn Ile Lys Thr Asp Lys Asn Gly Thr Val Thr Phe
        995                 1000                1005

Gly Ile Asn Thr Thr Ser Gly Leu Lys Ala Gly Lys Ser Thr Leu Asn
    1010                1015                1020

Asp Gly Gly Leu Ser Ile Lys Asn Pro Thr Gly Ser Glu Gln Ile Gln
1025                1030                1035                1040

Val Gly Ala Asp Gly Val Lys Phe Ala Lys Val Asn Asn Asn Gly Val
                1045                1050                1055

Val Gly Ala Gly Ile Asp Gly Thr Thr Arg Ile Thr Arg Asp Glu Ile
```

-continued

```
            1060                1065                1070

Gly Phe Thr Gly Thr Asn Gly Ser Leu Asp Lys Ser Lys Pro His Leu
        1075                1080                1085

Ser Lys Asp Gly Ile Asn Ala Gly Gly Lys Lys Ile Thr Asn Ile Gln
    1090                1095                1100

Ser Gly Glu Ile Gln Ala Asn Ser His Asp Ala Val Thr Gly Gly Lys
1105                1110                1115                1120

Ile Tyr Asp Leu Lys Thr Glu Leu Glu Asn Lys Ile Ser Ser Thr Ala
                1125                1130                1135

Lys Thr Ala Gln Asn Ser Leu His Glu Phe Ser Val Ala Asp Glu Gln
            1140                1145                1150

Gly Asn Asn Phe Thr Val Ser Asn Pro Tyr Ser Ser Tyr Asp Thr Ser
        1155                1160                1165

Lys Thr Ser Asp Val Ile Thr Phe Ala Gly Glu Asn Gly Ile Thr Thr
    1170                1175                1180

Lys Val Asn Lys Gly Val Val Arg Val Gly Ile Asp Gln Thr Lys Gly
1185                1190                1195                1200

Leu Thr Thr Pro Lys Leu Thr Val Gly Asn Asn Asn Gly Lys Gly Ile
                1205                1210                1215

Val Ile Asp Ser Gln Asn Gly Gln Asn Thr Ile Thr Gly Leu Ser Asn
            1220                1225                1230

Thr Leu Ala Asn Val Thr Asn Asp Lys Gly Ser Val Arg Thr Thr Glu
        1235                1240                1245

Gln Gly Asn Ile Ile Lys Asp Glu Asp Lys Thr Arg Ala Ala Ser Ile
    1250                1255                1260

Val Asp Val Leu Ser Ala Gly Phe Asn Leu Gln Gly Asn Gly Glu Ala
1265                1270                1275                1280

Val Asp Phe Val Ser Thr Tyr Asp Thr Val Asn Phe Ala Asp Gly Asn
                1285                1290                1295

Ala Thr Thr Ala Lys Val Thr Tyr Asp Asp Thr Ser Lys Thr Ser Lys
            1300                1305                1310

Val Val Tyr Asp Val Asn Asp Asp Thr Thr Ile Glu Val Lys Asp Lys
        1315                1320                1325

Lys Leu Gly Val Lys Thr Thr Thr Leu Thr Ser Thr Gly Thr Gly Ala
    1330                1335                1340

Asn Lys Phe Ala Leu Ser Asn Gln Ala Thr Gly Asp Ala Leu Val Lys
1345                1350                1355                1360

Ala Ser Asp Ile Val Ala His Ser Leu Asn Thr Leu Ser Gly Asp Ile
                1365                1370                1375

Gln Thr Ala Lys Gly Ala Ser Gln Ala Asn Asn Ser Ala Gly Tyr Val
            1380                1385                1390

Asp Ala Asp Gly Asn Lys Ile Val Ile Tyr Asp Ser Thr Asp Asn Lys
        1395                1400                1405

Tyr Tyr Gln Ala Lys Asn Asp Gly Thr Val Asp Lys Thr Lys Glu Val
    1410                1415                1420

Ala Lys Asp Lys Leu Val Ala Gln Ala Gln Thr Pro Asp Gly Thr Leu
1425                1430                1435                1440

Ala Gln Met Asn Val Lys Ser Val Ile Asn Lys Glu Gln Val Asn Asp
                1445                1450                1455

Ala Asn Lys Lys Gln Gly Ile Asn Glu Asp Asn Ala Phe Val Lys Gly
            1460                1465                1470

Leu Glu Lys Ala Ala Ser Asp Asn Lys Thr Lys Asn Ala Ala Val Thr
        1475                1480                1485
```

-continued

```
Val Gly Asp Leu Asn Ala Val Ala Gln Thr Pro Leu Thr Phe Ala Gly
    1490                1495                1500

Asp Thr Gly Thr Thr Ala Lys Lys Leu Gly Glu Thr Leu Thr Ile Lys
1505                1510                1515                1520

Gly Gly Gln Thr Asp Thr Asn Lys Leu Thr Asp Asn Asn Ile Gly Val
                1525                1530                1535

Val Ala Gly Thr Asp Gly Phe Thr Val Lys Leu Ala Lys Asp Leu Thr
            1540                1545                1550

Asn Leu Asn Ser Val Asn Ala Gly Gly Thr Lys Ile Asp Asp Lys Gly
        1555                1560                1565

Val Ser Phe Val Asp Ser Ser Gly Gln Ala Lys Ala Asn Thr Pro Val
    1570                1575                1580

Leu Ser Ala Asn Gly Leu Asp Leu Gly Gly Lys Val Ile Ser Asn Val
1585                1590                1595                1600

Gly Lys Gly Thr Lys Asp Thr Asp Ala Ala Asn Val Gln Gln Leu Asn
                1605                1610                1615

Glu Val Arg Asn Leu Leu Gly Leu Gly Asn Ala Gly Asn Asp Asn Ala
            1620                1625                1630

Asp Gly Asn Gln Val Asn Ile Ala Asp Ile Lys Lys Asp Pro Asn Ser
        1635                1640                1645

Gly Ser Ser Ser Asn Arg Thr Val Ile Lys Ala Gly Thr Val Leu Gly
    1650                1655                1660

Gly Lys Gly Asn Asn Asp Thr Glu Lys Leu Ala Thr Gly Gly Ile Gln
1665                1670                1675                1680

Val Gly Val Asp Lys Asp Gly Asn Ala Asn Gly Asp Leu Ser Asn Val
                1685                1690                1695

Trp Val Lys Thr Gln Lys Asp Gly Ser Lys Lys Ala Leu Leu Ala Thr
            1700                1705                1710

Tyr Asn Ala Ala Gly Gln Thr Asn Tyr Leu Thr Asn Asn Pro Ala Glu
        1715                1720                1725

Ala Ile Asp Arg Ile Asn Glu Gln Gly Ile Arg Phe Phe His Val Asn
    1730                1735                1740

Asp Gly Asn Gln Glu Pro Val Val Gln Gly Arg Asn Gly Ile Asp Ser
1745                1750                1755                1760

Ser Ala Ser Gly Lys His Ser Val Ala Ile Gly Phe Gln Ala Lys Ala
                1765                1770                1775

Asp Gly Glu Ala Ala Val Ala Ile Gly Arg Gln Thr Gln Ala Gly Asn
            1780                1785                1790

Gln Ser Ile Ala Ile Gly Asp Asn Ala Gln Ala Thr Gly Asp Gln Ser
        1795                1800                1805

Ile Ala Ile Gly Arg Thr Asn Val Val Ala Gly Lys His Ser Gly Ala
    1810                1815                1820

Ile Gly Asp Pro Ser Thr Val Lys Ala Asp Asn Ser Tyr Ser Val Gly
1825                1830                1835                1840

Asn Asn Asn Gln Phe Thr Asp Ala Thr Gln Thr Asp Val Phe Gly Val
                1845                1850                1855

Gly Asn Asn Ile Thr Val Thr Glu Ser Asn Ser Val Ala Leu Gly Ser
            1860                1865                1870

Asn Ser Ala Ile Ser Ala Gly Thr His Ala Gly Thr Gln Ala Lys Lys
        1875                1880                1885

Ser Asp Gly Thr Ala Gly Thr Thr Thr Thr Ala Gly Ala Thr Gly Thr
    1890                1895                1900
```

-continued

```
Val Lys Gly Phe Ala Gly Gln Thr Ala Val Gly Ala Val Ser Val Gly
1905                1910                1915                1920

Ala Ser Gly Ala Glu Arg Arg Ile Gln Asn Val Ala Ala Gly Glu Val
                1925                1930                1935

Ser Ala Thr Ser Thr Asp Ala Val Asn Gly Ser Gln Leu Tyr Lys Ala
            1940                1945                1950

Thr Gln Ser Ile Ala Asn Ala Thr Asn Glu Leu Asp His Arg Ile His
        1955                1960                1965

Gln Asn Glu Asn Lys Ala Asn Ala Gly Ile Ser Ser Ala Met Ala Met
    1970                1975                1980

Ala Ser Met Pro Gln Ala Tyr Ile Pro Gly Arg Ser Met Val Thr Gly
1985                1990                1995                2000

Gly Ile Ala Thr His Asn Gly Gln Gly Ala Val Ala Val Gly Leu Ser
                2005                2010                2015

Lys Leu Ser Asp Asn Gly Gln Trp Val Phe Lys Ile Asn Gly Ser Ala
            2020                2025                2030

Asp Thr Gln Gly His Val Gly Ala Ala Val Gly Ala Gly Phe His Phe
        2035                2040                2045


<210> SEQ ID NO 49
<211> LENGTH: 2314
<212> TYPE: PRT
<213> ORGANISM: Haemophilus influenzae

<400> SEQUENCE: 49

Met Asn His Lys Tyr Lys Val Ile Phe Asn Lys Ala Thr Gly Thr Phe
  1               5                  10                  15

Met Ala Val Ala Glu Cys Ala Lys Ser His Ser Gly Gly Ser Ser Ser
             20                  25                  30

Ser Thr Ala Gly Gln Val Gly Ser Ser Pro Val Ile Arg Leu Thr Arg
         35                  40                  45

Val Ala Thr Leu Ala Ile Leu Val Ile Gly Ala Thr Leu Asn Gly Ser
     50                  55                  60

Ala Tyr Ala Gln Asn Asn Ser Lys Ile Ala Phe Gly Thr Thr Gly Asn
 65                  70                  75                  80

Asn Asp Asn Ala Ser Ala Ser Asn Glu Ala Ser Ile Ala Ile Gly Ser
                 85                  90                  95

Leu Ala Lys Ala His Ala Asn Gln Ala Ile Ala Ile Gly Gly Ser Lys
            100                 105                 110

Pro Asp Pro Arg Asn Gln Ala Ala Asn Gln Lys Ala Gly Ser His Ala
        115                 120                 125

Lys Gly Lys Glu Ser Ile Ala Ile Gly Gly Asp Val Leu Ala Glu Gly
    130                 135                 140

Asp Ala Ser Ile Ala Ile Gly Ser Asp Asp Leu Tyr Leu Asp Arg Asn
145                 150                 155                 160

Ser Thr Asn Ser Lys Tyr Pro Asn Gly Leu Leu Ser Thr Leu Ile Gln
                165                 170                 175

Asn His Thr Val Leu Arg Gln Ile Arg Asp Ser Asn Gly Ser Gln Lys
            180                 185                 190

Tyr Arg Arg Thr Ala Ala Glu Gly His Ala Ser Thr Ala Val Gly Ala
        195                 200                 205

Met Ala Tyr Ala Lys Gly His Phe Ala Asn Ala Phe Gly Thr Arg Ser
    210                 215                 220

Thr Ala Glu Gly Asn Tyr Ser Leu Ala Val Gly Leu Thr Ala Lys Ala
225                 230                 235                 240
```

-continued

```
Glu Lys Gly Tyr Thr Ile Ala Ile Gly Ser Asn Ala Gln Ala Ile Asn
                245                 250                 255

Tyr Gly Ala Leu Ala Leu Gly Ala Asp Thr Arg Val Asp Leu Asp Tyr
            260                 265                 270

Gly Ile Ala Leu Gly Tyr Gly Ser Gln Ile Leu Asn Asn Asn Asn Asn
        275                 280                 285

Asn Asn Asn Lys Ala Tyr Val Pro Glu Gly Asn Gly Ser Asn Ile Lys
    290                 295                 300

Ser Ser Lys Ala Thr Gly Asn Gly Leu Phe Ser Ile Gly Ser Ser Thr
305                 310                 315                 320

Ile Lys Arg Lys Ile Ile Asn Val Gly Ala Gly Tyr Glu Asp Thr Asp
                325                 330                 335

Ala Val Asn Val Ala Gln Leu Lys Ala Val Glu Asn Leu Ala Lys Arg
            340                 345                 350

Gln Ile Thr Phe Lys Gly Asp Asp Asn Gly Thr Gly Val Lys Lys Lys
        355                 360                 365

Leu Gly Glu Thr Leu Thr Ile Lys Gly Gly Glu Thr Gln Ala Asp Lys
    370                 375                 380

Leu Thr Asp Asn Asn Asn Ile Gly Val Val Thr Asp Asn Asn Thr Gly
385                 390                 395                 400

Leu Lys Val Lys Leu Ala Lys Asn Leu Ser Gly Leu Glu Thr Val Ser
                405                 410                 415

Thr Lys Asn Leu Thr Ala Ser Glu Lys Val Thr Val Gly Ser Gly Asn
            420                 425                 430

Asn Thr Ala Glu Leu Gln Ser Gly Gly Leu Thr Phe Thr Pro Thr Thr
        435                 440                 445

Asn Ala Ser Thr Asp Lys Thr Val Tyr Gly Thr Asp Gly Leu Lys Phe
    450                 455                 460

Thr Asp Asn Ser Asn Thr Ala Leu Glu Asp Thr Thr Arg Ile Thr Lys
465                 470                 475                 480

Asp Lys Ile Gly Phe Ser Asn Lys Ala Gly Thr Val Asp Glu Asn Lys
                485                 490                 495

Pro Tyr Leu Asp Lys Asp Lys Leu Lys Val Gly Asn Ser Thr Leu Asn
            500                 505                 510

Asn Gly Gly Leu Thr Val Asn Asn Thr Ile Gly Gly Ser Asn Lys Gln
        515                 520                 525

Ile Gln Val Gly Ala Asp Gly Ile Lys Phe Ala Asp Val Asn Val Asn
    530                 535                 540

Val Ser Asn Ala Ala Lys Phe Gly Thr Thr Arg Ile Thr Glu Glu Glu
545                 550                 555                 560

Ile Gly Phe Ala Asp Ala Asp Gly Lys Val Asp Lys Lys Ser Pro Tyr
                565                 570                 575

Leu Asp Lys Lys Gln Leu Gln Val Gly Gly Val Lys Ile Thr Lys Asp
            580                 585                 590

Ser Gly Ile Asn Ala Gly Asp Gln Lys Ile Ser Asn Val Lys Asp Ala
        595                 600                 605

Thr Asp Asp Thr Asp Ala Val Thr Tyr Lys Gln Leu Lys Gln Val Gln
    610                 615                 620

Gln Asp Ala Asp Gly Ala Leu Gln Ser Phe Ser Ile Arg Asp Glu Lys
625                 630                 635                 640

Gly Gln Glu Phe Thr Ile Ser Asn Leu Tyr Ser Asn Gly Asn Thr Pro
                645                 650                 655
```

-continued

```
Asn Thr Phe Glu Thr Ile Thr Phe Ala Gly Glu Asn Gly Ile Ser Ile
            660                 665                 670

Ser Asn Asp Ile Ala Lys Gly Lys Val Lys Val Gly Ile Asp Pro Ile
        675                 680                 685

Asn Gly Leu Thr Thr Pro Lys Leu Thr Val Gly Ser Asp Lys Asp Gly
    690                 695                 700

Lys Thr Gln Leu Val Ile Glu Gln Val Ala Ser Gly Asn Gly Thr Lys
705                 710                 715                 720

Asn Ile Ile Arg Gly Val Ser Pro Thr Leu Pro Ser Ile Thr Asn Ala
                725                 730                 735

Gly Gly Val Arg Thr Thr Glu Gln Gly Asn Thr Ile Thr Ser Asp Glu
            740                 745                 750

Asp Lys Ser Lys Ala Ala Ser Ile Gly Asp Ile Leu Asn Thr Gly Phe
        755                 760                 765

Asn Leu Lys Asn Asn Ser Asn Ser Val Gly Phe Val Ser Thr Tyr Asn
    770                 775                 780

Thr Val Asp Phe Ile Asp Gly Asn Ala Thr Thr Ala Lys Val Thr Tyr
785                 790                 795                 800

Asp Glu Thr Asn Gln Thr Ser Lys Val Thr Tyr Asp Val Asn Val Asp
                805                 810                 815

Glu Lys Thr Ile Glu Leu Thr Gly Asp Asn Gly Lys Thr Asn Lys Ile
            820                 825                 830

Gly Val Lys Thr Thr Thr Leu Thr Thr Thr Asn Ala Asn Gly Lys Ala
        835                 840                 845

Thr Asn Phe Ser Thr Thr Asp Asn Asp Ala Leu Val Asn Ala Lys Asp
    850                 855                 860

Ile Ala Glu Asn Leu Asn Thr Leu Ala Lys Glu Ile His Thr Thr Lys
865                 870                 875                 880

Gly Thr Ala Asp Thr Ala Leu Gln Thr Phe Lys Val Lys Lys Asp Gly
                885                 890                 895

Ala Thr Asp Asp Glu Thr Ile Thr Val Gly Lys Asp Gly Thr Gln Asn
            900                 905                 910

Gly Lys Thr Val Asn Thr Leu Lys Leu Lys Gly Glu Asn Gly Leu Thr
        915                 920                 925

Val Ala Thr Asn Lys Asp Gly Thr Val Thr Phe Gly Ile Asn Thr Gln
    930                 935                 940

Ser Gly Leu Lys Ala Gly Asp Ser Thr Thr Leu Asn Lys Asp Gly Leu
945                 950                 955                 960

Ser Ile Lys Asn Pro Ala Ser Asn Glu Gln Ile Gln Val Gly Ala Asp
                965                 970                 975

Gly Val Lys Phe Ala Lys Val Asp Lys Gly Asn Ser Ser Thr Gly Ile
            980                 985                 990

Asp Gly Thr Ser Arg Ile Thr Lys Asp Gln Ile Gly Phe Thr Gly Ala
        995                 1000                1005

Asn Gly Ser Leu Asp Thr Thr Lys Pro His Leu Thr Lys Asp Lys Leu
    1010                1015                1020

Lys Val Gly Glu Val Glu Ile Thr Asn Thr Gly Ile Asn Ala Gly Gly
1025                1030                1035                1040

Lys Lys Ile Thr Asn Ile Gln Ser Gly Asp Ile Thr Gln Asn Ser Asn
                1045                1050                1055

Asp Ala Val Thr Gly Gly Arg Val Tyr Asp Leu Lys Thr Glu Leu Glu
            1060                1065                1070

Ser Lys Ile Asn Ser Ala Ala Lys Thr Ala Gln Asn Ser Leu His Glu
```

-continued

```
        1075                1080                1085

Phe Ser Val Ala Asp Glu Gln Gly Asn His Phe Thr Val Ser Asn Pro
    1090                1095                1100

Tyr Ser Ser Tyr Asp Thr Ser Lys Thr Ser Asp Val Ile Thr Phe Ala
1105                1110                1115                1120

Gly Glu Asn Gly Ile Thr Thr Lys Val Asn Lys Gly Val Val Arg Val
                1125                1130                1135

Gly Ile Asp Gln Thr Lys Gly Leu Thr Thr Pro Lys Leu Thr Val Gly
            1140                1145                1150

Asn Asn Asn Gly Lys Gly Ile Val Ile Asp Ser Lys Asp Gly Gln Asn
        1155                1160                1165

Thr Ile Thr Gly Leu Ser Asn Thr Leu Ala Asn Val Thr Asn Asp Gly
    1170                1175                1180

Ala Gly His Ala Leu Ser Gln Gly Leu Ala Asn Asp Thr Asp Lys Thr
1185                1190                1195                1200

Arg Ala Ala Ser Ile Gly Asp Val Leu Asn Ala Gly Phe Asn Leu Gln
                1205                1210                1215

Gly Asn Gly Glu Ala Val Asp Phe Val Ser Thr Tyr Asp Thr Val Asp
            1220                1225                1230

Phe Ile Asp Gly Asn Ala Thr Thr Ala Lys Val Thr Tyr Asp Asp Thr
        1235                1240                1245

Ser Lys Thr Ser Lys Val Val Tyr Asp Val Asn Val Asp Asn Lys Thr
    1250                1255                1260

Ile Glu Val Thr Ser Asp Lys Lys Leu Gly Val Lys Thr Thr Thr Leu
1265                1270                1275                1280

Thr Lys Thr Ser Ala Asn Gly Asn Ala Thr Lys Phe Ser Ala Ala Asp
                1285                1290                1295

Gly Asp Ala Leu Val Lys Ala Ser Asp Ile Ala Thr His Leu Asn Thr
            1300                1305                1310

Leu Ser Gly Asp Ile Gln Thr Ala Lys Gly Ala Ser Gln Ala Ser Ser
        1315                1320                1325

Ser Ala Ser Tyr Val Asp Ala Asp Gly Asn Lys Val Ile Tyr Asp Ser
    1330                1335                1340

Thr Asp Lys Lys Tyr Tyr Gln Val Asn Asp Lys Gly Gln Val Asp Lys
1345                1350                1355                1360

Asn Lys Glu Val Ala Lys Asp Lys Leu Val Ala Gln Ala Gln Thr Pro
                1365                1370                1375

Asp Gly Thr Leu Ala Gln Met Asn Val Lys Ser Val Ile Val Lys Glu
            1380                1385                1390

Gln Val Asn Asp Ala Asn Lys Lys Gln Gly Ile Asn Glu Asp Asn Ala
        1395                1400                1405

Phe Ile Lys Gly Leu Glu Asn Ala Ala Lys Asp Thr Lys Thr Lys Asn
    1410                1415                1420

Ala Ala Val Thr Val Gly Asp Leu Asn Ala Val Ala Gln Thr Pro Leu
1425                1430                1435                1440

Thr Phe Ala Gly Asp Thr Gly Thr Thr Ala Lys Lys Leu Gly Glu Thr
                1445                1450                1455

Leu Thr Ile Lys Gly Gly Gln Thr Asp Thr Asn Lys Leu Thr Asp Asn
            1460                1465                1470

Asn Ile Gly Val Val Ala Gly Thr Asp Gly Phe Thr Val Lys Leu Ala
        1475                1480                1485

Lys Asp Leu Thr Asn Leu Asn Ser Val Asn Ala Gly Gly Thr Arg Ile
    1490                1495                1500
```

-continued

```
Asp Glu Lys Gly Ile Ser Phe Val Asp Ala Asn Gly Gln Ala Lys Ala
1505                1510                1515                1520

Asn Thr Pro Val Leu Ser Ala Asn Gly Leu Asp Leu Gly Gly Lys Arg
                1525                1530                1535

Ile Ser Asn Ile Gly Ala Ala Val Asp Asp Asn Asp Ala Val Asn Phe
            1540                1545                1550

Lys Gln Phe Asn Glu Val Ala Lys Thr Val Asn Asn Leu Asn Asn Gln
        1555                1560                1565

Ser Asn Ser Gly Ala Ser Leu Pro Phe Val Val Thr Asp Ala Asn Gly
    1570                1575                1580

Lys Pro Ile Asn Gly Thr Asp Gly Lys Pro Gln Lys Ala Ile Lys Gly
1585                1590                1595                1600

Ala Asp Gly Lys Tyr Tyr His Ala Asn Ala Asn Gly Val Pro Val Asp
                1605                1610                1615

Lys Asp Gly Lys Pro Ile Thr Asp Ala Asp Lys Leu Ala Asn Leu Ala
            1620                1625                1630

Ala His Gly Lys Pro Leu Asp Ala Gly His Gln Val Val Ala Ser Leu
        1635                1640                1645

Gly Gly Asn Ser Asp Ala Ile Thr Leu Thr Asn Ile Lys Ser Thr Leu
    1650                1655                1660

Pro Gln Ile Asp Thr Pro Asn Thr Gly Asn Ala Asn Ala Gly Gln Ala
1665                1670                1675                1680

Gln Ser Leu Pro Ser Leu Ser Ala Ala Gln Gln Ser Asn Ala Ala Ser
                1685                1690                1695

Val Lys Asp Val Leu Asn Val Gly Phe Asn Leu Gln Thr Asn His Asn
            1700                1705                1710

Gln Val Asp Phe Val Lys Ala Tyr Asp Thr Val Asn Phe Val Asn Gly
        1715                1720                1725

Thr Gly Ala Asp Ile Thr Ser Val Arg Ser Ala Asp Gly Thr Met Ser
    1730                1735                1740

Asn Ile Thr Val Asn Thr Ala Leu Ala Ala Thr Asp Asp Asp Gly Asn
1745                1750                1755                1760

Val Leu Ile Lys Ala Lys Asp Gly Lys Phe Tyr Lys Ala Asp Asp Leu
                1765                1770                1775

Met Pro Asn Gly Ser Leu Lys Ala Gly Lys Ser Ala Ser Asp Ala Lys
            1780                1785                1790

Thr Pro Thr Gly Leu Ser Leu Val Asn Pro Asn Ala Gly Lys Gly Ser
        1795                1800                1805

Thr Gly Asp Ala Val Ala Leu Asn Asn Leu Ser Lys Ala Val Phe Lys
    1810                1815                1820

Ser Lys Asp Gly Thr Thr Thr Thr Thr Val Ser Ser Asp Gly Ile Ser
1825                1830                1835                1840

Ile Gln Gly Lys Asp Asn Ser Ser Ile Thr Leu Ser Lys Asp Gly Leu
                1845                1850                1855

Asn Val Gly Gly Lys Val Ile Ser Asn Val Gly Lys Gly Thr Lys Asp
            1860                1865                1870

Thr Asp Ala Ala Asn Val Gln Gln Leu Asn Glu Val Arg Asn Leu Leu
        1875                1880                1885

Gly Leu Gly Asn Ala Gly Asn Asp Asn Ala Asp Gly Asn Gln Val Asn
    1890                1895                1900

Ile Ala Asp Ile Lys Lys Asp Pro Asn Ser Gly Ser Ser Ser Asn Arg
1905                1910                1915                1920
```

-continued

```
Thr Val Ile Lys Ala Gly Thr Val Leu Gly Gly Lys Gly Asn Asn Asp
                1925                1930                1935

Thr Glu Lys Leu Ala Thr Gly Gly Val Gln Val Gly Val Asp Lys Asp
            1940                1945                1950

Gly Asn Ala Asn Gly Asp Leu Ser Asn Val Trp Val Lys Thr Gln Lys
        1955                1960                1965

Asp Gly Ser Lys Lys Ala Leu Leu Ala Thr Tyr Asn Ala Ala Gly Gln
    1970                1975                1980

Thr Asn Tyr Leu Thr Asn Asn Pro Ala Glu Ala Ile Asp Arg Ile Asn
1985                1990                1995                2000

Glu Gln Gly Ile Arg Phe Phe His Val Asn Asp Gly Asn Gln Glu Pro
                2005                2010                2015

Val Val Gln Gly Arg Asn Gly Ile Asp Ser Ser Ala Ser Gly Lys His
            2020                2025                2030

Ser Val Ala Ile Gly Phe Gln Ala Lys Ala Asp Gly Glu Ala Ala Val
        2035                2040                2045

Ala Ile Gly Arg Gln Thr Gln Ala Gly Asn Gln Ser Ile Ala Ile Gly
    2050                2055                2060

Asp Asn Ala Gln Ala Thr Gly Asp Gln Ser Ile Ala Ile Gly Thr Gly
2065                2070                2075                2080

Asn Val Val Thr Gly Lys His Ser Gly Ala Ile Gly Asp Pro Ser Thr
                2085                2090                2095

Val Lys Ala Asp Asn Ser Tyr Ser Val Gly Asn Asn Asn Gln Phe Ile
            2100                2105                2110

Asp Ala Thr Gln Thr Asp Val Phe Gly Val Gly Asn Asn Ile Thr Val
        2115                2120                2125

Thr Glu Ser Asn Ser Val Ala Leu Gly Ser Asn Ser Ala Ile Ser Ala
    2130                2135                2140

Gly Thr His Ala Gly Thr Gln Ala Lys Lys Ser Asp Gly Thr Ala Gly
2145                2150                2155                2160

Thr Thr Thr Thr Ala Gly Ala Thr Gly Thr Val Lys Gly Phe Ala Gly
                2165                2170                2175

Gln Thr Ala Val Gly Ala Val Ser Val Gly Ala Ser Gly Ala Glu Arg
            2180                2185                2190

Arg Ile Gln Asn Val Ala Ala Gly Glu Val Ser Ala Thr Ser Thr Asp
        2195                2200                2205

Ala Val Asn Gly Ser Gln Leu Tyr Lys Ala Thr Gln Gly Ile Ala Asn
    2210                2215                2220

Ala Thr Asn Glu Leu Asp His Arg Ile His Gln Asn Glu Asn Lys Ala
2225                2230                2235                2240

Asn Ala Gly Ile Ser Ser Ala Met Ala Met Ala Ser Met Pro Gln Ala
                2245                2250                2255

Tyr Ile Pro Gly Arg Ser Met Val Thr Gly Gly Ile Ala Thr His Asn
            2260                2265                2270

Gly Gln Gly Ala Val Ala Val Gly Leu Ser Lys Leu Ser Asp Asn Gly
        2275                2280                2285

Gln Trp Val Phe Lys Ile Asn Gly Ser Ala Asp Thr Gln Gly His Val
    2290                2295                2300

Gly Ala Ala Val Gly Ala Gly Phe His Phe
2305                2310
```

<210> SEQ ID NO 50
<211> LENGTH: 62
<212> TYPE: DNA

-continued

<213> ORGANISM: Haemophilus influenzae

<400> SEQUENCE: 50

```
gacccgttta gaggccccaa ggggttatgc tagttattgc tcagcggtgg cagcagcgtg     60

ca                                                                    62
```

<210> SEQ ID NO 51
<211> LENGTH: 47
<212> TYPE: DNA
<213> ORGANISM: Haemophilus influenzae

<400> SEQUENCE: 51

```
tccggggttc cccaatacga tcaataacga gtcgccaccg tcgtcgc                   47
```

<210> SEQ ID NO 52
<211> LENGTH: 110
<212> TYPE: DNA
<213> ORGANISM: Haemophilus influenzae

<400> SEQUENCE: 52

```
tatgaacaaa atttttaacg ttatttggaa tgttatgact caaacttggg ctgtcgtatc     60

tgaactcact cgcgcccaca ccaaacgtgc ctccgcaacc gtggcagccg               110
```

<210> SEQ ID NO 53
<211> LENGTH: 105
<212> TYPE: DNA
<213> ORGANISM: Haemophilus influenzae

<400> SEQUENCE: 53

```
acttgtttta aaaattgcaa taaaccttac aatactgagt ttgaacccga cagcatagac     60

ttgagtgagc gcgggtgtgg tttgcacgga ggcgttggca ccgtc                    105
```

<210> SEQ ID NO 54
<211> LENGTH: 36
<212> TYPE: PRT
<213> ORGANISM: Haemophilus influenzae

<400> SEQUENCE: 54

```
Met Asn Lys Ile Phe Asn Val Ile Trp Asn Val Met Thr Gln Thr Trp
  1               5                  10                  15

Ala Val Val Ser Glu Leu Thr Arg Ala His Thr Lys Arg Ala Ser Ala
             20                  25                  30

Thr Val Ala Ala
         35
```